US012195780B2

(12) United States Patent
Gabant

(10) Patent No.: US 12,195,780 B2
(45) Date of Patent: Jan. 14, 2025

(54) METHODS AND COMPOSITIONS FOR MAKING BACTERIOCINS AND ANTIMICROBIAL PEPTIDES

(71) Applicant: Syngulon SA, Seraing (BE)

(72) Inventor: Philippe Gabant, Ottignies Louvain-La-Neuve (BE)

(73) Assignee: Syngulon SA, Seraing (BE)

( * ) Notice: Subject to any disclaimer, the term of this patent is extended or adjusted under 35 U.S.C. 154(b) by 55 days.

(21) Appl. No.: 18/052,519

(22) Filed: Nov. 3, 2022

(65) Prior Publication Data

US 2023/0279461 A1 Sep. 7, 2023

Related U.S. Application Data

(62) Division of application No. 16/642,342, filed as application No. PCT/US2018/048846 on Aug. 30, 2018, now Pat. No. 11,492,651.

(60) Provisional application No. 62/552,835, filed on Aug. 31, 2017, provisional application No. 62/720,804, filed on Aug. 21, 2018.

(51) Int. Cl.

| | |
|---|---|
| ***C12P 21/02*** | (2006.01) |
| ***A01N 63/50*** | (2020.01) |
| ***B01L 3/00*** | (2006.01) |
| ***C07K 14/195*** | (2006.01) |
| ***C07K 14/32*** | (2006.01) |
| ***C12M 1/00*** | (2006.01) |
| ***C12M 1/34*** | (2006.01) |
| ***C12M 1/36*** | (2006.01) |
| ***C12M 1/40*** | (2006.01) |
| ***C12M 3/06*** | (2006.01) |

(52) U.S. Cl.

CPC .............. *C12P 21/02* (2013.01); *A01N 63/50* (2020.01); *B01L 3/502738* (2013.01); *C07K 14/195* (2013.01)

(58) Field of Classification Search

CPC ..... C12Q 1/04; C07K 14/4723; C07K 14/195

See application file for complete search history.

(56) References Cited

U.S. PATENT DOCUMENTS

| | | | |
|---|---|---|---|
| 5,910,438 | A | 6/1999 | Bernard et al. |
| 6,180,407 | B1 | 1/2001 | Bernard et al. |
| 7,176,029 | B2 | 2/2007 | Bernard et al. |
| 7,183,097 | B1 | 2/2007 | Gerdes et al. |
| 9,333,227 | B2 | 5/2016 | Gabant |
| 9,737,592 | B1 | 8/2017 | Bermudes et al. |
| 10,188,114 | B2 | 1/2019 | Gabant |
| 11,427,800 | B2 | 8/2022 | Gabant |
| 11,492,651 | B2 | 11/2022 | Gabant |
| 11,932,672 | B2 | 3/2024 | Gabant et al. |
| 2003/0096365 | A1 | 5/2003 | Faye et al. |
| 2004/0052814 | A1 | 3/2004 | Shi et al. |
| 2006/0229244 | A1 | 10/2006 | Dorit et al. |
| 2010/0286030 | A1 | 11/2010 | Farris et al. |
| 2013/0052182 | A1 | 2/2013 | Miller |
| 2015/0050253 | A1 | 2/2015 | Gabant |
| 2016/0002611 | A1 | 1/2016 | Mershin et al. |
| 2016/0145558 | A1 | 5/2016 | Boedicker et al. |
| 2016/0235774 | A1 | 8/2016 | Vournakis et al. |
| 2019/0191709 | A1 | 6/2019 | Gabant |
| 2020/0263221 | A1 | 8/2020 | Gabant |
| 2021/0238645 | A1 | 8/2021 | Gabant |
| 2022/0017573 | A1 | 1/2022 | Mignolet et al. |
| 2023/0193191 | A1 | 6/2023 | Gabant et al. |
| 2023/0279461 | A1 | 9/2023 | Gabant et al. |
| 2023/0414707 | A1 | 12/2023 | Gabant et al. |
| 2023/0416797 | A1 | 12/2023 | Gabant et al. |

FOREIGN PATENT DOCUMENTS

| | | | |
|---|---|---|---|
| CN | 1807645 | A | 7/2006 |
| CN | 101974546 | A | 2/2011 |
| JP | 2013-503159 | | 1/2013 |
| JP | 2016-512426 | | 4/2016 |
| WO | WO 2016028700 | | 2/2016 |
| WO | WO 2022/104320 | | 5/2022 |
| WO | WO 2022/104321 | | 5/2022 |
| WO | WO 2023/235682 | | 12/2023 |

OTHER PUBLICATIONS

Adetunji et al., Fungicidal effect of bacteriocins harvested from *Bacillus* spp., Malaysian Journal of Microbiology, vol. 9, No. 2, pp. 130-134, 2013.

Altschul, S.F., et al. Basic local alignment search tool, Journal of Molecular Biology, vol. 215, pp. 403-410, 1990.

Cotter, P.D. et al., Bacteriocins- a viable alternative to antibiotics, Nature Reviews Microbiology, vol. 11, pp. 95-105, 2013.

Damiati etal. (2018) Cell-Free Approaches in Synthetic Biology Utilizing Microfluidics Genes, vol. 9, issue 144), pp. 1-17.

Extended European Search Report in European Application No. 18852336.9 in 17 pages.

File History of U.S. Appl. No. 14/459,810, filed Jun. 14, 2014.

File History of U.S. Appl. No. 15/087,706, filed Mar. 31, 2016.

File History of U.S. Appl. No. 16/227,371, filed Dec. 20, 2018.

File History of U.S. Appl. No. 17/822,663, filed Aug. 26, 2022.

(Continued)

*Primary Examiner* — Suzanne M Noakes

*Assistant Examiner* — Jae W Lee

(74) *Attorney, Agent, or Firm* — KNOBBE, MARTENS, OLSON & BEAR, LLP

(57) ABSTRACT

Methods and compositions for making bacteriocins are described in some embodiments herein. In some embodiments, pro-polypeptide comprising the bacteriocins in the desired ratios in cis, and separated by cleavage sited can be produced by a microbial cell comprising a nucleic acid encoding the pro-polypeptide. In some embodiments microfluidic devices and methods for making specified mixtures of antimicrobial peptides and/or bacteriocins are described.

10 Claims, 8 Drawing Sheets

Specification includes a Sequence Listing.

(56) References Cited

OTHER PUBLICATIONS

File History of U.S. Appl. No. 16/642,342, filed Feb. 26, 2020.
File History of U.S. Appl. No. 16/972,553, filed Dec. 4, 2020.
Gajic et al, (2003) Novel Mechanism of Bacteriocin Secretion and Immunity Carried Out by Lactococcal Multidrug Resistance Proteins, J. Biol. Chem., vol. 278, No. 36, pp. 34291-34298.
Georgi et al. (2016) On-chip automation of cell-free protein synthesis: New opportunities due to a novel reaction mode. Lab Chip vol. 16, pp. 269-281.
Gibson et al., Creation of a Bacterial Cell Controlled by a Chemically Synthesized Genome, Science, vol. 329, pp. 52-56, 2010.
Goni-Moreno, et al., Multicellular Computing Using Conjugation for Wiring. PLoS ONE, vol. 8, No. 6, e65986, 2013.
International Search Report and Written Opinion in International Application No. PCT/US2018/048846 Dated Dec. 20, 2018 in 12 pages.
Jain et al. Current ADC Linker Chemistry, Pharmaceutical Research, vol. 32, pp. 3526-3540, 2015.
Jaramillo A., et al., Engineered Stable Ecosystems, Synthetic Biology, No. 2, vol. 17119, 2017.
Leonardo Acuna et al., A new hybrid bacteriocin, Ent35-MccV, displays antimicrobial activity against pathogenic Gram-positive and Gram-negative bacteria, FEBS Open Bio, vol. 2, No. 1, Jan. 1, 2012, pp. 12-19.
Li. Recombinant production of antimicrobial peptides in *Escherichia coli*: a review. Protein Expr Purif, Dec. 2011, vol. 80, No. 2, pp. 260-267.
Lohans Christopher T. et al., Development 1-4,6-H of Class IIa Bacteriocins as Therapeutic Agents, International Journal of Microbiology, vol. 2012, 386410, Jan. 1, 2012, pp. 1-13.
Mead et al. Nucleic Acids Res. Dec. 11, 1990; 18(23): 7167.
Michael Klocke et al., Heterologous Expression of Enterocin A, a Bacteriocin From Enterococcus Faecium, Fused to a Cellulose-Binding Domain in *Escherichia coli* Results in a Functional Protein With Inhibitory Activity Against Listeria., Applied Microbiology and Biotechnology, vol. 67, No. 4, Jun. 1, 2005, pp. 532-538.
Montalban-Lopez Manuel et al., Employing the promiscuity of lantibiotic biosynthetic machineries to produce novel antimicrobials FEMS Microbiology Reviews, vol. 41, No. 1, Sep. 2, 2016, pp. 5-18.
Nielsen et al., Genetic circuit design automation, Science, vol. 352, No. 6281, aac7341, 2016.
Office Action with English Translation dated Jul. 22, 2022, in Japanese Patent Application No. 2020-512860 in 11 pages.
Qingshan Ma et al., Expression and purification of lacticin Q by small ubiquitin-related modifier fusion in *Escherichia coli*, the Journal of Microbiology, the Microbiological Society of Korea, Heidelberg, vol. 50, No. 2, Apr. 27, 2012, pp. 326-331.
Rajput A. et al., Prediction and Analysis of Quorum Sensing Peptides Based on Sequence Features, PLoS One, vol. 10, No. 3, 2015.
Sahl et al. Biosynthesis and biological activities of lantibiotics with unique post-translational modifications. Eur J Biochem, Jun. 15, 1995, vol. 230, No. 3, pp. 827-853.
Shekh, R.M. et al., Biochemical characterization of an anti-Candida factor produced by Enterococcus, BMC Microbiology, vol. 12, No. 132, 2012.
Shenin et al., "Characteristics of Alirin B1, the major component of a fungicidal substance produced by Bacillus subtilis 10-VIZR". Antibiot Khimioter, vol. 50: pp. 3-7, 1995.
Shukla et al. (2010) Controlling the release of peptide antimicrobial agents from surfaces, Biomater., pp. 2348-1357.
Srivastava, S. et al., Antifungal Activity of Pseudomonas fluorescens Against Different Plant Pathogenic Fungi, the Internet Journal of Microbiology, vol. 7 No. 2, 2008.
Tomita et al. Twenty-Five Years of Research on Bovine Lactoferrin Applications, Biochimie, vol. 91, No. 1, pp. 52-57, 2009.
Van Heel Auke J. et al., Discovery, Production and Modification of Five Novel Lantibiotics Using the Promiscuous Nisin Modification Machinery, ACS Synthetic Biology, vol. 5, No. 10, Jul. 7, 2016, pp. 1146-1154.
Wang et al. APD3: The Antimicrobial Peptide Database as a Tool for Research and Education, Nucleic Acids Research, vol. 44, Issue D1, pp. D1087-D1093, 2016.
Wang et al. Genome Mining Demonstrates the Widespread Occurrence of Gene Clusters Encoding Bacteriocins in Cyanobacteria, PLoS ONE 6(7): e22384, 2011.
Wright, et al., Building-in biosafety for synthetic biology, Microbiology, vol. 159, pp. 1221-1235, 2013.
Zuber, P et al. Peptide Antibiotics, Bacillus subtilis and Other Gram-Positive Bacteria: Biochemistry, Physiology, and Molecular Genetics ed Sonenshein et al., pp. 897-916, American Society for Microbiology, 1993.
Office Action with English Translation dated Feb. 6, 2024, in Brazilian Patent Application No BR1120200041491 in 13 pages.
Office Action with English Translation dated Mar. 28, 2023, in Brazilian Patent Application No BR1120200041491 in 10 pages.
Office Action with English Translation dated Oct. 20, 2023, in Chinese Patent Application No. 201880060807.0 in 15 pages.
Office Action with English Summary dated Jun. 18, 2024 in Chinese Patent Application No. 201880060807.0 in 8 pages.
Extended European Search Report dated Jul. 30, 2021, in European Patent Application No. 18852336.9 in 17 pages.
Office Action with English Translation dated Dec. 8, 2022, in Japanese Patent Application No. 2020-512860 in 10 pages.
Office Action with English Translation dated Apr. 26, 2024, in Japanese Patent Application No. 2023-066616 in 6 pages.
International Preliminary Report on Patentability dated Mar. 3, 2020 in International Application No. PCT/US1848846 in 8 pages.
Wu Shanming et al. "Emerging and Recurrent Infectious Diseases" Shanghai Science and Technology Education Press, p. 538, Jul. 2010.
Office Action with English Translation dated Jun. 18, 2024 in Brazilian Application No. BR1120200041491 in 12 pages.
Office Action with English Translation dated Sep. 17, 2024 in Brazilian Application No. BR 12 2024 008921-1 in 12 pages.
Office Action with English Translation dated Oct. 17, 2024, in Japanese Patent Application No. 2023-066616 in 9 pages.

METHODS AND COMPOSITIONS FOR MAKING BACTERIOCINS AND ANTIMICROBIAL PEPTIDES

RELATED APPLICATIONS

This application is a divisional application of U.S. application Ser. No. 16/642,342, filed Feb. 26, 2020, now U.S. Pat. No. 11,492,651, issued Nov. 8, 2022, which is a U.S. national phase application under 35 U.S.C. § 371 of International Application No. PCT/US2018/048846, filed on Aug. 30, 2018, which claims the benefit of U.S. Provisional Application No. 62/720,804, filed Aug. 21, 2018, and U.S. Provisional Application No. 62/552,835, Filed Aug. 31, 2017. The contents of the aforementioned applications are expressly incorporated herein by reference in their entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SeqListingSYNG003D1.xml, created and last saved on Oct. 19, 2022, which is 865,276 bytes in size. The information in the electronic format of the Sequence Listing is incorporated herein by reference in its entirety.

BACKGROUND

Microbial organism-mediated processes can be used in a variety of industrial processes for the manufacture of products of interest, for example for fermentation in a feedstock. Additionally, microbial organisms can be used to manufacture products in sterile environments, such as in the manufacture of pharmaceuticals, biologics, and cosmetics. Additionally, populations of microbial organisms are involved in maintaining the health and metabolic functions of multicellular organisms, for example as cultures of microbial flora in the gut and skin of humans, or the roots of the plants. The efficiency and efficacy of these processes can be affected by culture conditions, as well as the phenotypic characteristics of microbial organisms present in the culture.

Tuning populations of microbial organisms, for example to reduce or eliminate undesired microbial organisms can be useful for maintaining the industrial processes and maintaining the health of tissues that comprise microbial organisms.

FIELD

Embodiments herein relate generally to producing gene products for the control of growth of microorganisms. More particularly, some embodiments relate to methods, reagents, and microfluidic devices for making bacteriocins. The bacteriocins can be produced in a composition, such as a specified mixture of bacteriocins, which can be useful for controlling the growth of populations of microbial organisms. In some embodiments antimicrobial peptides and/or bacteriocins are produced in desired ratios in a composition.

SUMMARY

Some embodiments include a method of making bacteriocins. The method can comprise expressing a nucleic acid comprising a bacteriocin coding sequence and a second polypeptide coding sequence in a single reading frame, in which the second polypeptide comprises, consists essentially of, or consists of a bacteriocin or signal molecule. The nucleic acid can further comprise cleavage site coding sequences disposed between the bacteriocin coding sequence and the second polypeptide coding sequence in the single reading frame. Thus, a pro-polypeptide comprising the bacteriocin, second polypeptide, and cleavage sites disposed between the bacteriocin and second polypeptide can be generated. In some embodiments, the method further comprises cleaving the cleavage site, thus separating the bacteriocin and second polypeptide from each other. The method can thus produce a composition comprising the bacteriocin and the second polypeptide. In some embodiments, the second polypeptide comprises, consists essentially of, or consists of a bacteriocin. In some embodiments, the second polypeptide comprises, consists essentially of, or consists of an antimicrobial peptide. In some embodiments, the second polypeptide comprises, consists essentially of, or consists of the signal molecule. In some embodiments, the expressing is performed by a microbial cell that does not produce a functional immunity modulator for at least one of the bacteriocins. In some embodiments, the microbial cell does not produce a functional immunity modulator for any of the bacteriocins. In some embodiments, the expressing is performed in vitro. In some embodiments, at least one of the bacteriocins is inactive when it is part of the pro-polypeptide. In some embodiments, the method further comprises isolating the pro-polypeptide prior to the cleaving. In some embodiments, the isolating comprises affinity purifying the pro-polypeptide, in which the affinity purification comprises binding an affinity tag encoded by the nucleic acid. In some embodiments, the nucleic acid comprises three bacteriocin coding sequences in the single reading frame. In some embodiments, at least two of the bacteriocins are different from each other. In some embodiments, the composition comprises a desired ratio of bacteriocins, or a desired ratio of signal molecules and bacteriocins. In some embodiments, at least a portion the desired ratio is achieved by a ratio of bacteriocin coding sequences, or bacteriocin and signal molecule coding sequences in the single reading frame of the nucleic acid. In some embodiments, the desired ratio is further achieved by a second nucleic acid comprising a ratio of bacteriocins coding sequences and further comprising cleavage sites between the bacteriocin coding sequences. In some embodiments, desired ratio is achieved by a ratio of bacteriocin coding sequences in the single reading frame of the nucleic acid. In some embodiments, the desired ratio of bacteriocins is selected to target an undesired microbial organism or population of undesired microbial organisms, and/or the desired ratio of bacteriocins is selected to balance a population of a microbiome of an animal, a human organ, a plant, a plant root, and/or soil (e.g. in the context of a plant root and soil). In some embodiments, the desired ratio of bacteriocins and signal molecules is selected to control genetic drift of a target microbial cell, and stimulate growth or production of a producing cell. In some embodiments, the desired ratio comprises a ratio of a first bacteriocin to a second bacteriocin of 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, in which the first bacteriocin is different from the second bacteriocin. In some embodiments, the cleavage sites are for a wild-type, variant, or synthetic cleavage enzyme, such as an endopeptidase. In some embodiments, the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, lodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. In some embodiments, the cleavage sites are for a single cleavage enzyme, and wherein the cleavage enzyme does not cleave within the bacteriocins. In some embodiments, at least one cleavage site is for a first cleavage enzyme, and another cleavage site is for a second cleavage enzyme, and neither the first nor the second cleavage enzyme cleaves within the bacteriocins. In some embodiments, the composition produced by the method further comprises a signal molecule (in which the nucleotide further comprises: a coding sequence for a signal molecule in the single reading frame), and a cleavage site sequence disposed between the signal molecule and a bacteriocin coding sequence. In some embodiments, the signal molecule is selected from the group consisting of: quorum sensing molecules, signal transduction receptor ligands, growth factors, hormones, and cytokines, and wherein the signal molecule can be wild-type, mutant, or synthetic. In some embodiments, the signal molecule comprises, consists of, or consists essentially of a quorum sensing peptide. In some embodiments, the pro-polypeptide has a length of no more than about 2000 amino acids. In some embodiments, the method further comprises expressing a second nucleic acid encoding a second pro-polypeptide comprising two bacteriocins and cleavage sites disposed therebetween, wherein the second pro-polypeptide is different from the first pro-polypeptide. In some embodiments, cleaving the pro-polypeptide comprises physical treatment of a peptide linker comprised by the cleavage site, wherein the peptide linker is chemical-sensitive or pH sensitive. In some embodiments, the method further comprises chemically modifying the bacteriocins. In some embodiments, the bacteriocins are chemically modified co-translationally. In some embodiments, the bacteriocins are chemically modified following the cleaving. In some embodiments, a pro-polypeptide as described herein comprises two or more antimicrobial peptides instead of bacteriocins, and upon cleavage, a composition comprising antimicrobial peptides is produced. In some embodiments, a pro-polypeptide as described herein comprises one or more antimicrobial peptides and one or more bacteriocins, and upon cleavage, a composition comprising a mixture of antimicrobial peptides and bacteriocins is produced.

Some embodiments include an isolated nucleic acid comprising a bacteriocin coding sequence and a second polypeptide coding sequence in a single reading frame, in which the second polypeptide comprises, consists essentially of, or consists of a bacteriocin or a signal molecule. The isolated nucleic acid can comprise cleavage site coding sequences disposed between the bacteriocin coding sequences and in the single reading frame. In some embodiments, the second polypeptide comprises, consists essentially of, or consists of the bacteriocin. In some embodiments, the second polypeptide comprises, consists essentially of, or consists of an antimicrobial peptide. In some embodiments, the second polypeptide comprises, consists essentially of, or consists of the signal molecule. In some embodiments, the cleavage site coding sequences encode cleavage sites for a cleavage enzyme, and in which the bacteriocin coding sequences do not comprise cleavage sites for the cleavage enzyme. In some embodiments, the nucleic acid comprises three bacteriocin coding sequences in the single reading frame. In some embodiments, the nucleic acid comprises at least 5, 10, 15, or 20 bacteriocin sequences in the single reading frame. In some embodiments, a cleavage site coding sequence is disposed in frame between any two adjacent bacteriocin and/or signal molecule coding sequences. In some embodiments, at least two of the bacteriocin sequences encode different bacteriocins from each other. In some embodiments, the three bacteriocin sequences are present in a desired ratio or portion of a desired ratio. In some embodiments, the desired ratio is selected to target an undesired microbial organism or population of undesired microbial organisms. In some embodiments, the desired ratio of bacteriocins is selected to balance a population of a microbiome of an animal, a human organ, a plant, a plant root, and/or soil (e.g., in the context of a plant root and soil). In some embodiments, the cleavage sites are for a wild-type, variant, or synthetic cleavage enzyme, such as an endopeptidase. In some embodiments, the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, lodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. In some embodiments, a first cleavage site coding sequence encodes a first cleavage site is for a first cleavage enzyme, and wherein a second cleavage site coding sequence encodes a cleavage site for a second cleavage enzyme that is different from the first cleavage enzyme, and wherein the bacteriocins do not comprise a cleavage site for any of the first or second cleavage enzyme. In some embodiments, the cleavage sites comprise a pH- or chemically-sensitive linker. In some embodiments, the isolated nucleic acid further comprises a coding sequence for a signal molecule in the single reading frame, in which a cleavage site coding sequences is disposed between the coding sequence for signal molecule and an adjacent bacteriocin coding sequence. In some embodiments, the signal molecule is selected from the group consisting of: quorum sensing molecules, signal transduction receptor ligands, growth factors, hormones, and cytokines, and in which the signal molecule can be wild-type, mutant, or synthetic. In some embodiments, an isolated nucleic acid as described herein comprises two or more antimicrobial peptide coding sequences instead of bacteriocin coding sequences, and encodes a pro-polypeptide comprising the antimicrobial peptides. In some embodiments, an isolated nucleic acid as described herein comprises one or more antimicrobial peptide coding sequences and one or more bacteriocin coding sequences, and encodes a pro-polypeptide comprising one or more antimicrobial peptides and one or more bacteriocins.

Some embodiments include a microbial cell, comprising a promoter operably linked to the isolated nucleic acid of any of the embodiments described herein, in which the isolated microbial cell does not produce a functional immunity modulator for a bacteriocin encoded by the isolated nucleic acid. In some embodiments, the cell does not produce a functional immunity modulator for any of the bacteriocins encoded by the isolated nucleic acid.

Some embodiments include an isolated pro-polypeptide comprising two bacteriocins, and/or a bacteriocin and a signal molecule, cleavage sites disposed between the bacteriocins and/or the bacteriocin and the signal molecule; and an affinity tag. In some embodiments, the pro-polypeptide comprises the two bacteriocins. In some embodiments, the pro-polypeptide comprises the bacteriocin and the signal molecule. In some embodiments, the pro-polypeptide comprises three bacteriocins. In some embodiments, the pro-polypeptide comprises at least 5, 10, 15, or 20 bacteriocins. In some embodiments, the pro-polypeptide comprises a signal molecule. In some embodiments, the cleavage sites are for a cleavage enzyme, and wherein the bacteriocin coding sequences do not comprise cleavage sites for the cleavage enzyme. In some embodiments, a cleavage site is for a first cleavage enzyme, in which another cleavage site is for a second cleavage enzyme different from the first cleavage enzyme, and in which the bacteriocins do not comprise a cleavage site for any of the first or second cleavage enzymes. In some embodiments, the isolated pro-polypeptide further comprises a co-translational or post-translational modification. In some embodiments, an isolated pro-polypeptide as described herein comprises two or more antimicrobial peptides instead of bacteriocins. In some embodiments, an isolated pro-polypeptide as described herein comprises one or more antimicrobial peptides and one or more bacteriocins.

In some embodiments, a composition comprising two more bacteriocins in a ratio selected to target a microbial cell or populations of microbial cells is described. Each of the bacteriocins of the composition can comprise, at its N-terminus, C-terminus, or N-terminus and C-terminus, a portion of a cleavage sequence that has been cleaved, in which the portions of cleavage sequences at the N-, C-, or N- and C-termini of the bacteriocins are for cleavage sites of the same or different cleavage enzyme. In some embodiments, at least some of the bacteriocins further comprise a tag. In some embodiments, the tag is selected from the group consisting of affinity tags, a signal sequence, or a stability tag. In some embodiments, the composition further comprises a signal molecule in a desired ratio with the bacteriocins, wherein the signal molecule comprises, at its N-terminus, C-terminus, or N-terminus and C-terminus, a portion of a cleavage sequence that has been cleaved, wherein the portions of cleavage sequences at the N-, C-, or N- and C-termini of the signal molecule are for cleavage sites of the same or different cleavage enzymes. In some embodiments, the ratio of bacteriocins is selected to target an undesired microbial organism or population of undesired microbial organisms. In some embodiments, the ratio of bacteriocins is selected to balance a population of a microbiome of an animal, a human organ, a plant, a plant root, and/or soil (e.g., in the context of a plant root and soil). In some embodiments, the composition is formulated for topical or oral administration to a human subject. In some embodiments, the composition is for use in balancing a population of a microbiome, for example, that of an animal, a human organ (such as a gut or skin), a plant, a plant root, and/or soil. In some embodiments, the isolated pro-polypeptide as described herein comprises one or more antimicrobial peptides. The pro-polypeptide can be cleaved, and the composition can comprise one or more antimicrobial peptides that comprise portions of cleavage sequences at the N-, C-, or N- and C-termini.

Some embodiments include a method for producing a specified mixture of bacteriocins and/or antimicrobial proteins, for example. The method can comprise selecting the mixture to comprise two or more different bacteriocins and/or antimicrobial proteins. The method can comprise, in a microfluidic device comprising discrete coding substrates that each encode an antimicrobial peptide or bacteriocin: placing discrete coding substrates that encode the antimicrobial peptides and/or bacteriocins of the specified mixture in fluid communication with an in vitro transcription/translation solution; incubating the discrete coding substrates with the in vitro transcription/translation solution, thus generating antimicrobial peptides and/or bacteriocins encoded by the discrete coding substrates; and mixing the antimicrobial peptides and/or bacteriocins in the microfluidic device, thus producing the specified mixture of antimicrobial peptides and/or bacteriocins. In some embodiments, the method further comprises producing two or more submixtures each comprising a subset of the specified mixture of antimicrobial peptides and/or bacteriocins and combining the submixtures to produce the specified mixture of antimicrobial peptides and/or bacteriocins. In some embodiments, selecting further comprises selecting a stoichiometry of the two or more different antimicrobial peptides and/or bacteriocins of the specified mixture. In some embodiments, the specified mixture of antimicrobial peptides and/or bacteriocins comprises a specified stoichiometry, and combining the submixtures results in the specified stoichiometry. In some embodiments, the discrete coding substrates are comprised within separate chambers. In some embodiments, the discrete coding substrates comprise nucleic acids immobilized thereon. In some embodiments, discrete coding substrates encoding antimicrobial peptides and/or bacteriocins of the specified mixture, but not other discrete coding substrates, are placed in fluidic communication with the in vitro transcription/translation solution. In some embodiments, incubating the discrete coding substrates with the in vitro transcription/translation solution comprises flowing the in vitro transcription/translation solution into each chamber. In some embodiments, the in vitro transcription/translation solution comprises an in vitro transcription reagent and/or an in vitro translation reagent. In some embodiments, placing the discrete coding substrates that encode the antimicrobial peptides and/or bacteriocins of the specified mixture in fluid communication with an in vitro transcription/translation solution comprises (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii). In some embodiments, mixing the antimicrobial peptides and/or bacteriocins in the microfluidic device comprises opening a valve to place the discrete coding substrates in fluid communication with a fluidic reservoir, in which the antimicrobial peptides and/or bacteriocins are mixed in the fluidic reservoir. In some embodiments, the method further comprises screening the mixture of antimicrobial peptides and/or bacteriocins in situ for a desired effect. In some embodiments, the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is performed in real time. For example, the screening can be performed withing 120 minutes, 60 minutes, 30 minutes, 15 minutes, 10 minutes, 5 minute, or 1 minute of the specified mixture of antimicrobial peptides and/or bacteriocins being generated. In some embodiments, the screening is for stabilization of an antimicrobial peptide and/or bacteriocin or for destruction of a microbial biofilm. In some embodiments, one or more of the discrete coding substrates encodes an auxiliary protein with anti-protease activity. In some embodiments, the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, one or more of the discrete coding substrates encodes an auxiliary protein that attracts the non-pathogenic microbial organism, or that enhances growth or reproduction of the non-pathogenic microbial organism in the microbiome of a subject. In some embodiments, the method further comprises delivering the specified mixture of antimicrobial peptides and/or bacteriocins to a wound via a tubing or membrane, thereby cleaning or dressing the wound. In some embodiments, the desired effect comprises antimicrobial activity. In some embodiments, the method further comprises screening 1, 2, 3, 4, 5, 6, 7, 8, 9, or 10 different mixtures against a microbial infection. In some embodiments, the method further comprises delivering the mixture of specified antimicrobial peptides and/or bacteriocins, in combination with a chemical antibiotic and/or a phage antibiotic, to a subject. In some embodiments, the in vitro transcription/translation solution is lyophyilized, and further comprising adding water to the in vitro transcription/translation solution. In some embodiments, the method comprises making a specified mixture of bacteriocins. As such the method can comprise, in a microfluidic device comprising discrete coding substrates that each encode a bacteriocin: placing discrete coding substrates that encode the bacteriocins of the specified mixture in fluid communication with an in vitro transcription/translation solution; incubating the discrete coding substrates with the in vitro transcription/translation solution, thus generating bacteriocins encoded by the discrete coding substrates; and mixing the bacteriocins in the microfluidic device, thus producing the specified mixture of bacteriocins. In some embodiments, the method comprises making a specified mixture of bacteriocins that does not comprise antimicrobial peptides. In some embodiments, the method comprises making a specified mixture of antimicrobial peptides. In some embodiments, the method comprises making a specified mixture of antimicrobial peptides that does not comprise bacteriocins. In some embodiments, the method comprises making a specified mixture of bacteriocins and antimicrobial peptides. It will be understood that if a method, microfluidic device or system as described herein is for making a specified mixture of bacteriocins that does not comprise antimicrobial peptides, such a method, microfluidic device or system need not comprise selecting antimicrobial peptides as part of a specified mixture, need not comprise discrete coding substrates encoding antimicrobial peptides, and need not produce or flow any antimicrobial peptides. It will be understood that if a method, microfluidic device or system as described herein is for making a specified mixture of antimicrobial peptides that does not comprise bacteriocins, such a method, microfluidic device or system need not comprise selecting bacteriocins as part of a specified mixture, need not comprise discrete coding substrates encoding bacteriocins, and need not produce or flow any bacteriocins.

Some embodiments include a microfluidic device for producing a specified mixture of antimicrobial peptides and/or bacteriocins. The device can comprise discrete coding substrates that each encode an antimicrobial peptide and/or bacteriocin; an in vitro transcription/translation solution; a fluidic reservoir; and valves each disposed on a fluidic path between a discrete coding substrate and the fluidic reservoir, each valve configured to regulate flow between the discrete coding substrate and the fluidic reservoir. The device can be configured to be placed in data communication with a processor configured to: based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, in which the flow comprises movement of the antimicrobial peptides and/or bacteriocins in the fluidic reservoir, thereby producing the specified mixture of antimicrobial peptides and/or bacteriocins in the fluidic reservoir. In some embodiments, the specified mixture of antimicrobial peptides and/or bacteriocins comprises two or more submixtures each comprising, consisting essentially of, or consisting of a subset of antimicrobial peptides and/or bacteriocins; and the processor is configured to permit flow of each submixture into the fluidic reservoir, thereby producing the specified mixture of antimicrobial peptides and/or bacteriocins. In some embodiments, the specified mixture of antimicrobial peptides and/or bacteriocins comprises a sum of the subsets of antimicrobial peptides and/or bacteriocins in a specified stoichiometry, and wherein combination of the submixtures yields the specified stoichiometry. In some embodiments, the discrete coding substrates are comprised within separate chambers. In some embodiments, the discrete coding substrates comprise nucleic acids immobilized thereon. In some embodiments, the discrete coding substrates comprise a material or product selected from the group consisting of a chip, bead, nanoparticle, well, membrane, matrix, plastic, metal, glass, polymer, polysaccharide, and paramagnetic compound. In some embodiments, the in vitro transcription/translation solution comprises an in vitro transcription reagent and/or an in vitro translation reagent. In some embodiments, the device is portable. In some embodiments, one or more of the discrete coding substrates encodes an auxiliary protein comprising, consisting essentially of, or consisting of a protein for stabilization of antimicrobial peptides and/or bacteriocins, a protein with anti-protease activity, or a protein for destruction of a microbial biofilm. In some embodiments, one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the fluidic reservoir is configured to be placed in fluid communication with a tissue of a subject. In some embodiments, the tissue comprises a microbiome, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the fluidic reservoir is configured to be placed in fluid communication with a wound of a subject. In some embodiments, the microfluidic device further comprises a fluidic passage such as a tube or membrane through which the fluidic reservoir is capable of being placed in fluid communication with the microbiome or wound, through which the specified mixture of antimicrobial peptides and/or bacteriocins is capable of being delivered to the microbiome or wound. In some embodiments, wherein each discrete coding substrate encodes a different bacteriocin. In some embodiments, a discrete coding substrate comprises the isolated nucleic acid comprising, consisting essentially of, or consisting of an antimicrobial peptide and/or bacteriocin coding sequence and a second polypeptide coding sequence in a single reading frame, as described herein. In some embodiments, a discrete coding substrate encodes an isolated pro-polypeptide as described herein. In embodiments, the microfluidic device further comprises the processor. In some embodiments, the microfluidic device further comprises a reservoir of chemical or phage antibiotics configured to mix with the mixture of specified antimicrobial peptides and/or bacteriocins. In some embodiments, the microfluidic device further comprise an antibiotic comprising, consisting essentially of, or consisting of chemical antibiotic and/or a phage antibiotic. In some embodiments, the in vitro transcription/translation solution is lyophiylized. In some embodiments, the microfluidic device is for producing a specified mixture of bacteriocins. As such, the device can comprise discrete coding substrates that each encode a bacteriocin; an in vitro transcription/translation solution; a fluidic reservoir; and valves each disposed on a fluidic path between a discrete coding substrate and the fluidic reservoir, each valve configured to regulate flow between the discrete coding substrate and the fluidic reservoir. In some embodiments, the microfluidic device is for producing a specified mixture of bacteriocins that does not comprise antimicrobial peptides. In some embodiments, the microfluidic device is for producing a specified mixture of antimicrobial peptides. In some embodiments, the microfluidic device is for producing a specified mixture of antimicrobial peptides that does not comprise bacteriocins. In some embodiments, the microfluidic device is for producing a specified mixture of bacteriocins and antimicrobial peptides.

Some embodiments include a system. The system can comprise a microfluidic device described herein, and a processor configured to: based on a specified mixture of antimicrobial peptides and/or bacteriocins (as described herein), configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thus producing the specified mixture of antimicrobial peptides and/or bacteriocins in the fluidic reservoir. In some embodiments, the microfluidic device is comprised by a cartridge, and the system comprises a coupling for placing the cartridge in data communication with the processor. In some embodiments, the system further comprises a reservoir of in vitro transcription/translation solution. In some embodiments, the system further comprise a reservoir of chemical and/or phage antibiotics configured to mix with the mixture of specified antimicrobial peptides and/or bacteriocins. In some embodiments, the system further comprise an antibiotic comprising, consisting essentially of, or consisting of a chemical antibiotic and/or a phage. In some embodiments, the in vitro transcription/translation solution is lyophiylized. In some embodiments, the system is for producing a specified mixture of bacteriocins. As such, the processor can be configured to, based on a specified mixture of antimicrobial peptides and/or bacteriocins (as described herein), configure the valves to place the discrete coding substrates that encode the bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the bacteriocins of the specified mixture are produced. In some embodiments, the system is for producing a specified mixture of bacteriocins that does not comprise antimicrobial peptides. In some embodiments, the system is for producing a specified mixture of antimicrobial peptides. In some embodiments, the system is for producing a specified mixture of antimicrobial peptides. In some embodiments, the system is for producing a specified mixture of antimicrobial peptides that does not comprise bacteriocins. In some embodiments, the system is for producing a specified mixture of bacteriocins and antimicrobial peptides.

Some embodiments include a microfluidic device for producing a specified mixture of antimicrobial peptides and/or bacteriocins. The device can comprises discrete coding substrates that each encode an antimicrobial peptide and/or bacteriocin, and valves each disposed on a fluidic path connected to a discrete coding substrate. Each valve can be configured to regulate flow to or from the discrete coding substrate. The device can be configured to be placed in fluid communication with a fluidic reservoir and/or an in vitro transcription/translation solution. In some embodiments, the device further comprises a fluidic reservoir or an in vitro transcription/translation solution. Some embodiments include a microfluidic device for producing a specified mixture of bacteriocins. The device can comprise discrete coding substrates that each encode a bacteriocin, and valves each disposed on a fluidic path to or from a discrete coding substrate, configured to place the discrete coding substrate in fluid communication with a fluidic reservoir and/or an in vitro transcription/translation solution.

DETAILED DESCRIPTION

Figure 1:
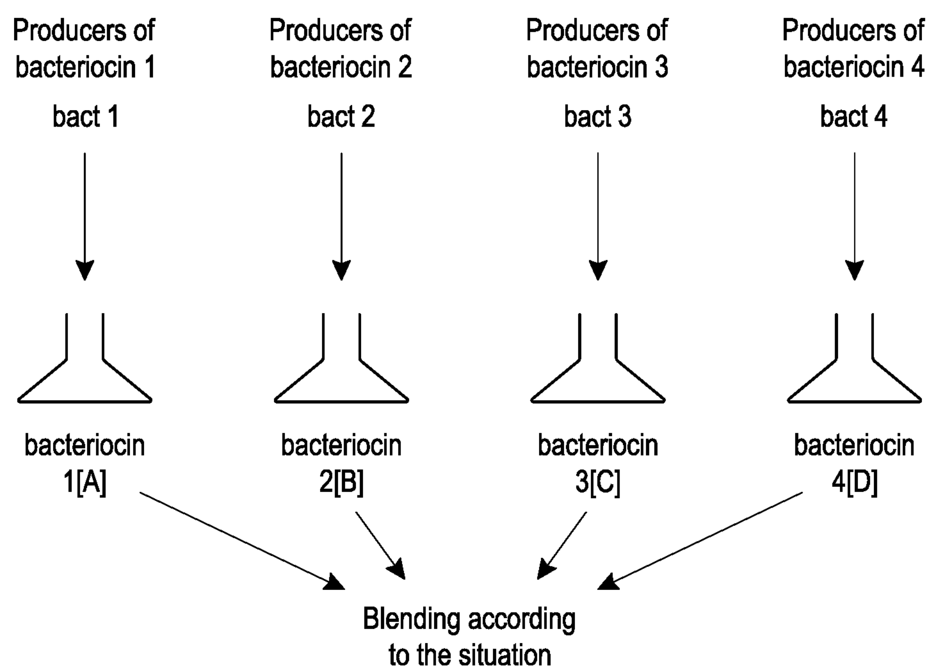
FIG. 1 is a schematic diagram of a conventional method for making a composition comprising bacteriocins. As shown, there are multiple strains for the production of a bacteriocin mixture. However, it is contemplated that there is a very high likelihood that the different bacteriocins will be of different concentrations ([A]≠[B]≠[C]≠[D]). Additionally, it is contemplated that the bacteriocins produced may be toxic to the host so as to cause production problems

Described in accordance with some embodiments herein are methods and compositions for making bacteriocins in a desired ratio. Some embodiments include compositions comprising bacteriocins in precise ratios or stoichiometries, which can be useful for tuning the population of microbial organisms in a number of applications, for example in industrial biotechnology manufacturing processes, pharmaceutical, biologic, and cosmetic manufacturing, and medical applications. In some embodiments, a single pro-polypeptide containing multiple bacteriocins separated by cleavage sites is encoded by a nucleic acid, and produced (see, for example, FIG. 2) by a genetically-engineered microbial cell containing the nucleic acid. In some embodiments, the pro-polypeptide can further comprise signal molecules that can modulate the growth of microbial cells and/or cells of a multicellular host. The bacteriocins in the pro-polypeptide can be in an inactive form, and thus the microbial cell does not require immunity against these bacteriocins. The pro-polypeptide can be isolated, for example by affinity purification. The cleavage sites of the pro-polypeptide can be cleaved (see, for example, FIG. 3), thus producing a mixture of active bacteriocins. Conceptually, the pro-polypeptide can be envisioned as a strand of "spaghetti," containing multiple component bacteriocins, which can then be cleaved into the individual bacteriocins. It is noted that in this Application, for brevity, a pro-polypeptide may also be referred to as "spaghetti." Some embodiments include microfluidic devices and methods for making specified mixtures of bacteriocins. The "specified mixtures" of bacteriocins of methods and microfluidic devices of some embodiments herein can be specified according to parameters that include, but are not limited to, the composition of bacteriocins (so that the comprise specified bacteriocins and/or do not comprise other bacteriocins), the stoichiometry of the bacteriocins of the mixture, and optionally, the presence of auxiliary proteins. The microfluidic device can comprise discrete coding substrates that each encode a bacteriocin (See, for example, FIG. 5). Discrete coding substrates encoding the bacteriocins of the specified mixture can be placed in fluid communication with an in vitro transcription/translation solution, so that the discrete coding substrates encoding the bacteriocins of the specified mixture are incubated with the in vitro transcription/translation solution, thus producing the bacteriocins of the specified mixture. The bacteriocins of the specified mixture can then be placed in fluid communication with a fluidic reservoir of the microfluidic device, and the bacteriocins fluidically move to the fluidic reservoir, thus producing the specified mixture of antimicrobial peptides and/or bacteriocins in the fluidic reservoir. In some embodiments, each discrete coding substrate encodes a different bacteriocin. In some embodiments, a discrete coding substrate encodes two or more different bacteriocins. In some embodiments, at least one or all of the discrete coding substrates encode a "spaghetti" pro-polypeptide as described herein. Optionally, the discrete coding substrate can comprise or encode a protease as described herein, which can cleave the cleavage sites of the pro-polypeptide so that the discrete coding substrate can produce two or more bacteriocins in a specified stoichiometry. The microfluidic device can comprise an outlet, configured to place the specified mixture of antimicrobial peptides and/or bacteriocins in fluidic communication with a tissue, a wound, a host microbiome, or a vessel. The specified mixture of bactericins can be used, for example, as a point-of-care antimicrobial composition, and/or to test the effects of the specified mixture on a host tissue and/or host microbiome, for example one comprising an undesired microbial organism.

Advantageously, the relative quantities of different bacteriocins in the pro-polypeptide will precisely determine the ratio of bacteriocins in the mixture after cleavage, and this ratio will be maintained regardless of the rate of expression of the polypeptide within or among different microbial cells. In contrast, conventional methods in which bacteriocins are translated as separate peptides or produced by different cells (see FIG. 1) can be subject to variations in transformation efficiency, genetic engineering efficiency, and/or gene expression efficiency (for example if some bacteriocin-encoding plasmids replicate and/or initiate transcription more efficiently than others), so that the final ratios of bacteriocins will be less precise than embodiments herein. As another advantage, since each nucleic acid can encode many bacteriocins, some embodiments herein provide for a much more efficient genetic modification of a host cell than conventional approaches that would involve introducing multiple constructs each encoding a particular bacteriocin. As another advantage, since the bacteriocins can be produced in their inactive form in the pro-polypeptide, the "workhorse" microbial organism that produces the bacteriocins does not need to be configured with immunity to all, some, or any of these bacteriocins, and thus can readily be used to produce mixtures of any of a number of different bacteriocins. Although in some embodiments, the producing microbial organism can naturally or artificially be configured with immunity to one or more or all of the bacteriocins included in the pro-polypeptide.

Populations of microbial organisms targeted by bacteriocin compositions of some embodiments herein can exist in a number in commercially useful environments such as industrial cultures, fermenters, pharmaceutical, biological, and cosmetic manufacturing, in microbiomes, such as human organs, animals, and plants (e.g. on the roots or soil in which the plant grows), and in products, such as foods (for human and/or animals), drug products, and cosmetic products. Without being limited by theory, it is contemplated that populations of microbial organisms in any of these environments do not necessarily co-exist at a steady state. For example, as reviewed in Jaramillo et al., Nature Microbiology 2: 17119 (2017), as populations of microbial organisms interact with each other (directly or indirectly), they can affect each other in positive or negative ways, but are not expected to exist at steady state, which conventionally lead to challenges in maintaining a co-culture. In some embodiments, when certain populations of microbial organisms reach a quantity or density above a certain threshold, a mixture of bacteriocins produced according to methods, and/or through the use or pro-polypeptides and/or nucleic acids and/or microbial cells of some embodiments herein can be added to the environment so as to target the microbial cells of this population. For example, if a population contains a large excess of microbial organism #1, and a smaller excess of microbial organism #2, in accordance with some embodiments, a mixture comprising a relatively high ratio of bacteriocin #1 (targeting microbial organism #1) to bacteriocin #2 (targeting microbial organism #2) can be administered to the population, so as to reduce the growth of microbial organisms #1 and #2, with a greater reduction targeted to microbial organism #1.

Bacteriocins and Antimicrobial Peptides

As used herein, "bacteriocin," and variations of this root term, has its customary and ordinary meaning as understood by one of skill in the art in view of this disclosure. It refers to a polypeptide that is secreted by a host cell and can neutralize at least one cell other than the individual host cell in which the polypeptide is made, including cells clonally related to the host cell and other microbial cells. "Bacteriocin" also encompasses a cell-free or chemically synthesized version of such a polypeptide. A cell that expresses a particular "immunity modulator" (discussed in more detail herein) is immune to the neutralizing effects of a particular bacteriocin or group of bacteriocins. As such, bacteriocins can neutralize a cell producing the bacteriocin and/or other microbial cells, so long as these cells do not produce an appropriate immunity modulator. As such, a host cell can exert cytotoxic or growth-inhibiting effects on a plurality of other microbial organisms by secreting bacteriocins. Detailed descriptions of bacteriocins, including methods and compositions for using bacteriocins to control the growth of microbial cells can be found, for example, in U.S. Pat. No. 9,333,227, which is hereby incorporated by reference in its entirety. "Bacteriocin" is not limited by the origin of the polypeptide, and by way of example is contemplated to encompass any bacteriocin, such as naturally-occurring bacteriocins, synthetic bacteriocins, and variants and combinations thereof.

The bacteriocins of some embodiments are initially produced in a pro-polypeptide, which can then be cleaved as described herein to produce the individual bacteriocins. In some embodiments, the pro-polypeptide is produced by the translational machinery (e.g. a ribosome, etc.) of a microbial cell. In some embodiments, the pro-polypeptide is produced by an in vitro expression system. The pro-polypeptide can undergo cleavage (for example processing by a cleavage enzyme such as a naturally-occurring or synthetic protease) to yield the polypeptide of the bacteriocin itself. As such, in some embodiments, a bacteriocin is produced from a precursor polypeptide. In some embodiments, a bacteriocin comprises a polypeptide that has undergone post-translational modifications, for example cleavage, or the addition of one or more functional groups. In some embodiments, a pro-polypeptide comprising, consisting essentially of, or consisting of bacteriocins and cleavage sites as described herein is chemically synthesized.

"Antibiotic," and variations of this root term, has its customary and ordinary meaning as understood by one of skill in the art in view of this disclosure. It refers to a metabolite, or an intermediate of a metabolic pathway which can kill or arrest the growth of at least one microbial cell. Some antibiotics can be produced by microbial cells, for example bacteria. Some antibiotics can be synthesized chemically. It is understood that bacteriocins are distinct from antibiotics, at least in that bacteriocins refer to gene products (which, in some embodiments, undergo additional post-translational processing) or synthetic analogs of the same, while antibiotics refer to intermediates or products of metabolic pathways or synthetic analogs of the same.

Neutralizing activity of bacteriocins can include, for example, arrest of microbial reproduction, or cytotoxicity. Some bacteriocins have cytotoxic activity (e.g. "bacteriocide" effects), and thus can kill microbial organisms, for example bacteria, yeast, algae, synthetic microorganisms, and the like. Some bacteriocins can inhibit the reproduction of microbial organisms (e.g. "bacteriostatic" effects), for example bacteria, yeast, algae, synthetic microorganisms, and the like, for example by arresting the cell cycle. In some neutralizing comprises, consists of, or consists essentially of arrest of microbial reproduction, inhibition of reproduction of microbial organisms, and/or cytotoxicity.

In some embodiments, a particular neutralizing activity or ranges of activities (e.g. cytoxicity or arrest of microbial reproduction) is selected based on the type of microbial regulation that is desired and the particular strains or species of microbial organisms being targeted. As such, in some embodiments, particular bacteriocins or combinations of bacteriocins are selected. For example, in some embodiments, microbial cells are engineered to express particular bacteriocins based on the cells being regulated. In some embodiments, for example if contaminating cells are to be killed, at least one cytotoxic bacteriocin is provided. In some embodiments, a bacteriocin or combination of bacteriocins which is effective against contaminants which commonly occur in a particular culture, or a particular geographic location, or a particular type of culture grown in a particular geographic location are selected. In some embodiments, for example embodiments in which reversible regulation of microbial cell ratios is desired, a bacteriocin that inhibits microbial reproduction is provided. Without being limited by any particular theory, many bacteriocins can have neutralizing activity against microbial organisms that typically occupy the same ecological niche as the species that produces the bacteriocin. As such, in some embodiments, when a particular spectrum of bacteriocin activity is desired, a bacteriocin is selected from a host species that occupies the same (or similar) ecological niche as the microbial organism or organisms targeted by the bacteriocin. In some embodiments, a particular mixture and/or ratio is selected to target a single microbial organism (which can include targeting one or more than one microbial organisms of that type, for example clonally related microbial organisms). For example a particular type of microbial organism may be targeted more efficiently by a predetermined mixture and/or ratio of bacteriocins than by a single bacteriocin.

In some embodiments, one or more bacteriocin activities are selected in advance of culture growth, and a pro-polypeptide comprising the bacteriocins in a desired stoichiometry is prepared. A polynucleotide encoding the pro-polypeptide can be prepared, for example using nucleic acid synthesis and/or molecular cloning, and can be used to produce the pro-polypeptide. The polynucleotide can be transcribed (if a DNA) and translated using a number of suitable systems, for example in a microbial cell, or in an in vitro expression system. In some embodiments, bacteriocins (and ratios thereof) may be selected based on their ability to neutralize one or more invading organisms which are likely to attempt to grow in a particular culture. In some embodiments, bacteriocins (and ratios thereof) may be selected based on their ability to limit the growth of particular useful microbial strains in an environment, for example in an industrial feedstock, or in a fermenter, or in a food, pharmaceutical, or cosmetic manufacturing environment, or in a tissue environment such as a gut or skin microbiome, or in maintaining or tuning a microbial population in a plant, a plant root, and/or soil, or in preserving or maintaining the quality of a food, drug or cosmetic product. In some embodiments, one or more bacteriocin activities (and/or ratios) are selected based on one or more microbial strains or a population of microbial strains an existing environment. For example, in some embodiments, if particular invaders are identified in an environment, a panel of neutralizing bacteriocins (and ratios thereof) can be selected to neutralize the identified invaders. In some embodiments, the bacteriocins are selected to neutralize all or substantially all of the microbial cells in an environment, for example to eliminate an industrial culture in a culture environment so that a new industrial culture can be introduced to the culture environment, or to prevent or inhibit contamination of a pharmaceutical or cosmetic manufacturing environment, or to prevent or minimize contamination or spoilage of a food, drug, or cosmetic product.

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains (see Adetunji and Olaoye (2013) Malaysian Journal of Microbiology 9: 130-13, hereby incorporated by reference in its entirety), an *Enterococcus faecalis* peptide (WLPPAGLL-GRCGRWFRPWLLWLQ SGAQY KWLGNLFGLGPK, SEQ ID NO: 1) has been shown to have neutralizing activity against *Candida* species (see Shekh and Roy (2012) BMC Microbiology 12: 132, hereby incorporated by reference in its entirety), and bacteriocins from *Pseudomonas* have been shown to have neutralizing activity against fungi such as *Curvularia lunata, Fusarium* species, *Helminthosporium* species, and *Biopolaris* species (Shalani and Srivastava (2008) The Internet Journal of Microbiology. Volume 5 Number 2. DOI: 10.5580/27dd—accessible on the world-wide web at archive.ispub.com/journal/the-internet-journal-of-microbiology/volume-5-number-2/screening-for-antifungal-activity-of-pseudomonas-fluorescens-against-phytopathogenic-fungi.html#sthash.d0Ys03UO.1DKuT1US.dpuf, hereby incorporated by reference in its entirety). By way of example, botrycidin AJ1316 (see Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference in its entirety) and alirin B1 (see Shenin et al. (1995) Antibiot Khimioter 50: 3-7, hereby incorporated by reference in its entirety) from *B. subtilis* have been shown to have antifungal activities. As such, in some embodiments, for example embodiments in which neutralization of a fungal microbial organism is desired, a bacteriocin comprises at least one of botrycidin AJ1316 or alirin B1.

For example, in some embodiments, bacteriocin activity in a culture of a particular microorganism (or collection of different microorganisms) is desirable, and bacteriocins are selected in predetermined ratios in order to neutralize microorganisms other than the desired microorganism(s). Bacteriocins typically produced by the desired microorganisms can be selected, as the desired microbial organisms can already produce the relevant immunity modulators against these bacteriocins, or can readily be engineered to produce the immunity modulators. As such, the selected bacteriocins can target undesired microbial cells, while causing little or no neutralization of the desired microbial organisms. For example, in some embodiments, bacteriocins are selected in particular ratios in order to neutralize invading microbial organisms typically found in a cyanobacteria culture environment, while preserving the cyanobacteria. Clusters of conserved bacteriocin polypeptides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 1.2, as SEQ ID NO's 420, 422, 424, 426, 428, 430, 432, 434, 436, 438, 440, 442, 444, 446, 448, and 450.

In some embodiments, a microbial cell produces bacteriocins. In some embodiments, bacteriocins neutralize cells of a different species or strain from the microbial cell that produced bacteriocins. In some embodiments, bacteriocins neutralize cells of the same species or strain as the host cell if these cells lack an appropriate immunity modulator. As bacteriocins can mediate neutralization of both host and non-host microbial organisms, the skilled artisan will readily appreciate that a bacteriocin is distinct from poison-antidote systems, which involve an endogenous mechanism by which a host microorganism can neutralize only itself. In other words, bacteriocins can neutralize cells other than the cell in which they are produced (for example, bacteriocins can be selected and/or engineered to act as an ecological niche protector), while poison molecules kill only the individual cell in which they are produced (for example, to act as suicidal systems).

A number of bacteriocins have been identified and characterized. Without being limited by theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Table 1.1, which is adapted from Cotter, P. D. et al. "Bacteriocins—a viable alternative to antibiotics" *Nature Reviews Microbiology* (2013) 11: 95-105, hereby incorporated by reference in its entirety.

Without being limited by theory, bacteriocins can effect neutralization of a target microbial cell in a variety of ways. For example, a bacteriocin can permeabilize a cell wall, thus depolarizing the cell wall and interfering with respiration.

TABLE 1.1

| Classification of Exemplary Bacteriocins | | |
|---|---|---|
| Group | Distinctive feature | Examples |
| Class I (typically modified) | | |
| MccC7-C51-type bacteriocins | Is covalently attached to a carboxy-terminal aspartic acid | MccC7-C51 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |
| Proteusins | Contain multiple hydroxylations, epimerizations and methylations | Polytheonamide A |
| Sactibiotics | Contain sulphur-α-carbon linkages | Subtilosin A, thuricin CD |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin I, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 1.2. In some embodiments, at least one bacteriocin comprising, consisting essentially of, or consisting of a polypeptide sequence of Table 1.2 is provided. As shown in Table 1.2, some bacteriocins function as pairs of molecules. As such, it will be understood that unless explicitly stated otherwise, when a functional "bacteriocin" or "providing a bacteriocin," or the like is discussed herein, functional bacteriocin pairs are included along with bacteriocins that function individually. With reference to Table 1.2, "organisms of origin" listed in parentheses indicate alternative names and/or strain information for organisms known the produce the indicated bacteriocin. However, in some embodiments herein, bacteriocins are produced by a desired microbial organisms, and thus are not limited to the examples of organisms known to produce the bacteriocins shown in Table 1.2

Embodiments herein also include peptides and proteins with identity to bacteriocins described in Table 1.2. The term "identity" has its customary and ordinary meaning as understood by one of skill in the art in view of this disclosure. It is meant to include nucleic acid or protein sequence homology or three-dimensional homology. As used herein, a "variant" of a polypeptide, such as a bacteriocin, signal molecule, immunity modulator, tag (or any other component peptide of a pro-polypeptide as described herein) has its customary and ordinary meaning as understood by one of skill in the art in view of this disclosure. It will be understood to include identity as described herein to the reference sequence of at least about 70%, for example, at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%. Several techniques exist to determine nucleic acid or polypeptide sequence homology and/or three-dimensional homology to polypeptides. These methods are routinely employed to discover the extent of identity that one sequence, domain, or model has to a target sequence, domain, or model. Percent identity may be determined using the BLAST software (Altschul, S. F., et al. (1990) "Basic local alignment search tool." J. Mol. Biol. 215:403-410, accessible on the world wide web at blast.ncbi.nlm.nih.gov) with the default parameters.

A vast range of functional bacteriocins can incorporate features of bacteriocins disclosed herein, thus providing for a vast degree of identity to the bacteriocins in Table 1.2. In some embodiments, a bacteriocin has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 1.2, including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%.

In some embodiments, a bacteriocin with identity to a bacteriocin in Table 1.2 is provided, in which the bacteriocin has been modified to remove one or more cleavage sites that are being used in a pro-polypeptide as described herein. Without being limited by theory, it is contemplated that modifying bacteriocins to remove cleavage sites (for example by making conservative substitutions, such as small non-polar to small non-polar amino acid, e.g. Leu→Ile, or small polar to small polar amino acid, e.g., Ser→Thr) can prevent the bacteriocin itself from being cleaved when the pro-polypeptide is cleaved as described herein. As such, in some embodiments a bacteriocin in a pro-polypeptide as described herein (e.g., a bacteriocin of Table 1.2, or a variant thereof) does not contain any cleavage sites that are used to separate the bacteriocins (or other elements) of the pro-polypeptide.

TABLE 1.2

Exemplary Bacteriocins

| Polypeptide SEQ ID NO: | Name | Class | Organism of origin | Polynucleotide SEQ ID NO: |
|---|---|---|---|---|
| 4 | Acidocin 8912 | Unclassified | *Lactobacillus acidophilus* | 5 |
| 6 | Acidocin A | class IIA/YGNGV | *Lactobacillus acidophilus* | 7 |
| 8 | Acidocin B (AcdB) | Unclassified | *Lactobacillus acidophilus* | 9 |
| 10 | Acidocin LF221B (Gassericin K7 B) | Unclassified | *Lactobacillus gasseri* | 11 |
| 12 | Aureocin A53 | Unclassified | *Staphylococcus aureus* | 13 |
| 14 | Avicin A | class IIA/YGNGV | *Enterococcus avium* (*Streptococcus avium*) | 15 |
| 16 | Bacteriocin 31 | Unclassified | *Enterococcus faecalis* (*Streptococcus faecalis*) | 17 |
| 18 | Bacteriocin J46 | Unclassified | *Lactococcus lactis* | 19 |
| 20 | Bacteriocin T8 | class IIa | *Enterococcus faecium* (*Streptococcus faecium*) | 21 |
| 22 | Boticin B | Unclassified | *Clostridium botulinum* | 23 |
| 24 | Bovicin HJ50 | Lantibiotic | *Streptococcus equinus* (*Streptococcus bovis*) | 25 |
| 26 | Brochocin-c | Unclassified | *Brochothrix campestris* | 27 |
| 28 | Butyrivibriocin AR10 | Unclassified | *Butyrivibrio fibrisolvens* | 29 |
| 30 | Butyrivibriocin OR79 | Lantibiotic | *Butyrivibrio fibrisolvens* | 31 |
| 32 | Carnobacteriocin B2 (Carnocin CP52) | class IIA/YGNGV | *Carnobacterium maltaromaticum* (*Carnobacterium piscicola*) | 33 |
| 34 | Carnobacteriocin BM1 (Carnobacteriocin B1) | class IIA/YGNGV | *Carnobacterium maltaromaticum* (*Carnobacterium piscicola*) | 35 |
| 36 | Carnobacteriocin-A (Piscicolin-61) | class IIc, non subgrouped bacteriocins (problematic) | *Carnobacterium maltaromaticum* (*Carnobacterium piscicola*) | 37 |
| 38 | Carnocyclin-A | Unclassified | *Carnobacterium maltaromaticum* (*Carnobacterium piscicola*) | 39 |
| 40 | Carocin D | Unclassified | *Pectobacterium carotovorum* subsp. *carotovorum* (*Erwinia carotovora* subsp. *carotovora*) | 41 |
| 42 | Cerein 7B | Unclassified | *Bacillus cereus* | 43 |
| 44 | Cinnamycin (Lanthiopeptin) | Lantibiotic | *Streptoverticillium griseoverticillatum* | 45 |
| 46 | Circularin A | Unclassified | *Geobacillus kaustophilus* (strain HTA426) | 47 |
| 48 | Closticin 574 | Unclassified | *Clostridium tyrobutyricum* | 49 |
| 50 | Coagulin A | Unclassified | *Bacillus coagulans* | 51 |
| 52 | Colicin-10 | Unclassified | *Escherichia coli* | 53 |
| 54 | Colicin-E1 | Unclassified | *Escherichia coli* | 55 |
| 56 | Colicin-Ia | Unclassified | *Escherichia coli* | 57 |
| 58 | Colicin-Ib | Unclassified | *Escherichia coli* | 59 |
| 60 | Colicin-M | Unclassified | *Escherichia coli* | 61 |
| 62 | Colicin-N | Unclassified | *Escherichia coli* | 63 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 64 | Colicin-V (Microcin-V) | Unclassified | *Escherichia coli* | 65 |
| 66 | Columbicin A | Lantibiotic | *Enterococcus columbae* | 67 |
| 68 | Curvacin-A | class IIA/YGNGV | *Lactobacillus curvatus* | 69 |
| 70 | Cypemycin | Unclassified | *Streptomyces* sp. | 71 |
| 72 | Cytolysin | Lantibiotic | *Bacillus halodurans* (strain ATCC BAA-125/ DSM 18197/FERM 7344/ JCM 9153/C-125) | 73 |
| 74 | Divercin V41 | class IIa/YGNGV | *Carnobacterium divergens* (*Lactobacillus divergens*) | 75 |
| 76 | Divergicin 750 | Unclassified | *Carnobacterium divergens* (*Lactobacillus divergens*) | 77 |
| 78 | Divergicin A | Class IIc | *Carnobacterium divergens* (*Lactobacillus divergens*) | 79 |
| 80 | Durancin Q | Unclassified | *Enterococcus durans* | 81 |
| 82 | Durancin TW-49M | Unclassified | *Enterococcus durans* | 83 |
| 84 | Dysgalacticin | Unclassified | *Streptococcus dysgalactiae* subsp. *equisimilis* (*Streptococcus equisimilis*) | 85 |
| 86 | Enterocin 1071A | Unclassified | *Enterococcus faecalis* (*Streptococcus faecalis*) | 87 |
| 88 | Enterocin 7A (Enterocin L50A) | bacteriocins without sequence leader | *Enterococcus faecalis* (*Streptococcus faecalis*) | 89 |
| 90 | Enterocin 7B | Unclassified | *Enterococcus faecalis* (*Streptococcus faecalis*) | 91 |
| 92 | Enterocin 96 | Class II | *Enterococcus faecalis* (strain ATCC 700802/ V583) | 93 |
| 94 | Enterocin A | Class IIa, IIc (problematic) | *Enterococcus faecium* (*Streptococcus faecium*) | 95 |
| 96 | Enterocin AS-48 (BACTERIOCIN AS-48) | Unclassified | *Enterococcus faecalis* (*Streptococcus faecalis*) | 97 |
| 98 | Enterocin B | class IIc, non subgrouped bacteriocins (problematic) | *Enterococcus faecium* (*Streptococcus faecium*) | 99 |
| 100 | Enterocin CRL35 (Mundticin KS) | Class IIa | *Enterococcus mundtii* | 101 |
| 102 | Enterocin EJ97 | Unclassified | *Enterococcus faecalis* (*Streptococcus faecalis*) | 103 |
| 104 | Enterocin P | Class IIa, IIb and IIc (problematic) | *Enterococcus faecium* (*Streptococcus faecium*) | 105 |
| 106 | Enterocin Q | Class IIc | *Enterococcus faecium* (*Streptococcus faecium*) | 107 |
| 108 | Enterocin SE-K4 | Class IIa | *Enterococcus faecalis* (*Streptococcus faecalis*) | 109 |
| 110 | Enterocin W alfa | Class IIb | *Enterococcus faecalis* (*Streptococcus faecalis*) | 111 |
| 112 | Enterocin W beta | Class IIb | *Enterococcus faecalis* (*Streptococcus faecalis*) | 113 |
| 114 | Enterocin Xalpha | Class IIb | *Enterococcus faecium* (*Streptococcus faecium*) | 115 |
| 116 | Enterocin Xbeta | Class IIb | *Enterococcus faecium* (*Streptococcus faecium*) | 117 |
| 118 | Enterolysin A | class III | *Enterococcus faecalis* (*Streptococcus faecalis*) | 119 |
| 120 | Epicidin 280 | Lantibiotic | *Staphylococcus epidermidis* | 121 |
| 122 | Epidermicin NI01 | Unclassified | *Staphylococcus epidermidis* | 123 |
| 124 | Epidermin | Lantibiotic | *Staphylococcus epidermidis* | 125 |
| 126 | Epilancin K7 | Lantibiotic | *Staphylococcus epidermidis* | 127 |
| 128 | Gallidermin | Lantibiotic | *Staphylococcus gallinarum* | 129 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 130 | Garvicin A | IId | *Lactococcus garvieae* | 131 |
| 132 | Garvicin ML | Unclassified | *Lactococcus garvieae* | 133 |
| 134 | Gassericin A | Unclassified | *Lactobacillus gasseri* | 135 |
| 136 | Gassericin T (gassericin K7 B) | Unclassified | *Lactobacillus gasseri* | 137 |
| 138 | Glycocin F | Unclassified | *Lactobacillus plantarum* | 139 |
| 140 | Halocin H4 | Unclassified | *Haloferax mediterranei* (strain ATCC 33500/ DSM 1411/JCM 8866/ NBRC 14739/NCIMB 2177/R-4) (*Halobacterium mediterranei*) | 141 |
| 142 | Halocin-S8 | Unclassified | *Haloarchaeon* S8a | 143 |
| 144 | Helveticin-J | Unclassified | *Lactobacillus helveticus* (*Lactobacillus suntoryeus*) | 145 |
| 146 | Hiracin JM79 | Class II sec-dependent | *Enterococcus hirae* | 147 |
| 148 | Lactacin-F (lafA) | class IIB | *Lactobacillus johnsonii* (strain CNCM I-12250/ La1/NCC 533) | 149 |
| 150 | Lactacin-F (lafX) | class IIB | *Lactobacillus johnsonii* (strain CNCM I-12250/ La1/NCC 533) | 151 |
| 152 | Lacticin 3147 A1 | Lantibiotic | *Lactococcus lactis* subsp. *lactis* (*Streptococcus lactis*) | 153 |
| 154 | Lacticin 3147 A2 | Lantibiotic | *Lactococcus lactis* subsp. *lactis* (*Streptococcus lactis*) | 155 |
| 156 | Lacticin 481 (Lactococcin DR) | Lantibiotic | *Lactococcus lactis* subsp. *lactis* (*Streptococcus lactis*) | 157 |
| 158 | Lacticin Q | Unclassified | *Lactococcus lactis* | 159 |
| 160 | Lacticin Z | Unclassified | *Lactococcus lactis* | 161 |
| 162 | Lactobin-A (Amylovorin-L471) | class IIB | *Lactobacillus amylovorus* | 163 |
| 164 | Lactocin-S | Lantibiotic | *Lactobacillus sakei* L45 | 165 |
| 166 | Lactococcin 972 | Unclassified | *Lactococcus lactis* subsp. *lactis* (*Streptococcus lactis*) | 167 |
| 168 | Lactococcin-A | Unclassified | *Lactococcus lactis* subsp. *cremoris* (*Streptococcus cremoris*) | 169 |
| 170 | Lactococcin-B | Unclassified | *Lactococcus lactis* subsp. *cremoris* (*Streptococcus cremoris*) | 171 |
| 172 | Lactocyclicin Q | Unclassified | *Lactococcus* sp. QU 12 | 173 |
| 174 | Laterosporulin | Unclassified | *Brevibacillus* sp. GI-9 | 175 |
| 176 | Leucocin N | Class IId | *Leuconostoc pseudomesenteroides* | 177 |
| 178 | Leucocin Q | Class IId | *Leuconostoc pseudomesenteroides* | 179 |
| 180 | Leucocin-A (Leucocin A-UAL 187) | class IIA/YGNGV | *Leuconostoc gelidum* | 181 |
| 182 | Leucocin-B (Leucocin B-Ta11a) | class IIA/YGNGV | *Leuconostoc carnosum* | 183 |
| 184 | Leucocyclicin Q | Unclassified | *Leuconostoc mesenteroides* | 185 |
| 186 | Lichenicidin A1 | Lantibiotic (two-peptide) | *Bacillus licheniformis* (strain DSM 13/ATCC 14580) | 187 |
| 188 | Linocin M18 | Unclassified | *Brevibacterium linens* | 189 |
| 190 | Listeriocin 743A | Class IIa | *Listeria innocua* | 191 |
| 192 | Mersacidin | Lantibiotic, type B | *Bacillus* sp. (strain HIL-Y85/54728) | 193 |
| 194 | Mesentericin Y105 | class IIA/YGNGV | *Leuconostoc mesenteroides* | 195 |
| 196 | Michiganin-A | Lantibiotic | *Clavibacter michiganensis* subsp. *michiganensis* | 197 |
| 198 | Microcin B17 (MccB17) | Unclassified | *Escherichia coli* | 199 |
| 200 | Microcin C7 | Unclassified | *Escherichia coli* | 201 |
| 202 | Microcin E492 | Unclassified | *Klebsiella pneumoniae* | 203 |
| 204 | Microcin H47 | Unclassified | *Escherichia coli* | 205 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 206 | Microcin J25 | Unclassified | *Escherichia coli* | 207 |
| 208 | Microcin-24 | Unclassified | *Escherichia coli* | 209 |
| 210 | Mundticin KS | Unclassified | *Enterococcus mundtii* | 211 |
| 212 | Mundticin L | class IIA/YGNGV | *Enterococcus mundtii* | 213 |
| 214 | Mutacin 1140 (Mutacin III) | Lantibiotic | *Streptococcus mutans* | 215 |
| 216 | Mutacin-2 | Lantibiotic | *Streptococcus mutans* | 217 |
| 218 | Nisin A | Lantibiotic | *Lactococcus lactis* subsp. *lactis* (*Streptococcus lactis*) | 219 |
| 220 | Nisin F | Lantibiotic | *Lactococcus lactis* | 221 |
| 222 | Nisin Q | Lantibiotic | *Lactococcus lactis* | 223 |
| 224 | Nisin U | Lantibiotic | *Streptococcus uberis* | 225 |
| 226 | Nisin Z | Lantibiotic | *Lactococcus lactis* subsp. *lactis* (*Streptococcus lactis*) | 227 |
| 228 | Nukacin ISK-1 | Lantibiotic | *Staphylococcus warneri* | 229 |
| 230 | Paenicidin A | Lantibiotic | *Paenibacillus polymyxa* (*Bacillus polymyxa*) | 231 |
| 232 | Pediocin PA-1 (Pediocin ACH) | class IIA/YGNGV | *Pediococcus acidilactici* | 233 |
| 234 | Penocin A | class IIA/YGNGV | *Pediococcus pentosaceus* (strain ATCC 25745/183-1w) | 235 |
| 236 | Pep5 | Lantibiotic | *Staphylococcus epidermidis* | 237 |
| 238 | Piscicolin 126 | class IIA/YGNGV | *Carnobacterium maltaromaticum* (*Carnobacterium piscicola*) | 239 |
| 240 | Plantaricin 1.25 β | Unclassified | *Lactobacillus plantarum* | 241 |
| 242 | Plantaricin 423 | class IIa | *Lactobacillus plantarum* | 243 |
| 244 | Plantaricin ASM1 | Unclassified | *Lactobacillus plantarum* | 245 |
| 246 | Plantaricin E | Unclassified | *Lactobacillus plantarum* | 247 |
| 248 | Plantaricin F | Class IIb | *Lactobacillus plantarum* | 249 |
| 250 | Plantaricin J | Class IIb | *Lactobacillus plantarum* | 251 |
| 252 | Plantaricin K | Unclassified | *Lactobacillus plantarum* | 253 |
| 254 | Plantaricin NC8 α | Unclassified | *Lactobacillus plantarum* | 255 |
| 256 | Plantaricin NC8 β | Unclassified | *Lactobacillus plantarum* | 257 |
| 258 | Plantaricin S α | Unclassified | *Lactobacillus plantarum* | 259 |
| 260 | Plantaricin S β | Unclassified | *Lactobacillus plantarum* | 261 |
| 262 | Plantaricin W α | Lantibiotic (two-peptide) | *Lactobacillus plantarum* | 263 |
| 264 | Plantaricin W β | Lantibiotic (two-peptide) | *Lactobacillus plantarum* | 265 |
| 266 | Plantaricin-A | Unclassified | *Lactobacillus plantarum* (strain ATCC BAA-793/NCIMB 8826/WCFS1) | 267 |
| 268 | Propionicin SM1 | Unclassified | *Propionibacterium jensenii* | 269 |
| 270 | Propionicin T1 | Unclassified | *Propionibacterium thoenii* | 271 |
| 272 | Propionicin-F | Unclassified | *Propionibacterium freudenreichii* subsp. *freudenreichii* | 273 |
| 274 | Pyocin S1 | Unclassified | *Pseudomonas aeruginosa* | 275 |
| 276 | Pyocin S2 | colicin/pyosin nuclease family | *Pseudomonas aeruginosa* (strain ATCC 15692/PAO1/1C/PRS 101/LMG 12228) | 277 |
| 278 | Ruminococcin-A | Lantibiotic | *Ruminococcus gnavus* | 279 |
| 280 | Sakacin G | Class IIa | *Lactobacillus sakei* | 281 |
| 282 | Sakacin-A | class IIA/YGNGV | *Lactobacillus sakei* | 283 |
| 284 | Sakacin-P (Sakacin 674) | class IIA/YGNGV | *Lactobacillus sakei* | 285 |
| 286 | Salivaricin 9 | lantibiotic | *Streptococcus salivarius* | 287 |
| 288 | Salivaricin A | Lantibiotic | *Streptococcus pyogenes* serotype M28 (strain MGAS6180) | 289 |
| 290 | Salivaricin A3 | Lantibiotic | *Streptococcus salivarius* | 291 |
| 292 | Salivaricin-A sa | Lantibiotic | *Streptococcus salivarius* | 293 |
| 294 | Staphylococcin C55 alpha | Lantibiotic (two-peptide) | *Staphylococcus aureus* | 295 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 296 | Staphylococcin C55 beta | Lantibiotic (two-peptide) | *Staphylococcus aureus* | 297 |
| 298 | Streptin | lantibiotic | *Streptococcus pyogenes* | 299 |
| 300 | Streptococcin A-FF22 | Lantibiotic | *Streptococcus pyogenes* | 301 |
| 302 | Streptococcin A-M49 | Lantibiotic | *Streptococcus pyogenes* serotype M49 | 303 |
| 304 | Sublancin 168 | Lantibiotic | *Bacillus subtilis* (strain 168) | 305 |
| 306 | Subtilin | Lantibiotic | *Bacillus subtilis* | 307 |
| 308 | Subtilosin | Unclassified | *Bacillus subtilis* (strain 168) | 309 |
| 310 | Subtilosin-A | Unclassified | *Bacillus subtilis* (strain 168) | 311 |
| 312 | Thermophilin 1277 | Lantibiotic | *Streptococcus thermophilus* | 313 |
| 314 | Thermophilin 13 | Unclassified | *Streptococcus thermophilus* | 315 |
| 316 | Thermophilin A | Unclassified | *Streptococcus thermophilus* | 317 |
| 318 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | *Bacillus cereus* (strain ATCC 14579/DSM 31) | 319 |
| 320 | Thuricin CD alpha | two-peptide lantibiotic | *Bacillus cereus* 95/8201 | 321 |
| 322 | Thuricin CD beta | two-peptide lantibiotic | *Bacillus cereus* 95/8201 | 323 |
| 324 | Thuricin-17 | Class IId | *Bacillus thuringiensis* | 325 |
| 326 | Trifolitoxin | Unclassified | *Rhizobium leguminosarum* bv. *trifolii* | 327 |
| 328 | Ubericin A | Class IIa | *Streptococcus uberis* | 329 |
| 330 | Uberolysin | Unclassified | *Streptococcus uberis* | 331 |
| 332 | UviB | Unclassified | *Clostridium perfringens* | 333 |
| 334 | Variacin | Lantibiotic, Type A | *Micrococcus varians* | 335 |
| 336 | Zoocin A | Unclassified | *Streptococcus equi* subsp. *zooepidemicus* | 337 |
| 338 | Fulvocin-C | Unclassified | *Myxococcus fulvus* | 339 |
| 340 | Duramycin-C | Lantibiotic | *Streptomyces griseoluteus* | 341 |
| 342 | Duramycin (duramycin-B) (Leucopeptin) | Lantibiotic B | *Streptoverticillium griseoverticillatum* | 343 |
| 344 | Carnocin UI49 | lantibiotic | *Carnobacterium* sp. (strain UI49) | 345 |
| 346 | Lactococcin-G α | Unclassified | *Lactococcus lactis* subsp. *lactis* (*Streptococcus lactis*) | 347 |
| 348 | Lactococcin-G β | Unclassified | *Lactococcus lactis* subsp. *lactis* (*Streptococcus lactis*) | 349 |
| 350 | Ancovenin | Lantibiotic | *Streptomyces* sp. (strain A647P-2) | 351 |
| 352 | Actagardine (Gardimycin) | Lantibiotic | *Actinoplanes liguriae* | 353 |
| 354 | Curvaticin FS47 | Unclassified | *Lactobacillus curvatus* | 355 |
| 356 | Bavaricin-MN | class IIA/YGNGV | *Lactobacillus sakei* | 357 |
| 358 | Mutacin B-Ny266 | Lantibiotic | *Streptococcus mutans* | 359 |
| 360 | Mundticin | class IIA/YGNGV | *Enterococcus mundtii* | 361 |
| 362 | Bavaricin-A | class IIA/YGNGV | *Lactobacillus sakei* | 363 |
| 364 | Lactocin-705 | Class IIb | *Lactobacillus paracasei* | 365 |
| 366 | Leucocin-B | Unclassified | *Leuconostoc mesenteroides* | 367 |
| 368 | Leucocin C | class IIA/YGNGV | *Leuconostoc mesenteroides* | 369 |
| 370 | LCI | Unclassified | *Bacillus subtilis* | 371 |
| 372 | Lichenin | Unclassified | *Bacillus licheniformis* | 373 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 374 | Lactococcin MMFII | class IIA/YGNGV | *Lactococcus lactis* subsp. *lactis* (*Streptococcus lactis*) | 375 |
| 376 | Serracin-P | Phage-Tail-Like | *Serratia plymuthica* | 377 |
| 378 | Halocin-C8 | Unclassified | *Halobacterium* sp. (strain AS7092) | 379 |
| 380 | Subpeptin JM4-B | Unclassified | *Bacillus subtilis* | 381 |
| 382 | Curvalicin-28a | Unclassified | *Lactobacillus curvatus* | 383 |
| 384 | Curvalicin-28b | Unclassified | *Lactobacillus curvatus* | 385 |
| 386 | Curvalicin-28c | Unclassified | *Lactobacillus curvatus* | 387 |
| 388 | Thuricin-S | Unclassified | *Bacillus thuringiensis* subsp. *entomocidus* | 389 |
| 390 | Curvaticin L442 | Unclassified | *Lactobacillus curvatus* | 391 |
| 392 | Divergicin M35 | class IIa/YGNGV | *Carnobacterium divergens* (*Lactobacillus divergens*) | 393 |
| 394 | Enterocin E-760 | class IIb | *Enterococcus* sp. | 395 |
| 396 | Bacteriocin E50-52 | Unclassified | *Enterococcus faecium* (*Streptococcus faecium*) | 397 |
| 398 | Paenibacillin | Unclassified | *Paenibacillus polymyxa* (*Bacillus polymyxa*) | 399 |
| 400 | Epilancin 15x | Unclassified | *Staphylococcus epidermidis* | 401 |
| 402 | Enterocin-HF | class IIa | *Enterococcus faecium* (*Streptococcus faecium*) | 403 |
| 404 | Bacillocin 602 | Class IIa | *Paenibacillus polymyxa* (*Bacillus polymyxa*) | 405 |
| 406 | Bacillocin 1580 | Class IIa | *Bacillus circulans* | 407 |
| 408 | Bacillocin B37 | Unclassified | *Paenibacillus polymyxa* (*Bacillus polymyxa*) | 409 |
| 410 | Rhamnosin A | Unclassified | *Lactobacillus rhamnosus* | 411 |
| 412 | Lichenicidin A2 | Lantibiotic (two-peptide) | *Bacillus licheniformis* (strain DSM 13/ATCC 14580) | 413 |
| 414 | Plantaricin C19 | Class IIa | *Lactobacillus plantarum* | 415 |
| 416 | Acidocin J1132 β | Class IIb | *Lactobacillus acidophilus* | 417 |
| 418 | factor with anti-Candida activity | Unclassified | *Enterococcus faecalis* | 419 |
| 420 | Ava_1098 (putative heterocyst differentiation protein) | Unclassified | *Anabaena variabilis* ATCC 29413 | 421 |
| 422 | alr2818 (putative heterocyst differentiation protein) | Unclassified | *Nostoc* sp 7120 | 423 |
| 424 | Aazo_0724 (putative heterocyst differentiation protein) | Unclassified | *Nostoc azollae* 0708 | 425 |
| 426 | AM1_4010 (putative heterocyst differentiation protein) | Unclassified | *Acaryochloris marina* MBIC11017 | 427 |
| 428 | PCC8801_3266 (putative heterocyst differentiation protein) | Unclassified | *Cyanothece* PCC 8801 | 429 |
| 430 | Cyan8802_2855 (putative heterocyst differentiation protein) | Unclassified | *Cyanothece* PCC 8802 | 431 |
| 432 | PCC7424_3517 | Unclassified | *Cyanothece* PCC 7424 | 433 |
| 434 | cce_2677(putative HetP protein) | Unclassified | *Cyanothece* ATCC 51142 | 435 |
| 436 | CY0110_11572 (putative heterocyst differentiation protein) | Unclassified | *Cyanothece* CCY0110 | 437 |
| 438 | MC7420_4637 | Unclassified | *Microcoleus chthonoplastes* PCC 7420 | 439 |
| 440 | asr1611 (putative DUF37 family protein) | Unclassified | *Nostoc* sp 7120 | 441 |
| 442 | Ava_4222 (putative DUF37 family protein) | Unclassified | *Anabaena variabilis* ATCC 29413 | 443 |
| 444 | N9414_07129 (putative DUF37 family protein) | Unclassified | *Nodularia spumigena* CCY9414 | 445 |
| 446 | Aazo_0083 (putative DUF37 family protein) | Unclassified | *Nostoc azollae* 0708 | 447 |
| 448 | S7335_3409 (putative DUF37 family protein) | Unclassified | *Synechococcus* PCC 7335 | 449 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 450 | P9303_21151 (putative DUF37 family protein) | Unclassified | *Prochlorococcus marinus* MIT 9303 | 451 |
| 699 | Curvalicin-28c | Unclassified | *Lactobacillus curvatus* | 700 |
| 701 | thruicin-S | Unclassified | *Bacillus thuringiensis* | 702 |
| 703 | curvaticin L442 | Unclassified | *Lactobacillus curvatus* L442 | 704 |
| 705 | Bacteriocin divergicin M35 | P84962 | *Carnobacterium divergens* (*Lactobacillus divergens*) | 706 |
| 707 | Lantibiotic 107891 | P85065 | *Microbispora* sp. (strain 107891) | 708 |
| 709 | Enterocin E-760 (Bacteriocin E-760) | P85147 | *Enterococcus* sp. | 710 |
| 711 | Bacteriocin E50-52 | P85148 | *Enterococcus faecium* (*Streptococcus faecium*) | 712 |
| 713 | Lantibiotic paenibacillin | P86013 | *Paenibacillus polymyxa* (*Bacillus polymyxa*) | 714 |
| 715 | Lantibiotic epilancin 15X | P86047 | *Staphylococcus epidermidis* | 716 |
| 717 | Enterocin-HF | P86183 | *Enterococcus faecium* (*Streptococcus faecium*) | 718 |
| 719 | Bacteriocin SRCAM 602 | P86393 | *Paenibacillus polymyxa* (*Bacillus polymyxa*) | 720 |
| 721 | Bacteriocin SRCAM 1580 | P86394 | *Bacillus circulans* | 722 |
| 723 | Bacteriocin SRCAM 37 | P86395 | *Paenibacillus polymyxa* (*Bacillus polymyxa*) | 724 |
| 725 | Bacteriocin rhamnosin A (Fragment) | P86526 | *Lactobacillus rhamnosus* | 726 |
| 727 | Lantibiotic lichenicidin A2 (LchA2) (BliA2) | P86720 | *Bacillus licheniformis* (strain ATCC 14580/ DSM 13/JCM 2505/ NBRC 12200/NCIMB 9375/NRRL NRS-1264/ Gibson 46) | 728 |
| 729 | Pyocin-S2 (EC 3.1.—.—) (Killer protein) | | *Pseudomonas aeruginosa* (strain ATCC 15692/ DSM 22644/CIP 104116/ JCM 14847/LMG 12228/1C/PRS 101/ PAO1) | 730 |
| 731 | Plantaricin C19 (Fragment) | | *Lactobacillus plantarum* | 732 |
| 733 | LsbB | | *Lactococcus lactis* subsp. *lactis* (*Streptococcus lactis*) | 734 |
| 735 | ACIDOCIN J1132 beta peptide (Fragment) | | *Lactobacillus acidophilus* | 736 |
| 737 | Uncharacterized protein | | *Lactobacillus salivarius* cp400 | 738 |

As used herein, “bacteriocin polynucleotide” has its customary and ordinary meaning as understood by one of skill in the art in view of this disclosure. It refers to a polynucleotide encoding a bacteriocin. As used herein, “bacteriocin coding sequence” has its customary and ordinary meaning as understood by one of skill in the art in view of this disclosure. It refers to nucleic acid coding sequence (e.g., RNA or DNA) that encodes the polypeptide sequence of a bacteriocin. In some embodiments, the host cell comprises at least one bacteriocin.

Antimicrobial peptides are a class of peptides that confer innate immune activity to kill or arrest the growth of microbial organisms. As used herein “antimicrobial peptide” (including variations of this root term) has its customary and ordinary meaning as would be understood by one of ordinary skill in the art in view of this disclosure. Classically, antimicrobial peptides have been described as peptides produced by the innate immune systems of invertebrates and vertebrates. Thus, while bactericins have classically been referred to a class of microbial gene products that target microbial organisms, antimicrobial peptides have classically been referred to as a class of invertebrate and vertebrate gene products that target microbial organisms. Examples of antimicrobial peptides suitable for methods, microfluidic devices, and systems of some embodiments herein are known in the art, and can be founds, for example, at The Antimicrobial Peptide Database accessible on the world wide web at aps.unmc.edu/AP/, which is incorporated herein by reference in its entirety. Over 1000 antimicrobial peptides and variants thereof have been identified and cataloged. The Antimicrobial Peptide Database is described in Wang et al. (2016), Nucleic Acids Res. 44(Database issue): D1087-D1093, which is incorporated herein by reference in its entirety. Examples of antimicrobial peptides include bacteriocins, antibacterial, antiviral, anti-HIV, antifungal, antiparasitic and anticancer peptides, such as Dermaseptin-B2, Abaecin, Ct-AMP1, Andropin, Aurein 1.1, Lactoferricin B, and Heliomicin. Methods, compositions, systems, and microfluidic devices of some embodiments comprise naturally-occurring antimicrobial peptides, or a nucleic acid encoding the same. Methods, compositions, systems, and microfluidic devices of some embodiments comprise non-naturally occurring antimicrobial peptides, or nucleic acids encoding the same. Methods, compositions, systems, and microfluidic devices of some embodiments include antimicrobial peptides that comprise a mutation or variation in a naturally-occuring antimicrobial peptides, or a nucleic acid encoding the same. Methods, compositions, systems, and microfluidic devices of some embodiments comprise antimicrobial peptides comprising, consisting essentially of, or consisting of non-naturally occurring peptide sequences, or nucleic acids encoding the same.

It is further contemplated that methods, systems, and microfluidic devices of some embodiments herein can be in conjunction with naturally occurring antimicrobial peptides, variants of naturally occurring antimicrobial peptides, and/or synthetic antimicrobial peptides. As such, antimicrobial peptides of methods, systems, and device of some embodiments can comprise, consist essentially of, or consist of naturally occurring antimicrobial peptides, variants of naturally occurring antimicrobial peptides, and/or synthetic antimicrobial peptides. In some embodiments, a variant antimicrobial peptide has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to a reference antimicrobial peptide (for example Dermaseptin-B2, Abaecin, Ct-AMP1, Andropin, Aurein 1.1, Lactoferricin B, or Heliomicin), including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%. Wherever bacteriocins are mentioned herein, it is expressly contemplated that any antimicrobial peptide as described herein may be substituted for one, two or more, or all of the noted bacteriocins (although it will be appreciated that in some contexts, such as a bacteriocin-immunity modulator pair, the antimicrobial peptide will have different properties and interact differently than a bactericoin). Accordingly, some embodiments of the methods and microfluidic devices described herein include bacteriocins only, some embodiments of the methods and microfluidic devices described herein include antimicrobial peptides only, and some embodiments of the methods and microfluidic devices described herein include a combination of bacteriocins and antimicrobial peptides. Accordingly, in the methods and compositions of some embodiments, a pro-polypeptide comprises an antimicrobial peptide instead of a bacteriocin. Accordingly, in the methods and compositions of some embodiments, a pro-polypeptide comprises one or more antimicrobial peptides and one or more bacteriocins.

Bacteriocin Immunity Modulators

Exemplary bacteriocin immunity modulators are shown in Table 2. While the immunity modulators in Table 2 are naturally-occurring, the skilled artisan will appreciate that variants of the immunity modulators of Table 2, naturally-occurring immunity modulators other than the immunity modulators of Table 2, or synthetic immunity modulators can be used according to some embodiments herein. In some embodiments, a microbial cell that produced a pro-polypeptide comprising bacteriocins does not produce an immunity modulator for at least one of the bacteriocins. Without being limited by theory, it is contemplated that in some embodiments, the bacteriocins in the pro-polypeptide are inactive, and thus have little to no ability to neutralize the cell that produced them (or a cell clonally related to the cell that produced them), so that the cell does not require immunity against these bacteriocins of the pro-polypeptide.

In some embodiments, a particular immunity modulator or particular combination of immunity modulators confers immunity to a particular bacteriocin, particular class or category of bacteriocins, or particular combination of bacteriocins. Exemplary bacteriocins to which immunity modulators can confer immunity are identified in Table 2. While Table 2 identifies an "organism of origin" for exemplary immunity modulators, these immunity modulators can readily be expressed in other naturally-occurring, genetically modified, or synthetic microorganisms to provide a desired bacteriocin immunity activity in accordance with some embodiments herein. As such, as used herein "immunity modulator" has its customary and ordinary meaning as understood by one of skill in the art in view of this disclosure, and refers not only to structures expressly provided herein, but also to structure that have substantially the same effect as the "immunity modulator" structures described herein, including fully synthetic immunity modulators, and immunity modulators that provide immunity to bacteriocins that are functionally equivalent to the bacteriocins disclosed herein.

Exemplary polynucleotide sequences encoding the polypeptides of Table 2 are indicated in Table 2. The skilled artisan will readily understand that the genetic code is degenerate, and moreover, codon usage can vary based on the particular organism in which the gene product is being expressed, and as such, a particular polypeptide can be encoded by more than one polynucleotide. In some embodiments, a polynucleotide encoding a bacteriocin immunity modulator is selected based on the codon usage of the organism expressing the bacteriocin immunity modulator. In some embodiments, a polynucleotide encoding a bacteriocin immunity modulator is codon optimized based on the particular organism expressing the bacteriocin immunity modulator. A vast range of functional immunity modulators can incorporate features of immunity modulators disclosed herein, thus providing for a vast degree of identity to the immunity modulators in Table 2. In some embodiments, an immunity modulator has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 2, or a range of identity defined by any two of the preceding values.

TABLE 2

| Exemplary bacteriocin immunity modulators | | | |
|---|---|---|---|
| Polypeptide SEQ ID NO: | Name | Organism of origin | Polynucleotide SEQ ID NO: |
| 452 | Microcin H47 immunity modulator Mchl | *Escherichia coli* | 453 |
| 454 | Colicin-E3 immunity modulator (Colicin-E3 chain B) (ImmE3) (Microcin-E3 immunity modulator) | *Escherichia coli* | 455 |
| 456 | Colicin-E1 immunity modulator (ImmE1) (Microcin-E1 immunity modulator) | *Escherichia coli* | 457 |
| 458 | Cloacin immunity modulator | *Escherichia coli* | 459 |
| 460 | Colicin-E2 immunity modulator (ImmE2) (Microcin-E2 immunity modulator) | *Escherichia coli* | 461 |
| 462 | Colicin-A immunity modulator (Microcin-A immunity modulator) | *Citrobacter freundii* | 463 |
| 464 | Colicin-Ia immunity modulator | *Escherichia coli* | 465 |
| 466 | Colicin-Ib immunity modulator | *Escherichia coli* | 467 |
| 468 | Colicin-N immunity modulator (Microcin-N immunity modulator) | *Escherichia coli* | 469 |
| 470 | Colicin-E8 immunity modulator (ImmE8) (Microcin-E8 immunity modulator) | *Escherichia coli* | 471 |
| 472 | Lactococcin-A immunity modulator | *Lactococcus lactis* subsp. *lactis* (*Streptococcus lactis*) | 473 |
| 474 | Lactococcin-A immunity modulator | *Lactococcus lactis* subsp. *cremoris* (*Streptococcus cremoris*) | 475 |
| 476 | Colicin-D immunity modulator (Microcin-D immunity modulator) | *Escherichia coli* | 477 |
| 478 | Colicin-E5 immunity modulator (ImmE5) (Microcin-E5 immunity modulator) | *Escherichia coli* | 479 |
| 480 | Colicin-E6 immunity modulator (ImmE6) (Microcin-E6 immunity modulator) | *Escherichia coli* | 481 |
| 482 | Colicin-E8 immunity modulator in ColE6 (E8Imm[E6]) | *Escherichia coli* | 483 |
| 484 | Colicin-E9 immunity modulator (ImmE9) (Microcin-E9 immunity modulator) | *Escherichia coli* | 485 |
| 486 | Colicin-M immunity modulator (Microcin-M immunity modulator) | *Escherichia coli* | 487 |
| 488 | Colicin-B immunity modulator (Microcin-B immunity modulator) | *Escherichia coli* | 489 |
| 490 | Colicin-V immunity modulator (Microcin-V immunity modulator) | *Escherichia coli* | 491 |
| 492 | Colicin-E1* immunity modulator (ImmE1) (Microcin-E1* immunity modulator) | *Shigella sonnei* | 493 |
| 494 | Colicin-E1 immunity modulator (ImmE1) (Microcin-E1 immunity modulator) | *Escherichia coli* | 495 |
| 496 | Probable leucocin-A immunity modulator | *Leuconostoc gelidum* | 497 |
| 498 | Lactococcin-B immunity modulator | *Lactococcus lactis* subsp. *cremoris* (*Streptococcus cremoris*) | 499 |
| 500 | Pediocin PA-1 immunity modulator (Pediocin ACH immunity modulator) | *Pediococcus acidilactici* | 501 |
| 502 | Putative carnobacteriocin-BM1 immunity modulator | *Carnobacterium maltaromaticum* (*Carnobacterium piscicola*) | 503 |
| 504 | Putative carnobacteriocin-B2 immunity modulator (Carnocin-CP52 immunity modulator) | *Carnobacterium maltaromaticum* (*Carnobacterium piscicola*) | 505 |

TABLE 2-continued

Exemplary bacteriocin immunity modulators

| Polypeptide SEQ ID NO: | Name | Organism of origin | Polynucleotide SEQ ID NO: |
|---|---|---|---|
| 506 | Nisin immunity modulator | *Lactococcus lactis* subsp. *lactis* (*Streptococcus lactis*) | 507 |
| 508 | Trifolitoxin immunity modulator | *Rhizobium leguminosarum* bv. *trifolii* | 509 |
| 510 | Antilisterial bacteriocin subtilosin biosynthesis protein AlbD | *Bacillus subtilis* (strain 168) | 511 |
| 512 | Putative ABC transporter ATP-binding protein AlbC (Antilisterial bacteriocin subtilosin biosynthesis protein AlbC) | *Bacillus subtilis* (strain 168) | 513 |
| 514 | Antilisterial bacteriocin subtilosin biosynthesis protein AlbB | *Bacillus subtilis* (strain 168) | 515 |
| 516 | Colicin-E7 immunity modulator (ImmE7) (Microcin-E7 immunity modulator) | *Escherichia coli* | 517 |
| 518 | Pyocin-S1 immunity modulator | *Pseudomonas aeruginosa* | 519 |
| 520 | Pyocin-S2 immunity modulator | *Pseudomonas aeruginosa* (strain ATCC 15692/ PAO1/1C/PRS 101/LMG 12228) | 521 |
| 522 | Hiracin-JM79 immunity factor | *Enterococcus hirae* | 523 |
| 524 | Probable mesentericin-Y105 immunity modulator | *Leuconostoc mesenteroides* | 525 |
| 526 | Microcin-24 immunity modulator | *Escherichia coli* | 527 |
| 528 | Colicin-K immunity modulator | *Escherichia coli* | 529 |
| 530 | Microcin C7 self-immunity modulator MccF | *Escherichia coli* | 531 |
| 532 | Sakacin-A immunity factor | *Lactobacillus sakei* | 533 |
| 534 | Colicin-E5 immunity modulator in ColE9 (E5Imm[E91) | *Escherichia coli* | 535 |
| 536 | Antilisterial bacteriocin subtilosin biosynthesis protein AlbD | *Bacillus subtilis* | 537 |
| 538 | Microcin-J25 export ATP-binding/permease protein McjD (Microcin-J25 immunity modulator) (Microcin-J25 secretion ATP-binding protein McjD) | *Escherichia coli* | 539 |
| 540 | Microcin E492 immunity modulator | *Klebsiella pneumoniae* | 541 |

Promoters

Promoters are well known in the art. A promoter can be used to drive the transcription of one or more genes. In some embodiments, a promoter drives expression of polynucleotide encoding a desired gene product as described herein. In some embodiments, a promoter drives expression of a polynucleotide encoding a pro-polypeptide comprising two or more bacteriocins as described herein. In some embodiments, a promoter drives expression of an immunity modulator polynucleotide as described herein. In some embodiments, a promoter drives expression of a polynucleotide encoding a pro-polypeptide comprising two or more bacteriocins in a microbial cell, but the microbial cell does not express immunity modulators for one or more of these bacteriocins (for example, the cell can lack a promoter driving transcription of the immunity modulator, or can lack nucleic acid encoding the immunity modulator). Some promoters can drive transcription at all times ("constitutive promoters"). Some promoters can drive transcription under only select circumstances ("conditional promoters"), for example depending on the presence or absence of an environmental condition, chemical compound, gene product, stage of the cell cycle, or the like.

The skilled artisan will appreciate that depending on the desired expression activity, an appropriate promoter can be selected, and placed in cis with a nucleic acid sequence to be expressed. Exemplary promoters with exemplary activities, and useful in some embodiments herein are provided in Tables 3.1-3.11 herein. The skilled artisan will appreciate that some promoters are compatible with particular transcriptional machinery (e.g. RNA polymerases, general transcription factors, and the like). As such, while compatible "species" are identified for some promoters described herein, it is contemplated that in some embodiments, these promoters can readily function in microorganisms other than the identified species, for example in species with compatible endogenous transcriptional machinery, genetically modified species comprising compatible transcriptional machinery, or fully synthetic microbial organisms comprising compatible transcriptional machinery.

The promoters of Tables 3.1-3.11 herein are publicly available from the Biobricks foundation. It is noted that the Biobricks foundation encourages use of these promoters in accordance with BioBrick™ Public Agreement (BPA).

It should be appreciated that any of the "coding" polynucleotides described herein (for example a bacteriocin polynucleotide, immunity polynucleotide, or nucleotide encoding a pro-polypeptide comprising two or more bacteriocins) is generally amenable to being expressed under the control of a desired promoter. In some embodiments, a single "coding" polynucleotide is under the control of a single promoter. In some embodiments, two or more "coding" polynucleotides are under the control of a single promoter, for example two, three, four, five, six, seven, eight, nine, or ten polynucleotides.

Generally, translation initiation for a particular transcript is regulated by particular sequences at or 5' of the 5' end of the coding sequence of a transcript. For example, a coding sequence can begin with a start codon configured to pair with an initiator tRNA. While naturally-occurring translation systems typically use Met (AUG) as a start codon, it will be readily appreciated that an initiator tRNA can be engineered to bind to any desired triplet or triplets, and accordingly, triplets other than AUG can also function as start codons in certain embodiments. Additionally, sequences near the start codon can facilitate ribosomal assembly, for example a Kozak sequence ((gcc)gccRccAUGG, SEQ ID NO: 542, in which R represents "A" or "G") or Internal Ribosome Entry Site (IRES) in typical eukaryotic translational systems, or a Shine-Delgarno sequence (GGAGGU, SEQ ID NO: 543) in typical prokaryotic translation systems. As such in some embodiments, a transcript comprising a "coding" polynucleotide sequence, for example a bacteriocin polynucleotide or immunity polynucleotide, or nucleotide encoding a pro-polypeptide comprising two or more bacteriocins, comprises an appropriate start codon and translational initiation sequence. In some embodiments, for example if two or more "coding" polynucleotide sequences are positioned in cis on a transcript, each polynucleotide sequence comprises an appropriate start codon and translational initiation sequence(s). In some embodiments, for example if two or more "coding" polynucleotide sequences are positioned in cis on a transcript, the two sequences are under control of a single translation initiation sequence, and either provide a single polypeptide that can function with both encoded polypeptides in cis.

TABLE 3.1

Exemplary Metal-Sensitive Promoters

| SEQ ID NO: | Name | Description |
|---|---|---|
| 544 | BBa_I721001 | Lead Promoter |
| 545 | BBa_I731004 | FecA promoter |
| 546 | BBa_I760005 | Cu-sensitive promoter |
| 547 | BBa_I765000 | Fe promoter |
| 548 | BBa_I765007 | Fe and UV promoters |
| 549 | BBa_J3902 | PrFe (PI + PII rus operon) |

TABLE 3.2

Exemplary Cell Signaling-Responsive Promoters

| SEQ ID NO: | Name | Description |
|---|---|---|
| 550 | BBa_I1051 | Lux cassette right promoter |
| 551 | BBa_I14015 | P(Las) TetO |
| 552 | BBa_I14016 | P(Las) CIO |
| 553 | BBa_I14017 | P(RhI) |
| 554 | BBa_I739105 | Double Promoter (LuxR/HSL, positive/cl, negative) |
| 555 | BBa_I746104 | P2 promoter in agr operon from *S. aureus* |
| 556 | BBa_I751501 | plux-cl hybrid promoter |
| 557 | BBa_I751502 | plux-lac hybrid promoter |
| 558 | BBa_I761011 | CinR, CinL and glucose controlled promotor |
| 559 | BBa_J06403 | RhIR promoter repressible by CI |
| 560 | BBa_J102001 | Reverse Lux Promoter |
| 561 | BBa_J64000 | rhII promoter |
| 562 | BBa_J64010 | lasI promoter |
| 563 | BBa_J64067 | LuxR + 3OC6HSL independent R0065 |
| 564 | BBa_J64712 | LasR/LasI Inducible & RHLR/RHLI repressible Promoter |
| 565 | BBa_K091107 | pLux/cl Hybrid Promoter |
| 566 | BBa_K091117 | pLas promoter |
| 567 | BBa_K091143 | pLas/cl Hybrid Promoter |
| 568 | BBa_K091146 | pLas/Lux Hybrid Promoter |
| 569 | BBa_K091156 | pLux |
| 570 | BBa_K091157 | pLux/Las Hybrid Promoter |
| 571 | BBa_K145150 | Hybrid promoter: HSL-LuxR activated, P22 C2 repressed |
| 572 | BBa_K266000 | PAI + LasR -> LuxI (AI) |
| 573 | BBa_K266005 | PAI + LasR -> LasI & AI + LuxR --\| LasI |
| 574 | BBa_K266006 | PAI + LasR -> LasI + GFP & AI + LuxR --\| LasI + GFP |
| 575 | BBa_K266007 | Complex QS -> LuxI & LasI circuit |
| 576 | BBa_K658006 | position 3 mutated promoter lux pR-3 (luxR & HSL regulated) |
| 577 | BBa_K658007 | position 5 mutated promoter lux pR-5 (luxR & HSL regulated) |
| 578 | BBa_K658008 | position 3&5 mutated promoter lux pR-3/5 (luxR & HSL regulated) |
| 579 | BBa_R0061 | Promoter (HSL-mediated luxR repressor) |
| 580 | BBa_R0062 | Promoter (luxR & HSL regulated -- lux pR) |
| 581 | BBa_R0063 | Promoter (luxR & HSL regulated -- lux pL) |
| 582 | BBa_R0071 | Promoter (RhIR & C4-HSL regulated) |
| 583 | BBa_R0078 | Promoter (cinR and HSL regulated) |

TABLE 3.2-continued

| Exemplary Cell Signaling-Responsive Promoters | | |
|---|---|---|
| SEQ ID NO: | Name | Description |
| 584 | BBa_R0079 | Promoter (LasR & PAI regulated) |
| 585 | BBa_R1062 | Promoter, Standard (luxR and HSL regulated -- lux pR) |

TABLE 3.3

| Exemplary Constitutive *E. coli* $\sigma^{70}$ Promoters | | |
|---|---|---|
| SEQ ID NO: | Name | Description |
| 586 | BBa_I14018 | P(Bla) |
| 587 | BBa_I14033 | P(Cat) |
| 588 | BBa_I14034 | P(Kat) |
| 589 | BBa_I732021 | Template for Building Primer Family Member |
| 590 | BBa_I742126 | Reverse lambda cl-regulated promoter |
| 591 | BBa_J01006 | Key Promoter absorbs 3 |
| 592 | BBa_J23100 | constitutive promoter family member |
| 593 | BBa_J23101 | constitutive promoter family member |
| 594 | BBa_J23102 | constitutive promoter family member |
| 595 | BBa_J23103 | constitutive promoter family member |
| 596 | BBa_J23104 | constitutive promoter family member |
| 597 | BBa_J23105 | constitutive promoter family member |
| 598 | BBa_J23106 | constitutive promoter family member |
| 599 | BBa_J23107 | constitutive promoter family member |
| 600 | BBa_J23108 | constitutive promoter family member |
| 601 | BBa_J23109 | constitutive promoter family member |
| 602 | BBa_J23110 | constitutive promoter family member |
| 603 | BBa_J23111 | constitutive promoter family member |
| 604 | BBa_J23112 | constitutive promoter family member |
| 605 | BBa_J23113 | constitutive promoter family member |
| 606 | BBa_J23114 | constitutive promoter family member |
| 607 | BBa_J23115 | constitutive promoter family member |
| 608 | BBa_J23116 | constitutive promoter family member |
| 609 | BBa_J23117 | constitutive promoter family member |
| 610 | BBa_J23118 | constitutive promoter family member |
| 611 | BBa_J23119 | constitutive promoter family member |
| 612 | BBa_J23150 | 1 bp mutant from J23107 |
| 613 | BBa_J23151 | 1 bp mutant from J23114 |
| 614 | BBa_J44002 | pBAD reverse |
| 615 | BBa_J48104 | NikR promoter, a protein of the ribbon helix-helix family of trancription factors that repress expre |
| 616 | BBa_J54200 | lacq_Promoter |
| 617 | BBa_J56015 | lacIQ - promoter sequence |
| 618 | BBa_J64951 | *E. Coli* CreABCD phosphate sensing operon promoter |
| 619 | BBa_K088007 | GlnRS promoter |
| 620 | BBa_K119000 | Constitutive weak promoter of lacZ |
| 621 | BBa_K119001 | Mutated LacZ promoter |
| 622 | BBa_K137029 | constitutive promoter with (TA)10 between −10 and −35 elements |
| 623 | BBa_K137030 | constitutive promoter with (TA)9 between −10 and −35 elements |
| 624 | BBa_K137031 | constitutive promoter with (C)10 between −10 and −35 elements |
| 625 | BBa_K137032 | constitutive promoter with (C)12 between −10 and −35 elements |
| 626 | BBa_K137085 | optimized (TA) repeat constitutive promoter with 13 bp between −10 and −35 elements |
| 627 | BBa_K137086 | optimized (TA) repeat constitutive promoter with 15 bp between −10 and −35 elements |
| 628 | BBa_K137087 | optimized (TA) repeat constitutive promoter with 17 bp between −10 and −35 elements |
| 629 | BBa_K137088 | optimized (TA) repeat constitutive promoter with 19 bp between −10 and −35 elements |
| 630 | BBa_K137089 | optimized (TA) repeat constitutive promoter with 21 bp between −10 and −35 elements |
| 631 | BBa_K137090 | optimized (A) repeat constitutive promoter with 17 bp between −10 and −35 elements |
| 632 | BBa_K137091 | optimized (A) repeat constitutive promoter with 18 bp between −10 and −35 elements |

TABLE 3.3-continued

| Exemplary Constitutive *E. coli* $\sigma^{70}$ Promoters | | |
|---|---|---|
| SEQ ID NO: | Name | Description |
| 633 | BBa_K256002 | J23101:GFP |
| 634 | BBa_K256018 | J23119:IFP |
| 635 | BBa_K256020 | J23119:HO1 |
| 636 | BBa_K256033 | Infrared signal reporter (J23119:1FP:J23119:HO1) |
| 637 | BBa_K292000 | Double terminator + constitutive promoter |
| 638 | BBa_K292001 | Double terminator + Constitutive promoter + Strong RBS |
| 639 | BBa_K418000 | IPTG inducible Lac promoter cassette |
| 640 | BBa_K418002 | IPTG inducible Lac promoter cassette |
| 641 | BBa_K418003 | IPTG inducible Lac promoter cassette |
| 642 | BBa_M13101 | M13K07 gene I promoter |
| 643 | BBa_M13102 | M13K07 gene II promoter |
| 644 | BBa_M13103 | M13K07 gene III promoter |
| 645 | BBa_M13104 | M13K07 gene IV promoter |
| 646 | BBa_M13105 | M13K07 gene V promoter |
| 647 | BBa_M13106 | M13K07 gene VI promoter |
| 648 | BBa_M13108 | M13K07 gene VIII promoter |
| 649 | BBa_M13110 | M13110 |
| 650 | BBa_M31519 | Modified promoter sequence of g3. |
| 651 | BBa_R1074 | Constitutive Promoter I |
| 652 | BBa_R1075 | Constitutive Promoter II |
| 653 | BBa_S03331 | --Specify Parts List-- |

TABLE 3.4

| Exemplary Constitutive *E. coli* $\sigma^{S}$ Promoters | | |
|---|---|---|
| SEQ ID NO: | Name | Description |
| 654 | BBa_J45992 | Full-length stationary phase osmY promoter |
| 655 | BBa_J45993 | Minimal stationary phase osmY promoter |

TABLE 3.5

| Exemplary Constitutive *E. coli* $\sigma^{32}$ Promoters | | |
|---|---|---|
| SEQ ID NO: | Name | Description |
| 656 | BBa_J45504 | htpG Heat Shock Promoter |

TABLE 3.6

| Exemplary Constitutive *B. subtilis* $\sigma^{A}$ Promoters | | |
|---|---|---|
| SEQ ID NO: | Name | Description |
| 657 | BBa_K143012 | Promoter veg a constitutive promoter for *B. subtilis* |
| 658 | BBa_K143013 | Promoter 43 a constitutive promoter for *B. subtilis* |
| 659 | BBa_K780003 | Strong constitutive promoter for *Bacillus subtilis* |
| 660 | BBa_K823000 | PliaG |
| 661 | BBa_K823002 | PlepA |
| 662 | BBa_K823003 | Pveg |

TABLE 3.7

| Exemplary Constitutive *B. subtilis* $\sigma^{B}$ Promoters | | |
|---|---|---|
| SEQ ID NO: | Name | Description |
| 663 | BBa_K143010 | Promoter ctc for *B. subtilis* |
| 664 | BBa_K143011 | Promoter gsiB for *B. subtilis* |
| 665 | BBa_K143013 | Promoter 43 a constitutive promoter for *B. subtilis* |

TABLE 3.8

| Exemplary Constitutive Promoters from miscellaneous prokaryotes | | |
|---|---|---|
| SEQ ID NO: | Name | Description |
| 666 | a_K112706 | Pspv2 from *Salmonella* |
| 667 | BBa_K112707 | Pspv from *Salmonella* |

TABLE 3.9

| Exemplary Constitutive Promoters from bacteriophage T7 | | |
|---|---|---|
| SEQ ID NO: | Name | Description |
| 668 | BBa_I712074 | T7 promoter (strong promoter from T7 bacteriophage) |
| 669 | BBa_I719005 | T7 Promoter |
| 670 | BBa_J34814 | T7 Promoter |
| 671 | BBa_J64997 | T7 consensus −10 and rest |
| 672 | BBa_K113010 | overlapping T7 promoter |
| 673 | BBa_K113011 | more overlapping T7 promoter |
| 674 | BBa_K113012 | weaken overlapping T7 promoter |
| 675 | BBa_R0085 | T7 Consensus Promoter Sequence |
| 676 | BBa_R0180 | T7 RNAP promoter |
| 677 | BBa_R0181 | T7 RNAP promoter |
| 678 | BBa_R0182 | T7 RNAP promoter |
| 679 | BBa_R0183 | T7 RNAP promoter |
| 680 | BBa_Z0251 | T7 strong promoter |

TABLE 3.9-continued

| Exemplary Constitutive Promoters from bacteriophage T7 | | |
|---|---|---|
| SEQ ID NO: | Name | Description |
| 681 | BBa_Z0252 | T7 weak binding and processivity |
| 682 | BBa_Z0253 | T7 weak binding promoter |

TABLE 3.10

| Exemplary Constitutive Promoters from yeast | | |
|---|---|---|
| SEQ ID NO: | Name | Description |
| 683 | BBa_I766555 | pCyc (Medium) Promoter |
| 684 | BBa_I766556 | pAdh (Strong) Promoter |
| 685 | BBa_I766557 | pSte5 (Weak) Promoter |
| 686 | BBa_J63005 | yeast ADH1 promoter |
| 687 | BBa_K105027 | cyc100 minimal promoter |
| 688 | BBa_K105028 | cyc70 minimal promoter |
| 689 | BBa_K105029 | cyc43 minimal promoter |
| 690 | BBa_K105030 | cyc28 minimal promoter |
| 691 | BBa_K105031 | cyc16 minimal promoter |
| 692 | BBa_K122000 | pPGK1 |
| 693 | BBa_K124000 | pCYC Yeast Promoter |
| 694 | BBa_K124002 | Yeast GPD (TDH3) Promoter |
| 695 | BBa_K319005 | yeast mid-length ADH1 promoter |
| 696 | BBa_M31201 | Yeast CLB1 promoter region, G2/M cell cycle specific |

TABLE 3.11

| Exemplary Constitutive Promoters from miscellaneous eukaryotes | | |
|---|---|---|
| SEQ ID NO: | Name | Description |
| 697 | BBa_I712004 | CMV promoter |
| 698 | BBa_K076017 | Ubc Promoter |

The above-referenced promoters are provided by way of non-limiting example only. The skilled artisan will readily recognize that many variants of the above-referenced promoters, and many other promoters (including promoters isolated from naturally existing organisms, variations thereof, and fully synthetic promoters) can readily be used in accordance with some embodiments herein.

Cleavage Sites

As used herein, "cleavage site" has its customary and ordinary meaning as understood by one of skill in the art in view of this disclosure. It refers to a polypeptide sequence that mediates the cleavage of a polypeptide (for example by hydrolysis of a peptide bond) to separate a single polypeptide into two or more discrete polypeptides. In some embodiments, a cleavage site comprises, consists of, or consists essentially of a consensus polypeptide sequence for cleavage by a "cleavage enzyme," such as a peptidase. In some embodiments, the cleavage enzyme is a wild-type, a variant, or a synthetic cleavage enzyme, for example a wild-type, variant, or synthetic endopeptidase. A number of example cleavage enzymes and their corresponding cleavage sites are described herein. For reference, the cleavage sites are described with reference to formula (I), below:

Pn-P4-P3-P2-P1-||Cleavage||-P1'-P2'-P3'-P4'-Pm' (I)

in which amino acid residues in a substrate undergoing cleavage are designated P1, P2, P3, P4 etc. in the N-terminal (or "upstream") direction from the cleaved bond. Likewise, the residues in C-terminal (or "downstream") direction of the cleavage site are designated P1', P2', P3', P4'. etc.

Example cleavage enzymes and their cleavage sites useful in accordance with some embodiments herein are described in Table 4, below.

It is noted that a number of cleavage enzymes cleave at consensus sequences, and thus, a particular cleavage enzyme can cut at two or more particular polypeptide sequences that fall within the scope of a consensus sequence (or consensus sequences) for that cleavage enzyme. As such, for convenience herein, unless explicitly stated otherwise, two cleavage sites may be referred to as the "same" when they are both cut by the same cleavage enzyme under the same conditions, even if they are two different sequences (which may fall within the scope of that cleavage enzyme's consensus sequence(s)). For example, the sequences DVADL (SEQ ID NO: 739) and DVADI (SEQ ID NO: 740) may both be referred to as the "same" cleavage site for the purposes of cleavage by Caspase 2 because they both fall within the scope of consensus sequence for Caspase 2, even though these cleavage sites are not identical. On the other hand, also for convenience herein, unless explicitly stated otherwise, two cleavage sites may be referred to as "different" when they are each cut by different cleavage enzymes, but would not be cut by the same cleavage enzyme.

TABLE 4

| Example Cleavage Enzymes and Cleavage Sites | | | | | | |
|---|---|---|---|---|---|---|
| Cleavage Enzyme | Cleavage Site (with reference to Formula (I)) | | | | | |
| Name | P4 | P3 | P2 | P1 | P1' | P2' |
| Arg-C proteinase | — | — | — | R | — | — |
| Asp-N endopeptidase | — | — | — | — | D | — |
| BNPS-Skatole | — | — | — | W | — | — |
| Caspase 1 | F, W, Y, or L | | H, A or T | D | not P, E, D, Q, K or R | — |
| Caspase 2 | D | V | A | D | not P, E, D, Q, K or R | — |
| Caspase 3 | D | M | Q | D | not P, E, D, Q, K or R | — |
| Caspase 4 | L | E | V | D | not P, E, D, Q, K or R | — |
| Caspase 5 | L or W | E | H | D | — | — |
| Caspase 6 | V | E | H or I | D | not P, E, D, Q, K or R | — |

TABLE 4-continued

| Example Cleavage Enzymes and Cleavage Sites | | | | | | |
|---|---|---|---|---|---|---|
| Cleavage Enzyme | Cleavage Site (with reference to Formula (I)) | | | | | |
| Name | P4 | P3 | P2 | P1 | P1' | P2' |
| Caspase 7 | D | E | V | D | not P, E, D, Q, K or R | — |
| Caspase 8 | I or L | E | T | D | not P, E, D, Q, K or R | — |
| Caspase 9 | L | E | H | D | — | — |
| Caspase 10 | I | E | A | D | — | — |
| Chymotrypsin-high | — | — | — | F or Y | not P | — |
| specificity (C-term | — | — | — | W | not M or P | — |
| to [FYW], not | — | — | — | F, L or Y | not P | — |
| before P) | — | — | — | W | not M or P | — |
| Chymotrypsin-low | — | — | — | M | Not P or Y | — |
| specificity (C-term to [FYWML], not before P | — | — | — | H | not D, M, P, or W | — |
| Clostripain (Clostridiopeptidase B) | — | — | — | R | — | — |
| CNBr | — | — | — | M | — | — |
| Enterokinase | D or E | D or E | D or E | K | — | — |
| Factor Xa | A, F, G, I, L, T, V or M | D or E | G | R | — | — |
| Formic acid | — | — | — | D | — | — |
| Glutamyl endopeptidase | — | — | — | E | — | — |
| GranzymeB | I | E | P | D | — | — |
| Hydroxylamine | — | — | — | N | G | — |
| Iodosobenzoic acid | — | — | — | W | — | — |
| LysC | — | — | — | K | — | — |
| Neutrophil elastase | — | — | — | A or V | — | — |
| NTCB (2-nitro-5-thiocyanobenzoic acid) | — | — | — | — | C | — |
| Pepsin (pH 1.3) | — | not H, K, or R | not P | not R | F or L | not P |
| | — | not H, K, or R | not P | F or L | — | not P |
| Pepsin (pH > 2) | — | not H, K, or R | not P | not R | F, L, W, or Y | not P |
| | — | not H, K, or R | not P | F, L, W, or Y | — | not P |
| Proline-endopeptidase | — | — | H, K or R | P | not P | — |
| Proteinase K | — | — | — | A, E, F, I, L T, V, W or Y | — | — |
| Staphylococcal peptidase I | — | — | not E | E | — | — |
| Thermolysin | — | — | — | not D or E | A, F, I, L, M or V | — |
| Thrombin | A, F, G, I, L, T, V or M | A, F, G, I, L, T, V, W or A | P | R | not D or E | Not DE |
| Trypsin (please | — | — | | K or R | not P | — |
| note the exceptions | — | — | W | K | P | — |
| in the following | — | — | M | R | P | — |
| rows) | | | | | | |
| Exceptions to the | — | — | C or D | K | D | — |
| Trypsin Consensus | — | — | C | K | H or Y | — |
| Site Noted in the | — | — | C | R | K | — |
| rows above | — | — | R | R | H or R | — |

Additional information about cleavage sites can be found on the world wide web at web.expasy.org/peptide_cutter/peptidecutter_enzymes.html, which is herein incorporated by reference in its entirety.

In some embodiments the cleavage site comprises, consists essentially of, or consists of a cleavage site of Table 4. As such, in some embodiments, the cleavage site comprises, consists essentially of, or consists of a cleavage site for Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. As such, in the methods of some embodiments herein, one or more of the listed enzymes is used to cleave the cleavage sites.

In some embodiments the cleavage site comprises, consists essentially of, or consists of a chemical- or pH-sensitive linker. Such linkers can undergo cleavage in the presence of a suitable chemical (in the case of chemical-sensitive linkers), or at a suitable pH (in the case of pH linkers). In some embodiments, the pH-sensitive linker undergoes enzyme-mediated cleavage when the pH is in a suitable range. For example, the pH-sensitive linkers such as the valine-citrulline (vc) dipeptide is cleaved in a pH-sensitive manner by cathepsin B at acidic pH's (e.g., in the 4.8-6 range) (See, e.g., Jain et al. Pharmaceutical Research, 32: 3526-3540, (2015)), which is hereby incorporated by reference in its entirety). In some embodiments, the pH-sensitive linker undergoes a cleavage event when the pH is in a particular range. For example, tunable pH sensitive linkers based on a phosphoraamidate backbone have also been described, which can undergo hydrolysis at a pH of less than 7.4 are described in PCT Pub. No. WO 2016028700, which is hereby incorporated by reference it its entirety). In some embodiments, the chemical-sensitive linker undergoes a cleavage event in the present of a chemical. For example, linkers comprising, consisting essentially or, consisting of disulfide bridges can be released upon the introduction of glutathione (See, e.g., Jain et al. Pharmaceutical Research, 32: 3526-3540, (2015)).

Signal Molecules

In some embodiments, pro-polypeptides comprise one or more signal molecules. As used herein, a "signal molecule" has its customary and ordinary meaning as understood by one of skill in the art in view of this disclosure. It refers to a secreted molecule that is capable of modulating, inducing, or inhibiting an activity or process in the cell that produced it, or in a different cell (a subject cell can be a microbial cell or a non-microbial cell, for example a cell of a multicellular organism such as an animal or plant). Example signal molecules include, but are not limited to, signaling peptides, quorum sensing molecules (for example, quorum sensing peptides), signal transduction receptor ligands, growth factors, hormones, and cytokines. In some embodiments, a signal molecule comprises, consists essentially of, or consists of a signaling peptides, quorum sensing molecules (for example, quorum sensing peptides), signal transduction receptor ligands, growth factors, hormones, or cytokine. In some embodiments, a signal molecule comprises, consists essentially of, or consists of a combination of two or more of signaling peptides, quorum sensing molecules (for example, quorum sensing peptides), signal transduction receptor ligands, growth factors, hormones, and cytokines, which can include combinations of two or more of the same type of molecule (for example a combination of two signaling peptides or a combination of two receptor ligands), as well as combinations of two different kinds of molecules (e.g., a combination of a cytokine and a hormone). In some embodiments, the signal molecule is for microbe-host dialog, and as such, the signal molecule is selected to target one or more cells of a host organism, for example a plant or animal. In some embodiments, the signal molecule stimulates, inhibits, increases, or decreases the production of bacteriocins and/or the growth rate of a subpopulation of a flora. In some embodiments, the signal molecule comprises, consists of, or consists essentially of a quorum sensing peptide, or a variant thereof as described herein.

Example quorum sensing peptides suitable for pro-polypeptides, methods, and/or encoded by nucleic acids of some embodiments include, but are not limited to, quorum sensing peptides such as the peptides shown in Table 5 below, including variants of these peptides, and combinations of two or more of any of these peptides. Without being limited by theory, it is contemplated that microbial cells, such as gram-positive bacteria use quorum sensing peptides to orchestrate cell-to-cell communication. A review of quorum sensing peptides can be found in Rajput et al., PLoS One DOI:10.1371/journal.pone.0120066 Mar. 17, 2015, pp. 1-16, which is hereby incorporated by reference in its entirety. The quorum sensing peptides can induce activation of downstream response regulators and/or transcription factors in a target microbial cell. It is noted that in some embodiments, the downstream response regulators or transcription factors can be configured to activate or repress transcription of a target nucleic acid of interest. Accordingly, in some embodiments, a target microbial cell is genetically engineered to express or repress transcription (and subsequent expression) of a gene product of interest upon stimulation by a signal peptide of a pro-polypeptide.

In some embodiments, the signal molecule of the pro-polypeptide comprises, consists essentially of, or consists of a signal molecule (e.g., a quorum sensing molecule such as a quorum sensing peptide), which stimulates transcription of one or more bacteriocin polynucleotides in the target microbial cell. The target microbial cell can be genetically engineered to place one or more bacteriocin polynucleotides under the control of a transcription factor that responds to the quorum sensing molecule. In some embodiments, transcription of one or more bacteriocin polynucleotides is configured to be induced by a transcription factor (e.g., a transcriptional activator) that responds to the quorum sensing molecule. As such, signaling by the signal molecule (e.g. quorum sensing molecule) of the pro-polypeptide can stimulate the production of one or more additional bacteriocins by the target microbial cell.

In some embodiments, the target microbial cell is genetically modified to place one or more molecules of a poison-antidote system under the control of a transcription factor or response regulator that responds to a signal molecule (e.g., a quorum sensing molecule such as a quorum sensing peptide) so as to induce a suicidal response in target cell upon signaling by the signal molecule. Poison-antidote systems, which are distinct from bacteriocins, can be useful for accomplishing such a suicidal response, which in turn can be useful for containment and/or selective growth of microbial cells. Exemplary poison antidote systems are described in U.S. Pat. Nos. 5,910,438, 6,180,407, 7,176,029, and 7,183,097, each of which is hereby incorporated by reference in its entirety. In some embodiments, a poison-antidote system comprises a cytotoxic (poison) polypeptide, and a corresponding antitoxin (antidote) polypeptide in a single cell. As used herein, a "poison polynucleotide" has its customary and ordinary meaning as understood by one of skill in the art in view of this disclosure, and can refer to a polynucleotide encoding a poison polypeptide. An "antidote polynucleotide" has its customary and ordinary meaning as understood by one of skill in the art in view of this disclosure, and can refer to a polynucleotide encoding an antidote polypeptide. As such, in some embodiments, the target microbial cell is configured to induce transcription of a poison polynucleotide in response to a signal molecule such as a quorum sensing molecule, so as to induce a suicidal response in the target microbial cell. In some embodiments, the target microbial cell is configured to transcriptionally repress an antibody polynucleotide (while continuing to express a corresponding poison polypeptide) in response to a signal molecule such as a quorum sensing molecule, so as to induce a suicidal response in the target microbial cell.

In some embodiments, the quorum sensing peptides are naturally-occurring. In some embodiments, the quorum sensing peptide comprises, consists essentially of, or consists of a variant of a naturally-occurring quorum sensing peptide. In some embodiments, the quorum sensing peptide comprises, consists essentially of, or consists of a synthetic peptide. Information on quorum sensing peptides, including example sequences, can be found on the quorumpeps database, accessible on the world wide web at quorumpeps.ugent.be., which is hereby incorporated by reference in its entirety.

TABLE 5

| Name | Species | SEQ ID NO: (if peptide shown) |
|---|---|---|
| phrANTH3 | *Bacillus anthracis* | — |
| phrANTH1 | *Bacillus anthracis* | — |
| phrANTH2 | *Bacillus anthracis* | — |
| PapR5I | *Bacillus cereus* | — |
| PapR5IV | *Bacillus cereus* | — |
| PapR5II | *Bacillus cereus* | — |
| PapR7III | *Bacillus cereus* | — |
| PapR7IV | *Bacillus cereus* | — |
| PapR7II | *Bacillus cereus* | — |
| PapR5III | *Bacillus cereus* | — |
| PapR7I | *Bacillus cereus, Bacillus thuringiensis* | — |
| Phr0662 | *Bacillus halodurans* | — |
| phr1988 | *Bacillus halodurans* | — |
| ComX RO-B-2 | *Bacillus mojavensis* | — |
| ComX RO-H-1 | *Bacillus mojavensis* | — |
| ComX RO-C-2 | *Bacillus mojavensis* | — |
| Phr-pPL10-1, PhrPUM | *Bacillus pumilus* | — |
| PHRBST1 | *Bacillus stearothermophilus* | — |
| PhrA | *Bacillus subtilis* | — |
| ComX 168 | *Bacillus subtilis* | — |
| Mersacidin | *Bacillus subtilis* | — |
| PhrI | *Bacillus subtilis* | — |
| PhrG | *Bacillus subtilis* | — |
| PhrK | *Bacillus subtilis* | — |
| ComX RO-E-2 | *Bacillus subtilis* | — |
| Subtilin | *Bacillus subtilis* | — |
| ComX RS-B-1 | *Bacillus subtilis* | — |
| Phr-pLS20 | *Bacillus subtilis* | — |
| PhrF | *Bacillus subtilis* | — |
| Phr-pTA1040 | *Bacillus subtilis* | — |
| Phr-pPOD2000, Phr-pTA1060 | *Bacillus subtilis* | — |
| PhrE | *Bacillus subtilis* | — |
| BsEDF | *Bacillus subtilis* | — |
| ComX natto | *Bacillus subtilis* | — |
| Entianin | *Bacillus subtilis* | — |
| Competence and Sporulation Factor, CSF, PhrC | *Bacillus subtilis, Bacillus mojavensis* | — |
| NprRB | *Bacillus thuringiensis* | — |
| PisN | *Carnobacterium maltaromaticum* | — |
| CbaX | *Carnobacterium maltaromaticum* | — |
| Carnobacteriocin B2, CB2, CbnB2 | *Carnobacterium piscicola* | — |
| CbnS, CS | *Carnobacterium piscicola, Carnobacterium maltaromaticum* | — |
| AIP, Autoinducing peptide | *Clostridium acetobutylicum* | — |
| PHRCACET4 | *Clostridium acetobutylicum* | — |
| PHRCACET1 | *Clostridium acetobutylicum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |
| AgrD1, AIP, Autoinducing peptide | *Clostridium botulinum* | — |
| AgrDCp | *Clostridium perfringens* | — |
| WS9326A | *Clostridium perfringens* | — |
| WS9326B | *Clostridium perfringens* | — |

TABLE 5-continued

| Name | Species | SEQ ID NO: (if peptide shown) |
|---|---|---|
| Cochinmicin II/III | *Clostridium perfringens* | — |
| AgrD2, AIP, Autoinducing peptide | *Clostridium sporogenes* | — |
| AgrD1, AIP, Autoinducing peptide | *Clostridium sporogenes* | — |
| AgrD | *Clostridium thermocellum* | — |
| QSP1 | *Cryptococcus neoformans* | — |
| QSP24 | *Cryptococcus neoformans* | — |
| QSP2 | *Cryptococcus neoformans* | — |
| — | *Eikenella corodens* | — |
| cAM373 | *Enterococcus faecalis* | — |
| iCF10 | *Enterococcus faecalis* | — |
| iPD1 | *Enterococcus faecalis* | — |
| cPD1 | *Enterococcus faecalis* | — |
| GBAP, Gelatinase Biosynthesis-Activating Pheromone | *Enterococcus faecalis* | — |
| cAD1 | *Enterococcus faecalis* | — |
| iAD1 | *Enterococcus faecalis* | — |
| cCF10 | *Enterococcus faecalis* | — |
| iAM373 | *Enterococcus faecalis* | — |
| cOB1 | *Enterococcus faecalis* | — |
| EntF | *Enterococcus faecium* | — |
| EDF, Extracellular death factor | *Escherichia coli* | — |
| LamD | *Lactobacillus plantarum* | — |
| PltA | *Lactobacillus plantarum* | — |
| Plantaricin A, PlnA | *Lactobacillus plantarum* | — |
| IP-TX | *Lactobacillus sakei* | — |
| IP-673 | *Lactobacillus sakei* | — |
| Orf4 | *Lactobacillus sakei* | — |
| Nisin A | *Lactococcus lactis* | — |
| AIP | *Listeria monocytogenes* | — |
| PaEDF-1 | *Pseudomonas aeruginosa* | — |
| PaEDF-2 | *Pseudomonas aeruginosa* | — |
| PaEDF-3 | *Pseudomonas aeruginosa* | — |
| AIP, Autoinducing peptide | *Staphylococcus arlettae* | — |
| AIP2, Autoinducing peptide 2 | *Staphylococcus aureus* | — |
| AIP3, Autoinducing peptide 3 | *Staphylococcus aureus* | — |
| AIP1, Autoinducing peptide 1 | *Staphylococcus aureus* | — |
| AIP4, Autoinducing peptide 4 | *Staphylococcus aureus* | — |
| AIP, Autoinducing peptide | *Staphylococcus auricularis* | — |
| AIP, Autoinducing peptide | *Staphylococcus auricularis* | — |
| AIP, Autoinducing peptide | *Staphylococcus capitis* | — |
| AIP, Autoinducing peptide | *Staphylococcus capitis* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus carnosus* | — |
| AIP, Autoinducing peptide | *Staphylococcus cochnii* subsp. *cochnii* | — |
| AIP, Autoinducing peptide | *Staphylococcus cochnii* subsp. *urealyticum* | — |
| AIP2, Autoinducing peptide 2 | *Staphylococcus epidermidis* | — |
| AIP, Autoinducing peptide | *Staphylococcus epidermidis* | — |
| AIP, Autoinducing peptide | *Staphylococcus epidermidis* | — |
| AIP, Autoinducing peptide | *Staphylococcus epidermidis* | — |
| Pep5 | *Staphylococcus epidermidis* | — |
| AIP4, Autoinducing peptide 4 | *Staphylococcus epidermidis* | — |
| AIP1, Autoinducing peptide 1 | *Staphylococcus epidermidis* | — |
| AIP3, Autoinducing peptide 3 | *Staphylococcus epidermidis* | — |
| AIP-II | *Staphylococcus epidermidis* | — |
| AIP-III | *Staphylococcus epidermidis* | — |
| AIP, Autoinducing peptide | *Staphylococcus gallinarum* | — |
| AIP, Autoinducing peptide | *Staphylococcus lugdunensis* | — |
| AIP, Autoinducing peptide | *Staphylococcus lugdunensis* | — |
| AIP, Autoinducing peptide | *Staphylococcus simulans* | — |
| AIP, Autoinducing peptide | *Staphylococcus simulans* | — |
| AIP, Autoinducing peptide | *Staphylococcus simulans* | — |
| AIP, Autoinducing peptide | *Staphylococcus warneri* | — |
| AIP, Autoinducing peptide | *Staphylococcus xylosus* | — |
| Short Hydrophobic Peptide 3, SHP3 | *Streptococcus agalactiae* | — |
| Competence Stimulating Peptide, CSP | *Streptococcus crista* | — |

TABLE 5-continued

| Name | Species | SEQ ID NO: (if peptide shown) |
|---|---|---|
| SilCR | *Streptococcus dysgalactiae* | — |
| Competence Stimulating Peptide, CSP | *Streptococcus gordonii* | — |
| Competence Stimulating Peptide, CSP | *Streptococcus gordonii* | — |
| Competence Stimulating Peptide, CSP | *Streptococcus milleri* | — |
| Competence Stimulating Peptide, CSP | *Streptococcus mitis* | — |
| Competence Stimulating Peptide, CSP | *Streptococcus mitis* | — |
| Competence Stimulating Peptide, CSP | *Streptococcus mitis* | — |
| Competence Stimulating Peptide, CSP | *Streptococcus mitis* | — |
| Competence Stimulating Peptide, CSP | *Streptococcus mitis* | — |
| Competence Stimulating Peptide, CSP | *Streptococcus mitis* | — |
| Competence Stimulating Peptide, CSP | *Streptococcus mitis, Streptococcus pneumoniae, Streptococcus oralis* | — |
| 18-CSP, Competence Stimulating Peptide | *Streptococcus mutans* | — |
| 21-CSP, Competence Stimulating Peptide | *Streptococcus mutans* | — |
| Short Hydrophobic Peptide, SHP1509 | *Streptococcus mutans* | — |
| ComS | *Streptococcus mutans* | — |
| Competence Stimulating Peptide, CSP | *Streptococcus oralis* | — |
| Competence Stimulating Peptide, CSP | *Streptococcus oralis* | — |
| Competence Stimulating Peptide, CSP | *Streptococcus pneumoniae* | — |
| Competence Stimulating Peptide, CSP | *Streptococcus pneumoniae* | — |
| Bacteriocin Inducing Peptide, BIP | *Streptococcus pneumoniae* | — |
| Bacteriocin Inducing Peptide, BIP, BIP-2, BIpC | *Streptococcus pneumoniae* | — |
| Bacteriocin Inducing Peptide, BIP-1, BIpC | *Streptococcus pneumoniae* | — |
| Streptin 1 | *Streptococcus pyogenes* | — |
| XIP | *Streptococcus pyogenes* | — |
| XIP | *Streptococcus pyogenes* | — |
| SHP2-C10 | *Streptococcus pyogenes* | — |
| SHP2-C9 | *Streptococcus pyogenes* | — |
| SHP2-C7 | *Streptococcus pyogenes* | — |
| SHP3-C10 | *Streptococcus pyogenes* | — |
| SHP3-C9 | *Streptococcus pyogenes* | — |
| SHP3-C7 | *Streptococcus pyogenes* | — |
| Competence Stimulating Peptide, CSP | *Streptococcus pyogenes, Streptococcus pneumoniae* | — |
| Competence Stimulating Peptide, CSP | *Streptococcus sanguis* | — |
| STP | *Streptococcus thermophilus* | — |
| SHP1358(15-23) | *Streptococcus thermophilus* | — |
| ComS, SHP0316(18-24) | *Streptococcus thermophilus* | — |
| Short Hydrophobic Peptide; SHP1299 | *Streptococcus thermophilus* | — |
| Competence Stimulating Peptide, CSP | *Streptococcus thermophilus, Streptococcus constellatus, Streptococcus anginosus* | — |
| Siamycin I | *Streptomyces* species | — |
| TM0504 | *Thermotoga maritima* | — |
| Synthetic RAP-binding peptide, RBP | Synthetic (FHWWQTSPAHFS) | 741 |
| Synthetic RAP-binding peptide, RBP | Synthetic (WPFAHWPWQYPR) | 742 |
| Synthetic AgrC ligand | Synthetic (GDSVCASYF, thiolacton linkage between C5 and F9) | 743 |
| Synthetic AgrC ligand | Synthetic (SVCASYF, thiolacton linkage between C3 and F7) | 744 |
| Synthetic Cry1Aa ligand | Synthetic (SKADT) | 745 |
| Synthetic Cry1Aa ligand | Synthetic (SKPAD) | 746 |

TABLE 5-continued

| Name | Species | SEQ ID NO: (if peptide shown) |
|---|---|---|
| Synthetic Fsr ligand | Synthetic (benzyloxycarbonyl-QNSAAAFAAWA, lacton linkage between S3 and A11) | 747 |
| Synthetic Fsr ligand | Synthetic (benzyloxycarbonyl-QNSAAAFGQWA, lacton linkage between S3 and A11) | 748 |
| Synthetic AgrC1, AgrC2 | Synthetic (YSTC(alpha-aminobutyric acid)FIM, thiolacton linkage between C4 and M7) | 749 |
| Synthetic AgrC1, AgrC2 | Synthetic (N-4-(4-benzoylphenoxy)butyryl-STCAFIM, thiolacton linkage between C3 and M7) | 750 |

Cytokines are a class of signal molecules that are typically produced by cells, such as cells of the immune system, and capable of inducing a response in other cells. A number of different cytokines can be used in pro-polypeptides, methods, and/or encoded by nucleic acids of some embodiments herein. It is contemplated that a pro-polypeptide comprising a bacteriocin and a cytokine in accordance with some embodiments can be useful to induce antimicrobial activity (by the bacteriocin(s)), and a host response, for example immune cell suppression or immune cell stimulation (by the cytokine(s)). In some embodiments, the cytokine comprises, consists essentially of, or consists of a naturally-occurring cytokine, variant of a naturally occurring, or synthetic cytokine. A number of suitable cytokines can be used in pro-polypeptides, methods, compositions, cells, or encoded by nucleic acids in accordance with some embodiments herein, including, but not limited to IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-22, IL-23, IFN-α, IFN-β, IFN-γ, TNF-α, TNF-β, TGF-β1, M-CSF, G-CSF, and GM-CSF, variants of any of these, or any combination of two or more of these.

Hormones are a class of signal molecules that are typically produced by cells of multicellular organisms, and signal to other cells, frequently circulating through different tissues and/or organs of a multicellular organism. A number of different hormones can be used in pro-polypeptides, methods, and/or be encoded by nucleic acids of some embodiments herein. It is contemplated that a pro-polypeptide comprising a bacteriocin and a hormone in accordance with some embodiments can be useful to induce antimicrobial activity (by the bacteriocin(s)), along with a host response, for example cell growth or proliferation (by the hormone(s)). In some embodiments, the cytokine comprises, consists essentially of, or consists of a naturally-occurring hormone, variant of a naturally occurring hormone, or synthetic hormone. Example hormones suitable for pro-polypeptides, methods, and/or encoded by nucleic acids of some embodiments include, but are not limited to, protein and peptide hormones, for example activin and inhibin, adiponectin, adipose-derived hormones, adrenocorticotropic hormone, agouti gene, agouti signaling peptide, allatostatin, amylin, amylin family, angiotensin, ANGPTL8, asprosin, atrial natriuretic peptide, big gastrin, bovine somatotropin, bradykinin, brain-derived neurotrophic factor, calcitonin, ciliary neurotrophic factor, corticotropin-releasing hormone, crustacean neurohormone family, endothelin, enteroglucagon, erythroferrone, fellutamide, FGF15, FGF15/19, FGF19, FNDC5, follicle-stimulating hormone, gastrin, gastroinhibitory peptide, ghrelin, glucagon-like peptide-1, gonadotropin, gonadotropin release inhibitor, gonadotropin-releasing hormone, granulocyte colony-stimulating factor, growth hormone, growth hormone-releasing hormone, hepcidin, human chorionic gonadotropin, human placental lactogen, incretin, insulin, insulin analog, insulin aspart, insulin degludec, insulin glargine, insulin lispro, insulin-like growth factor, insulin-like growth factor 1, insulin-like growth factor 2, leptin, limostatin, liraglutide, little gastrin I, luteinizing hormone, melanocortin, melanocyte-stimulating hormone, alpha-melanocyte-stimulating hormone, beta-melanocyte-stimulating hormone, gamma-melanocyte-stimulating hormone, minigastrin, N-terminal prohormone of brain natriuretic peptide, nerve growth factor, neuropeptide VF precursor, neurotrophin-3, neurotrophin-4, NPH insulin, obestatin, osteocalcin, parathyroid hormone, peptide hormone, peptide YY, plasma renin activity, pramlintide, preprohormone, prolactin, relaxin, relaxin family peptide hormones, renin, salcatonin, sauvagine, secretin, secretin family, sincalide, stanniocalcin, teleost leptins, temporin, thyroid-stimulating hormone, thyrotropin-releasing hormone, urocortin, urocortin II, urocortin III, vasoactive intestinal peptide, vitellogenin, variants of any of these, or any combination of two or more of these.

Affinity Tags

In pro-polypeptides, methods, and nucleic acids encoding pro-polypeptides of some embodiments herein, a pro-polypeptide, or component peptide thereof (e.g. a bacteriocin or signal molecule) comprises an affinity tag. Optionally, one or more cleavage sites can be positioned between the affinity tag and the rest of the pro-polypeptide to facilitate removal of the affinity tag after affinity purification. Affinity tags can be used in purification, for example by contact with a molecule that binds the affinity tag immobilized on a solid phase, such as a bead. Example affinity tags suitable for pro-polypeptides, methods, and encoding by nucleic acids of some embodiments herein can comprise, consist essentially of, or consist of His-tags, glutathione-S-transferase (GST) tags, FLAG tags, strep tags, maltose binding protein (MBP), chitin binding protein (CBP), myc tags, HA tags, NE tags, and V5 tags, variants of any of these, or any combination of two or more of these.

Microbial Organisms

In some embodiments, genetically engineered microorganisms are provided. As used herein, genetically engineered "microbial organism," "microorganism," and variations of these root terms (such as pluralizations and the like), have their customary and ordinary meanings as understood by one of skill in the art in view of this disclosure. They encompass genetic modification of any naturally-occurring species or fully synthetic prokaryotic or eukaryotic unicellular organism, as well as Archae species. Thus, this expression can refer to cells of bacterial species, fungal species, and algae.

Exemplary microorganisms that can be used in accordance with embodiments herein include, but are not limited to, bacteria, yeast, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, hereby incorporated by reference in its entirety). As such, in some embodiments, the microorganism is fully synthetic. A desired combination of genetic elements, including elements that regulate gene expression, and elements encoding gene products (for example bacteriocins, immunity modulators, poison, antidote, and industrially useful molecules) can be assembled on a desired chassis into a partially or fully synthetic microorganism. Description of genetically engineered microbial organisms for industrial applications can also be found in Wright, et al. (2013) "Building-in biosafety for synthetic biology" Microbiology 159: 1221-1235.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, Cyanobacteria species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli.*

A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces* japonicas), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises photosynthetic microalgae. Exemplary algae species that can be useful for biofuels, and can be used in accordance with embodiments herein, include *Botryococcus braunii, Chlorella species, Dunaliella tertiolecta, Gracilaria species, Pleurochrysis carterae*, and Sargassum species. Additionally, many algaes can be useful for food products, fertilizer products, waste neutralization, environmental remediation, and carbohydrate manufacturing (for example, biofuels).

Design of Pro-Polypeptides and Nucleic Acids Encoding Pro-Polypeptides

Pro-polypeptides comprising selected bacteriocins in desired ratios in accordance with some embodiments herein can be designed using a variety of approaches. For example, one option is to design a nucleic acid coding sequence comprising the bacteriocins, cleavage sites, and other features of the pro-polypeptide such as affinity tags and/or signal molecules in a single open reading frame. A polynucleotide having this sequence can then be sequenced. Additionally, computational tools are available to facilitate the design of pro-polypeptides (and nucleic acids encoding them) in accordance with some embodiments. For example, as described in Nielsen et al., "Genetic circuit design automation" Science (2016) 352: aac7341 (hereby incorporated by reference in its entirety), a computer-based design environment, Cello, permits a user to writes Verilog code that is automatically transformed into a DNA sequence. Accordingly, in some embodiments, text-based approach can readily be used to produce a nucleic acid encoding the desired elements of a pro-polypeptide, such as a particular combination and/or ratio of bacteriocins and cleavage sites separating the bacteriocins, and in a manner where bacteriocins are not cleaved by a cleavage enzyme that cleaves the cleavage sites. In some embodiments, the pro-polypeptide comprises selected bacteriocins and antimicrobial peptides in desired ratios. In some embodiments, the pro-polypeptide comprises selected antimicrobial peptides in desired ratios. In some embodiments, the pro-polypeptide comprises selected bacteriocins in desired ratios.

Genetic Modification of Microbial Organisms for Expression of Nucleic Acids

Techniques of genetically modifying microorganisms are well known in the art. In methods and compositions of some embodiments, a microorganism is genetically modified to comprise nucleic acid sequence regulating the expression of, and encoding, bacteriocins, for example pro-polypeptides comprising bacteriocins as described herein. In methods and compositions of some embodiments herein, polynucleotides encoding pro-polypeptides can be delivered to microorganisms, and can be stably integrated into the chromosomes of these microorganisms, or can exist free of the genome, for example in a plasmid, extrachromosomal array, episome, minichromosome, or the like.

Exemplary vectors for genetic modification of microbial cells include, but are not limited to, plasmids, viruses (including bacteriophage), and transposable elements. Additionally, it will be appreciated that entire microbial genomes comprising desired sequences can be synthesized and assembled in a cell (see, e.g. Gibson et al. (2010), Science 329: 52-56). As such, in some embodiments, a microbial genome (or portion thereof) is synthesized with desired features such as bacteriocin polynucleotide(s), and introduced into a microbial cell.

In some embodiments, a cassette for inserting one or more desired bacteriocin and/or immunity modulator polynucleotides into a polynucleotide sequence (for example inserting, into an expression vector, a cassette encoding a pro-polypeptide comprising bacteriocins) is provided. Exemplary cassettes include, but are not limited to, a Cre/lox cassette or FLP/FRT cassette. In some embodiments, the cassette is positioned on a plasmid, so that a plasmid with the desired polynucleotide encoding the desired pro-polypeptide can be readily introduced to the microbial cell. In some embodiments, the cassette is positioned in a desired position in the genome of the microbial cell.

In some embodiments, plasmid conjugation can be used to introduce a desired plasmid from a "donor" microbial cell to a recipient microbial cell. Goñi-Moreno, et al. (2013) Multicellular Computing Using Conjugation for Wiring. PLoS ONE 8(6): e65986, hereby incorporated by reference in its entirety. In some embodiments, plasmid conjugation can genetically modify a recipient microbial cell by introducing a conjugation plasmid from a donor microbial cell to a recipient microbial cell. Without being limited by any particular theory, conjugation plasmids that comprise the same or functionally same set of replication genes typically cannot coexist in the same microbial cell. As such, in some embodiments, plasmid conjugation "reprograms" a recipient microbial cell by introducing a new conjugation plasmid to supplant another conjugation plasmid that was present in the recipient cell. In some embodiments, plasmid conjugation is used to engineer (or reengineer) a microbial cell with a particular nucleic acid encoding a pro-polypeptide, or combination of different nucleic acids encoding different pro-polypeptide. According to some embodiments, a variety of conjugation plasmids comprising different nucleic acids comprising a variety of different pro-polypeptides is provided. The plasmids can comprise additional genetic elements as described herein, for example promoters, translational initiation sites, and the like. In some embodiments the variety of conjugation plasmids is provided in a collection of donor cells, so that a donor cell comprising the desired plasmid can be selected for plasmid conjugation. In some embodiments, a particular combination and/or ratio of bacteriocins is selected, and an appropriate donor cell (encoding the particular pro-polypeptide) is conjugated with a microbial cell of interest to introduce a conjugation plasmid comprising that combination into a recipient cell.

Pro-Polypeptides

Figure 2:
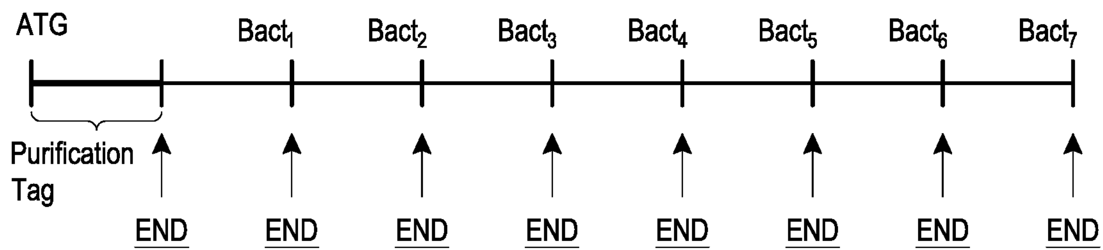
FIG. 2 is a schematic diagram of an embodiment of a nucleic acid encoding a pro-polypeptide comprising bacteriocins and cleavage sites in accordance with some embodiments herein. As shown, a single bacteria may produce a pro-polypeptide encoded by a synthetic gene. It is contemplated that the molecular ratio of one bacteriocin can be changed by putting multiple copies of it in the pro-polypeptide.
Figure 2:
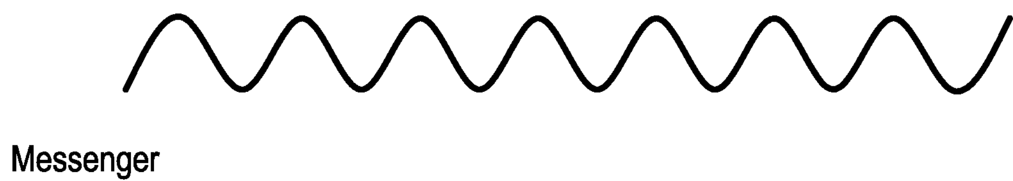
Figure 2:
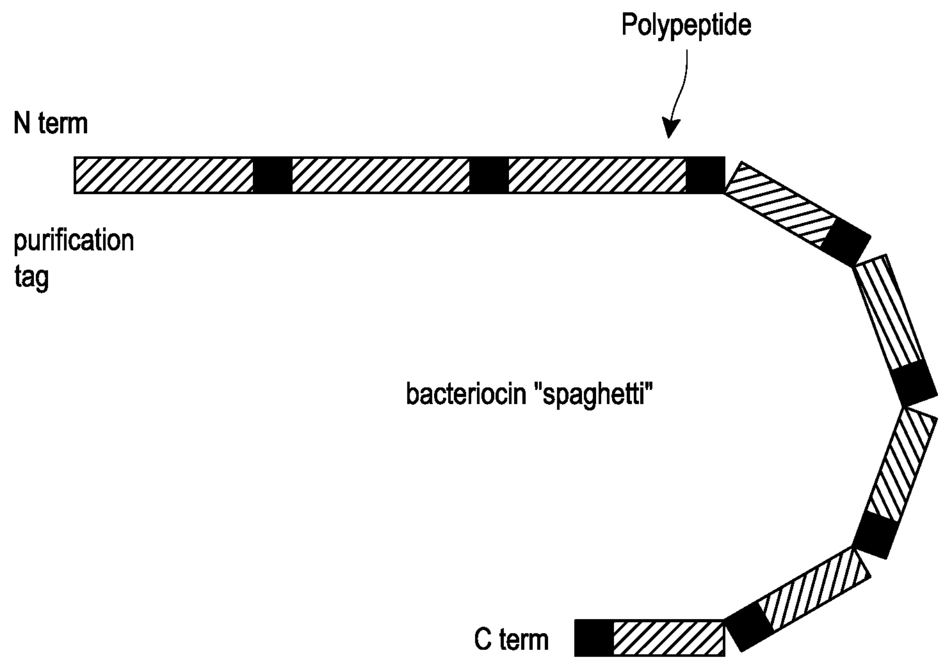

As used herein, "pro-polypeptide" has its customary and ordinary meaning as understood by one of skill in the art in view of this disclosure. It refers to a precursor polypeptide comprising, consisting essentially of, or consisting of at least two component peptides in a desired ratio (e.g., at least one bacteriocin and at least one signal molecule, or two or more bacteriocins, and optionally one or more other peptides disclosed herein (for example, a signaling peptide, a quorum sensing molecule such as a quorum sensing peptide, a signal transduction receptor ligand, a growth factor, a hormones, a cytokine, or a combination of two or more of any of the listed items), and at least one cleavage site separating the component peptides of the pro-polypeptide. An example pro-polypeptide in accordance with some embodiments is schematically illustrated in FIG. 2. The component peptides can be separated from each other by cleavage sites so that, upon cleavage, the component peptides are separated from each other and present in ratios that are determined by the number of copies of each component peptide in the pro-polypeptide (See FIG. 3). In some embodiments, one or more component peptides of the pro-polypeptide are in an inactive form, and become active upon cleavage from surrounding polypeptide sequences. Without being limited by theory, it is contemplated that in some embodiments, at least some, or in some embodiments all, of the bacteriocins are inactive when they are part of the pro-polypeptide so that, advantageously, the pro-polypeptide can be produced and/or modified by microbial cells that do not require immunity to those bacteriocins that are inactive. It is expressly contemplated that the pro-polylpeptides described herein can be used in conjunction with any of the methods and kits as described herein. Furthermore, it will be appreciated that for any pro-polypeptide described herein, the polynucleotide or polynucleotides (to the extent that there are multiple possible codons) will be readily appreciated based on the skilled artisan's understanding of the genetic code.

Figure 4A:
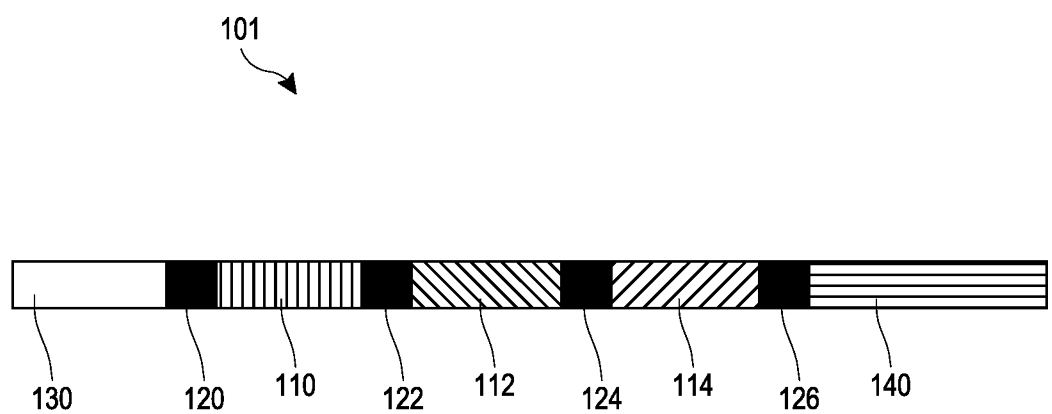
FIG. 4A is a schematic diagram of an embodiment of a pro-polypeptide comprising bacteriocins, cleavage sites, and a signal molecule in accordance with some embodiments herein.

FIG. 4A is a schematic diagram illustrating a pro-polypeptide 100 in accordance with some embodiments herein. The pro-polypeptide can comprise bacteriocins 110, 112, 114. The bacteriocins can be the same or different (e.g. all of the bacteriocins can be the same, or some bacteriocins can be the same while others are different, or all of the bacteriocins can be different from each other). The pro-polypeptide can further include one or more cleavage sites 120, 122, 124, and 126 disposed between the bacteriocins, and/or other polypeptides o the pro-polypeptide. In some embodiments, the pro-polypeptide further comprise a tag 130. In some embodiments, the pro-polypeptide further comprises a signal molecule 140 such as described herein, for example a quorum sensing molecule such as a quorum sensing peptide. In some embodiments, cleavage sites 120, 122, 124, and 126 are disposed between the bacteriocins, tag, and signal molecule. In some embodiments, the tag is useful for purifying the pro-polypeptide. In some embodiments, a cleavage site (e.g., 120, 122, 124, and 126) includes two or more consensus sites for an enzyme such as an endopeptidase. It is contemplated that in some embodiments, a cleavage site contains two or more cleavage consensus sequences (which can be the same or different), at least one of which is immediately downstream of the C-terminal of an upstream peptide and/or at least one of is immediately upstream of the N-terminal of a downstream polypeptide, so that the any vestiges can of the cleavage site can essentially eliminated or entirely eliminated of that peptide. In some embodiments, a "cleavage site" includes two or more consensus sequences, at least one of which is configured to be immediately upstream or downstream of a peptide (e.g., a bacteriocin) so as to remove any vestiges of that cleavage site from the peptide upon cleavage. In some embodiments, a "cleavage site" includes two consensus sequences, one of which is configured to be immediately downstream of an upstream peptide (e.g., a bacteriocin), and the other of which is immediately upstream of a downstream peptide (e.g. a bacteriocin) so as to remove any vestiges of that cleavage site from the C-terminal portion of the upstream peptide and from the N-terminal portion of the downstream peptide upon cleavage of both cleavage sites. Optionally, additional cleavage sites are positioned between these two cleavage sites.

Figure 4B:
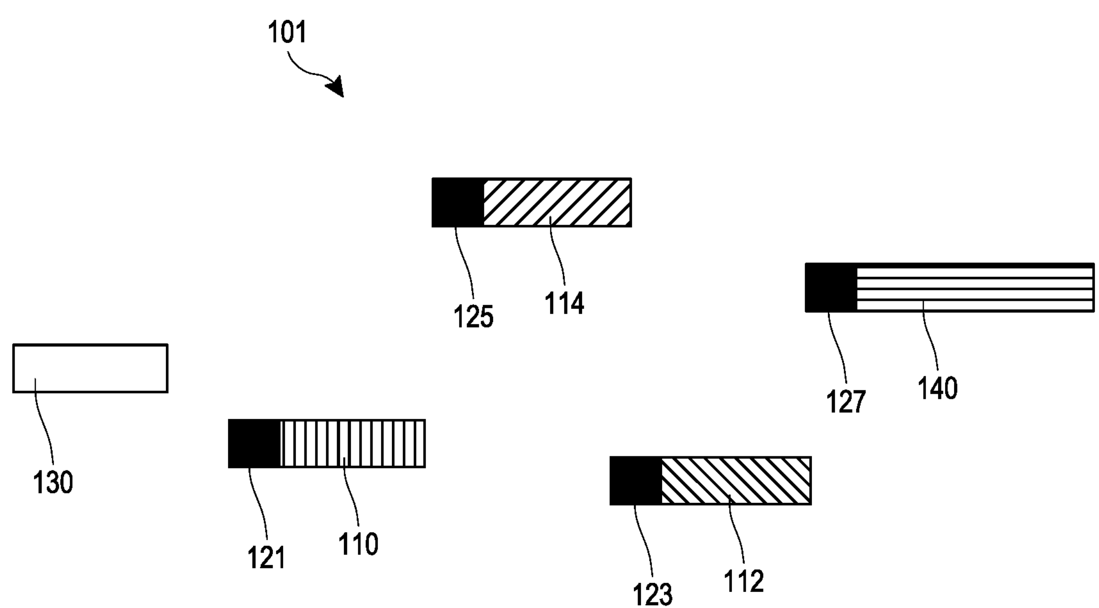
FIG. 4B is a schematic diagram of an embodiment of a composition comprising bacteriocins and a signal molecule following cleavage of a pro-polypeptide in accordance with some embodiments herein.

FIG. 4B is a schematic diagram illustrating a composition comprising bacteriocins 101 made from pro-polypeptide 100 in accordance with some embodiments herein. The composition can comprise bacteriocins 110, 112, 114. The bacteriocins can be the same or different (e.g. all of the bacteriocins can be the same, or some bacteriocins can be the same while others are different, or all of the bacteriocins can be different from each other). Optionally, some of the bacteriocins 110, 112, 114, can further comprise vestiges of cleavage sites, 121, 123, 125, 127. In some embodiments, the composition further comprises a tag 130, and/or a signal molecule 140 as described herein. Some of the bacteriocins 110, 112, 114, and/or the tag 130, and/or the signal molecule 140 can further comprise vestiges of cleavage sites, 121, 123, 125, 127. In some embodiments, following cleavage, a bacteriocin comprises no more than 0, 1, 2, 3, 4, 5, 6, 7, 8, 9, or 10, amino acids as a vestige of a cleavage site, including ranges between any two of the listed values. In some embodiments, bacteriocin does not comprise any vestiges od cleavage sites. In some embodiments, a bacteriocin comprises a vestige of a cleavage site on its N-terminal, on its C-terminal, or on its N- and C-termini. It is contemplated that in some embodiments, a signal molecule and/or tag also comprises vestiges as described herein. In some embodiments, a signal molecule and/or tag does not comprise any vestiges as described herein.

In some embodiments, a pro-polypeptide comprises, consists essentially of, or consists of at least one bacteriocin, at least one signal molecule, and one or more cleavage sites disposed between the bacteriocins and signal molecules, so that each bacteriocin or signal molecule can be separated from the rest of the pro-polypeptide by cleavage of the cleavage sites. In some embodiments, the bacteriocin(s) and signal molecule(s) are in a desired ratio.

In some embodiments, a pro-polypeptide comprises first component peptide comprising, consisting essentially of, or consisting of a bacteriocin, at least one additional component peptide (bacteriocin or signal molecule), and cleavage sites disposed between the component peptides. The pro-polypeptide can further comprise an affinity tag. In some embodiments, the affinity tag is separated from the bacteriocins (and/or other component peptides) of the pro-polypeptide by a cleavage site, so that after affinity purification of the pro-polypeptide, the affinity tag can be cleaved so as to remove it from the pro-polypeptides. In some embodiments, the pro-polypeptide comprises, consists essentially of, or consists of at least two bacteriocins, and optionally at least one signal molecule. In some embodiments, the isolated pro-polypeptide comprises three or more bacteriocins, for example, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocins, including ranges between any two of the listed values, for example, 3-10, 3-20, 3-30, 3-50, 5-10, 5-20, 5-30, 5-50, 7-10, 7-20, 7-30, 7-50, 10-20, 10-30, or 10-50 bacteriocins. In some embodiments, the pro-polypeptide comprises at least five bacteriocins.

It is further contemplated that the pro-polypeptide can include a signal molecule, which can facilitate communication to microbial cells, or to a host organism. Accordingly, in pro-polypeptides, methods, and nucleic acids of some embodiments, the pro-polypeptide further comprises a signal molecule. The signal molecule can be separated from other component peptides of the pro-polypeptide by a cleavage site. In some embodiments, the signal molecule comprises, consists essentially of, or consists of a quorum sensing molecule (e.g., a quorum sensing peptide), a cytokine, or a hormone as described herein. In some embodiments, a target cell is configured to produce additional gene products, for example bacteriocins, in response to the quorum sensing molecule. The target cell can be genetically engineered so that one or more bacteriocin polynucleotides are under the control of a transcription factor that responds to the quorum sensing molecule, so that, upon signaling by the quorum sensing molecule, the bacteriocin polynucleotides are transcribed, and the target cell produces additional bacteriocins.

In some embodiments, one or more cleavage sites are disposed in frame between any two adjacent component peptides (e.g., bacteriocins, signal molecules) of the pro-polypeptide. In some embodiments, one or more cleavage sites are disposed in frame between any two adjacent bacteriocins of the pro-polypeptide. It is noted that in pro-polypeptides, methods, and nucleic acids of some embodiments, component peptides (e.g., bacteriocins and/or signal molecules) or affinity tags positioned at or near the N- or C-terminus of a pro-polypeptide may be positioned near a cleavage site to separate them from the rest of the pro-polypeptide, but they are not flanked by cleavage sites on both sides. For example, for a bacteriocin on the N-terminus of a bacteriocin, there may be a cleavage site in the C-terminal direction from the bacteriocin, but no cleavage site on the N-terminal side of the bacteriocin. In some embodiments, for example, if a component peptide or affinity tag is near the N- or C-terminus of the pro-polypeptide, but there is additional N- or C-terminal sequence beyond the component peptide or affinity tag, the component peptide may comprise cleavage sites on both sides so as to facilitate removal of the additional N- or C-terminal sequence. In some embodiments, some additional N- or C-terminal sequences can remain on the component polypeptide.

It is noted that in some embodiments, the cleavage sites can comprise sequences targeted by a cleavage enzyme. In order to minimize or avoid cleavage of the bacteriocins or other component peptides (e.g., signal molecules) of the pro-polypeptide, it is contemplated that in some embodiments, the component peptides themselves do not contain cleavage sites for the cleavage enzyme(s) that target cleavage sites between the component peptides. As such, in some embodiments, the bacteriocins do not comprise cleavage sites for the cleavage enzyme or enzymes that target the cleavage sites between the bacteriocins. In some embodiments, two or more cleavage enzymes are used to target all of the cleavage sites between the component peptides of the pro-polypeptide, but the bacteriocins do not contain cleavage sites targeted by any of these cleavage enzymes. In some embodiments, at least one cleavage site is for a first cleavage enzyme, and another cleavage site is for a second cleavage enzyme different from the first cleavage enzyme, and the bacteriocins do not comprise a cleavage site for any of the first or second cleavage enzymes In some embodiments, the signal molecule(s) do not comprise the cleavage sites for the cleavage enzyme or enzymes that target the cleavage sites between the bacteriocins and signal molecules. It is noted that as in some embodiments, cleavage is performed after affinity purifying the pro-polypeptide. Consequently, it can be acceptable for an affinity tag itself to comprise one or more cleavage sites, as the affinity tag may be dispensable by the time cleavage is performed.

In some embodiments, the cleavage sites separating the component peptides of the pro-polypeptide are all targeted by the same cleavage enzyme so that a single enzyme can be used to cleave the pro-polypeptide into separate bacteriocins (and optionally, other peptides) in the desired ratios. In some embodiments, the cleavage sites separating the component peptides of the pro-polypeptide are collectively targeted by a combination of cleavage enzyme so that the number of cleavage enzymes that is smaller than the number of cleavage sites in the pro-polypeptide. In some embodiments, the cleavage sites separating the component peptides of the pro-polypeptide are collectively targeted by one, two, three, four, five, six, seven, eight, nine, or ten cleavage enzymes. In some embodiments, the cleavage sites comprise a chemical or pH-sensitive linker. As such, in some of these embodiments, the cleavage sites separating the component peptides of the pro-polypeptide are collectively cleaved by the same chemical and/or same pH conditions.

In some embodiments, the bacteriocins themselves comprise tags, for example affinity tags, signal sequences (for secretion, internalization, nuclear localization, etc.), or stability tags. Optionally, the tags can be cleavable from the pro-polypeptides. As such, the bacteriocin can comprise a cleavage site between itself and the tag. It can be useful for the tag to remain affixed to the bacteriocin after the component peptides are cleaved from the pro-polypeptide. As such, in some embodiments, the cleavage site between the bacteriocin and the tag can be targeted by different cleavage enzymes (and/or cleaved under different chemical or pH conditions) than the cleavage sites separating the component peptides from each other.

In some embodiments, the pro-polypeptide further comprises a post-translational or co-translation modification, for example, glycosylation, acetylation, methylation, PEGYlation, SUMOylation, ubiquitination, or two or more of any of these.

In some embodiments, the pro-polypeptide comprises a quantity of two or more different component peptides (e.g., bacteriocins and/or signal molecules) in a desired ratio, or portion of a desired ratio. For example, the ratio of a first bacteriocin to a second (different) bacteriocin, or to a signal molecule can be about 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10. In some embodiments, the pro-polypeptide comprises a quantity of two or more different bacteriocins in a desired ratio, or portion of a desired ratio. In some embodiments, the desired ratio of bacteriocins is selected to target an undesired microbial organism or population of undesired microbial organisms. In some embodiments, the desired ratio of bacteriocins is selected to balance a population of a microbiome of an animal, a human organ, a plant root, and/or soil. In some embodiments, the bacteriocins and/or signal molecules are present in a portion of a desired ratio, and the desired ratio can be achieved by adding an additional bacteriocin and/or signal molecule in a suitable ratio (for example, if the products of two different pro-polypeptides are combined, together, they can yield the desired ratio of component polypeptides such as bacteriocins and/or signal molecules).

In some embodiments, the pro-polypeptide has a length of no more than 20,000 amino acids, for example, no more than 20,000, 15,000, 10,000, 9000, 8000, 7000, 6000, 5000, 4000, 3000, 2000, 1000, 900, 800, 700, 600, 500, 400, 300, 200, or 100 amino acids, including between any two of the listed values, for example 100-20,000; 100-10,000; 100-5000; 100-2000; 100-1000; 500-20,000; 500-10,000; 500-5000; 500-2000; 500-1000; 1000-20,000; 1000-10,000; 1000-5000; or 1000-2000 amino acids. In some embodiments, the pro-polypeptide has a length of no more than 5000 amino acids. In some embodiments, the pro-polypeptide has a length of no more than 2000 amino acids.

Nucleic Acids

Methods, kits, microbial cells, and/or nucleic acids of some embodiments herein include a nucleic acid encoding a pro-polypeptide. In some embodiments, the nucleic acid encodes a bacteriocin and a signal molecule in a single reading frame, and encodes a cleavage site coding sequences disposed between the bacteriocin and signal molecule coding sequences. In some embodiments, an isolated nucleic acid comprises two bacteriocin coding sequences in a single reading frame. The isolated nucleic acid can further comprise cleavage site coding sequences disposed between the bacteriocin coding sequences and in the single reading frame. In methods, nucleic acids, microbial cells, and/or kits of some embodiments herein, a nucleic acid encodes any pro-polypeptide described herein. In some embodiments, a kit comprises a nucleic acid composing one or more pro-polypeptides as described herein. In some embodiments, the kit further comprises a microbial cell capable of expression the pro-polypeptide.

As noted herein, for nucleic acids of some embodiments, it can be advantageous for the bacteriocins (or other polypeptides) encoded by the nucleic acids to remain intact after cleavage. As such, in some embodiments, the nucleic acid encodes cleavage sites for a cleavage enzyme, and its bacteriocin and/or signal molecule coding sequences encode bacteriocins and/or signal molecules (respectively) that do not comprise cleavage sites for the cleavage enzyme. In some embodiments, the cleavage site coding sequences of the nucleic acid encode cleavage sites for a cleavage enzyme, and the bacteriocin coding sequences encode bacteriocins that do not comprise cleavage sites for the cleavage enzyme.

In some embodiments, the nucleic acid comprises three or more bacteriocin coding sequences in the single reading frame, for example 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocin coding sequences, including ranges between any two of the listed values, for example, 3-10, 3-20, 3-30, 3-50, 5-10, 5-20, 5-30, 5-50, 7-10, 7-20, 7-30, 7-50, 10-20, 10-30, or 10-50 bacteriocin coding sequences. In some embodiments, the nucleic acid comprises at least three bacteriocin sequences in the single reading frame. In some embodiments, the nucleic acid comprises at least five bacteriocin sequences in the single reading frame. In some embodiments, at least two of the bacteriocin coding sequences encode different bacteriocins from each other.

In some embodiments, one or more cleavage site coding sequences are disposed in frame between any two adjacent bacteriocin coding sequences of the isolated nucleic acid. As noted herein, it can be advantageous for a single cleavage enzyme to be able to separate multiple, or all, of the component peptides of a pro-polypeptide. Accordingly, in some embodiments, each of the bacteriocin coding sequences (and, if present, signal molecule coding sequence(s)) are separated from each other by in-frame cleavage site coding sequences for the same enzyme. As such, upon translation of the nucleic acid, the resultant pro-polypeptide can be cleaved into its component peptides by a single enzyme.

In some embodiments, a cleavage site coding sequence encodes a cleavage site for a first cleavage enzyme, and another cleavage site coding sequence encodes another cleavage site for a different cleavage enzyme. In some embodiment, the bacteriocins encoded by the bacteriocin coding sequences do not comprise a cleavage site for any of the first or second cleavage enzymes. In some embodiment, no bacteriocins encoded by the isolated nucleic acids comprises a cleavage site for any of the cleavage enzymes that cleave the interspersed cleavage sites.

In some embodiments, all of the bacteriocin coding sequences (and, if present, signal molecule coding sequence(s)) are separated from each other by in-frame cleavage site coding sequences, which are collective cleaved by a combination of two, three, four, five, six, seven, eight, nine, or ten cleavage enzymes. As such, upon translation of the nucleic acid, that combination of cleavage enzymes can be used to cleave the pro-polypeptide into its component peptides.

In some embodiments, the cleavage site coding sequence encodes a cleavage site for a cleavage enzyme as described herein, for example in Table 4. In some embodiments the cleavage site coding sequence encodes a cleavage site that is chemically and/or pH-sensitive as described herein.

In some embodiments, the component peptide (e.g., bacteriocin and/or signal molecule) coding sequences of the isolated nucleic acid are present in a desired ratio, or portion of a desired ratio. In some embodiments, three of more bacteriocin sequences are present in a desired ratio or portion of a desired ratio. In some embodiments, the desired ratio is selected to target an undesired microbial organism or population of undesired microbial organisms. In some embodiments, the desired ratio of bacteriocins is selected to balance a population of a microbiome of an animal, a human organ, or a plant root and/or soil.

In some embodiments, the isolated nucleic acid further comprises a coding sequence for a signal molecule in the single reading frame. A cleavage site coding sequences can be disposed between the coding sequence for signal molecule and an adjacent bacteriocin coding sequence or sequences. In some embodiments, the signal molecule comprises a quorum sensing molecule, a signal transduction receptor ligand, a growth factor, a hormone, or a cytokine. In some embodiments, the signal molecule can be wild-type, mutant, or synthetic.

Microbial Cells for Making Bacteriocins

Methods, kits, and microbial cells of some embodiments comprise a microbial cell comprising an isolated nucleic acid as described herein. Such microbial cells can be useful for producing pro-polypeptides comprising bacteriocins in desired ratios as described herein. The microbial cell can comprise a promoter as described herein. The promoter can be operably linked to the isolated nucleic acid. Thus, the microbial cell can be configured to transcribe the isolated nucleic acid and translate it into a pro-polypeptide comprising bacteriocins. As noted herein, the bacteriocins of the pro-polypeptide can be inactive while they are part of the pro-polypeptide. Accordingly in some embodiments, the isolated microbial cell does not produce a functional immunity modulator for a bacteriocin encoded by the isolated nucleic acid. For example, the microbial cell can lack a coding sequence for the immunity modulator, or if it does comprise coding sequence for the immunity modulator, the coding sequence can be transcriptionally silent (e.g. due to lack of a promoter), and/or the coding sequence can be mutated so that any immunity modulator produced by the coding sequence is nonfunctional. In some embodiments, the promoter operationally linked to the nucleic acid comprises, consists essentially of, or consists of any of the promoters of Tables 3.1-3.11.

Methods of Making Bacteriocins

Figure 8:
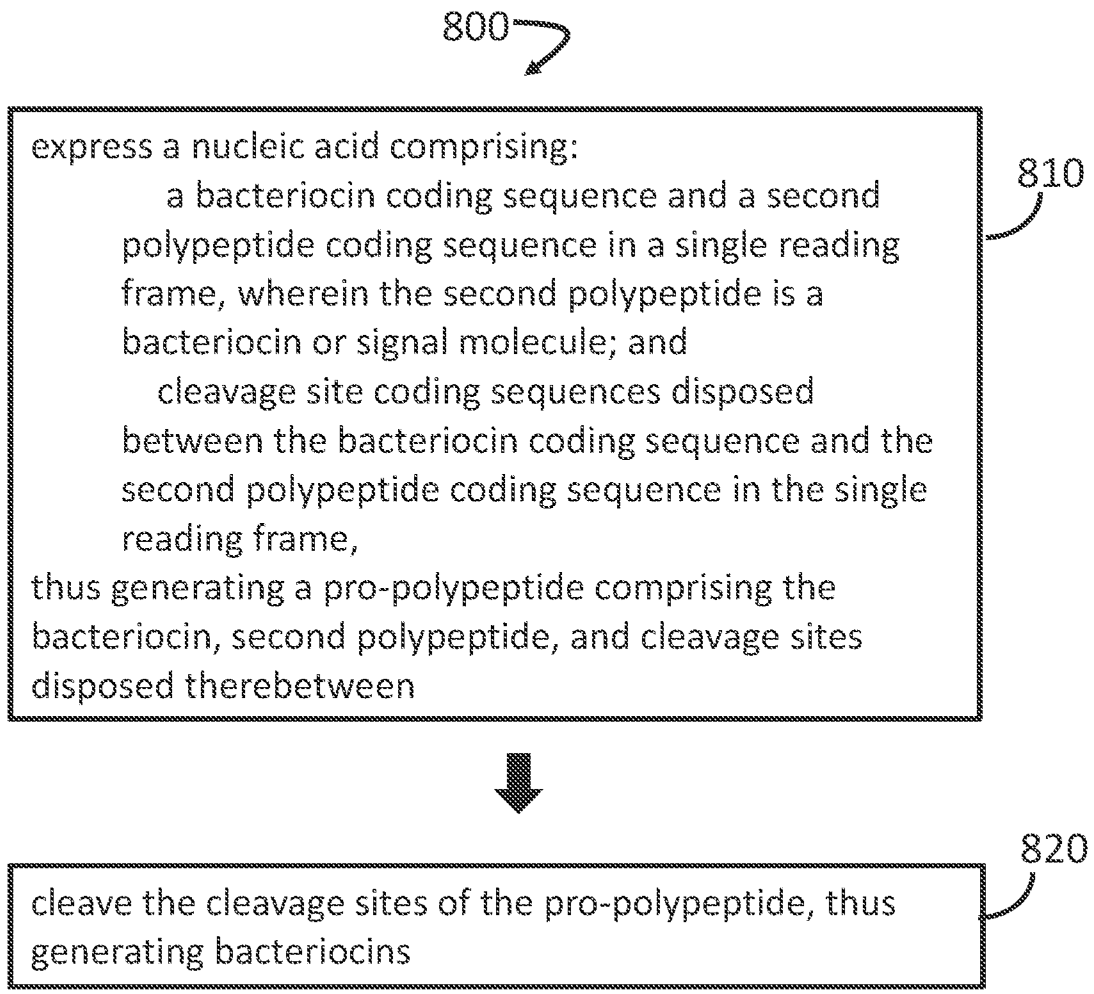
FIG. 8 is a flow diagram illustrating a method for making antimicrobial peptides and/or bacteriocins according to some embodiments herein.

Some embodiments include methods of making bacteriocins. The methods can be useful for making compositions comprising bacteriocins (and optionally, other molecules such as signal molecules) in a desired ratio. In some embodiments, a method of making bacteriocins comprises expressing a nucleic acid. The nucleic acid can comprise two bacteriocin coding sequences in a single reading frame, or a bacteriocin and a signal molecule coding sequence in a single reading frame (see, for example, FIG. 8). The nucleic acid can further comprise cleavage site coding sequences disposed between the bacteriocin coding sequences (or between the bacteriocin and signal molecule coding sequences) and in the single reading frame. The nucleic acid can be expressed to generate a pro-polypeptide comprising the bacteriocins and cleavage sites disposed therebetween. In some embodiments, nucleic acids encoding bacteriocins (and/or signal molecules) as described herein are expressed by a gene expression system to as to produce pro-polypeptides as described herein.

In some embodiments, for example, when producing bacteriocins for a semi-controlled environment as in biopharma production, the pro-polypeptide comprises a bacteriocin coding sequence, a signal molecule coding sequence, and a cleavage site disposed between the bacteriocin and signal molecule coding sequences. It is contemplated that such a pro-polypeptide can be used to produce a composition comprising the bacteriocin and signal molecule in a desired ratio, which can be useful for inhibiting genetically drifting microbial organisms (via the bacteriocin; for example if the immunity of the target organisms is tied to their maintenance of a certain genetic state; this approach is described in additional detail in U.S. Pat. No. 9,333,227). Additionally, the signal molecule can promote the growth, proliferation, or production of a desired product by producing cells in environment (for example, genetically engineered microbial cells, or mammalian cell culture such as CHO or BHK cells).

In some embodiments, the method further comprises cleaving the cleavage site, thus separating the bacteriocins (and/or signal molecules) from each other. Upon separation of the bacteriocins (and/or signal molecules), a composition comprising bacteriocins (or combination of bacteriocins and signal molecules) is thus produced. In some embodiments, the cleavage sites are cleaved by a cleavage enzyme or combination of cleavage enzymes as described herein, for example in Table 4. In some embodiments, the cleavage sites are cleaved by exposing a peptide comprising a pH-sensitive or chemically-sensitive linker to pH or chemical conditions that induce cleavage. In some embodiments, the pro-polypeptide is stored for period of time before cleaving, for example, at least 1 day, 2 days, 3 days, 4 days, 5 days, 6 days, 1 week, 2 weeks, 3 weeks, 4 weeks, 1 month, 2 months, or 3 three months, including ranges between any two of the listed values.

In some embodiments, bacteriocins are inactive when they are part of a pro-polypeptide. Accordingly, in some embodiments, the microbial cell does not produce a functional immunity modulator for at least one of the bacteriocins, for example, the microbial cell can lack a coding sequence for the immunity modulator, or if it does comprise coding sequence for the immunity modulator, the coding sequence can be transcriptionally silent (e.g. due to lack of a promoter), and/or the coding sequence can be mutated so that any immunity modulator produced by the coding sequence is nonfunctional. In some embodiments, the microbial cell comprises *E. coli* or *B. subtilis*.

In some embodiments, at least one of the bacteriocins is inactive when it is part of the pro-polypeptide.

In some embodiments, the nucleic acid is expressed in vitro. Cell-free expression systems can be used to transcribe and/or translate nucleic acids in vitro. In some embodiments, the in vitro expression system comprises, consists of, or consists essentially of cell extracts. In some embodiments, the in vitro expression system comprises an RNA polymerase, ribosomes, tRNAs (and the corresponding amino acids), an energy source, and enzymatic cofactors. The in vitro expression system can further comprise enzymes for co- or post-translational modification, and/or cellular components that mediate protein folding such as heat shock proteins.

In some embodiments, the method further comprises isolating the pro-polypeptide prior to the cleaving. The pro-polypeptide can be isolated from the microbial cell, or from the in vitro expression system as described herein. In some embodiments, isolation comprises purifying the pro-polypeptide. In some embodiments, isolating comprises affinity purifying the pro-polypeptide. The affinity purification can be performed using an affinity tag as described herein. The nucleic acid can encode an affinity tag on the pro-polypeptide. The affinity tag can be bound by a suitable binding agent specific for the affinity tag (e.g., an anti-myc antibody for a myc tag, or GSH-coated beads for the GST, or nickel or cobalt for a His tag). The binding agent can be immobilized on a solid phase, so that, upon binding of the affinity tag, the pro-polypeptide will be immobilized on the solid phase. The solid phase can be removed from the microbial cell and/or in vitro expression system. Optionally, the solid phase can be washed. The affinity tagged pro-polypeptide can then be released from the solid phase. For example, the pro-polypeptide can be isolated by immuno-precipitation, affinity chromatography, and the like.

In some embodiments, the nucleic acid comprises at least three bacteriocin coding sequences in a single reading frame, for example at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocins, including ranges between any two of the listed values, for example, about 3-10, 3-20, 3-30, 3-50, 5-10, 5-20, 5-30, 5-50, 7-10, 7-20, 7-30, 7-50, 10-20, 10-30, or 10-50 bacteriocins. As such, the nucleic acid can produce a pro-polypeptide comprising the indicated number of bacteriocins.

In some embodiments, at least two of the bacteriocins are different from each other. In some embodiments, two or more of the bacteriocins are the same. In some embodiments, at least two of the bacteriocins are different from each other, and at least two of the bacteriocins are the same.

Upon cleavage of the pro-polypeptide, a composition comprising bacteriocins can be produced. In some embodiments, the composition comprises a desired ratio of bacteriocins. In some embodiments, at least a portion the desired ratio is achieved by a ratio of bacteriocin coding sequences in the single reading frame of the nucleic acid. Without being limited by theory, it is contemplated that in some embodiments, the nucleic acid encodes desired relative quantities of two or more different bacteriocins coding sequences in cis, the corresponding pro-polypeptide will also have these ratios of bacteriocins. For example, if the nucleic acid comprises two coding sequences for "bacteriocin A," and three coding sequences of "bacteriocin B," each separated by cleavage sites, the resultant pro-polypeptide will comprise a ratio of bacteriocin A to bacteriocin B of 2:3. Upon cleavage, the solution will comprise the bacteriocins in these ratios. It is noted that in some embodiments, additional proteins or polypeptides encoded by the nucleic acid are also produced in desired ratios, for example signal molecules. As such, a solution can be produced comprising bacteriocins and signal molecules in a predetermined ratio or range of ratios. In some embodiments, the predetermined ratio is achieved by a ratio of bacteriocin coding sequences in the single reading frame of the nucleic acid.

In some embodiments, the nucleic acid encodes bacteriocins (and optionally additional peptides such as signal molecules) in a portion of a desired ratio. Additional components can be added to achieve the final desired ratio. For example, a second, different pro-polypeptide can comprise bacteriocins and/or signal molecules in a second ratio. The two different polypeptides can together provide the final desired ratio of bacteriocins (and optionally other peptides, such as signal molecules) of interest. As such, in some embodiments, the desired ratio is further achieved by a second nucleic acid comprising a ratio of bacteriocin coding sequences and further comprising cleavage sites between the bacteriocin coding sequences.

A desired ratio can be selected for a number of applications. In some embodiments, a desired ratio of bacteriocins is selected to target an undesired microbial organism or population of undesired microbial organisms. For example, if an environment such as a culture medium, feedstock, fermenter, bioreactor, or microbiome contains, or is at risk of containing a population of undesired microbial organisms, a ratio of bacteriocins can be selected to target those undesired microbial organisms. In some embodiments, the desired ratio of bacteriocins is selected to balance a population of a microbiome of an animal (for example a horse, cow, sheep, pig, donkey, dog, cat, or non-human primate), a human organ (e.g., skin or a gut), or a plant root and/or soil microbiome, or to preserve a product such as a food product (human or non-human animal), pharmaceutical, or cosmetic product. In some embodiments, the desired ratio comprises a ratio between two bacteriocins in a pro-polypeptide (e.g., a first to second bacteriocin, first to third, second to third, or third to fourth, or fourth to fifth) of about 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, in which the first (or second, or third, or fourth) bacteriocin is different from the second (or third, or fourth, or fifth) bacteriocin. It is noted that different pairs of bacteriocins in the pro-polypeptide can have different ratios to each other. Therefore, it is contemplated that the ratios three or more bacteriocins to each other can be ascertained by the individual (pair-wise) ratios of the bacteriocins to each other. For example, a first and second bacteriocin can have a ratio of 1:2, and a second and third bacteriocin can have a ratio of 2:5, so that the ratio of the first to the second to the third bacteriocin is 1:2:5, respectively. In some embodiments, the desired ratio comprises a ratio of a first bacteriocin to a second bacteriocin to a third bacteriocin of about 1:1:2, 1:2:2, 1:1:3, 1:2:3, 1:3:3, 2:2:3, or 2:3:3.

As noted herein, it can be advantageous for the bacteriocins to remain intact following cleavage of the pro-polypeptide. As such, in some embodiments, the bacteriocins of the pro-polypeptide do not contain any of the cleavage sites that separate the bacteriocins (or optional other polypeptides such as signal molecules). Upon cleavage of the cleavage sites, the bacteriocins can remain intact. In some embodiments, the cleavage sites are for a single cleavage enzyme, and the cleavage enzyme does not cleave within the bacteriocins. In some embodiments, at least one cleavage site is for a first cleavage enzyme, and another cleavage site is for a second cleavage enzyme, and neither the first nor the second cleavage enzyme cleaves within the bacteriocins.

In some embodiments, the composition produced by the method comprises a signal molecule as described herein. The nucleic acid can encode the signal molecule in the same reading frame as the other component(s) of the pro-polypeptide (e.g., the bacteriocins). A cleavage site sequence disposed between the signal molecule and the bacteriocin coding sequence or sequences. As such, upon cleavage of the cleavage sites, the signal molecule can be separate from the bacteriocin. In some embodiments, the signal molecule comprises, consists essentially of, or consists of a quorum sensing molecule, signal transduction receptor ligand, growth factor, hormones, or cytokine, or a combination of two or more of these. In some embodiments, the signal molecule is wild-type, mutant, or synthetic.

In some embodiments, the pro-polypeptide has a length of no more than 20,000 amino acids, for example, no more than 20,000, 15,000, 10,000, 9000, 8000, 7000, 6000, 5000, 4000, 3000, 2000, 1000, 900, 800, 700, 600, 500, 400, 300, 200, or 100 amino acids, including between any two of the listed values, for example 100-20,000; 100-10,000; 100-5000; 100-2000; 100-1000; 500-20,000; 500-10,000; 500-

5000; 500-2000; 500-1000; 1000-20,000; 1000-10,000; 1000-5000; or 1000-2000 amino acids. In some embodiments, the pro-polypeptide has a length of no more than 5000 amino acids. In some embodiments, the pro-polypeptide has a length of no more than 2000 amino acids.

As noted herein, the ratios of bacteriocins (and other polypeptides such as signal molecules) can be further tuned by using two or more different pro-polypeptides to obtain particular ratios and/or combinations of molecules (e.g., bacteriocins, signal molecules). In some embodiments, the method comprises expressing a second nucleic acid encoding a second pro-polypeptide comprising two bacteriocins and cleavage sites disposed between the bacteriocins. The second pro-polypeptide can be different from the first pro-polypeptide, so cleavage of the second pro-polypeptide produces a different ratio of bacteriocins and/or signal molecules than the first pro-polypeptide once it has been cleaved.

In some embodiments, the method further comprises chemically modifying the bacteriocins. Example chemical modifications include, but are not limited to glycosylation, acetylation, methylation, PEGYlation, SUMOylation, ubiquitination, or two or more of any of these. In some embodiments, the bacteriocins are chemically modified co-translationally. In some embodiments, the bacteriocins are chemically modified post-translationally. For example, the microbial cell can comprise, or can be genetically engineered to comprise enzymes for co-translational modification or post-translational modification. For example, the in vitro expression system can comprise enzymes for co-translational or post-translational modification. For example, the in vitro expression system can comprise enzymes for post-translational modification, and/or, following isolation of the pro-polypeptide from the expression system (in vitro or microbial cell), the pro-polypeptide can be contacted with enzymes that produce the desired post-translational modification. In some embodiments, bacteriocins are chemically modified after the pro-polypeptide has been cleaved.

Figure 3:
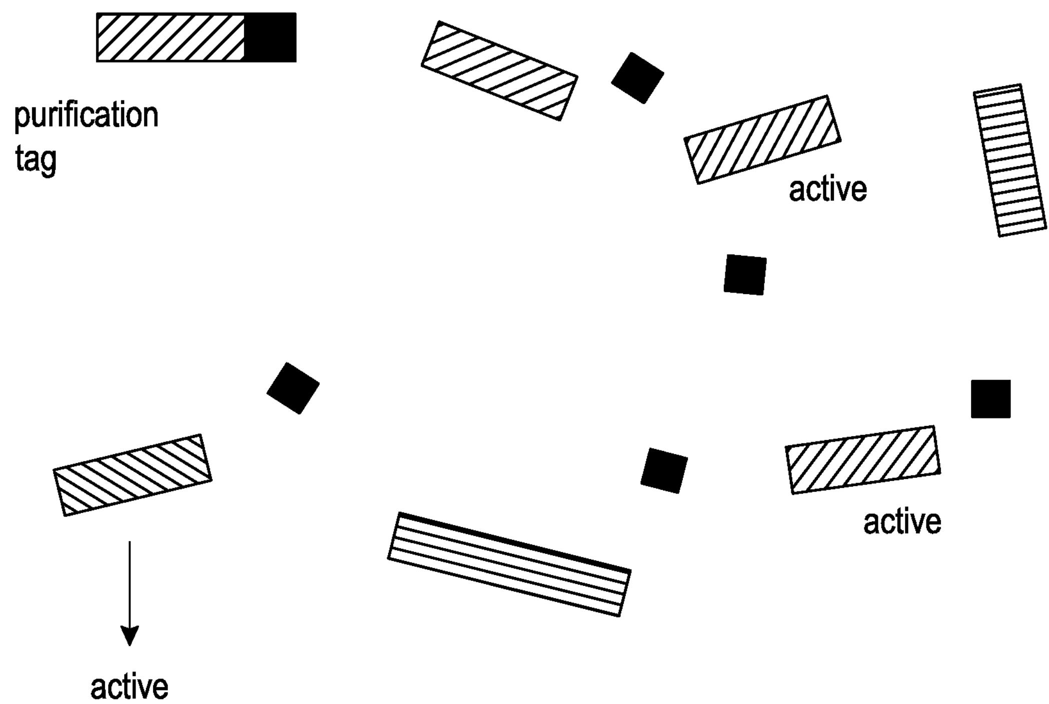
FIG. 3 is a schematic diagram of an embodiment of a composition comprising bacteriocins and cleavage sites in accordance with some embodiments herein.

Some embodiment include a composition comprising bacteriocins, which can be made according to methods of some embodiments herein is shown in FIG. 3. In some embodiments, the composition is produced by the cleavage of a pro-polypeptide as described herein. It is contemplated that the bacteriocins can be released by cleavage of the pro-polypeptide, for example via an endopeptidase. The result can be a mixture with the correct molecular blend according to a predetermined and/or desired result in terms of bacterial killing. In some embodiments, one strain of host cell can produce a multi-bacteriocin mixture in one fermentation. It is contemplated that there can be no toxic effect during production (and thus, no need of immunity in the host cell). Optionally, purification of the pro-polypeptide (and/or "cleaved" bacteriocins) can be performed purification via a tag. Optionally molecular adjustment between bacteriocins can be performed.

Compositions Comprising Bacteriocins

In some embodiments, compositions comprising bacteriocins in desired ratios are provided. Optionally, the composition can further comprise additional polypeptides, for example signal molecules, in desired ratios with the bacteriocins and/or each other.

In some embodiments, a composition comprises two or more bacteriocins in a ratio selected to target a microbial cell or populations of microbial cells. Each of the bacteriocins can comprise, at its N-terminus, C-terminus, or N-terminus and C-terminus, a portion of a cleavage sequence that has been cleaved. It is contemplated that when a pro-polypeptide comprising multiple bacteriocins as described herein is cleaved at its cleavage sites, at least some of the bacteriocins will comprise the vestiges of the cleavage site at their N- and/or C-termini, depending on the cleavage site. As such, it is contemplated that not only will the bacteriocins of the composition be in desired ratios with a very high degree of accuracy, but further, the bacteriocins will be structurally distinct in that many or all of the bacteriocins will comprise N- and/or C-terminal vestiges of cleavage sites, for example partial cleavage sites. In some embodiments, the portions of cleavage sequences at the N-, C-, or N- and C-termini of the bacteriocins are for cleavage sites of the same cleavage enzyme. In some embodiments, the portions of cleavage sequences at the N-, C-, or N- and C-termini of the bacteriocins are for cleavage sites of two or more different cleavage enzymes.

In some embodiments, some or all of the bacteriocins of the composition further comprise a tag. In some embodiments, the tag is selected from the group consisting of affinity tags, a signal sequence, or a stability tag. In some embodiments, a cleavage site is disposed between the tag and the bacteriocin.

In some embodiments, the composition further comprises a signal molecule as described herein. The signal molecule can also be in the desired ratio. The signal molecule can also comprise vestiges of cleavage sites at its N- and/or C-termini.

In some embodiments, the ratio of bacteriocins in the composition is selected to target an undesired microbial organism or population of undesired microbial organisms in an environment, such as an industrial manufacturing environment, a fermenter, a food, drug, or cosmetic manufacturing environment, or a product to be preserved (e.g., a food, drug, or cosmetic product). In some embodiments, the ratio of bacteriocins is selected to balance a population of a microbiome of an animal, a human organ, or a plant root and/or soil, or to preserve a product (such as a food, drug, or cosmetic product). In some embodiments, the composition is formulated for topical or oral administration to a human subject.

Coding Substrates

In accordance with methods and microfluidic devices and systems of some embodiments described herein, coding substrates are provided. A coding substrate can comprise a nucleic acid encoding a protein or peptide such as an antimicrobial peptide and/or bacteriocin (and, optionally, an auxiliary protein) as described herein. The coding substrates of methods and microfluidic devices of some embodiments encode antimicrobial peptides and/or bacteriocins, and can be used to produce a specified mixture of antimicrobial peptides and/or bacteriocins. The coding substrates can be discrete, and capable of being placed in fluidic isolation from each other (which may be referred to herein as "discrete" coding substrates). For example, in a method or microfluidic device of some embodiments, several discrete coding substrates may be used to produce a specified mixture of antimicrobial peptides and/or bacteriocins by way of in vitro transcription/translation, in which (i) only discrete coding substrates encoding the antimicrobial peptides and/or bacteriocins of the specified mixture are contacted and incubated with an in vitro transcription/translation solution, (ii) only coding substrates that have produced antimicrobial peptides and/or bacteriocins of the specified mixture are placed in fluidic communication with a fluidic reservoir where the specified mixture is formed, or (i) and (ii). For example, valves as described herein can control the flow of in vitro transcription/translation solution to, and/or antimicrobial peptides and/or bacteriocins from discrete coding substrates (or chambers housing the discrete coding substrates). In methods and microfluidic devices of some embodiments, different coding substrates, encoding different antimicrobial peptides and/or bacteriocins from each other may be housed in separate chambers (of a microfluidic device as described herein), each of which may be placed in fluid communication with an in vitro transcription/translation solution by a valve. As such, in methods and microfluidic devices some embodiments, the discrete coding substrates of a microfluidic device are comprised within separate chambers. In some embodiments, the discrete coding substrates comprise, consist essentially of, or consist of beads. By way of example, beads encoding the antimicrobial peptides and/or bacteriocins of the specified mixture (but not beads encoding other antimicrobial peptides and/or bacteriocins) can be placed in fluid communication with an in vitro transcription/translation solution, either mechanically, or through the opening and/or closing of valve to direct fluids to the appropriate beads. In some embodiments, different discrete coding substrates encode different antimicrobial peptides and/or bacteriocins from each other. Some embodiments comprise a system comprising a processor. The system can be configured to be placed in fluid and/or data communication with a microfluidic device as described herein. Optionally, the system comprises a pump, and/or reservoirs of reagents (e.g., in vitro transcription/translation solution) which can be placed in fluid communication with the microfluidic device. In some embodiments, the microfluidic device is formatted as a cartridge for insertion into the system. In some embodiments, the coding substrates encode bacteriocins, but not antimicrobial peptides. In some embodiments, the coding substrates encode antimicrobial peptides, but not bacteriocins. In some embodiments, the coding substrates encode a combination of antimicrobial peptides and bacteriocins.

In accordance with the methods and microfluidic devices and systems of some embodiments described herein, the coding substrates are discrete coding substrates. In some embodiments, a discrete coding substrate is comprised within a chamber. Accordingly, in some embodiments, multiple discrete coding substrates are each comprised within a separate chamber. In some embodiments, two or more discrete coding substrates are comprised within the same chamber, so that a single chamber contains two or more discrete coding substrates, and thus can produce a mixture and/or stoichiometry of antimicrobial peptides and/or bacteriocins. In some embodiments, a chamber comprises at least 1, 2, 3, 4, 5, 6, 7, 8, 9, 10, 20, 30, 40, 50, 60, 70, 80, 90, 100, 100, 1000, 5000, 10,000, 500,000, 1,000,000, 10,000,000, or 100,000,000 discrete coding substrates, including ranges between any two of the listed values, for example 1-3, 1-5, 1-10, 1-50, 2-3, 2-5, 2-10, 2-20, 2-50, 2-100, 10-50, 50-100, 50-500, 50-1000, 100-500, 100-1000, 500-1000, 1000-5000, 5000-10,000, 10,000-50,000, 50,000-100,000, 100,000-500,000, 500,000-1,000,000, 1,000,000-10,000,000, 10,000,000-100,000,000, or 100,000,000-1,000,000,000 discrete coding substrates.

In accordance with the methods and microfluidic devices and systems of some embodiments described herein, the chambers of the microfluidic device comprising the discrete coding substrates are micro-scale chambers. For example, the chambers may each have a volume of no more than 1, 5, 10, 20, 50, 100, 250 or 500 microliters, including ranges between any two of the listed values, for example, 1-5 microliters, 1-10 microliters, 1-20 microliters, 1-50 microliters, 1-100 microliters, 1-500 microliters, 5-10 microliters, 5-20 microliters, 5-50 microliters, 5-100 microliters, 5-500 microliters, 10-20 microliters, 10-50 microliters, 10-100 microliters, 10-500 microliters, 50-100 microliters, or 50-500 microliters. In some embodiments, the chambers comprise, consist essentially of, or consist of a material or product selected from the group consisting of a well, nanowell, membrane, matrix, plastic, metal, glass, polymer, polysaccharide, and paramagnetic compound, or a combination of two or more of these. In accordance with the methods and microfluidic devices of some embodiments described herein, the coding substrates comprise, consist essentially of, or consist of a material or product selected from the group consisting of a chip, bead, nanoparticle, well, nanowell, membrane, matrix, plastic, metal, glass, polymer, polysaccharide, and paramagnetic compound, or a combination of two or more of these. Some embodiments include a microfluidic device comprising separate microchambers, each comprising one or more beads, each of which comprises, consstins essentially of, or consists of a coding substrate. The beads can each comprise nucleic acids encoding antimicrobial peptides and/or bacteriocins. In some embodiments, the device includes 1, 2, 3, 4, 5, 6, 7, 8, 9, 10, 10-50, 50-100, 100-500, 500-1000 or 1000-5000 chambers, or any number therebetween.

In accordance with the methods and microfluidic devices and systems of some embodiments described herein, the coding substrates comprise nucleic acids immobilized thereon. For example, the nucleic acids can be covalently bound to the coding substrate, hybridized to the coding substrate, and/or associated with the coding substrate via one or more force, such as an electrostatic force. In some embodiments, the nucleic acid comprises DNA. In some embodiments, the nucleic acid comprises RNA.

In some embodiments, a coding substrate further encodes or comprises an auxiliary protein, such as a protein for stabilization of antimicrobial peptides and/or bacteriocins, a protein with anti-protease activity (for example a serpentin), a protein for stabilization of antimicrobial peptides and/or bacteriocins, a protein for destruction of a microbial biofilm (for example a biofilm breaker such as Dispersin B), a pheromone protein, a protein that attracts a non-pathogenic microbial organism, or a protein that enhances growth or reproduction of the non-pathogenic microbial organism in a microbiome of a subject. Without being limited by theory it is contemplated that such an auxiliary protein can enhance expression and/or activity of an antimicrobial peptide and/or bacteriocin, for example, by stabilizing the antimicrobial peptide and/or bacteriocinin a particular environment, by inhibiting a protease from a particular environment that would degrade an antimicrobial peptide and/or bacteriocin, and/or by degrading fibrils of a microbial biofilm to enhance bacterial contact by the antimicrobial peptide and/or bacteriocin. In some embodiments, a discrete coding substrate encodes an antimicrobial peptide and/or bacteriocinin addition to an auxiliary protein. In some embodiments, a first coding substrate encodes an auxiliary protein and a second coding substrate encodes an antimicrobial peptide and/or bacteriocin. In some embodiments, the auxiliary proteins are selected with the antimicrobial peptides and/or bacteriocins. For example, if a mixture of antimicrobial peptides and/or bacteriocins is for an environment comprising a particular protease, for example trypsin, a coding substrate encoding an inhibitor of that protease can be selected along with coding substrates encoding the mixture of antimicrobial peptides and/or bacteriocins. In some embodiments, a coding substrate encodes an auxiliary protein with anti-protease activity. In some embodiments, the auxiliary protein with anti-protease is a protein for stabilization of antimicrobial peptides and/or bacteriocins. In some embodiments, one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the auxiliary protein is a pheromone peptide that induces an antimicrobial peptide and/or bacteriocin of a desired microbial organism such as a non-pathogenic microbial organism (although in some embodiments, a pathogenic microbial organism is a desired microbial organism). Thus, for example, in some embodiments a discrete coding substrate encodes an auxiliary protein that induces or causes a bacteria to secrete an antimicrobial peptide and/or bacteriocin that inhibits growth or reproduction of another bacteria. In some embodiments, one or more of the discrete coding substrates encodes a protein that attracts the non-pathogenic microbial organism, or that enhances growth or reproduction of the non-pathogenic microbial organism in the microbiome of a subject. In some embodiments, bacteriocins, and not antimicrobial peptides are used.

Inhibition of growth or reproduction has its customary and ordinary meaning as understood by one of skill in the art in view of this disclosure. It refers to a decrease in or arrest of proliferation of microbial organisms (or a decrease in the rate of proliferation of microbial organisms), for example, arrest of the cell cycle and/or killing of microbial organisms. Similarly, enhancement of growth or reproduction refers to an increase in proliferation or the rate of proliferation of microbial organisms. Any method known in the art may be used to detect inhibition or enhancement of growth or reproduction.

In Vitro Transcription/Translation Solutions

In accordance with the methods, systems and microfluidic devices of some embodiments described herein, a transcription/translation solution can be used to produce an antimicrobial peptide and/or bacteriocin encoded by a coding substrate. As such, the transcription/translation solution may be useful for generating peptides, or antimicrobial peptides and/or bacteriocins, in a method or microfluidic device for producing a specified mixture of antimicrobial peptides and/or bacteriocins The term, “in vitro transcription/translation solution” encompasses an in vitro transcription solution and/or an in vitro translation solution sufficient to produce an antimicrobial peptide and/or bacteriocin from a coding substrate. By way of example, in embodiments in which the coding substrate comprises RNA transcripts encoding antimicrobial peptides and/or bacteriocins, it is contemplated that an “in vitro transcription/translation solution” comprising, consisting essentially of, or consisting of a translation solution is sufficient (since it will be understood that the RNA is already a transcript). By way of example, in embodiments in which the coding substrate comprises DNAs encoding antimicrobial peptides and/or bacteriocins, it is contemplated that an “in vitro transcription/translation solution” comprises a transcription solution (for transcribing the DNAs into RNAs) and a translation solution (for translating the RNAs into polypeptides). In some embodiments, the transcription and translation solution are together in a single solution. In some embodiments, the transcription and translation solution are in separate solutions, for example in vesicles suspended in a single solution, and/or in separate solutions that are applied sequentially. In some embodiments, components of the in vitro transcription/translation solution are lyophilized, and configured to be reconstituted into the in vitro transcription/translation solution upon the addition of water. In some embodiments, the in vitro transcription/translation solution is reconstituted by adding water to lyophilized components.

Translation solutions can be useful for translating nucleic acids in accordance with the methods, systems and/or microfluidic devices described herein. Suitable translation solutions can comprise, consist essentially of, or consist of reagents for in vitro translation (which, for convenience, may be referred to herein as “translation reagents”), and as such can be configured for in vitro translation of a transcript such as an RNA. Some embodiments include a transcription solution comprising reagents for transcription (which, for convenience, may be referred to herein as “transcription reagents”), and thus is configured for in vitro transcription and translation, for example to transcribe and translate a nucleic acid encoding an antimicrobial peptide and/or bacteriocin or other peptides as described herein. It is contemplated that in vitro transcription and translation in a single solution (such as a transcription solution further comprising a translation solution as described herein) can facilitate efficient in vitro production of antimicrobial peptides and/or bacteriocins or other peptides in accordance with methods and microfluidic devices of some embodiments. Thus, in accordance with the methods and microfluidic devices of some embodiments described herein, the in vitro transcription/translation solution comprises an in vitro transcription reagent and/or an in vitro translation reagent.

In accordance with the methods and microfluidic devices of some embodiments described herein, the translation solution comprises, consists essentially of, or consists of one or more translation reagents or in vitro translation reagents. Examples of translation reagents include, but are not limited to, a ribosome, a buffer, an amino acid, a tRNA (which may be conjugated to an amino acid), a lysate or extract such as an *E. coli* lysate or *E. coli* extract, and a cofactor or metallic ion such as $Mg^{2+}$, or a combination of two or more of any of the listed items. In accordance with the methods, systems and kits of some embodiments described herein the translation solution further comprises a transcription solution, and thus is configured for in vitro transcription and translation. As described herein, a transcription solution further comprising a translation solution contemplates a single solution that is suitable for in vitro transcription and translation. As such, a transcription solution further comprising a translation solution encompasses a single transcription/translation solution. It will be appreciated that some components of a transcription and/or translation solution, for example ribosomes, may not be liquids, and could potentially be isolated from the transcription and/or translation solution, for example by filtration and/or centrifugation. Translation solutions of methods and microfluidic devices of some embodiments described herein (and which can be comprised by translation solutions as described herein) can comprise, consist essentially or, or consist of one or more transcription reagents. Examples of transcription reagents include an RNA polymerase, a buffer, a nucleic acid mix (for example, NTPs including ATP, GTP, CTP, and UTP), a cofactor or metallic ion such as $Mg^{2+}$, a transcription inducer (such as a transcription factor, IPTG, or lactose), a polyadenylation enzyme, a capping enzyme, a lysate or extract such as a bacterial lysate or extract such as an *E. coli* lysate or *E. coli* extract, an SP6 polymerase, a T3 polymerase, a T7 RNA polymerase, or a mixture of two or more of any of the listed items. The transcription solution can be useful for transcribing a template, such as a candidate nucleic acid as described herein. Translation solutions of methods and microfluidic devices of some embodiments include one or more transcription reagents in combination with one or more translation reagents. In some embodiments, a microfluidic device and/or system comprises a reservoir comprising an in vitro transcription/translation solution as described herein. In some embodiments, the reservoir comprises an in vitro transcription solution and an in vitro translation solution which can be combined to produce the in vitro transcription/translation solution.

In some embodiments, the translation solution comprises a post-translational modification enzyme. Examples of post-translational modification enzymes include, but are not limited to a cleavage enzyme, a kinase, a phosphatase, a glycosyltransferase, or a mixture of any two of the listed items.

In accordance with the systems, methods and microfluidic devices of some embodiments described herein, the translation solution is provided to a coding substrate at a microliter-scale. For example, the translation solution may have a volume of 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, or 500 μl-1000 μl.

In accordance with the systems, methods and microfluidic devices of some embodiments described herein, the in vitro transcription/translation solution is lyophyilized. In some embodiments, the in vitro transcription/translation solution is configured be reconstituted in a solution such as water. As such, a microfluidic device of some embodiments can be stably stored for periods of time at ambient temperature, without substantial impact on the efficacy of the in vitro transcription/translation solution. Accordingly, it is contemplated that the microfluidic device of some embodiments is suitable for point-of-care treatment, and can be used to prepare specified mixtures of antimicrobial peptides and/or bacteriocins as needed (for example, in response to particular injuries, infections, and/or surgical procedures).

Microfluidic Devices and Systems

A fluidic system comprising a microfluidic device can be useful for producing specified mixtures of antimicrobial peptides and/or bacteriocins in accordance with the methods and microfluidic devices and systems of some embodiments described herein. In some embodiments, a system is configured to receive a microfluidic device comprising discrete coding substrates as described herein, so that the system can direct the microfluidic device to produce a specified mixture of antimicrobial peptides and/or bacteriocins via in vitro transcription/translation. In some embodiments, the system is configured to be in fluid and/or data communication with the device. For example, disposable cartridge can comprise, consist essentially of, or consist of a microfluidic device for use in conjunction with systems as described herein. As it is contemplated that specified mixtures of antimicrobial peptides and/or bacteriocins can be customized for particular applications, for example, to interact with a particular microbiome of a particular subject, or to target a particular infection, it is contemplated that single-use disposable microfluidic devices can minimize contamination (for example from residual bacteriocins) that may interfere with the stoichiometry and composition of the specified mixture of antimicrobial peptides and/or bacteriocins, and can be useful for maintaining sterility for medical use on a subject. As such, in some embodiments, the microfluidic device is sterile. In the methods and microfluidic devices of some embodiments, the fluidic device comprises a microfluidic device. As it will be understood that a "microfluidic device" is a kind of "fluidic device," a microfluidic device is expressly contemplated wherever a "fluidic device" is mentioned herein. Additionally, unless expressly stated otherwise, any disclosure of a fluidic device (such as a microfluidic device) herein is understood to be applicable to a microfluidic device of some embodiments, as well as methods comprising microfluidic devices as described herein.

In some embodiments, a microfluidic device for producing a specified mixture of antimicrobial peptides and/or bacteriocins is provided. In some embodiments, the device comprises discrete coding substrates, as described herein, that each encode an antimicrobial peptide and/or bacteriocin. The device can further comprise an in vitro transcription/translation solution as described herein. The device can further comprise a fluidic reservoir, one or more valves, and/or can be configured to be placed in data communication with a processor as described herein. The valves can regulate fluidic communication between the transcription/translation solution, the discrete coding substrates, and/or the fluidic reservoir. The processor can be configured to control the valves, so as to place coding substrates encoding the antimicrobial peptides and/or bacteriocins of the specified mixture in fluid communication with the in vitro transcription/translation solution so that the antimicrobial peptides and/or bacteriocins of the specified mixture are produced. The processor can be configured to control the valves (and, in some embodiments, fluidic flow) in the microfluidic device to place the antimicrobial peptides and/or bacteriocins of the mixture in fluid communication with the fluidic reservoir so that the antimicrobial peptides and/or bacteriocins of the specified mixture flow to the fluidic reservoir, thus providing the specified mixture of antimicrobial peptides and/or bacteriocins in the fluidic reservoir. Optionally, the antimicrobial peptides and/or bacteriocins of the specified mixture are actively mixed in the fluidic reservoir. In some embodiments, the antimicrobial peptides and/or bacteriocins of the specified mixture mix passively (but are not actively mixed) in the fluidic reservoir. In some embodiments, the microfluidic device comprises the processor. In some embodiments, the microfluidic device does not itself comprise the processor, but is configured to be placed in data communication with the processor. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Some embodiments of the methods and microfluidic devices described herein include a microfluidic device for producing a specified mixture of antimicrobial peptides and/or bacteriocins. The device can comprise: discrete coding substrates that each encode a bacteriocin and/or an antimicrobial peptide; an in vitro transcription/translation solution; a fluidic reservoir; valves each disposed on a fluidic path between a discrete coding substrate and the fluidic reservoir, each valve configured to regulate flow between the discrete coding substrate and the fluidic reservoir. The device can be configured to be placed in data communication with a processor configured to: based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, wherein the flow comprises movement of a fluid comprising the specified antimicrobial peptides and/or bacteriocins in the fluidic reservoir, thus producing the specified mixture of antimicrobial peptides and/or bacteriocins. In some embodiments, the microfluidic device comprises the processor. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

In accordance with the methods and microfluidic devices of some embodiments described herein, the microfluidic device comprises discrete coding substrates but not a fluidic reservoir and/or an in vitro transcription/translation solution. As such, the microfluidic device can be placed in fluid and data communication with a system as described herein, and the system can provide the fluidic reservoir and/or the in vitro transcription/translation solution so that the specified mixture of antimicrobial peptides and/or bacteriocins can be produced. Accordingly, in some embodiments, the system comprises a fluidic reservoir and/or an in vitro transcription/translation solution as described herein. In some embodiments, the microfluidic device does not comprise the fluidic reservoir, the in vitro transcription/translation solution, and/or any other components of the system, and is separate from these components of the system until it is placed in data and/or fluid communication with the system. In some embodiments, the microfluidic device is configured to be attached to the fluidic reservoir, the in vitro transcription/translation solution, and/or another component of the system. For example, the device may comprise a cartridge that is configured to be inserted into the system to place the discrete coding substrates of the cartridge in fluid communication with an external (to the cartridge) to the fluidic reservoir, in vitro transcription/translation solution, and/or other component of the system. In some embodiments, the cartridges are consumable. For example, a cartridge may comprise discrete coding substrates, be configured to be inserted into the system described herein to produce a mixture of specified antimicrobial peptides and/or bacteriocins, and then be discarded, after which another cartridge that includes other discrete coding substrates may be inserted into the system to produce a different mixture of specified antimicrobial peptides and/or bacteriocins. In some embodiments, a cartridge is configured to receive an in vitro transcription/translation solution from the system, so that the in vitro transcription/translation solution contacts the discrete coding substrates of the cartridge that encode the bacteriocins and/or antimicrobial peptides of the specified mixture. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Also contemplated are embodiments in which the system and/or microfluidic device is dry. In some embodiments, the system or microfluidic device comprises a lyophilized reagent configured to be dissolved in a fluid such as water.

Figure 5:
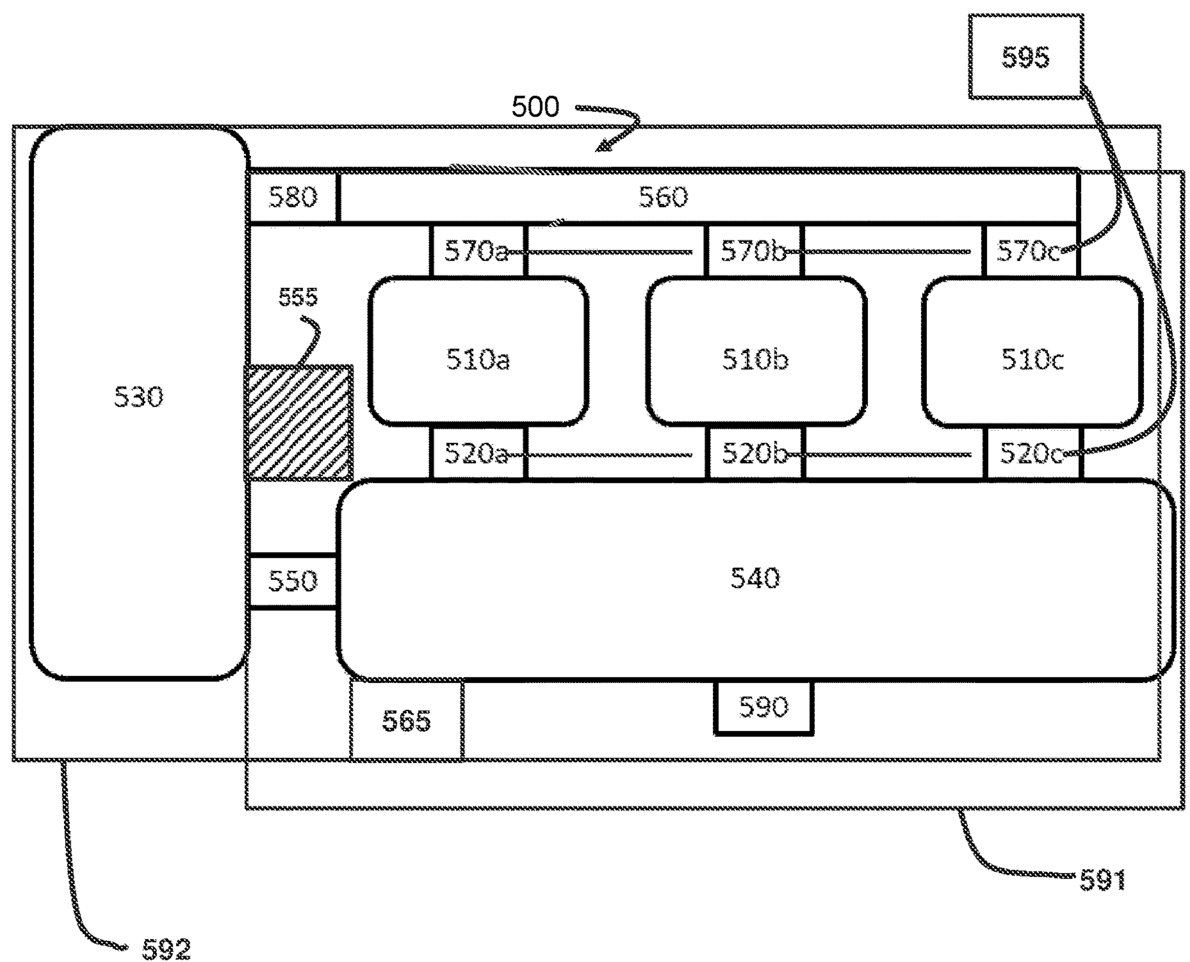
FIG. 5 is a schematic diagram depicting a microfluidic device in accordance with some embodiments herein.

FIG. 5 is a schematic diagram depicting a microfluidic device 500 of some embodiments herein. The microfluidic device 500 can comprise discrete coding substrates 510*a*, 510*b*, 510*c* (while three discrete coding substrates are shown by way of example, it is contemplated that microfluidic devices of embodiments herein can comprise other quantities of discrete coding substrates, as described herein). The device can comprise a fluidic reservoir 540, which, by way of example, can receive antimicrobial peptides and/or bacteriocins produced from the discrete coding substrates 510*a*, 510*b*, 510*c*, and thus can contain a specified mixture of antimicrobial peptides and/or bacteriocins as described herein. Valves 520*a*, 520*b*, 520*c*, and/or 570*a*, 570*b*, 570*c* can regulate fluidic flow to and from the discrete coding substrates 510*a*, 510*b*, 510*c*. In some embodiments, the microfluidic device further comprises an outlet 590, which can permit flow from the fluidic reservoir 540 out of the microfluidic device. For example, the specified mixture of antimicrobial peptides and/or bacteriocins can flow through the outlet 590 to a tissue, wound, microbiome of a subject, and/or vessel as described herein. In some embodiments, a processor 595 as described herein is in data communication with the device, and controls flow through valves 520*a*, 520*b*, 520*c*, and/or 570*a*, 570*b*, 570*c* and/or 550 and/or 580. In some embodiments, the device does not itself comprise a processor 595, and is configured to placed in data communication with a processor 595 as described herein so as to controls flow through valves 520*a*, 520*b*, 520*c*, and/or 570*a*, 570*b*, 570*c* and/or 550 and/or 580. It is contemplated that in accordance with microfluidic devices and methods of some embodiments herein, the production of antimicrobial peptides and/or bacteriocins of a specified mixture can be achieved by contacting only a subset of discrete coding substrates 510*a*, 510*b*, 510*c* with an in vitro transcription/translation solution in the first place (so that only some discrete coding substrates are used to produce an antimicrobial peptide and/or bacteriocin), and/or by only permitting a subset of antimicrobial peptides and/or bacteriocins produced from discrete coding substrates 510*a*, 510*b*, 510*c* to enter the fluidic reservoir 540. It is noted that contacting only a subset of the discrete coding substrates with in vitro transcription/translation solution can enhance efficiency by avoiding the use of in vitro transcription/translation solution on coding substrates that do not encode antimicrobial peptides and/or bacteriocins of the specified mixture. In some embodiments, the microfluidic device is part of a cartridge 591 that does not comprise a reservoir of in vitro transcription/translation solution. The cartridge 591 can be configured to place the microfluidic device in data communication with a system comprising a processor 595. Optionally the cartridge can also be placed in fluid communication with the system. In some embodiments, the microfluidic device is part of a cartridge 592 that comprises a reservoir of in vitro transcription/translation solution 530. The cartridge 592 can be configured to place the microfluidic device in data communication with a system comprising a processor 595. In some embodiments, the microfluidic device comprises, consists essentially of, or consists of the microfluidic device 600 shown in FIG. 6, which includes discrete coding substrates 610*a*, 610*b*, 610*c*, a channel 660, and valves 620*a*, 620*b*, 620*c*, 670*a*, 670*b*, 670*c*, and/or 680, similar to the microfluidic device 500 in FIG. 5. The microfluidic device optionally does not include In some embodiments, the microfluidic device 600 can be placed in fluid communication with a system comprising a reservoir of in vitro transcription/translation solution 530 or a fluidic reservoir 540, or in data communication with a heating element 555. For example, a disposable cartridge can comprise, consist essentially of, or consist of the microfluidic device 600, and can be configured to be placed in fluid communication with a system comprising in vitro transcription/translation solution 530 and a fluidic reservoir 540. The microfluidic device 600 can also be placed in data communication with a processor 595 and/or a heating element 555 of the system. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Figure 6:
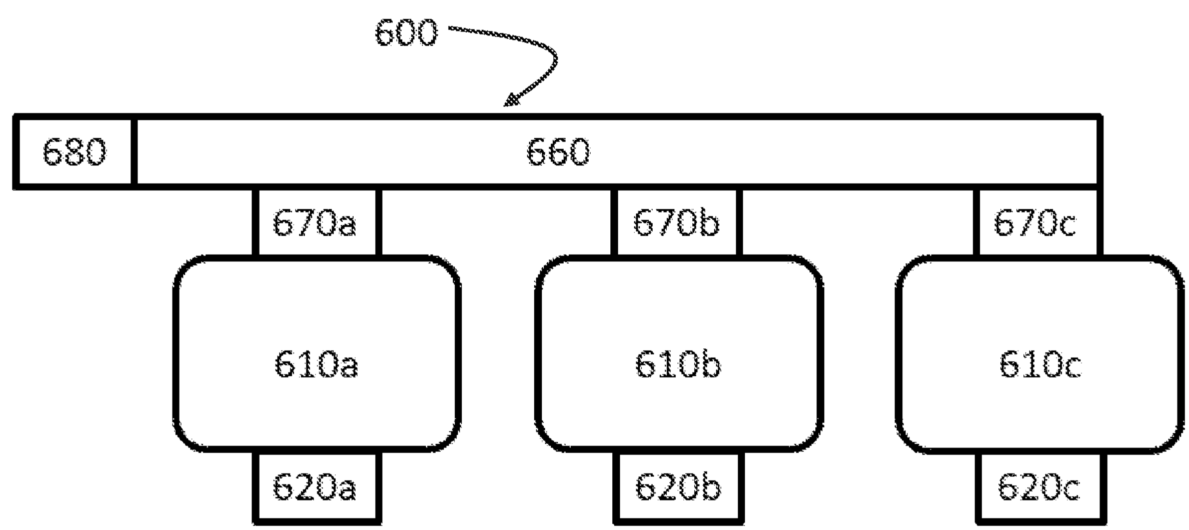
FIG. 6 is a schematic diagram depicting a microfluidic device in accordance with some embodiments herein.

In some embodiments, valves 520*a*, 520*b*, and 520*c* regulate flow between the discrete coding substrates 510*a*, 510*b*, 510*c* and the fluidic reservoir 540. Valves 570*a*, 570*b*, and 570*c* are optional, and/or valves 550 and 580 are optional, and/or the channel 560 is optional. In some embodiments, the reservoir of in vitro transcription/translation solution 530 can be in fluidic communication with the fluidic reservoir 540. Optionally, valve 550 is disposed between the reservoir of in vitro transcription/translation solution 530 and the fluidic reservoir 540, and regulates flow of in vitro transcription/translation solution to the fluidic reservoir 540. In some embodiments, the microfluidic device 600 of FIG. 6 is part of a cartridge.

In some embodiments, for example if only the antimicrobial peptides and/or bacteriocins of the specified mixture are permitted to enter the fluidic reservoir 540 from the coding substrates 510*a*, 510*b*, 510*c*, valves 570*a*, 570*b*, and 570*c* regulate flow between a reservoir of in vitro transcription/translation solution 530 and the discrete coding substrates 510*a*, 510*b*, 510*c*, and valves 520*a*, 520*b*, 520*c* are optional, and/or valve 550 is optional and/or valve 580 is optional. A channel 560 can connect the reservoir of in vitro transcription/translation solution 530 to the discrete coding substrates 510*a*, 510*b*, 510*c*, with optional intervening valve 580 between the reservoir 530 and the channel 560, and/or optional intervening valves 570*a*, 570*b*, 570*c* between the channel 560 and the discrete coding substrates 510*a*, 510*b*, 510*c*. In some embodiments, valves 570*a*, 570*b*, and 570*c* regulate flow between a reservoir of in vitro transcription/translation solution 530 and the discrete coding substrates 510*a*, 510*b*, 510*c*, and valves 520*a*, 520*b*, 520*c* regulate flow between the discrete coding substrates 510*a*, 510*b*, 510*c* and the fluidic reservoir 540. Optionally, channel 560 can connect the reservoir 530 to the discrete coding substrates 510*a*, 510*b*, 510*c*. Valve 580 is optional and/or valve 550 is optional.

The microfluidic device can further comprise an outlet 590. The outlet 590 can place the fluidic reservoir (and any mixture of antimicrobial peptides and/or bacteriocins therein) in fluidic communication with a tissue of a subject, a wound, and/or a microbiome of a subject as described herein. In some embodiments, the outlet 590 comprises a valve. In some embodiments, the outlet 590 can be placed in fluid communication with a vessel for storing a specified mixture of antimicrobial peptides and/or bacteriocins, for example a test tube, bag, or well.

In some embodiments, the in vitro transcription/translation solution reservoir 530 is in fluid communication with channel 560. Optional valve 580 controls from from the reservoir 530 to the channel 560. In some embodiments, valves 570*a*, 570*b*, and 570*c* regulate flow of transcription/translation solution from the channel 560 into discrete coding substrates 510*a*, 510*b*, 510*c*. By way of example, to produce a specified mixture of antimicrobial peptides and/or bacteriocins comprising antimicrobial peptides and/or bacteriocins encoded by discrete coding substrates 510*a* and 510*b* (but not 510*c*), valves 570*a* and 570*b* can be open, while valve 570*c* is closed, to permit flow of transcription/translation solution 530 into discrete coding substrates 510*a* and 510*b*, but not 510*c*. In some embodiments, discrete coding substrates 510*a*, 510*b*, and/or 510*c* are incubated with the in vitro transcription/translation solution to produce a specified mixture of antimicrobial peptides and/or bacteriocins that is released via valves 520*a*, 520*b*, and/or 520*c* into the fluidic reservoir 540.

In some embodiments, in vitro transcription/translation solution flows to the discrete coding substrates 510*a*, 510*b*, and/or 510*c* through the fluidic reservoir 540. The reservoir of in vitro transcription/translation solution 530 can be in fluid communication with the fluidic reservoir 540, optionally with flow regulated by intervening valve 550. Optionally, valves 520*a*, 520*b*, 520*c* regulate flow from the fluidic reservoir 540 to the discrete coding substrates 510*a*, 510*b*, and 510*c*. As such, the in vitro transcription/translation solution can be incubated with the appropriate discrete coding substrates to produce antimicrobial peptides and/or bacteriocins, and antimicrobial peptides and/or bacteriocins can then flow through valves 520*a*, 520*b*, and 520*c* to the fluidic reservoir 540. Valves 570*a*, 570*b*, 570*c*, the channel 560, and valve 580 can be optional. In some embodiments, discrete coding substrates 510*a*, 510*b*, and/or 510*c* are incubated with the in vitro transcription/translation solution to produce a specified mixture of antimicrobial peptides and/or bacteriocins that is released via valves 520*a*, 520*b*, and/or 520*c* into the fluidic reservoir 540. In some embodiments, the specified mixture of antimicrobial peptides and/or bacteriocins flows through the outlet 590 to a wound, tissue, microbiome of a subject, and/or vessel as described herein.

In some embodiments, valve 550 regulates flow from the in vitro transcription/translation solution reservoir 530 into fluidic reservoir 540, and valves 520*a*, 520*b*, and/or 520*c* regulate flow from discrete coding substrates 510*a*, 510*b*, and/or 510*c* to fluidic reservoir 540. Valves 570*a*, 570*b*, 570*c*, and 580, and channel 560 are optional. As such, in vitro transcription/translation solution can flow from the fluidic reservoir 540 to the discrete coding substrates 510*a*, 510*b*, and/or 510*c*, can be incubated with the discrete coding substrates 510*a*, 510*b*, and/or 510*c* to produce antimicrobial peptides and/or bacteriocins, and antimicrobial peptides and/or bacteriocins can flow to the fluidic reservoir 540. In some embodiments, the processor 595 regulates flow of in vitro transcription/translation solution through valves 520*a*, 520*b*, and 520*c* to the discrete coding substrates 510*a*, 510*b*, and/or 510*c* so that only discrete coding substrates encoding antimicrobial peptides and/or bacteriocins of the specified mixture receive in vitro transcription translation/solution. In some embodiments, the processor 595 permits flow of in vitro transcription translation/solution from the fluidic reservoir 540 to the discrete coding substrates 510*a*, 510*b*, and/or 510*c* encoding the antimicrobial peptides and/or bacteriocins of the specified mixture through valves 520*a*, 520*b*, and 520*c*, and after the antimicrobial peptides and/or bacteriocins have ben produced by in vitro transcription translation, the processor 595 regulates valves 520*a*, 520*b*,

520*c*, so that only the antimicrobial peptides and/or bacteriocins of the specified mixture to enter the fluidic reservoir 540.

It can be appreciated that in some embodiments of the fluidic device 500 depicted in FIG. 5, valves 550, 570*a*, 570*b*, 570*c*, 580, and channel 560, are optional. For example, some embodiments of the fluidic device include valves 580, 570*a*, 570*b* and 570*c*, and flow means 560, but not valve 550. In some other embodiments, the fluidic device includes valve 550, but not valves 570*a*, 570*b*, 570*c*, or 580, or flow means 560. In some embodiments, the fluidic device includes valves 550, 570*a*, 570*b*, 570*c*, and 580, and flow means 560. In some embodiments, valve 580 is included, and valves 570*a*, 570*b*, and 570*c* are excluded. In some embodiments, valve 580 is excluded, and valves 570*a*, 570*b*, and 570*c* are included. It can also be appreciated that in some embodiments of the fluidic device 500, the outlet 590 does not comprise a valve.

In some embodiments, the outlet 590 permits a wash fluid into the fluidic reservoir 540, and any of the other valves may be opened to permit flow of the wash fluid into any other fluidically connected portion of the device. In some embodiments, the wash fluid comprises a buffer or a detergent. It can be appreciated that additional valves may be present in the microfluidic device to allow the inflow or outflow of fluids in any of the fluidic portions of the device.

In some embodiments, channel 560 comprises, consists essentially of, or consists of a microchannel, tube, pipe, and a hose, and as such, can contain and/or direct flow of a fluid. In some embodiments, the channel 560 comprises material such as rubber, plastic, metal.

In accordance with the methods and microfluidic devices of some embodiments described herein, the microfluidic device is portable. For example, some embodiments of the device may be removed from a laboratory and taken into a natural environment where a scientist performs tests with various mixtures of specified antimicrobial peptides and/or bacteriocins.

In accordance with the methods and microfluidic devices of some embodiments described herein, the microfluidic device comprises an outlet 590 through which the specified mixture of antimicrobial peptides and/or bacteriocins are delivered to a wound. For example, the outlet 590 can be connected to the wound via a membrane or tube. Thus, in some embodiments, the device comprises a wound dressing or wound cleaning device.

In some embodiments, fluid is passively transferred from one component of the device to another. The microfluidic devices of some embodiments include a pump 565 that actively pumps fluid from one component of the device to another.

In accordance with the methods and microfluidic devices of some embodiments described herein, the microfluidic device comprises a heating element 555 such as a heating block. In some embodiments, the heating element is configured to heat parts of the microfluidic device, such as the fluidic reservoir 540 and/or the discrete coding substrates 510*a*, 510*b*, and/or 510*c* to perform incubation step. In some embodiments, the incubation step is at at least about 0° C., 4° C., 25° C., 30° C., 37° C., 38° C., 40° C., including ranges between any two of the listed values, for example 0-40° C., or 36-38° C., or 4-40° C. In some embodiments, the incubation with the in vitro transcription/translation solution at least 1, 10, 30, 60 second, or at least 2, 3, 4, 5, 6, 7, 8, 9, 10, 15, 20, 25, or 30 minutes, including ranges between any two of the listed valued, for example 1-30 seconds, 30-60 seconds, 1-2 minutes, 2-5 minutes, 5-10 minutes, 10-15 minutes, 15-30 minutes, or 30-60 minutes, 1-2 hours, 2-5 hours, 5-10 hours, 10-15 hours, 15-24 hours, 24-48 hours, or 48-72 hours. In some embodiments, the incubation with the in vitro transcription/translation solution comprises more than one temperature at different times.

In accordance with the methods and microfluidic devices of some embodiments described herein, the microfluidic device comprises a reservoir of chemical and/or phage antibiotics configured to mix with the mixture of specified antimicrobial peptides and/or bacteriocins. In some embodiments, the microfluidic device comprises an antibiotic comprising a chemical antibiotic and/or a phage. In some embodiments, the system comprises a reservoir of chemical or phage antibiotics configured to mix with the mixture of specified antimicrobial peptides and/or bacteriocins. In accordance with the methods and microfluidic devices of some embodiments described herein, the microfluidic device comprises an antibiotic comprising a chemical antibiotic and/or a phage.

Fluidic Reservoirs

In methods and microfluidic devices of some embodiments herein, the microfluidic device comprise a fluidic reservoir 540. In some embodiments, the fluidic reservoir is or is configured to be in fluid communication with at least one discrete coding substrate (optionally, separated by a valve as described herein). In some embodiments, the fluidic reservoir is in fluid communication with discrete coding substrates or chambers housing the discrete coding substrates, as described herein. In some embodiments, the fluidic reservoir is placed in fluid communication with the discrete coding substrates (or chambers) by a channel, tubing, microfluidic tubing, membrane, mesh, opening, passageway, or two or more of these. By way of example, the channel, tubing, microfluidic tubing, membrane, mesh, opening, and/or passageway of some embodiments can comprise a material such as rubber, glass, plastic, metal, an organic compound, or two or more of these. In some embodiments, the fluidic reservoir is configured to receive antimicrobial peptides and/or bacteriocins of the specified mixture of antimicrobial peptides and/or bacteriocins. The specified antimicrobial peptides and/or bacteriocins can be mixed in the fluidic reservoir, forming the mixture, for example by passive mixing and/or by active mixing. In some embodiments, the microfluidic device comprises more than one fluidic reservoirs. In some embodiments, the fluidic reservoir has a volume of at least 1 μl, for example, at least 1, 5, 10, 100, 500, or 1000 μl, including ranges between any two of the listed values, for example, 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, 500 μl-1000 μl, 1 ml-1000 ml, 1 ml-50 ml, 1 ml-500 ml, 1 ml-900 ml, 50 ml-100 ml, 50 ml-500 ml, 50 ml-1000 ml, 100 ml-200 ml, 100 ml-500 ml, 100 ml-1000 ml, 200 ml-500 ml, 200 ml-1000 ml, 500 ml-900 ml, 500 ml-1000 ml.

Valves

In methods and microfluidic devices of some embodiments, the microfluidic device comprise one or more valves. As used herein, "valve" encompasses mechanical valves, as well as electromagnetic fields, conditional diffusion membranes, and other devices understood in the art to permit and restrict liquid flow. In some embodiments, a valve separates the fluidic reservoir from a discrete coding substrate, and controls the flow of fluids between the discrete coding substrate and fluidic reservoir. Each valve may be disposed on a fluidic path between a discrete coding substrate and the fluidic reservoir. Each valve may be configured to regulate flow between the discrete coding substrate and the fluidic reservoir. In some embodiments, each discrete coding substrate is separated from the fluidic reservoir by a valve configured to control the flow of fluid from the discrete coding substrate to the fluidic reservoir. In some embodiments, a valve as described herein comprises a hydraulic, pneumatic, manual, solenoid, motor valve, or socket ball valve, or a combination of two or more of these. In some embodiments, a valve as described herein comprises a two-port, three-port, or four-port valve. In some embodiments, a valve as described herein comprises a microfluidic valve or microvalve, such as a solenoid microvalve, screw microvalve, pneumatic microvalve, or a combination of two or more of these. In some embodiments, a valve is binary, so that flow through the valve is either "on" or "off." In some embodiments, a valve regulates the rate of flow though the valve.

In some embodiments, valves 520*a*, 520*b*, 520*c* are disposed between the fluidic reservoir 540 and the coding substrates 510*a*, 510*b*, 510*c*. For example, in some embodiments, valves are disposed between the fluidic reservoir and the coding substrates, and between the coding substrates and the fluidic reservoir. A single valve between the fluidic reservoir and the coding substrates may be opened to flush some or all of the coding substrates with a transcription/translation fluid, and then only valves between coding substrates of interest and the reservoir are opened after incubation, so that only antimicrobial peptides and/or bacteriocins of interest are included in a specified mixture of antimicrobial peptides and/or bacteriocins are permitted to flow into the fluidic reservoir.

In some embodiments, separate valves are disposed between the transcription/translation solution and the discrete coding substrates, so that separate valves can be opened and closed to place only discrete coding substrates of interest in contact with the transcription/translation solution, and thus produce a specified antimicrobial peptides and/or bacteriocins mixture upon incubation of the discrete coding substrates of interest with the transcription/translation solution. In view of this disclosure, the skilled artisan will appreciate that there are multiple ways for valves to regulate flow to and from the discrete coding substrates so that only antimicrobial peptides and/or bacteriocins of the specified mixture of antimicrobial peptides and/or bacteriocins are obtained in a mixture in the fluidic reservoir 540.

Smart bandages can comprise a processor, a sensor (such as a pH and/or temperature sensor), and a source of therapeutic agent, in which the processor is configured to control the administration of therapeutic agent. For example, the sensor can detect inflammation, and the processor can administer quantities of anti-inflammatory agent in response to the detected inflammation. Examples of suitable smart bandages may be found on the world wide web at www.cnet.com/news/this-smart-bandage-can-deliver-drugs-monitor-chronic-wounds, which is hereby incorporated by reference in its entirety. In some embodiments, the microfluidic device as described herein comprises a smart bandage. In some embodiments, the microfluidic device or system is configured to be placed in fluid communication with a smart bandage. For example, the port of the microfluidic device can be placed in fluid communication with a reservoir of a smart bandage, so that the smart bandage can control delivery of the specified mixture of antimicrobial peptides and/or bacteriocins to a subject. In some embodiments, the microfluidic device is comprised by a disposable cartridge that further comprises a smart bandage, and is in fluid communication with the fluidic reservoir, so that a specified mixture of antimicrobial peptides and/or bacteriocins can be delivered to a subject via the smart bandage. Optionally, the disposable cartridge comprising the smart bandage and the microfluidic device comprises an adhesive for direct application to a tissue of a subject, for example skin. As such, the microfluidic device of some embodiments is for medical use. In some embodiments, the smart bandage monitors a wound or site of inflammation and delivers a specified mixture of antimicrobial peptides and/or bacteriocins as described herein to the skin or to a wound site.

Processors

A processor 595 can regulate valves in microfluidic devices and methods of some embodiments. The processor can be configured to, based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir. In some embodiments, the processor is configured to permit incubation of the in vitro transcription/translation solution with the discrete coding substrates that encode the antimicrobial peptides and/or bacteriocins of the mixture, so that the specified antimicrobial peptides and/or bacteriocins of the mixture are produced. In some embodiments, the processor is configured to permit flow of the specified antimicrobial peptides and/or bacteriocins through the valves into the fluidic reservoir. In some embodiments, the processor is configured to control flow of fluid in the fluidic reservoir. In some embodiments, the flow comprises movement of a fluid comprising the specified antimicrobial peptides and/or bacteriocins into and/or within the fluidic reservoir, thus producing the specified mixture of antimicrobial peptides and/or bacteriocins. For example, the flow can mix bacteriocins from different coding substrates once they are present in the fluidic reservoir, thus producing the specified mixture of antimicrobial peptides and/or bacteriocins. In some embodiments, the microfluidic device comprises a processor. In some embodiments, the microfluidic device does not itself comprise a processor, but is configured to be placed in data communication with the processor.

It is contemplated that a specified mixture of antimicrobial peptides and/or bacteriocins according to methods and microfluidic devices of some embodiments herein can be formed from two or more submixtures. For example, a first submixture of bacteriocins A and B in a ratio of 1:1 can be combined with the same quantity of a second submixture of bacteriocins B and C in a ratio of 1:1, thus producing a mixture of bacteriocins A, B, and C in ratios of 1:2:1. In accordance with the methods and microfluidic devices of some embodiments described herein, the specified mixture of antimicrobial peptides and/or bacteriocins comprises two or more submixtures each comprising a subset of antimicrobial peptides and/or bacteriocins, and the processor is configured to permit flow of each submixture into the fluidic reservoir, thereby producing the specified mixture of antimicrobial peptides and/or bacteriocins. In some embodiments, the specified mixture of antimicrobial peptides and/or bacteriocins comprises a sum of the submixtures of bacteriocins in a specified stoichiometry, and combination of the submixtures yields the mixture in the specified stoichiometry.

Methods for Producing a Specified Mixture of Antimicrobial Peptides and/or Bacteriocins In some embodiments, a method for producing a specified mixture of antimicrobial peptides and/or bacteriocins is provided. The method may include producing bacteriocins of the specified mixture, but not other bacteriocins, by in vitro transcription and translation of bacteriocins encoded by discrete coding substrates, and then mixing the selected bacteriocins from the in vitro transcription and translation to produce the specified mixture of antimicrobial peptides and/or bacteriocins. In some embodiments, the method includes producing bacteriocins by in vitro transcription and translation of bacteriocins encoded by discrete coding substrates, and then mixing bacteriocins of the specified mixture, but not other bacteriocins (if any) to produce the specified mixture of antimicrobial peptides and/or bacteriocins. In some embodiments, the method for producing a specified mixture of antimicrobial peptides and/or bacteriocins is performed on a microfluidic device as described herein. In some embodiments, the method is for producing a specified mixture of bacteriocins, and not antimicrobial peptides. In some embodiments, the method is for producing a specified mixture of antimicrobial peptides, and not bacteriocins. In some embodiments, the method is for producing a specified mixture of bacteriocins and antimicrobial peptides.

Figure 7:
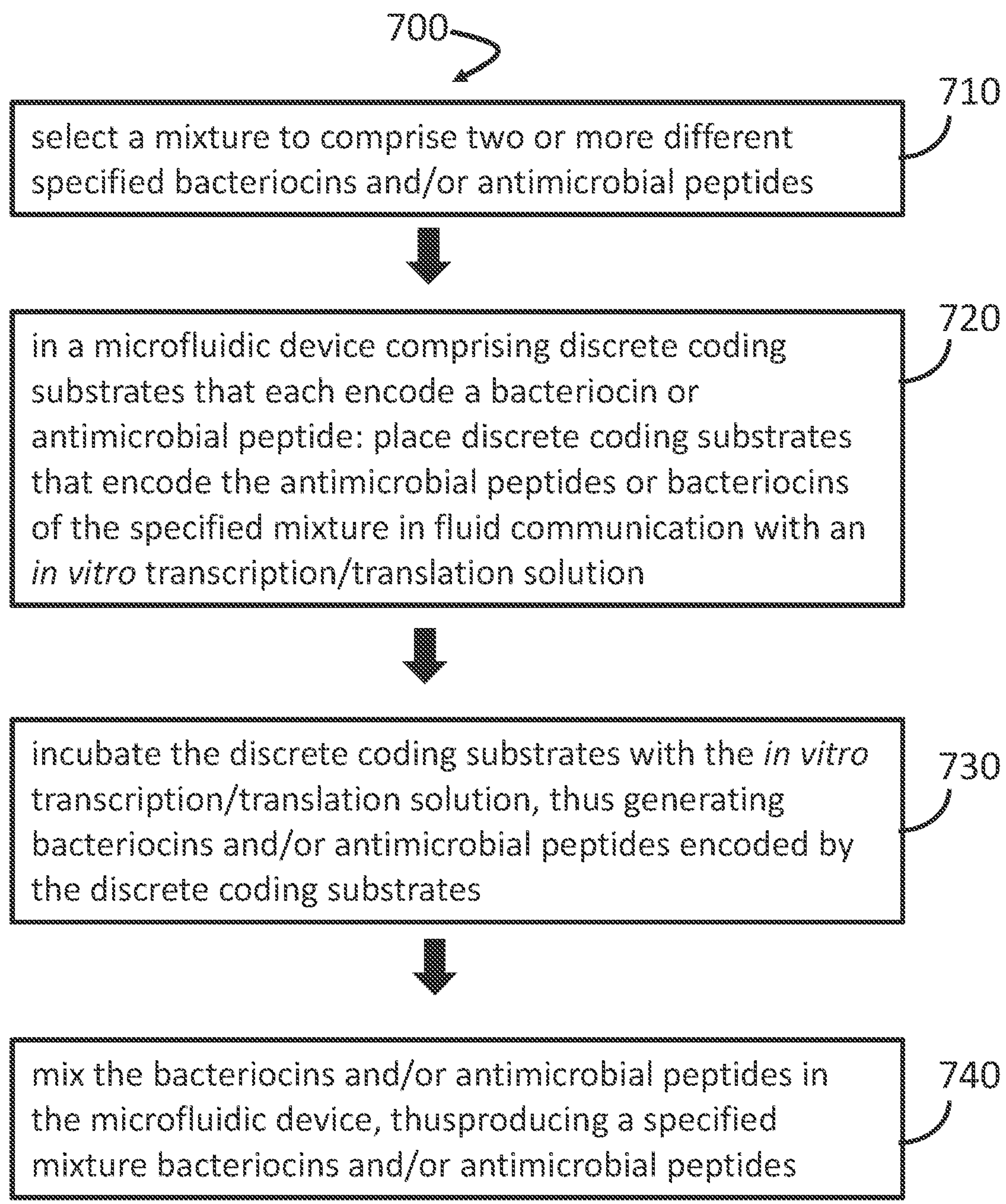
FIG. 7 is a flow diagram illustrating a method for producing a specified mixture of antimicrobial peptides and/or bacteriocins according to some embodiments herein.

FIG. 7 is a flow diagram illustrating a method for producing a specified mixture of antimicrobial peptides and/or bacteriocins 700 of some embodiments. The method can comprise selecting the specified mixture to comprise two or more different specified bacteriocins 710; in a microfluidic device comprising discrete coding substrates that each encode an antimicrobial peptide and/or bacteriocin: placing discrete coding substrates that encode the antimicrobial peptides and/or bacteriocins of the mixture, but not other discrete coding substrates, in fluid communication with an in vitro transcription/translation solution 720; incubating the discrete coding substrates with the in vitro transcription/translation solution, thus generating antimicrobial peptides and/or bacteriocins encoded by the discrete coding substrates 730; and mixing the bacteriocins in the microfluidic device, thus producing the specified mixture of antimicrobial peptides and/or bacteriocins 740.

In some embodiments, the method of producing a specified mixture of antimicrobial peptides and/or bacteriocins further comprises producing two or more submixtures each comprising a subset of the specified mixture of antimicrobial peptides and/or bacteriocins, and combining the submixtures to produce the specified mixture of antimicrobial peptides and/or bacteriocins. For example, the method can comprise performing (a) through (d) as follows to produce a first specified submixture of antimicrobial peptides and/or bacteriocins: (a) selecting a submixture to comprise two or more different specified antimicrobial peptides and/or bacteriocins; (b) in a microfluidic device comprising discrete coding substrates that each encode an antimicrobial peptide and/or bacteriocin: placing discrete coding substrates that encode the antimicrobial peptides and/or bacteriocins of the submixture, but not other discrete coding substrates, in fluid communication with an in vitro transcription/translation solution; (c) incubating the discrete coding substrates with the in vitro transcription/translation solution, thereby generating antimicrobial peptides and/or bacteriocins encoded by the discrete coding substrates; (d) mixing the antimicrobial peptides and/or bacteriocins in the microfluidic device, thereby producing the specified submixture of antimicrobial peptides and/or bacteriocins; repeating (a) through (d) to produce a second specified submixture of antimicrobial peptides and/or bacteriocins; and combining the first specified submixture of antimicrobial peptides and/or bacteriocins the second specified submixture of antimicrobial peptides and/or bacteriocins to produce the specified mixture of antimicrobial peptides and/or bacteriocins.

In some embodiments of the method of producing a specified mixture of antimicrobial peptides and/or bacteriocins, the selecting further comprises selecting a stoichiometry of the two or more different specified antimicrobial peptides and/or bacteriocins. In some embodiments, the specified mixture of antimicrobial peptides and/or bacteriocins comprises a specified stoichiometry, and combining the submixtures results in the specified stoichiometry. For example, a first submixture of bacteriocin "A" can be combined with a second submixture of bacteriocins "A" and "B" in a ratio of 1:1, to produce a specified mixture of antimicrobial peptides and/or bacteriocins "A" and "B" in a ratio of 2:1.

In some embodiments of the method of producing a specified mixture of antimicrobial peptides and/or bacteriocins, incubating the discrete coding substrates with the in vitro transcription/translation solution comprises flowing the in vitro transcription/translation solution to each discrete coding substrate encoding a bacteriocin of the mixture. In some embodiments, the method comprises placing the discrete coding substrates that encode the antimicrobial peptides and/or bacteriocins of the mixture, but not other discrete coding substrates, in fluid communication with an in vitro transcription/translation solution, comprising (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii). In some embodiments, mixing the antimicrobial peptides and/or bacteriocins in the microfluidic device comprises opening a valve to place the discrete coding substrates in fluid communication with a fluidic reservoir, wherein the antimicrobial peptides and/or bacteriocins are mixed in the fluidic reservoir.

In some embodiments, the method of producing a specified mixture of antimicrobial peptides and/or bacteriocins further comprises screening the mixture of antimicrobial peptides and/or bacteriocins in situ for a desired effect. In some embodiments, the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. For example, the pathogenic bacteria can be a rapidly evolving bacteria or a bacteria exhibiting antibiotic resistance, for example MRSA. In some embodiments, the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is performed in real time. For example, the screening can be performed withing 120 minutes, 60 minutes, 30 minutes, 15 minutes, 10 minutes, 5 minute, or 1 minute of the specified mixture of antimicrobial peptides and/or bacteriocins being generated. In some embodiments, the screening is for stabilization of a antimicrobial peptides and/or bacteriocins or for destruction of a microbial biofilm. In some embodiments, the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

Some microbial organisms can evolve quickly. Advantageously, the methods, devices and systems described herein can be used to combat rapidly evolving microbial organisms by rapidly producing mixtures of specified bacteriocins that are tailored to an infection of a subject by the microbial organism. In some embodiments, the subject is infected with a *Staphylococcus* such as MRSA, influenza virus, West Nile virus, or Zika virus. In some embodiments, the subject is diabetic and/or has an infection in an extremity such as a hand or foot.

Also envisioned is the use of antimicrobial peptides and/or bacteriocins in conjunction with conventional chemical antibiotics and/or phage antibiotics. In some embodiments, a method as described herein includes treatment of a microbial infection with a combination of a mixture of specified antimicrobial peptides and/or bacteriocins and a chemical antibiotic and/or a phage. Some embodiments comprise delivering the mixture of specified antimicrobial peptides and/or bacteriocins, in combination with a chemical antibiotic and/or a phage antibiotic, to a subject. Moreover, in some embodiments, a microfluidic device and/or system as described herein further comprises a conventional antibiotic, for example, an phage antibiotic or a small-molecule antibiotic such as a metabolite. In some embodiments, the microfluidic device and/or system further comprises a reservoir of antibiotic. The antibiotic can be selected from the group consisting of Amoxicillin, Amoxicillin/clavulanic acid (amoxicillin+clavulanic acid), Ampicillin, Benzathine benzylpenicillin, Benzylpenicillin, Cefalexin, Cefazolin, Cefixime, Cefotaxime, Ceftriaxone, Cloxacillin, Penicillin, Phenoxymethylpenicillin (penicillin V), Piperacillin/tazobactam, Procaine benzylpenicillin, Ceftazidimeα, Meropenemα, Aztreonamα, Imipenem/cilastatin, Amikacin, Azithromycin[, Chloramphenicol, Ciprofloxacin, Clarithromycin, Clindamycin, Doxycycline, Erythromycin, Gentamicin, Metronidazole, Nitrofurantoin, Spectinomycin, Trimethoprim/sulfamethoxazole, Trimethoprim, Vancomycin, Clofazimine, Dapsone, Rifampicin, Ethambutol/isoniazid, Ethambutol/isoniazid/pyrazinamide/rifampicin, Ethambutol/isoniazid/rifampicin, Isoniazid, Isoniazid/pyrazinamide/rifampicin, Isoniazid/rifampicin, Pyrazinamide, Rifabutin, Rifampicin, Rifapentine, Amikacin, Bedaquiline, Capreomycin, Clofazimine, Cycloserine, Delamanid, Ethionamide, Kanamycin, Levofloxacin, Linezolid, Moxifloxacin, p-aminosalicylic acid, rifabutin, rifapentine, rifalazil, rifaximin. Streptomycin, a phage, or a combination of two or more of these antibiotics.

Some embodiments of the method of producing a specified mixture of antimicrobial peptides and/or bacteriocins further comprise delivering the specified mixture of antimicrobial peptides and/or bacteriocins to a wound via a tubing or membrane, thereby cleaning or dressing the wound. For example, the specified mixture of antimicrobial peptides and/or bacteriocins may be placed on a cut or open sore, and then the cut or sore may be closed and/or bandaged.

Some embodiments of the method of producing a specified mixture of antimicrobial peptides and/or bacteriocins include a wash of the microfluidic device. The wash can be with a wash fluid. For example, some embodiments include an incubation step with a transcription solution, followed by a wash step, followed by a separate incubation with a translation solution.

In some embodiments, the method further comprises administering the specified mixture of antimicrobial peptides and/or bacteriocins to a subject in need of treatment. For example, the subject can have an infection such as an infected wound, a surgical incision, and infection of the extremities associated with diabetes, and/or a biofilm. The specified mixture of antimicrobial peptides and/or bacteriocins can be selected to target the microbial organism(s) of the infection (or selected as a candidate to target the microbial organism(s) of the infection), and can be produced in a microfluidic device as described herein. The specified mixture of antimicrobial peptides and/or bacteriocins can be administered to the subject as described herein, for example at or near the site of infection. In some embodiments, the microfluidic device itself is directly applied to the infection (for example, as a smart bandage as described herein). In some embodiments, the method further comprises selecting the subject as having an infection in need of treatment. The method can further comprise selecting a specified mixture of antimicrobial peptides and/or bacteriocins to target the infection, and producing the specified mixture in a microfluidic device as described herein. Also contemplated are medical uses of the microfluidic device for treating, inhibiting, preventing and/or reducing the risk of an infection. In some embodiments, the method (or medical use) comprises administering the specified mixture of antimicrobial peptides and/or bacteriocins and an antibiotic as described herein (for example a small molecule antibiotic and/or a phage) to the subject.

In some embodiments, the microfluidic device is for veterinary use, for example to produce a specified mixture of antimicrobial peptides and/or bacteriocins to treat an infection of a domestic animal or a farm animal, and/or to promote growth of the animal. Advantageously, uses of the specified mixture of antimicrobial peptides and/or bacteriocins in farm animals can avoid the use of antibiotics in food production. As noted in World Health Organization recommendations, doing so can reduce the development and proliferation of antibiotic-resistant microbial o.

In some embodiments, the microfluidic device is for use in a small fermenter (e.g., a fermenter less than or equal to 100 liters, 50 liters, 40 liters, 30 liters, 20 liters, 10 liters, 5 liters, 2 liters, or 1 liters in volume, including ranges between any two of the listed values), for example to produce specified mixtures of bacteriocins to target a contaminating organism in the small fermenter.

In some embodiments, the microfluidic device is for use in sterilizing medical devices. For example, the specified mixture of antimicrobial peptides and/or bacteriocins can be selected to target contaminants, such as MRSA on the medical device, and can be applied to the medical device on-site, for example at a hospital. In some embodiments, the microfluidic device is for use in pre-treating an implant with a specified mixture of antimicrobial peptides and/or bacteriocins, so as to inhibit or prevent infection and/or biofilm formation.

In some embodiments, the microfluidic device is for use in defense against a pathogen, for example in an epidemic, or in bioterrorism defense. Specified mixtures of bacteriocins directed against the pathogen (e.g., bioterrorism agent) can be distributed to systems as described herein manually or automatically, and the specified mixtures of bacteriocins targeting the pathogen (e.g., bioterrorism agent) can be produced in microfluidic devices at or near the site of the pathogen (e.g., bioterrorism agent).

In some embodiments, the method further comprises mixing the specified mixture of antimicrobial peptides and/or bacteriocins with another reagent or antimicrobial compound to produce a final mixture. For example, the specified mixture of antimicrobial peptides and/or bacteriocins may be combined with a chemical or a natural fluid. In some embodiments, the specified mixture of antimicrobial peptides and/or bacteriocins is combined with an antibiotic drug or phage to produce the final mixture. In some embodiments, the final mixture is part of a formulation for a therapy such as, for example, an anti-pain therapy.

Example 1

A nucleic acid is provided encoding one copy of the coding sequence of the bacteriocin Subtilin, two copies of the coding sequence of the bacteriocin Bavaricin-MN, and one copy of the coding sequence for the quorum sensing factor BsEDF all in a single reading frame. The nucleic acid further encodes cleavage sites for Caspase 2 in the same reading frame, which flank each bacteriocin coding sequence and the BsEDF coding sequence. As such, the nucleic acid encodes a pro-polypeptide that comprises one copy of Subtilin, two copies of Bavaricin-MN, and one copy of BsEDF, each flanked by Caspase 2 cleavage sites. The nucleic acid is expressed in an *E. coli* cell, which does not comprise coding sequence for the immunity modulators for either of Subtilosin-A or Bavaricin-MN, and thus does not produce functional immunity modulators for these bacteriocins. The pro-polypeptide is produced by the *E. coli*, and contains Subtilin and Bavaricin-MN in their inactive forms. The pro-polypeptide is purified by way of its His tag using a nickel-containing substrate. The purified pro-polypeptide is then cleaved using Caspase 2, producing a composition that comprises Subtilin, Bavaricin-MN, and BsEDF in a 1:2:1 ratio. The composition is added to an industrial feedstock to prevent the proliferation of undesired microbial organisms (via the bacteriocins), and to control the growth of genetically modified *B. subtilis* (via the BsEDF).

Example 2

It is determined that a ratio of the bacteriocins Mundticin, Serracin-P, Thuricin-17, and Plantaricin J of 1:2:3:4 is useful for targeting a population of undesired microbial cells in animal food during storage. A nucleic acid encoding one copy of the coding sequence of Mundticin, two copies of the coding sequence of Serracin-P, three copies of the coding sequence of Thuricin-17, and four copies of the coding sequence Plantaricin J is synthesized. All of the bacteriocin coding sequences are in a single reading frame, and each bacteriocin coding sequence is separated from the other bacteriocin coding sequences by sequences encoding Granzyme B cleavage sites. The nucleic acid also encodes GST on the 3' end of the open reading frame, and immediately downstream of a Granzyme B cleavage site coding sequence. Thus, the nucleic acid encodes a pro-peptide comprising Mundticin, Serracin-P, Thuricin-17, Plantaricin J in a 4:3:2:1 ratio, respectively, along with a C-terminal GST tag. The nucleic acid is expressed in an in vitro translation system, so as to produce the pro-polypeptide. The pro-polypeptide is purified using GSH-coated beads. The pro-polypeptide is then cleaved by GranzymeB, producing a solution comprising active Mundticin, Serracin-P, Thuricin-17, and Plantaricin J in a ratio of 1:2:3:4, respectively. The cleavage site immediately adjacent to the GST tag is also cleaved, so that none of the bacteriocins comprises GST. The composition comprising the bacteriocins in the 1:2:3:4 ratio is added to the animal food, thus targeting the population of undesired microbial cells in the animal food.

Example 3

A microfluidic device is provided that comprises 244 chambers. Each chamber comprises a discrete coding substrate. Each discrete coding substrate is a chip, each chip comprising 10,000-20,000 DNAs. Molecules, each encoding a bacteriocin of Table 1.2. The DNA molecules in each chamber encode separate bacteriocins compared to the DNA molecules in each of the other chambers. Each of the chambers is connected by a valve to a fluidic reservoir. The fluidic reservoir is also connected by a valve to a transcription/translation solution housed in a transcription/translation solution chamber. The device includes a processor configured to open the valve connecting the fluidic reservoir to the transcription/translation solution to allow the transcription/translation solution to flow into the fluidic reservoir, close the valve connecting the fluidic reservoir to the transcription/translation solution to prevent fluid from flowing back into the transcription/translation solution chamber, open valves connecting the fluidic reservoir to chambers housing the selected coding substrates to allow transcription/translation solution to flow from the fluidic reservoir into the chambers housing the selected coding substrates, incubate selected coding substrates the at 37° C. thereby producing bacteriocins from the selected coding substrates, and open one or more valves such as the valves connecting the coding substrates to the fluidic reservoir, to release bacteriocins into the fluidic reservoir and/or a receptacle.

The device is connected electronically or wirelessly to a user input device such as a phone, touchscreen, keyboard, button, mouse, or computer. The processor selects bacteriocins based on user input entered into the user input device, or according to a pre-programmed set of instructions.

Example 4

A device as described herein is used to make a first specified mixture of bacteriocins. The bacteriocins are applied to a transdermal patch that is applied to a subject with a burn. If the burn on the subject does not heal, the device is used to make a second specified mixture of bacteriocins different from the first specified mixture of bacteriocins. The second specified mixture of bacteriocins is then applied to a new transdermal patch that is applied to the burn. Multiple variations of specified mixtures of bacteriocins may be applied to the burn, or to burns of various subjects, depending on whether a particular formulation of bacteriocins is expected to be beneficial for the healing of the burn, or on whether a particular formulation is desired to be tested.

OPTIONS

In addition to the items above, the following options are set forth:

1. A method of making bacteriocins, the method comprising expressing a nucleic acid comprising:

a bacteriocin coding sequence and a second polypeptide coding sequence in a single reading frame, wherein the second polypeptide is a bacteriocin or signal molecule; and cleavage site coding sequences disposed between the bacteriocin coding sequence and the second polypeptide coding sequence in the single reading frame, thereby generating a pro-polypeptide comprising the bacteriocin, second polypeptide, and cleavage sites disposed therebetween.

2. The method of option 1, further comprising cleaving the cleavage site, thereby separating the bacteriocin and second polypeptide from each other, and thereby producing a composition comprising the bacteriocin and the second polypeptide.

3. The method of any one of options 1 or 2, wherein the second polypeptide is the bacteriocin.

4. The method of any one of options 1 or 2, wherein the second polypeptide is the signal molecule.

5. The method of any one of options 1-4, wherein the expressing is performed by a microbial cell that does not produce a functional immunity modulator for at least one of the bacteriocins.

6. The method of option 5, wherein the microbial cell does not produce a functional immunity modulator for any of the bacteriocins.

7. The method of any one of options 1-4, wherein the expressing is performed in vitro.

8. The method of any one of options 1-7, wherein at least one of the bacteriocins is inactive when it is part of the pro-polypeptide.

9. The method of any one of options 2-8, further comprising isolating the pro-polypeptide prior to the cleaving.

10. The method of option 9, wherein said isolating comprises affinity purifying the pro-polypeptide, wherein the affinity purification comprises binding an affinity tag encoded by the nucleic acid.

11. The method of any one of options 1-8, wherein the nucleic acid comprises three bacteriocin coding sequences in the single reading frame.

12. The method of any one of options 1-3 or 5-11, wherein at least two of the bacteriocins are different from each other.

13. The method of any one of options 2-12, wherein the composition comprises a desired ratio of bacteriocins, or a desired ratio of signal molecules and bacteriocins.

14. The method of option 13, wherein at least a portion the desired ratio is achieved by a ratio of bacteriocin coding sequences, or bacteriocin and signal molecule coding sequences in the single reading frame of the nucleic acid.

15. The method of any one of options 12-14, wherein the desired ratio is further achieved by a second nucleic acid comprising a ratio of bacteriocins coding sequences and further comprising cleavage sites between the bacteriocin coding sequences.

16. The method of option 15, wherein the desired ratio is achieved by a ratio of bacteriocin coding sequences in the single reading frame of the nucleic acid.

17. The method of any one of options 12-16, wherein the desired ratio of bacteriocins is selected to target an undesired microbial organism or population of undesired microbial organisms, and/or wherein the desired ratio of bacteriocins is selected to balance a population of a microbiome of an animal, a human organ, a plant root, or soil.

18. The method of any one of options 12-16, wherein the desired ratio of bacteriocins and signal molecules is selected to control genetic drift of a target microbial cell, and stimulate growth or production of a producing cell.

19. The method of any one of options 10-18, wherein the desired ratio comprises a ratio of a first bacteriocin to a second bacteriocin of 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, wherein the first bacteriocin is different from the second bacteriocin.

20. The method of any one of options 1-18, wherein the cleavage sites are for a wild-type, variant, or synthetic cleavage enzyme, such as an endopeptidase.

21. The method of any one of options 1-20, wherein the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, lodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin.

22. The method of any one of options 1-21, wherein the cleavage sites are for a single cleavage enzyme, and wherein the cleavage enzyme does not cleave within the bacteriocins.

23 The method of any one of options 1-22, wherein at least one cleavage site is for a first cleavage enzyme, and another cleavage site is for a second cleavage enzyme, and wherein neither the first nor the second cleavage enzyme cleaves within the bacteriocins.

24. The method of any one of options 1-23, wherein the composition further comprises a signal molecule, and wherein the nucleotide further comprises:

a coding sequence for a signal molecule in the single reading frame; and a cleavage site sequence disposed between the signal molecule and a bacteriocin coding sequence.

25. The method of any one of options 1-2 or 4-24, wherein the signal molecule is selected from the group consisting of: quorum sensing molecules, signal transduction receptor ligands, growth factors, hormones, and cytokines, and wherein the signal molecule can be wild-type, mutant, or synthetic.

26. The method of any one of options 1-25, wherein the pro-polypeptide has a length of no more than about 2000 amino acids.

27. The method of any one of options 1-26, further comprising expressing a second nucleic acid encoding a second pro-polypeptide comprising two bacteriocins and cleavage sites disposed therebetween, wherein the second pro-polypeptide is different from the first pro-polypeptide.

28. The method of any one of options 2-19 or 24-27, wherein cleaving the pro-polypeptide comprises physical treatment of a peptide linker comprised by the cleavage site, wherein the peptide linker is chemical-sensitive or pH sensitive.

29. The method of any one of options 1-28, further comprising chemically modifying the bacteriocins.

30. The method of option 29, wherein the bacteriocins are chemically modified co-translationally.

31. The method of any one of options 2-30, further comprising chemically modifying the bacteriocins following the cleaving.

32. An isolated nucleic acid comprising:

a bacteriocin coding sequence and a second polypeptide coding sequence in a single reading frame, wherein the second polypeptide is a bacteriocin or a signal molecule; and cleavage site coding sequences disposed between the bacteriocin coding sequences and in the single reading frame.

33. The isolated nucleic acid of option 32, wherein the second polypeptide is the bacteriocin.

34. The isolated nucleic acid of option 32, wherein the second polypeptide is the signal molecule.

35. The isolated nucleic acid of any one of options 32-34, wherein the cleavage site coding sequences encode cleavage sites for a cleavage enzyme, and wherein the bacteriocin coding sequences do not comprise cleavage sites for the cleavage enzyme.

35. The isolated nucleic acid of any one of options 32-35, wherein the nucleic acid comprises three bacteriocin coding sequences in the single reading frame.

36. The isolated nucleic acid of any one of options 32-35, wherein the nucleic acid comprises at least 5, 10, 15, or 20 bacteriocin sequences in the single reading frame.

37. The isolated nucleic acid of any one of options 32-36, wherein a cleavage site coding sequence is disposed in frame between any two adjacent bacteriocin and/or signal molecule coding sequences.

38. The isolated nucleic acid of any one of options 32-36, wherein at least two of the bacteriocin sequences encode different bacteriocins from each other.

39. The isolated nucleic acid of option 35, wherein the three bacteriocin sequences are present in a desired ratio or portion of a desired ratio.

40. The isolated nucleic acid of option 39, wherein the desired ratio is selected to target an undesired microbial organism or population of undesired microbial organisms.

41. The isolated nucleic acid of option 39 wherein the desired ratio of bacteriocins is selected to balance a population of a microbiome of an animal, a human organ, a plant root, or soil.

42. The isolated nucleic acid of any one of options 32-41, wherein the cleavage sites are for a wild-type, variant, or synthetic cleavage enzyme, such as an endopeptidase.

43. The isolated nucleic acid of any one of options 32-42, wherein the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, lodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin.

44. The isolated nucleic acid of any one of options 42-43, wherein a first cleavage site coding sequence encodes a first cleavage site is for a first cleavage enzyme, and wherein a second cleavage site coding sequence encodes a cleavage site for a second cleavage enzyme that is different from the first cleavage enzyme, and wherein the bacteriocins do not comprise a cleavage site for any of the first or second cleavage enzyme.

45. The isolated nucleic acid of any one of options 32-41, wherein the cleavage sites comprise a pH- or chemically-sensitive linker.

46. The isolated nucleic acid of any one of options 32, 33, or 35-44, wherein the isolated nucleic acid further comprises a coding sequence for a signal molecule in the single reading frame, wherein a cleavage site coding sequences is disposed between the coding sequence for signal molecule and an adjacent bacteriocin coding sequence.

47. The isolated nucleic acid of any one of options 32 or 24-46, wherein the signal molecule is selected from the group consisting of: quorum sensing molecules, signal transduction receptor ligands, growth factors, hormones, and cytokines, and wherein the signal molecule can be wild-type, mutant, or synthetic.

48. A microbial cell, comprising a promoter operably linked to the isolated nucleic acid of any one of options 32-47, wherein the isolated microbial cell does not produce a functional immunity modulator for a bacteriocin encoded by the isolated nucleic acid.

49. The microbial cell of option 48, wherein the cell does not produce a functional immunity modulator for any of the bacteriocins encoded by the isolated nucleic acid.

50. An isolated pro-polypeptide comprising:

two bacteriocins, and/or a bacteriocin and a signal molecule;

cleavage sites disposed between the bacteriocins and/or the bacteriocin and the signal molecule; and an affinity tag.

51. The isolated pro-polypeptide of option 50, wherein the pro-polypeptide comprises the two bacteriocins.

52. The isolated pro-polypeptide of option 50, wherein the pro-polypeptide comprises the bacteriocin and the signal molecule.

53. The isolated pro-polypeptide of any one of options 50-52, wherein the pro-polypeptide comprises three bacteriocins.

54. The isolated pro-polypeptide of any one of options 50-52, wherein the pro-polypeptide comprises at least 5, 10, 15, or 20 bacteriocins.

55. The isolated pro-polypeptide of any one of options 50, 51, 53, or 54, wherein the pro-polypeptide comprises a signal molecule.

56. The isolated pro-polypeptide of any one of options 50-55, wherein the cleavage sites are for a cleavage enzyme, and wherein the bacteriocin coding sequences do not comprise cleavage sites for the cleavage enzyme.

57. The isolated pro-polypeptide of any one of options 50-55, wherein a cleavage site is for a first cleavage enzyme, and wherein another cleavage site is for a second cleavage enzyme different from the first cleavage enzyme, and wherein the bacteriocins do not comprise a cleavage site for any of the first or second cleavage enzymes.

58. The isolated pro-polypeptide of any one of options 50-57, further comprising a co-translational or post-translational modification.

59. A composition comprising two more bacteriocins in a ratio selected to target a microbial cell or populations of microbial cells, wherein each of the bacteriocins comprises, at its N-terminus, C-terminus, or N-terminus and C-terminus, a portion of a cleavage sequence that has been cleaved, wherein the portions of cleavage sequences at the N-, C-, or N- and C-termini of the bacteriocins are for cleavage sites of the same or different cleavage enzyme.

60. The composition of option 59, wherein at least some of the bacteriocins further comprise a tag.

61. The composition of option 60, wherein the tag is selected from the group consisting of affinity tags, a signal sequence, or a stability tag.

62. The composition of any one of options 59-61, further comprising a signal molecule in a desired ratio with the bacteriocins, wherein the signal molecule comprises, at its N-terminus, C-terminus, or N-terminus and C-terminus, a portion of a cleavage sequence that has been cleaved, wherein the portions of cleavage sequences at the N-, C-, or N- and C-termini of the signal molecule are for cleavage sites of the same or different cleavage enzymes 63. The composition of any one of options 59-62, wherein the ratio of bacteriocins is selected to target an undesired microbial organism or population of undesired microbial organisms.

64. The composition of any one of options 59-63, wherein the ratio of bacteriocins is selected to balance a population of a microbiome of an animal, a human organ, a plant root, or soil.

65. The composition of option 64, wherein the composition is formulated for topical or oral administration to a human subject.

66. The composition of option 64 or 65, wherein the composition is formulated for use in balancing a population of a microbiome of an animal, a human organ, a plant root, or soil.

67. A method for producing a specified mixture of bacteriocins and/or antimicrobial peptides, the method comprising:

selecting the mixture to comprise two or more different bacteriocins and/or antimicrobial peptides;

in a microfluidic device comprising discrete coding substrates that each encode a bacteriocin or antimicrobial peptide: placing discrete coding substrates that encode the antimicrobial peptides or bacteriocins of the specified mixture in fluid communication with an in vitro transcription/translation solution;

incubating the discrete coding substrates with the in vitro transcription/translation solution, thereby generating antimicrobial peptides and/or bacteriocins encoded by the discrete coding substrates; and mixing the antimicrobial peptides and/or bacteriocins in the microfluidic device, thereby producing the specified mixture of antimicrobial peptides and/or bacteriocins.

68. The method of option 67, further comprising:

producing two or more submixtures each comprising a subset of the specified mixture of antimicrobial peptides and/or bacteriocins; and combining the submixtures to produce the specified mixture of antimicrobial peptides and/or bacteriocins.

69. The method of option 67 or 68, wherein selecting further comprises selecting a stoichiometry of the two or more different antimicrobial peptides and/or bacteriocins of the specified mixture.

70. The method of any one of options 68-69, wherein the specified mixture of antimicrobial peptides and/or bacteriocins comprises a specified stoichiometry, and wherein combining the submixtures results in the specified stoichiometry.

71. The method of any one of options 67-70, wherein the discrete coding substrates are comprised within separate chambers.

72. The method of any one of options 67-71, wherein the discrete coding substrates comprise nucleic acids immobilized thereon.

73. The method of any one of options 67-72, wherein discrete coding substrated encoding antimicrobial peptides and/or bacteriocins of the specified mixture, but not other discrete coding substrates, are placed in fluidic communication with the in vitro transcription/translation solution.

74. The method of any one of options 67-73, wherein incubating the discrete coding substrates with the in vitro transcription/translation solution comprises flowing the in vitro transcription/translation solution into each chamber.

75. The method of any one of options 67-74, wherein the in vitro transcription/translation solution comprises an in vitro transcription reagent and/or an in vitro translation reagent.

76. The method of any one of options 67-75, wherein placing the discrete coding substrates that encode the antimicrobial peptides and/or bacteriocins of the specified mixture in fluid communication with an in vitro transcription/translation solution comprises (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii).

77. The method of any one of options 67-76, wherein mixing the antimicrobial peptides and/or bacteriocins in the microfluidic device comprises opening a valve to place the discrete coding substrates in fluid communication with a fluidic reservoir, wherein the antimicrobial peptides and/or bacteriocins are mixed in the fluidic reservoir.

78. The method of any one of options 67-77, further comprising screening the mixture of antimicrobial peptides and/or bacteriocins in situ for a desired effect.

79. The method of option 78, wherein the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

80. The method of option 78, wherein the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

81. The method of option 78, wherein said screening is performed in real time.

82. The method of option 78, the screening is for stabilization of an antimicrobial peptide and/or bacteriocin or for destruction of a microbial biofilm.

83. The method of option 82, wherein one or more of the discrete coding substrates encodes an auxiliary protein with anti-protease activity.

84. The method of option 78, wherein the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

85. The method of option 84, wherein one or more of the discrete coding substrates encodes an auxiliary protein that attracts the non-pathogenic microbial organism, or that enhances growth or reproduction of the non-pathogenic microbial organism in the microbiome of a subject.

86. The method of any one of options 67-85, further comprising delivering the specified mixture of antimicrobial peptides and/or bacteriocins to a wound via a tubing or membrane, thereby cleaning or dressing the wound.

87. A microfluidic device for producing a specified mixture of antimicrobial peptides and/or bacteriocins, the device comprising:

discrete coding substrates that each encode an antimicrobial peptide and/or bacteriocin;

an in vitro transcription/translation solution;

a fluidic reservoir; and valves each disposed on a fluidic path between a discrete coding substrate and the fluidic reservoir, each valve configured to regulate flow between the discrete coding substrate and the fluidic reservoir, wherein the device is configured to be placed in data communication with a processor configured to:

based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir;

permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;

permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

88. The microfluidic device of option 87, wherein:

the specified mixture of antimicrobial peptides and/or bacteriocins comprises two or more submixtures each comprising a subset of antimicrobial peptides and/or bacteriocins; and the processor is configured to permit flow of each submixture into the fluidic reservoir, thereby producing the specified mixture of antimicrobial peptides and/or bacteriocins.

89. The microfluidic device of option 88, wherein the specified mixture of antimicrobial peptides and/or bacteriocins comprises a sum of the subsets of antimicrobial peptides and/or bacteriocins in a specified stoichiometry, and wherein combination of the submixtures yields the specified stoichiometry.

90. The microfluidic device of any one of options 87-89, wherein the discrete coding substrates are comprised within separate chambers.

91. The microfluidic device of any one of options 87-90, wherein the discrete coding substrates comprise nucleic acids immobilized thereon.

92. The microfluidic device of option 91, wherein the discrete coding substrates comprise a material or product selected from the group consisting of a chip, bead, nanoparticle, well, membrane, matrix, plastic, metal, glass, polymer, polysaccharide, and paramagnetic compound.

93. The microfluidic device of any one of options 87-92, wherein the in vitro transcription/translation solution comprises an in vitro transcription reagent and/or an in vitro translation reagent.

94. The microfluidic device of any one of options 87-93, wherein the device is portable.

95. The microfluidic device of any one of options 87-94, wherein one or more of the discrete coding substrates encodes an auxiliary protein comprising a protein for stabilization of antimicrobial peptides and/or bacteriocins, a protein with anti-protease activity, or a protein for destruction of a microbial biofilm.

96. The microfluidic device of any one of options 87-95, wherein one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

97. The microfluidic device of any one of options 87-96, wherein the fluidic reservoir is configured to be placed in fluid communication with a tissue of a subject.

98. The microfluidic device of any one of option 97, wherein the tissue comprises a microbiome, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

99. The microfluidic device of any one of options 87-98, wherein the fluidic reservoir is configured to be placed in fluid communication with a wound of a subject.

100. The microfluidic device of any one of options 97-99, further comprising a fluidic passage such as a tube or membrane through which the fluidic reservoir is in fluid communication with the microbiome or wound, through which the specified mixture of antimicrobial peptides and/or bacteriocins is capable of being delivered to the microbiome or wound.

101. The microfluidic device of any one of options 87-100, wherein each discrete coding substrate encodes a different antimicrobial peptide and/or bacteriocin.

102. The microfluidic device of any one of options 87-102, wherein a discrete coding substrate comprises the isolated nucleic acid of any of options 32-49.

103. The microfluidic device of any one of options 87-102, wherein a discrete coding substrate encodes the isolated pro-polypeptide of any one of options 50-58.

104. The microfluidic device of any one of options 87-103, further comprising the processor.

105. A system comprising:

the microfluidic device of any one of options 87-104, and a processor configured to:

based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir;

permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;

permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

106. The system of option 105, wherein the microfluidic device is comprised by a cartridge (or is a cartridge), the system comprising a coupling for placing the cartridge in data communication with the processor.

107. The system of any one of options 105-106 further comprising a reservoir of in vitro transcription/translation solution.

108. A microfluidic device for producing a specified mixture of antimicrobial peptides and/or bacteriocins, the device comprising:

discrete coding substrates that each encode an antimicrobial peptide and/or bacteriocin;

valves each disposed on a fluidic path connected to a discrete coding substrate, each valve configured to regulate flow to or from the discrete coding substrate, and wherein the device is configured to be placed in fluid communication with a fluidic reservoir or an in vitro transcription/translation solution.

109. The microfluidic device of option 108 further comprising a fluidic reservoir or an in vitro transcription/translation solution.

110. The method of option 78, wherein the desired effect comprises antimicrobial activity.

111. The method of option 110, further comprising screening 1, 2, 3, 4, 5, 6, 7, 8, 9, or 10 different mixtures against a microbial infection.

112. The method of any one of options 67-86 further comprising delivering the mixture of specified antimicrobial peptides and/or bacteriocins, in combination with a chemical antibiotic and/or a phage antibiotic, to a subject.

113. The method of any one of options 67-86 wherein the in vitro transcription/translation solution is lyophyilized, and further comprising adding water to the in vitro transcription/translation solution.

114. The microfluidic device of any one of claims 87-104, further comprising a reservoir of chemical or phage antibiotics configured to mix with the mixture of specified antimicrobial peptides and/or bacteriocins.

115. The microfluidic device of any one of options 87-104, further comprising an antibiotic comprising a chemical antibiotic and/or a phage.

116. The microfluidic device of any one of options 87-104, wherein the in vitro transcription/translation solution is lyophyilized.

117. The system of any one of options 105-107 further comprising a reservoir of chemical or phage antibiotics configured to mix with the mixture of specified antimicrobial peptides and/or bacteriocins.

118. The system of any one of options 105-107 further comprising an antibiotic comprising a chemical antibiotic and/or a phage.

119. The system of option 107 wherein the in vitro transcription/translation solution is lyophyilized.

120. The method of any one of options 67-86 and 110-113, wherein the method is for making a specified mixture of antimicrobial peptides that does not comprise bacteriocins.

121. The method of any one of options 67-86 and 110-113, wherein the method is for making a specified mixture of bacteriocins that does not comprise antimicrobial peptides.

122. The method of any one of options 67-86 and 110-113, wherein the method is for making a specified mixture of bacteriocins and antimicrobial peptides.

123. The microfluidic device of any one of options 87-104, 108, 109, and 114-116, wherein the device is for producing a specified mixture of bacteriocins that does not comprise antimicrobial peptides.

124. The microfluidic device of any one of options 87-104, 108, 109, and 114-116, wherein the device is for producing a specified mixture of antimicrobial peptides that does not comprise bacteriocins.

125. The microfluidic device of any one of options 87-104, 108, 109, and 114-116, wherein the device is for producing a specified mixture of antimicrobial peptides and bacteriocins.

126. The system of any one of options 105-107 and 117-119, wherein the system is for producing a specified mixture of bacteriocins that does not comprise antimicrobial peptides.

127. The system of any one of options 105-107 and 117-119, wherein the system is for producing a specified mixture of antimicrobial peptides that does not comprise bacteriocins.

128. The system of any one of options 105-107 and 117-119, wherein the system is for producing a specified mixture of antimicrobial peptides and bacteriocins.

In at least some of the embodiments described herein, one or more elements used in an embodiment can interchangeably be used in another embodiment unless such a replacement is not technically feasible. It will be appreciated by those skilled in the art that various other omissions, additions and modifications may be made to the methods and structures described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase “A or B” will be understood to include the possibilities of “A” or “B” or “A and B.”

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

SEQUENCE LISTING

```
Sequence total quantity: 750
SEQ ID NO: 1            moltype = AA  length = 40
FEATURE                 Location/Qualifiers
source                  1..40
                        mol_type = protein
                        organism = Enterococcus faecalis
SEQUENCE: 1
WLPPAGLLGR CGRWFRPWLL WLQSGAQYKW LGNLFGLGPK                         40

SEQ ID NO: 2            moltype = AA  length = 5
FEATURE                 Location/Qualifiers
REGION                  1..5
                        note = N-terminal motif of class terminal IIa
VARIANT                 3
                        note = Xaa = any amino acid
source                  1..5
                        mol_type = protein
                        organism = synthetic construct
SEQUENCE: 2
YGXGV                                                               5

SEQ ID NO: 3            moltype = AA  length = 135
FEATURE                 Location/Qualifiers
REGION                  1..135
                        note = Hybrid bacteriocin Ent35-MccV
source                  1..135
                        mol_type = protein
                        organism = synthetic construct
SEQUENCE: 3
GKYYGNGVSC NKKGCSVDWG RAIGIIGNNS AANLATGGAA GWKSGGGASG RDIAMAIGTL  60
SGQFVAGGIG AAAGGVAGGA IYDYASTHKP NPAMSPSGLG GTIKQKPEGI PSEAWNYAAG  120
RLCNWSPNNL SDVCL                                                    135

SEQ ID NO: 4            moltype = AA  length = 46
FEATURE                 Location/Qualifiers
source                  1..46
                        mol_type = protein
                        organism = Lactobacillus acidophilus
SEQUENCE: 4
MISSHQKTLT DKELALISGG KTHYPTNAWK SLWKGFWESL RYTDGF                  46

SEQ ID NO: 5            moltype = DNA  length = 141
FEATURE                 Location/Qualifiers
source                  1..141
                        mol_type = genomic DNA
                        organism = Lactobacillus acidophilus
SEQUENCE: 5
atgatttcat ctcatcaaaa aacgttaact gataaagaat tagcattaat ttctgggggg  60
aaaacgcact acccgactaa tgcatggaaa agtctttgga aaggtttctg ggaaagcctt  120
cgttatactg acggttttta g                                             141
```

```
SEQ ID NO: 6            moltype = AA  length = 81
FEATURE                 Location/Qualifiers
source                  1..81
                        mol_type = protein
                        organism = Lactobacillus acidophilus
SEQUENCE: 6
MISMISSHQK TLTDKELALI SGGKTYYGTN GVHCTKKSLW GKVRLKNVIP GTLCRKQSLP  60
IKQDLKILLG WATGAFGKTF H                                            81

SEQ ID NO: 7            moltype = DNA  length = 246
FEATURE                 Location/Qualifiers
source                  1..246
                        mol_type = genomic DNA
                        organism = Lactobacillus acidophilus
SEQUENCE: 7
atgatttcaa tgatttcatc tcatcaaaaa acgttaactg ataaagaatt agcattaatt  60
tctgggggga aaacgtacta tggtactaat ggtgtgcatt gtactaaaaa gagtctttgg  120
ggtaaagtac gcttaaaaaa cgtgattcct ggaactcttt gtcgtaagca atcgttgccg  180
atcaaacagg atttaaaaat tttactgggc tgggctacag gtgcttttgg caagacattt  240
cattaa                                                             246

SEQ ID NO: 8            moltype = AA  length = 60
FEATURE                 Location/Qualifiers
source                  1..60
                        mol_type = protein
                        organism = Lactobacillus acidophilus
SEQUENCE: 8
MDKKTKILFE VLYIICIIGP QFILFVTAKN NMYQLVGSFV GIVWFSYIFW YIFFKQHKKM  60

SEQ ID NO: 9            moltype = DNA  length = 183
FEATURE                 Location/Qualifiers
source                  1..183
                        mol_type = genomic DNA
                        organism = Lactobacillus acidophilus
SEQUENCE: 9
atggataaga aaacaaaaat attatttgaa gtattataca tcatctgtat aataggccct  60
caatttatat tatttgtgac tgcaaaaaac aatatgtatc agttggtggg ttcgtttgtt  120
ggaatagtat ggttttcgta tattttttgg tatatttttt tcaaacaaca taaaaaaatg  180
tag                                                                183

SEQ ID NO: 10           moltype = AA  length = 65
FEATURE                 Location/Qualifiers
source                  1..65
                        mol_type = protein
                        organism = Lactobacillus gasseri
SEQUENCE: 10
MALKTLEKHE LRNVMGGNKW GNAVIGAATG ATRGVSWCRG FGPWGMTACA LGGAAIGGYL  60
GYKSN                                                              65

SEQ ID NO: 11           moltype = DNA  length = 198
FEATURE                 Location/Qualifiers
source                  1..198
                        mol_type = genomic DNA
                        organism = Lactobacillus gasseri
SEQUENCE: 11
atggctttaa aaacattaga aaaacatgaa ttaagaaatg taatgggtgg aaacaagtgg  60
gggaatgctg taataggagc tgctacggga gctactcgcg gagtaagttg gtgcagagga  120
ttcggaccat ggggaatgac tgcctgtgcg ttaggaggtg ctgcaattgg aggatatctg  180
ggatataaga gtaattaa                                                198

SEQ ID NO: 12           moltype = AA  length = 51
FEATURE                 Location/Qualifiers
source                  1..51
                        mol_type = protein
                        organism = Staphylococcus aureus
SEQUENCE: 12
MSWLNFLKYI AKYGKKAVSA AWKYKGKVLE WLNVGPTLEW VWQKLKKIAG L           51

SEQ ID NO: 13           moltype = DNA  length = 156
FEATURE                 Location/Qualifiers
source                  1..156
                        mol_type = genomic DNA
                        organism = Staphylococcus aureus
SEQUENCE: 13
atgagttggt taaatttttt aaaatacatc gctaaatatg gcaaaaaagc ggtatctgct  60
gcttggaagt acaaaggtaa agtattagaa tggcttaatg ttggtcctac tcttgaatgg  120
gtatggcaaa aattaaagaa aattgctgga ttataa                            156
```

```
SEQ ID NO: 14          moltype = AA  length = 61
FEATURE                Location/Qualifiers
source                 1..61
                       mol_type = protein
                       organism = Enterococcus avium
SEQUENCE: 14
MTRSKKLNLR EMKNVVGGTY YGNGVSCNKK GCSVDWGKAI SIIGNNSAAN LATGGAAGWK  60
S                                                                 61

SEQ ID NO: 15          moltype = DNA  length = 186
FEATURE                Location/Qualifiers
source                 1..186
                       mol_type = genomic DNA
                       organism = Enterococcus avium
SEQUENCE: 15
atgacaagat caaaaaaatt aaatttacgc gaaatgaaga atgttgttgg tggtacctac  60
tatggaaatg gtgtatcttg taacaagaaa ggctgttcag ttgactgggg caaagccatc  120
agtattatag gaaataattc cgcagcaaac ttagcaactg gtggtgctgc tggttggaag  180
tcataa                                                            186

SEQ ID NO: 16          moltype = AA  length = 67
FEATURE                Location/Qualifiers
source                 1..67
                       mol_type = protein
                       organism = Enterococcus faecalis
SEQUENCE: 16
MKKKLVICGI IGIGFTALGT NVEAATYYGN GLYCNKQKCW VDWNKASREI GKIIVNGWVQ  60
HGPWAPR                                                           67

SEQ ID NO: 17          moltype = DNA  length = 204
FEATURE                Location/Qualifiers
source                 1..204
                       mol_type = genomic DNA
                       organism = Enterococcus faecalis
SEQUENCE: 17
atgaaaaaga aattagttat ttgtggcatt attgggattg gttttacagc attaggaaca  60
aatgtagaag ctgctacgta ttacggaaat ggtttatatt gtaataagca aaaatgttgg  120
gtagactgga ataaagcttc aagggaaatt ggaaaaatta ttgttaatgg ttgggtacaa  180
catggccctt gggctcctag atag                                        204

SEQ ID NO: 18          moltype = AA  length = 51
FEATURE                Location/Qualifiers
source                 1..51
                       mol_type = protein
                       organism = Lactococcus lactis
SEQUENCE: 18
MKEQNSFNLL QEVTESELDL ILGAKGGSGV IHTISHEVIY NSWNFVFTCC S          51

SEQ ID NO: 19          moltype = DNA  length = 156
FEATURE                Location/Qualifiers
source                 1..156
                       mol_type = genomic DNA
                       organism = Lactococcus lactis
SEQUENCE: 19
atgaaagaac aaaactcttt taatcttctt caagaagtga cagaaagtga attggacctt  60
attttaggtg caaaaggcgg cagtggagtt attcatacaa tttctcatga agtaatatat  120
aatagctgga actttgtatt tacttgctgc tcttaa                           156

SEQ ID NO: 20          moltype = AA  length = 74
FEATURE                Location/Qualifiers
source                 1..74
                       mol_type = protein
                       organism = Enterococcus faecium
SEQUENCE: 20
MKKKVLKHCV ILGILGTCLA GIGTGIKVDA ATYYGNGLYC NKEKCWVDWN QAKGEIGKII  60
VNGWVNHGPW APRR                                                   74

SEQ ID NO: 21          moltype = DNA  length = 225
FEATURE                Location/Qualifiers
source                 1..225
                       mol_type = genomic DNA
                       organism = Enterococcus faecium
SEQUENCE: 21
atgaaaaaga aagtattaaa acattgtgtt attctaggaa tattaggaac ttgtctagct  60
ggcatcggta caggaataaa agttgatgca gctacttact atggaaatgg tctttattgt  120
aacaaagaaa aatgttgggt agattggaat caagctaaag gagaaattgg aaaaattatt  180
gttaatggtt gggttaatca tggtccatgg gcacctagaa ggtag                 225

SEQ ID NO: 22          moltype = AA  length = 50
```

```
FEATURE                 Location/Qualifiers
source                  1..50
                        mol_type = protein
                        organism = Clostridium botulinum
SEQUENCE: 22
MQKPEIISAD LGLCAVNEFV ALAAIPGGAA TFAVCQMPNL DEIVSNAAYV           50

SEQ ID NO: 23           moltype = DNA  length = 153
FEATURE                 Location/Qualifiers
source                  1..153
                        mol_type = genomic DNA
                        organism = Clostridium botulinum
SEQUENCE: 23
atgcaaaaac cagaaattat tagtgctgat ttagggcttt gtgcagttaa tgaatttgta  60
gctcttgctg ccattcctgg tggtgctgct acatttgcag tatgccaaat gccaaacttg  120
gatgagattg ttagtaatgc agcatatgtt taa                               153

SEQ ID NO: 24           moltype = AA  length = 58
FEATURE                 Location/Qualifiers
source                  1..58
                        mol_type = protein
                        organism = Streptococcus equinus
SEQUENCE: 24
MMNATENQIF VETVSDQELE MLIGGADRGW IKTLTKDCPN VISSICAGTI ITACKNCA    58

SEQ ID NO: 25           moltype = DNA  length = 177
FEATURE                 Location/Qualifiers
source                  1..177
                        mol_type = genomic DNA
                        organism = Streptococcus equinus
SEQUENCE: 25
atgatgaatg ctactgaaaa ccaaattttt gttgagactg tgagtgacca agaattagaa  60
atgttaattg gtggtgcaga tcgtggatgg attaagactt taacaaaaga ttgtccaaat  120
gtaatttctt caatttgtgc aggtacaatt attacagctt gtaaaaattg tgcttaa     177

SEQ ID NO: 26           moltype = AA  length = 77
FEATURE                 Location/Qualifiers
source                  1..77
                        mol_type = protein
                        organism = Brochothrix campestris
SEQUENCE: 26
MHKVKKLNNQ ELQQIVGGYS SKDCLKDIGK GIGAGTVAGA AGGGLAAGLG AIPGAFVGAH  60
FGVIGGSAAC IGGLLGN                                                 77

SEQ ID NO: 27           moltype = DNA  length = 234
FEATURE                 Location/Qualifiers
source                  1..234
                        mol_type = genomic DNA
                        organism = Brochothrix campestris
SEQUENCE: 27
atgcacaagg taaaaaaatt aaacaatcaa gagttacaac agatcgtggg aggttacagt  60
tcaaaagatt gtctaaaaga tattggtaaa ggaattggtg ctggtacagt agctggggca  120
gccggcggtg gcctagctgc aggattaggt gctatcccag gagcattcgt tggagcacat  180
tttggagtaa tcggcggatc tgccgcatgc attggtggat tattaggtaa ctag        234

SEQ ID NO: 28           moltype = AA  length = 80
FEATURE                 Location/Qualifiers
source                  1..80
                        mol_type = protein
                        organism = Butyrivibrio fibrisolvens
SEQUENCE: 28
MSKKQIMSNC ISIALLIALI PNIYFIADKM GIQLAPAWYQ DIVNWVSAGG TLTTGFAIIV  60
GVTVPAWIAE AAAAFGIASA                                              80

SEQ ID NO: 29           moltype = DNA  length = 243
FEATURE                 Location/Qualifiers
source                  1..243
                        mol_type = genomic DNA
                        organism = Butyrivibrio fibrisolvens
SEQUENCE: 29
atgagtaaaa aacaaattat gagtaactgt atatcaattg cattattaat agcactaatt  60
cctaatatct attttattgc agataaaatg ggaattcagt tagcacctgc ttggtatcaa  120
gatattgtga attgggtatc tgctggtgga acacttacta ctggttttgc gattattgta  180
ggagttacag taccggcatg gatagcagaa gcagctgcag cttttggtat agcttcagca  240
tga                                                                243

SEQ ID NO: 30           moltype = AA  length = 48
FEATURE                 Location/Qualifiers
source                  1..48
```

```
                         mol_type = protein
                         organism = Butyrivibrio fibrisolvens
SEQUENCE: 30
MNKELNALTN PIDEKELEQI LGGGNGVIKT ISHECHMNTW QFIFTCCS              48

SEQ ID NO: 31            moltype = DNA  length = 147
FEATURE                  Location/Qualifiers
source                   1..147
                         mol_type = genomic DNA
                         organism = Butyrivibrio fibrisolvens
SEQUENCE: 31
atgaacaaag aacttaatgc acttacaaat cctattgacg agaaggagct tgagcagatc  60
ctcggtggtg gcaatggtgt catcaagaca atcagccacg agtgccacat gaacacatgg  120
cagttcattt tcacatgttg ctcttaa                                     147

SEQ ID NO: 32            moltype = AA  length = 66
FEATURE                  Location/Qualifiers
source                   1..66
                         mol_type = protein
                         organism = Carnobacterium maltaromaticum
SEQUENCE: 32
MNSVKELNVK EMKQLHGGVN YGNGVSCSKT KCSVNWGQAF QERYTAGINS FVSGVASGAG  60
SIGRRP                                                            66

SEQ ID NO: 33            moltype = DNA  length = 201
FEATURE                  Location/Qualifiers
source                   1..201
                         mol_type = genomic DNA
                         organism = Carnobacterium maltaromaticum
SEQUENCE: 33
atgaatagcg taaaagaatt aaacgtgaaa gaaatgaaac aattacacgg tggagtaaat  60
tatggtaatg gtgtttcttg cagtaaaaca aaatgttcag ttaactgggg acaagccttt  120
caagaaagat acacagctgg aattaactca tttgtaagtg gagtcgcttc tggggcagga  180
tccattggta ggagaccgta a                                           201

SEQ ID NO: 34            moltype = AA  length = 61
FEATURE                  Location/Qualifiers
source                   1..61
                         mol_type = protein
                         organism = Carnobacterium maltaromaticum
SEQUENCE: 34
MKSVKELNKK EMQQINGGAI SYGNGVYCNK EKCWVNKAEN KQAITGIVIG GWASSLAGMG  60
H                                                                 61

SEQ ID NO: 35            moltype = DNA  length = 186
FEATURE                  Location/Qualifiers
source                   1..186
                         mol_type = genomic DNA
                         organism = Carnobacterium maltaromaticum
SEQUENCE: 35
atgaaaagcg ttaaagaact aaataaaaaa gaaatgcaac aaattaatgg tggagctatc  60
tcttatggca atggtgttta ttgtaacaaa gagaaatgtt gggtaaacaa ggcagaaaac  120
aaacaagcta ttactggaat agttatcggt ggatgggctt ctagtttagc aggaatggga  180
cattaa                                                            186

SEQ ID NO: 36            moltype = AA  length = 71
FEATURE                  Location/Qualifiers
source                   1..71
                         mol_type = protein
                         organism = Carnobacterium maltaromaticum
SEQUENCE: 36
MNNVKELSIK EMQQVTGGDQ MSDGVNYGKG SSLSKGGAKC GLGIVGGLAT IPSGPLGWLA  60
GAAGVINSCM K                                                      71

SEQ ID NO: 37            moltype = DNA  length = 216
FEATURE                  Location/Qualifiers
source                   1..216
                         mol_type = genomic DNA
                         organism = Carnobacterium maltaromaticum
SEQUENCE: 37
atgaataatg taaaagagtt aagtattaaa gaaatgcaac aagttactgg tggagaccaa  60
atgtcagatg gtgtaaatta tggaaaaggc tctagcttat caaaaggtgg tgccaaatgt  120
ggtttaggga tcgtcggcgg attagctact atcccttcag gtcctttagg ctggttagcc  180
ggagcagcag gtgtaattaa tagctgtatg aaataa                           216

SEQ ID NO: 38            moltype = AA  length = 64
FEATURE                  Location/Qualifiers
source                   1..64
                         mol_type = protein
```

```
                          organism = Carnobacterium maltaromaticum
SEQUENCE: 38
MLYELVAYGI AQGTAEKVVS LINAGLTVGS IISILGGVTV GLSGVFTAVK AAIAKQGIKK  60
AIQL                                                              64

SEQ ID NO: 39             moltype = DNA  length = 195
FEATURE                   Location/Qualifiers
source                    1..195
                          mol_type = genomic DNA
                          organism = Carnobacterium maltaromaticum
SEQUENCE: 39
atgttatatg aattagttgc atatggtatc gcacaaggta cagctgaaaa ggttgtaagt  60
ctaattaacg caggtttaac agtagggtct attatttcaa ttttgggtgg ggtcacagtc  120
ggtttatcag gtgtcttcac agcagttaaa gcagcaattg ctaaacaagg aataaaaaaa  180
gcaattcaat tataa                                                   195

SEQ ID NO: 40             moltype = AA  length = 836
FEATURE                   Location/Qualifiers
source                    1..836
                          mol_type = protein
                          note = subsp. carotovorum
                          organism = Pectobacterium carotovorum
SEQUENCE: 40
MIKYRLYAPN DGDTMTVSGG GGWVSNDDRK GGNDRDNGKG GSAVDFSKNP EKQAIVNPYL  60
AIAIPMPVYP LYGKLGFTIN TTAIETELAN VRAAINTKLA TLSAVIGRSL PVVGRVFGVT  120
AAGMWPSSTA PSSLDSIYNQ AHQQALAQLA AQQGVLNKGY NVTAMPAGFV SSLPVSEIKS  180
LPTAPASLLA QSVINTELSQ RQLALTQPTT NAPVANIPVV KAEKTAMPGV YSAKIIAGEP  240
AFQIKVDNTK PALAQNPPKV KDDIQVSSFL SSPVADTHHA FIDFGSDHEP VYVSLSKIVT  300
AEEEKKQVEE AKRREQEWLL RHPITAAERK LTEIRQVISF AQQLKESSVA TISEKTKTVA  360
VYQEQVNTAA KNRDNFYNQN RGLLSAGITG GPGYPIYLAL WQTMNNFHQA YFRANNALEQ  420
ESHVLNLARS DLAKAEQLLA ENNRLQVETE RTLAEEKEIK RNRVNVSTFG TVQTQLSKLL  480
SDFYAVTSLS QSVPSGALAS FSYNPQGMIG SGKIVGKDVD VLFSIPVKDI PGYKSPINLD  540
DLAKKNGSLD LPIRLAFSDE NGERVLRAFK ADSLRIPSSV RGVAGSYDKN TGIFSAEIDG  600
VSSRLVLENP AFPPTGNVGN TGNTAPDYKA LLNTGVDVKP VDKITVTVTP VADPVDIDDY  660
IIWLPTASGS GVEPIYVVFN SNPYGGTEKG KYSKRYYNPD KAGGPILELD WKNVKIDHAG  720
VDNVKLHTGR FKASVENKVM IERLENILNG QITATDTDKR FYTHELRELN RYRNLGIKDG  780
EVPSSIQEES AVWNDTHTAT LEDYKINEKE QPLYTDAALQ AAYEQELKDA LGGKHG      836

SEQ ID NO: 41             moltype = DNA  length = 2511
FEATURE                   Location/Qualifiers
source                    1..2511
                          mol_type = genomic DNA
                          note = subsp. carotovorum
                          organism = Pectobacterium carotovorum
SEQUENCE: 41
atgattaaat accgtttata tgctccaaat gatggagaca ccatgacagt gagtggtggt  60
ggtggttggg tttcaaacga tgatcgcaaa ggtggtaatg acagggacaa tggcaaaggt  120
ggttctgccg ttgattttag taaaaatcca gaaaagcagg ctatcgttaa tccctatttg  180
gcaatcgcga taccgatgcc ggtctaccct ctttatggaa agctagggtt cacaataaat  240
acgacggcaa ttgagactga actcgcaaat gtcagagcag caattaacac taaacttgca  300
acactcagtg cagtgattgg cagatcactt ccggtcgttg ggcgggtatt tggtgttact  360
gccgccggaa tgtggccttc tagtaccgct cccagtagtc tcgattctat atacaatcaa  420
gcacatcagc aggctttagc ccagttagct gctcaacagg gagtattaaa taaagggtat  480
aacgttacag caatgcctgc aggtttcgtc agcagtttgc ctgttagtga aatcaaatca  540
ttgccaacag ctcccgccag tttactggca caaagtgtga ttaataccga actttcccag  600
cgtcaactgg ctcttactca gcccacgacg aatgcaccag tcgcgaatat tcccgtagtt  660
aaagcagaga aaacagcaat gccaggtgtg tattcagcga aaattattgc tggtgagcct  720
gcattccaaa tcaaggtcga taataccaaa cctgctttgg cacagaatcc gccgaaagta  780
aaagatgata ttcaggtatc ttctttcctt tcctcgccag tagctgatac gcaccatgca  840
tttattgatt ttggcagcga tcatgaaccg gtatacgtgt ctctttcaaa gatcgtgaca  900
gccgaggagg agaaaaaaca ggttgaagag gccaagcgcc gtgagcagga gtggttgttg  960
cgtcatccaa ttacagctgc ggagcgaaaa ttaactgaaa tccgccaagt gatctctttt  1020
gctcaacagc taaaagaaag ctctgtcgca accatttcag aaaaaactaa aactgttgcg  1080
gtttaccaag aacaggtgaa taccgctgca aaaaatcgcg acaattttta taatcaaaat  1140
agaggtctgt taagtgcggg tataactggg ggaccgggat atcctattta tcttgcttta  1200
tggcaaacga tgaataactt tcatcaggct tatttcagag caaataatgc attggaacaa  1260
gagagtcatg ttctgaacct ggctcgttct gatctggcta aggctgagca attgcttgct  1320
gagaataatc gacttcaggt tgaaacggag cgaacgcttg ccgaagaaaa agagataaaa  1380
cgcaacaggg ttaatgtatc aacatttggc acagtgcaaa ctcaacttag taaattgctg  1440
tcagattttt atgctgttac atcactttcc caaagtgttc cttcgggggc attagcctct  1500
ttttcatata atccacaagg gatgattggc agcggtaaga ttgttgggaa ggatgtcgat  1560
gttttatttt ccatcccagt aaaagatatt ccgggatata aatctcctat taacttggac  1620
gatttagcca agaaaaatgg aagtctggat cttcccattc gtctggcatt ttctgatgag  1680
aatggagaaa gggttcttcg ggcattcaaa gcggatagtc tgcgaatccc ttcgagtgtc  1740
agaggtgtag cgggcagtta tgacaaaaat acgggtattt ttagtgcaga aattgatggt  1800
gtttcatctc gccttgtact ggaaaaccca gcgtttcctc cgaccggaaa tgtcggtaat  1860
acgggtaata ctgcacctga ctataaagca ttactgaata ctggtgttga tgttaaacct  1920
gttgataaaa tcacagttac ggtaacacca gttgctgatc cagtggatat tgatgactat  1980
ataatctggt tgccaactgc gtctggttct ggcgtggaac ccatttatgt cgtgtttaac  2040
```

```
agtaatccgt atggtgggac ggaaaaagga aaatatagca aacgttatta taatccagat  2100
aaggcaggcg gtccgatctt ggagctggat tggaaaaacg ttaagattga ccatgcaggt  2160
gtggacaatg ttaaattaca cacagggcgt ttcaaagcgt cggttgaaaa caaagtgatg  2220
attgaacgtt tggaaaacat actgaatggt caaatcacgg ccacggatac tgacaagcga  2280
ttctatacgc atgaattaag agagttaaac cgctacagaa atttaggcat caaagacggt  2340
gaagtgccta gtagcattca agaagaaagc gctgtttgga acgacacaca cacagcgacg  2400
cttgaagact acaaaattaa tgagaaagag caaccgttgt acactgatgc tgctttgcag  2460
gcagcctacg aacaggaact caaagacgca ttaggaggga aacatggcta a           2511

SEQ ID NO: 42          moltype = AA  length = 74
FEATURE                Location/Qualifiers
source                 1..74
                       mol_type = protein
                       organism = Bacillus cereus
SEQUENCE: 42
MENLQMLTEE ELMEIEGGGW WNSWGKCVAG TIGGAGTGGL GGAAAGSAVP VIGTGIGGAI  60
GGVSGGLTGA ATFC                                                    74

SEQ ID NO: 43          moltype = DNA  length = 225
FEATURE                Location/Qualifiers
source                 1..225
                       mol_type = genomic DNA
                       organism = Bacillus cereus
SEQUENCE: 43
atggaaaact tacaaatgtt aactgaagaa gaattaatgg aaattgaagg tggaggctgg  60
tggaatagct ggggtaaatg tgttgctgga actatcggtg gagctggaac tggtggttta  120
ggtggagctg ctgcaggttc agctgttccg gttattggta ctggtattgg tggcgctatt  180
ggtggagtta gcggtggcct tacaggtgca gctacttttt gctaa                  225

SEQ ID NO: 44          moltype = AA  length = 78
FEATURE                Location/Qualifiers
source                 1..78
                       mol_type = protein
                       organism = Streptoverticillium griseoverticillatum
SEQUENCE: 44
MTASILQQSV VDADFRAALL ENPAAFGASA AALPTPVEAQ DQASLDFWTK DIAATEAFAC  60
RQSCSFGPFT FVCDGNTK                                                78

SEQ ID NO: 45          moltype = DNA  length = 237
FEATURE                Location/Qualifiers
source                 1..237
                       mol_type = genomic DNA
                       organism = Streptoverticillium griseoverticillatum
SEQUENCE: 45
atgaccgctt ccattcttca gcagtccgtc gtggacgccg acttccgcgc ggcgctgctt  60
gagaaccccg ccgccttcgg cgcttccgcc gcggccctgc ccacgcccgt cgaggcccag  120
gaccaggcgt cccttgactt ctggaccaag gacatcgccg ccacggaagc cttcgcctgc  180
cgccagagct gcagcttcgg cccgttcacc ttcgtgtgcg acggcaacac caagtaa     237

SEQ ID NO: 46          moltype = AA  length = 76
FEATURE                Location/Qualifiers
source                 1..76
                       mol_type = protein
                       organism = Geobacillus kaustophilus
SEQUENCE: 46
MSLLALVAGT LGVSQSIATT VVSIVLTGST LISIILGITA ILSGGVDAIL EIGWSAFVAT  60
VKKIVAERGK AAAIAW                                                  76

SEQ ID NO: 47          moltype = DNA  length = 231
FEATURE                Location/Qualifiers
source                 1..231
                       mol_type = genomic DNA
                       organism = Geobacillus kaustophilus
SEQUENCE: 47
atgagtttgc tggcgcttgt tgccgggacg ctcggcgtgt cacagtcaat cgcgacgacg  60
gttgtttcga ttgtgttgac cggctccact ctcatttcta ttattcttgg gatcaccgct  120
attttgtcag gtggagtcga cgccattttg gaaattgggt ggtcagcttt tgtcgcgacg  180
gtgaaaaaaa tagtggcgga acgaggaaaa gcggcagcga ttgcatggta a           231

SEQ ID NO: 48          moltype = AA  length = 309
FEATURE                Location/Qualifiers
source                 1..309
                       mol_type = protein
                       organism = Clostridium tyrobutyricum
SEQUENCE: 48
MRKVFLRSII STLVMCAFVS SSFSVNADES KPNDEKIINN IENVTTTKDI VKSNKNNIVY  60
LDEGVMSIPL SGRKPIAIKD DNNKEDLTVT LPIKNTGDIS KISSNGTILY KNNSSNSSNI  120
ALQPKNDGFK ALININDKLA NKEYEFTFNL PKNSKLISAA TYLGKEYDTK EVFVVDKNNI  180
ITSIISPAWA KDANGHNVST YYKIVSNNKL VQVVEFTENT AFPVVADPNW TKIGKCAGSI  240
```

```
AWAIGSGLFG GAKLIKIKKY IAELGGLQKA AKLLVGATTW EEKLHAGGYA LINLAAELTG  300
VAGIQANCF                                                          309

SEQ ID NO: 49          moltype = DNA  length = 930
FEATURE                Location/Qualifiers
source                 1..930
                       mol_type = genomic DNA
                       organism = Clostridium tyrobutyricum
SEQUENCE: 49
ttgagaaaag tatttttaag atcaataatt tcaacattag ttatgtgtgc atttgtttca  60
agcagctttt cagtaaatgc ggatgaaagc aaaccaaatg atgaaaaaat aattaataac  120
atagaaaacg ttactactac taaagatatt gtaaaaagta ataaaaataa tattgtatat  180
ttagatgaag gtgtaatgag tattccattg tctgggagaa aacccattgc tattaaagat  240
gataataata aagaagattt aactgttaca ttacctatta agaatactgg agatatatct  300
aaaattagta gtaatggtac tattctgtat aaaaataata gtagtaattc atctaatata  360
gctttacaac ctaaaaatga tggatttaag gctttaataa atattaatga taagttagct  420
aataaagaat atgaatttac atttaattta cccaaaaaca gtaaattaat tagtgctgcc  480
acatatttgg gtaaagaata tgatacaaaa gaagtatttg tagtagacaa aaataatata  540
attacgagta ttattagtcc agcttgggct aaagatgcaa atggacataa tgtttctact  600
tattataaga tagtatcgaa taataaatta gtacaagttg ttgaattcac agaaaatact  660
gcattcccgg tggtagctga tcctaattgg actaaaattg ggaaatgcgc tgggtcaata  720
gcatgggcta taggttctgg ccttttggt ggagcaaagc taattaaaat aaaaaaatat  780
atagcagagc ttggaggact tcaaaaagca gctaaattat tagttggtgc aaccacttgg  840
gaagaaaaat tacacgcagg cggttatgca ttaattaact tagctgctga gctaacaggt  900
gtagcaggta tacaagcaaa ttgtttttaa                                   930

SEQ ID NO: 50          moltype = AA  length = 62
FEATURE                Location/Qualifiers
source                 1..62
                       mol_type = protein
                       organism = Bacillus coagulans
SEQUENCE: 50
MKKIEKLTEK EMANIIGGKY YGNGVTCGKH SCSVDWGKAT TCIINNGAMA WATGGHQGTH  60
KC                                                                 62

SEQ ID NO: 51          moltype = DNA  length = 189
FEATURE                Location/Qualifiers
source                 1..189
                       mol_type = genomic DNA
                       organism = Bacillus coagulans
SEQUENCE: 51
atgaaaaaaa ttgaaaaatt aactgaaaaa gaaatggcca atatcattgg tggtaaatac  60
tacggtaatg ggttacttg tggcaaacat tcctgctctg ttgactgggg taaggctacc  120
acctgcataa tcaataatgg agctatggca tgggctactg gtggacatca aggtactcat  180
aaatgctag                                                          189

SEQ ID NO: 52          moltype = AA  length = 490
FEATURE                Location/Qualifiers
source                 1..490
                       mol_type = protein
                       organism = Escherichia coli
SEQUENCE: 52
MDKVTDNSPD VESTESTEGS FPTVGVDTGD TITATLATGT ENVGGGGGAF GGASESSAAI  60
HATAKWSTAQ LKKHQAEQAA RAAAAEAALA KAKSQRDALT QRLKDIVNDA LRANAARSPS  120
VTDLAHANNM AMQAEAERLR LAKAEQKARE EAEAAEKALR EAERQRDEIA RQQAETAHLL  180
AMAEAAAEAEK NRQDSLDEEH RAVEVAEKKL AEAKAELAKA ESDVQSKQAI VSRVAGELEN  240
AQKSVDVKVT GFPGWRDVQK KLERQLQDKK NEYSSVTNAL NSAVSIRDAK KTEVQNAEIK  300
LKEAKDALEK SQVKDSVDTM VGFYQYITEQ YGEKYSRIAQ DLAEKAKGSK FNSVDEALAA  360
FEKYKNVLDK KFSKVDRDDI FNALESITYD EWAKHLEKIS RALKVTGYLS FGYDVWDGTL  420
KGLKTGDWKP LFVTLEKSAV DFGVAKIVAL MFSFIVGAPL GFWGIAIITG IVSSYIGDDE  480
LNKLNELLGI                                                         490

SEQ ID NO: 53          moltype = DNA  length = 1473
FEATURE                Location/Qualifiers
source                 1..1473
                       mol_type = genomic DNA
                       organism = Escherichia coli
SEQUENCE: 53
atggataaag tcactgataa ttctccagat gtggagagca cagaatctac tgaggggtca  60
ttcccaactg ttggggttga tactggcgat acgattacag cgacgcttgc aactggaact  120
gaaaatgttg gtggaggcgg tggagcattt ggtggggcca gtgaaagttc tgctgcgata  180
catgcaaccg ctaaatggtc taccgcgcag ttgaaaaaac atcaggctga acaggctgcc  240
cgtgctgctg cggctgaggc agcattggca aaagcgaaat ctcagcgtga tgccctgact  300
caacgtctca aggatattgt taatgacgct ttacgtgcta atgccgctcg tagtccatca  360
gtaactgacc ttgctcatgc caataatatg gcaatgcagg cagaggctga gcgtttgcgc  420
cttgcgaagg cagagcaaaa agcccgtgaa gaagctgaag cagcagaaaa agcgctccgg  480
gaagcagaac gccaacgtga tgagattgcc cgccaacagg ctgaaaccgc gcatttgtta  540
gcaatggcgg aggcagcaga ggctgagaaa aatcgacagg attctcttga tgaagagcat  600
cgggctgtgg aagtggcaga gaagaagctg gctgaggcta aagctgaact ggcgaaggcc  660
```

```
gaaagcgatg tacagagtaa gcaagcgatt gtttccagag ttgcagggga gcttgaaaac  720
gctcaaaaaa gtgttgatgt gaaggttacc ggatttcctg gatggcgtga tgttcagaaa  780
aaactggaga gacaattgca ggataagaag aatgaatatt cgtcagtgac gaatgctctt  840
aattctgctg ttagcattag agatgctaaa aaaacagaag ttcagaatgc tgagataaaa  900
ttaaaagaag ctaaggatgc tcttgagaag agtcaggtaa aagactctgt tgatactatg  960
gttgggtttt atcaatatat aaccgaacaa tatggggaaa aatattccag aatagctcag  1020
gatttagctg aaaaggcgaa gggtagtaaa tttaatagtg ttgatgaagc acttgctgca  1080
tttgaaaagt ataaaaatgt actggataag aaattcagta aggttgatag ggatgatatt  1140
tttaatgctt tagagtctat tacttatgat gagtgggcca agcatctaga aaagatctct  1200
agggctctta aggttactgg atatttgtct ttcgggtatg atgtatggga tggtacccta  1260
aagggattaa aaacaggaga ctggaagcct ttatttgtca ctctggagaa gagcgcggta  1320
gatttcggcg tggcaaaaat tgtggcatta atgtttagtt ttattgttgg tgcgcctctt  1380
ggcttctggg gaattgcaat tatcacaggt attgtttctt cttacatagg ggatgatgag  1440
ttgaacaagc ttaatgaatt actaggtatt taa                               1473
```

```
SEQ ID NO: 54          moltype = AA  length = 522
FEATURE                Location/Qualifiers
source                 1..522
                       mol_type = protein
                       organism = Escherichia coli
SEQUENCE: 54
METAVAYYKD GVPYDDKGQV IITLLNGTPD GSGSGGGGGK GGSKSESSAA IHATAKWSTA  60
QLKKTQAEQA ARAKAAAEAQ AKAKANRDAL TQRLKDIVNE ALRHNASRTP SATELAHANN  120
AAMQAEDERL RLAKAEEKAR KEAEAAEKAF QEAEQRRKEI EREKAETERQ LKLAEAEEKR  180
LAALSEEAKA VEIAQKKLSA AQSEVVKMDG EIKTLNSRLS SSIHARDAEM KTLAGKRNEL  240
AQASAKYKEL DELVKKLSPR ANDPLQNRPF FEATRRRVGA GKIREEKQKQ VTASETRINR  300
INADITQIQK AISQVSNNRN AGIARVHEAE ENLKKAQNNL LNSQIKDAVD ATVSFYQTLT  360
EKYGEKYSKM AQELADKSKG KKIGNVNEAL AAFEKYKDVL NKKFSKADRD AIFNALASVK  420
YDDWAKHLDQ FAKYLKITGH VSFGYDVVSD ILKIKDTGDW KPLFLTLEKK AADAGVSYVV  480
ALLFSLLAGT TLGIWGIAIV TGILCSYIDK NKLNTINEVL GI                     522
```

```
SEQ ID NO: 55          moltype = DNA  length = 1569
FEATURE                Location/Qualifiers
source                 1..1569
                       mol_type = genomic DNA
                       organism = Escherichia coli
SEQUENCE: 55
atggaaaccg cggtagcgta ctataaagat ggtgttcctt atgatgataa gggacaggta  60
attattactc ttttgaatgg tactcctgac gggagtggct ctggcggcgg aggtggaaaa  120
ggaggcagta aaagtgaaag ttctgcagct attcatgcaa ctgctaaatg gtctactgct  180
caattaaaga aaacacaggc agagcaggct gcccgggcaa aagctgcagc ggaagcacag  240
gcgaaagcaa aggcaaacag ggatgcgctg actcagcgcc tgaaggatat cgtgaatgag  300
gctcttcgtc acaatgcctc acgtacgcct tcagcaacag agcttgctca tgctaataat  360
gcagctatgc aggcggaaga cgagcgtttg cgccttgcga aagcagaaga aaaagcccgt  420
aaagaagcgg aagcagcaga aaaggctttt caggaagcag aacaacgacg taaagagatt  480
gaacgggaga aggctgaaac agaacgccag ttgaaactgg ctgaagctga agagaaacga  540
ctggctgcat tgagtgaaga agctaaagct gttgagatcg cccaaaaaaa actttctgct  600
gcacaatctg aagtggtgaa aatggatgga gagattaaga ctctcaattc tcgtttaagc  660
tccagtatcc atgcccgtga tgcagaaatg aaaacgctcg ctggaaaacg aaatgaactg  720
gctcaggcat ccgctaaata taaagaactg gatgagctgg tcaaaaaact atcaccaaga  780
gccaatgatc cgcttcagaa ccgtcctttt tttgaagcaa ccagacgacg ggttggggcc  840
ggtaagatta gagaagaaaa acaaaaacag gtaacagcat cagaaacacg tattaaccgg  900
ataaatgctg atataactca gatccagaag gctatttctc aggtcagtaa taatcgtaat  960
gccggtatcg ctcgtgttca tgaagctgaa gaaaatttga aaaaagcaca gaataatctc  1020
cttaattcac agattaagga tgctgttgat gcaacagtta gcttttatca aacgctgact  1080
gaaaaatatg gtgaaaaata ttcgaaaatg gcacaggaac ttgctgataa gtctaaaggt  1140
aagaaaatcg gcaatgtgaa tgaagctctc gctgcttttg aaaaatacaa ggatgtttta  1200
aataagaaat tcagcaaagc cgatcgtgat gctattttta atgcgttggc atcggtgaag  1260
tatgatgact gggctaaaca tttagatcag tttgccaagt acttgaagat tacggggcat  1320
gtttcttttg gatatgatgt ggtatctgat atcctaaaaa ttaaggatac aggtgactgg  1380
aagccactat ttcttacatt agagaagaaa gctgcagatg caggggtgag ttatgttgtt  1440
gctttacttt ttagcttgct tgctggaact acattaggta tttggggtat tgctattgtt  1500
acaggaattc tatgctccta tattgataag aataaactta atactataaa tgaggtgtta  1560
gggatttaa                                                          1569
```

```
SEQ ID NO: 56          moltype = AA  length = 626
FEATURE                Location/Qualifiers
source                 1..626
                       mol_type = protein
                       organism = Escherichia coli
SEQUENCE: 56
MSDPVRITNP GAESLGYDSD GHEIMAVDIY VNPPRVDVFH GTPPAWSSFG NKTIWGGNEW  60
VDDSPTRSDI EKRDKEITAY KNTLSAQQKE NENKRTEAGK RLSAAIAARE KDENTLKTLR  120
AGNADAADIT RQEFRLLQAE LREYGFRTEI AGYDALRLHT ESRMLFADAD SLRISPREAR  180
SLIEQAEKRQ KDAQNADKKA ADMLAEYERR KGILDTRLSE LEKNGGAALA VLDAQQARLL  240
GQQTRNDRAI SEARNKLSSV TESLNTARNA LTRAEQQLTQ QKNTPDGKTI VSPEKFPGRS  300
STNHSIVVSG DPRFAGTIKI TTSAVIDNRA NLNYLLSHSG LDYKRNILND RNPVVTEDVE  360
GDKKIYNAEV AEWDKLRQRL LDARNKITSA ESAVNSARNN LSARTNEQKH ANDALNALLK  420
EKENIRNQLS GINQKIAEEK RKQDELKATK DAINFTTEFL KSVSEKYGAK AEQLAREMAG  480
```

```
QAKGKKIRNV EEALKTYEKY RADINKKINA KDRAAIAAAL ESVKLSDISS NLNRFSRGLG  540
YAGKFTSLAD WITEFGKAVR TENWRPLFVK TETIIAGNAA TALVALVFSI LTGSALGIIG  600
YGLLMAVTGA LIDESLVEKA NKFWGI                                       626

SEQ ID NO: 57          moltype = DNA  length = 1881
FEATURE                Location/Qualifiers
source                 1..1881
                       mol_type = genomic DNA
                       organism = Escherichia coli
SEQUENCE: 57
atgtctgacc ctgtacgtat tacaaatccc ggtgcagaat cgctggggta tgattcagat  60
ggccatgaaa ttatggccgt tgatatttat gtaaaccctc cacgtgtcga tgtctttcat  120
ggtaccccgc ctgcatggag ttccttcggg aacaaaacca tctggggcgg aaacgagtgg  180
gttgatgatt ccccaacccg aagtgatatc gaaaaaaggg acaaggaaat cacagcgtac  240
aaaaacacgc tcagcgcgca gcagaaagag aatgagaata agcgtactga agccggaaaa  300
cgcctctctg cggcgattgc tgcaagggaa aaagatgaaa acacactgaa aacactccgt  360
gccggaaacg cagatgccgc tgatattaca cgacaggagt tcagactcct gcaggcagag  420
ctgagagaat acggattccg tactgaaatc gccggatatg acgccctccg gctgcataca  480
gagagccgga tgctgtttgc tgatgctgat tctcttcgta tatctccccg ggaggccagg  540
tcgttaatcg aacaggctga aaaacggcag aaggatgcgc agaacgcaga caagaaggcc  600
gctgatatgc ttgctgaata cgagcgcaga aaaggtattc tggacacccg gttgtcagag  660
ctggaaaaaa atggcggggc agcccttgcc gttcttgatg cacaacaggc ccgtctgctc  720
gggcagcaga cacggaatga cagggccatt tcagaggccc ggaataaact cagttcagtg  780
acggaatcgc ttaacacggc ccgtaatgca ttaaccagag ctgaacaaca gctgacgcaa  840
cagaaaaaca cgcctgacgg caaaacgata gtttcccctg aaaaattccc ggggcgttca  900
tcaacaaatg attctattgt tgtgagcggt gatccgagat ttgccggtac gataaaaatc  960
acaaccagcg cagtcatcga taaccgtgca aacctgaatt atcttctgag ccattccggt  1020
ctggactata aacgcaatat tctgaatgac cggaatccgg tggtgacaga ggatgtggaa  1080
ggtgacaaga aaatttataa tgctgaagtt gctgaatggg ataagttacg gcaaagattg  1140
cttgatgcca gaaataaaat cacctctgct gaatctgcgg taaattcggc gagaaataac  1200
ctcagtgcca gaacaaatga gcaaaagcat gcaaatgacg ctcttaatgc cctgttgaag  1260
gaaaaagaga atatccgtaa ccagctttcc ggcatcaatc agaagatagc ggaagagaaa  1320
agaaaacagg atgaactgaa ggcaacgaaa gacgcaatta atttcacaac agagttcctg  1380
aaatcagttt cagaaaaata tggtgcaaaa gctgagcagt tagccagaga gatggccggg  1440
caggctaaag ggaagaaaat acgtaatgtt gaagaggcat taaaaacgta tgaaaagtac  1500
cgggctgaca ttaacaaaaa aattaatgca aaagatcgtg cagcgattgc cgcagccctt  1560
gagtctgtga agctgtctga tatatcgtct aatctgaaca gattcagtcg ggactggga  1620
tatgcaggaa aatttacaag tcttgctgac tggatcactg agtttggtaa ggctgtccgg  1680
acagagaact ggcgtcctct ttttgttaaa acagaaacca tcatagcagg caatgccgca  1740
acggctcttg tggcactggt cttcagtatt cttaccggaa gcgctttagg cattatcggg  1800
tatggtttac tgatggctgt caccggtgcg ctgattgatg aatcgcttgt ggaaaaagcg  1860
aataagttct ggggtattta a                                            1881

SEQ ID NO: 58          moltype = AA  length = 626
FEATURE                Location/Qualifiers
source                 1..626
                       mol_type = protein
                       organism = Escherichia coli
SEQUENCE: 58
MSDPVRITNP GAESLGYDSD GHEIMAVDIY VNPPRVDVFH GTPPAWSSFG NKTIWGGNEW  60
VDDSPTRSDI EKRDKEITAY KNTLSAQQKE NENKRTEAGK RLSAAIAARE KDENTLKTLR  120
AGNADAADIT RQEFRLLQAE LREYGFRTEI AGYDALRLHT ESRMLFADAD SLRISPREAR  180
SLIEQAEKRQ KDAQNADKKA ADMLAEYERR KGILDTRLSE LEKNGGAALA VLDAQQARLL  240
GQQTRNDRAI SEARNKLSSV TESLKTARNA LTRAEQQLTQ QKNTPDGKTI VSPEKFPGRS  300
STNHSIVVSG DPRFAGTIKI TTSAVIDNRA NLNYLLTHSG LDYKRNILND RNPVVTEDVE  360
GDKKIYNAEV AEWDKLRQRL LDARNKITSA ESAINSARNN VSARTNEQKH ANDALNALLK  420
EKENIRSQLA DINQKIAEEK RKRDEINMVK DAIKLTSDFY RTIYDEFGKQ ASELAKELAS  480
VSQGKQIKSV DDALNAFDKF RNNLNKKYNI QDRMAISKAL EAINQVHMAE NFKLFSKAFG  540
FTGKVIERYD VAVELQKAVK TDNWRPFFVK LESLAAGRAA SAVTAWAFSV MLGTPVGILG  600
FAIIMAAVSA LVNDKFIEQV NKLIGI                                       626

SEQ ID NO: 59          moltype = DNA  length = 1881
FEATURE                Location/Qualifiers
source                 1..1881
                       mol_type = genomic DNA
                       organism = Escherichia coli
SEQUENCE: 59
atgtctgacc ctgtacgtat tacaaatccc ggtgcagaat cgctgggata tgattcagat  60
ggccatgaaa ttatggccgt tgatatttat gtaaaccctc cacgtgtcga tgtctttcat  120
ggtaccccgc ctgcatggag ttccttcggg aacaaaacca tctggggtgg aaacgagtgg  180
gtcgatgatt ccccaacccg aagtgatatc gaaaaaaggg acaaggaaat cacagcgtac  240
aaaaacacgc tcagcgcgca gcagaaagag aatgagaata agcgtactga agctggaaaa  300
cgcctttctg cggcaattgc tgcaagggaa aaagatgaaa acacactgaa aacactccgt  360
gccggaaacg cagatgccgc tgatattaca cgacaggagt tcagactcct gcaggcagag  420
ctgagagaat acggattccg tactgaaatc gccggatatg atgccctccg gctgcataca  480
gagagccgga tgctgtttgc tgatgctgat tctcttcgta tatctccccg cgaggccagg  540
tcgttaatcg aacaggctga aaaacggcag aaggatgcgc agaacgcaga caagaaggcc  600
gctgatatgc ttgctgaata cgagcgcaga aaaggtattc tggacacgcg gttgtcagag  660
ctggaaaaaa atggcggggc agcccttgcc gttcttgatg cacaacaggc ccgtctgctc  720
```

```
gggcagcaga cacggaatga cagggccatt tcagaggccc ggaataaact cagttcggtg  780
acggaatcgc ttaagacggc ccgtaatgca ttaaccagag ctgaacaaca gctgacgcaa  840
cagaaaaaca cgcctgacgg caaaacgata gtttcccctg aaaaattccc ggggcgttca  900
tcaacaaatc attctattgt tgtgagtggt gatccgaggt ttgccggtac gataaaaatc  960
acaaccagcg cggtcatcga taaccgtgca aacctgaatt atcttctgac ccattccggt  1020
ctggactata aacgcaatat tctgaatgac cggaatccgg tggtgacaga ggatgtggaa  1080
ggtgacaaga aaatttataa tgctgaagtt gctgaatggg ataagttacg gcaacgattg  1140
cttgatgcca gaaataaaat cacctctgct gaatctgcga taaattcggc gagaaataac  1200
gtcagtgcca gaacaaatga acaaaagcat gcaaatgacg ctcttaatgc cctgttgaag  1260
gaaaaagaga atatccgtag ccagcttgct gacatcaatc agaaaatagc tgaagagaaa  1320
agaaaaaggg atgaaataaa tatggtaaag gatgccataa aactcacctc tgatttctac  1380
agaacgatat atgatgagtt cggtaaacaa gcatccgaac ttgctaagga gctggcttct  1440
gtatctcaag ggaaacagat taagagtgtg gatgatgcac tgaacgcttt tgataaattc  1500
cgtaataatc tgaacaagaa atataacata caagatcgca tggccatttc taaagccctg  1560
gaagctatta atcaggtcca tatggcggag aattttaagc tgttcagtaa ggcatttggt  1620
tttaccggaa aagttattga acgttatgat gttgctgtgg agttacaaaa ggctgtaaaa  1680
acggacaact ggcgtccatt ttttgtaaaa cttgaatcac tggcagcagg aagagctgct  1740
tcagcagtta cagcatgggc gttttccgtc atgctgggaa cccctgtagg tattctgggt  1800
tttgcaatta ttatggcggc tgtgagtgcg cttgttaatg ataagtttat tgagcaggtc  1860
aataaactta ttggtatctg a                                            1881
```

```
SEQ ID NO: 60          moltype = AA  length = 271
FEATURE                Location/Qualifiers
source                 1..271
                       mol_type = protein
                       organism = Escherichia coli
SEQUENCE: 60
METLTVHAPS PSTNLPSYGN GAFSLSAPHV PGAGPLLVQV VYSFFQSPNM CLQALTQLED  60
YIKKHGASNP LTLQIISTNI GYFCNADRNL VLHPGISVYD AYHFAKPAPS QYDYRSMNMK  120
QMSGNVTTPI VALAHYLWGN GAERSVNIAN IGLKISPMKI NQIKDIIKSG VVGTFPVSTK  180
FTHATGDYNV ITGAYLGNIT LKTEGTLTIS ANGSWTYNGV VRSYDDKYDF NASTHRGIIG  240
ESLTRLGAMF SGKEYQILLP GEIHIKESGK R                                 271
```

```
SEQ ID NO: 61          moltype = DNA  length = 816
FEATURE                Location/Qualifiers
source                 1..816
                       mol_type = genomic DNA
                       organism = Escherichia coli
SEQUENCE: 61
atggaaacct taactgttca tgcaccatca ccatcaacta acttaccaag ttatggcaat  60
ggtgcatttt ctctttcagc accacatgtg cctggtgctg gccctctttt agtccaggtt  120
gtttatagtt ttttccagag tccaaacatg tgtcttcagg ctttaactca acttgaggat  180
tacatcaaaa aacatggggc cagcaaccct ctcacattgc agatcatatc gacaaatatt  240
ggttacttct gtaacgccga ccgaaatctg gttcttcacc ctggaataag cgtttatgac  300
gcttaccact tcgcaaaacc agcgccaagt caatatgact atcgctcaat gaatatgaaa  360
caaatgagcg gtaatgtcac tacaccaatt gtggcgcttg ctcactattt atggggtaat  420
ggcgctgaaa ggagcgttaa tatcgccaac attggtctta aaatttcccc tatgaaaatt  480
aatcagataa aagacattat aaaatctggt gtagtaggca cattccctgt ttctacaaag  540
ttcacacatg ccactggtga ttataatgtt attaccggtg catatcttgg taatatcaca  600
ctgaaaacag aaggtacttt aactatctct gccaatggct cctggactta caatggcgtt  660
gttcgttcat atgatgataa atacgatttt aacgccagca ctcaccgtgg cattatcgga  720
gagtcgctca caaggctcgg ggcgatgttt tctggtaaag agtaccagat actgcttcct  780
ggtgaaattc acattaaaga aagtggtaag cgataa                            816
```

```
SEQ ID NO: 62          moltype = AA  length = 387
FEATURE                Location/Qualifiers
source                 1..387
                       mol_type = protein
                       organism = Escherichia coli
SEQUENCE: 62
MGSNGADNAH NNAFGGGKNP GIGNTSGAGS NGSASSNRGN SNGWSWSNKP HKNDGFHSDG  60
SYHITFHGDN NSKPKPGGNS GNRGNNGDGA SAKVGEITIT PDNSKPGRYI SSNPEYSLLA  120
KLIDAESIKG TEVYTFHTRK GQYVKVTVPD SNIDKMRVDY VNWKGPKYNN KLVKRFVSQF  180
LLFRKEEKEK NEKEALLKAS ELVSGMGDKL GEYLGVKYKN VAKEVANDIK NFHGRNIRSY  240
NEAMASLNKV LANPKMKVNK SDKDAIVNAW KQVNAKDMAN KIGNLGKAFK VADLAIKVEK  300
IREKSIEGYN TGNWGPLLLE VESWIIGGVV AGVAISLFGA VLSFLPISGL AVTALGVIGI  360
MTISYLSSFI DANRVSNINN IISSVIR                                      387
```

```
SEQ ID NO: 63          moltype = DNA  length = 51
FEATURE                Location/Qualifiers
source                 1..51
                       mol_type = genomic DNA
                       organism = Escherichia coli
SEQUENCE: 63
gcaaatcgag tttcgaatat aaataacatt atatctagtg ttattcgatg a           51
```

```
SEQ ID NO: 64          moltype = AA  length = 103
FEATURE                Location/Qualifiers
source                 1..103
```

```
                         mol_type = protein
                         organism = Escherichia coli
SEQUENCE: 64
MRTLTLNELD SVSGGASGRD IAMAIGTLSG QFVAGGIGAA AGGVAGGAIY DYASTHKPNP  60
AMSPSGLGGT IKQKPEGIPS EAWNYAAGRL CNWSPNNLSD VCL                    103

SEQ ID NO: 65            moltype = DNA  length = 312
FEATURE                  Location/Qualifiers
source                   1..312
                         mol_type = genomic DNA
                         organism = Escherichia coli
SEQUENCE: 65
atgagaactc tgactctaaa tgaattagat tctgtttctg gtggtgcttc agggcgtgat  60
attgcgatgg ctataggaac actatccgga caatttgttg caggaggaat tggagcagct  120
gctgggggtg tggctggagg tgcaatatat gactatgcat ccactcacaa acctaatcct  180
gcaatgtctc catccggttt aggaggaaca attaagcaaa aacccgaagg gataccttca  240
gaagcatgga actatgctgc gggaagattg tgtaattgga gtccaaataa tcttagtgat  300
gtttgtttat aa                                                      312

SEQ ID NO: 66            moltype = AA  length = 58
FEATURE                  Location/Qualifiers
source                   1..58
                         mol_type = protein
                         organism = Enterococcus columbae
SEQUENCE: 66
MMNATENQIF VETVSDQELE MLIGGAGRGW IKTLTKDCPN VISSICAGTI ITACKNCA    58

SEQ ID NO: 67            moltype = DNA  length = 177
FEATURE                  Location/Qualifiers
source                   1..177
                         mol_type = genomic DNA
                         organism = Enterococcus columbae
SEQUENCE: 67
atgatgaatg ctactgaaaa ccaaattttt gttgagactg tgagtgacca agaattagaa  60
atgttaattg gtggtgcagg tcgtggatgg attaagactt taacaaaaga ttgtccaaat  120
gtgatttctt caatttgtgc aggtacaatt attacagctt gtaaaaattg tgcttaa     177

SEQ ID NO: 68            moltype = AA  length = 59
FEATURE                  Location/Qualifiers
source                   1..59
                         mol_type = protein
                         organism = Lactobacillus curvatus
SEQUENCE: 68
MNNVKELSMT ELQTITGGAR SYGNGVYCNN KKCWVNRGEA TQSIIGGMIS GWASGLAGM   59

SEQ ID NO: 69            moltype = DNA  length = 180
FEATURE                  Location/Qualifiers
source                   1..180
                         mol_type = genomic DNA
                         organism = Lactobacillus curvatus
SEQUENCE: 69
atgaataatg taaaagaatt aagtatgaca gaattacaaa caattaccgg cggtgctaga  60
tcatatggca acggtgttta ctgtaataat aaaaaatgtt gggtaaatcg ggtgaagca  120
acgcaaagta ttattggtgg tatgattagc ggctgggcta gtggtttagc tggaatgtaa  180

SEQ ID NO: 70            moltype = AA  length = 64
FEATURE                  Location/Qualifiers
source                   1..64
                         mol_type = protein
                         organism = Streptomyces sp.
SEQUENCE: 70
MRSEMTLTST NSAEALAAQD FANTVLSAAA PGFHADCETP AMATPATPTV AQFVIQGSTI  60
CLVC                                                               64

SEQ ID NO: 71            moltype = DNA  length = 195
FEATURE                  Location/Qualifiers
source                   1..195
                         mol_type = genomic DNA
                         organism = Streptomyces sp.
SEQUENCE: 71
gtgcgatctg agatgactct tacgagcacg aattccgctg aggctctggc ggcgcaggac  60
tttgcgaaca ccgttctcag cgcggcggcc ccgggcttcc acgcggactg cgagacgccg  120
gccatggcca ccccggccac gccgaccgtc gcccagttcg tgatccaggg cagcacgatc  180
tgcctggtct gctga                                                   195

SEQ ID NO: 72            moltype = AA  length = 65
FEATURE                  Location/Qualifiers
source                   1..65
                         mol_type = protein
```

```
                          organism = Bacillus halodurans
SEQUENCE: 72
MVNSKDLRNP EFRKAQGLQF VDEVNEKELS SLAGSGDVHA QTTWPCATVG VSVALCPTTK  60
CTSQC                                                             65

SEQ ID NO: 73             moltype = DNA  length = 198
FEATURE                   Location/Qualifiers
source                    1..198
                          mol_type = genomic DNA
                          organism = Bacillus halodurans
SEQUENCE: 73
atggtaaatt caaaagattt gcgtaatcct gaattccgca aagcccaagg tctacaattc  60
gttgacgagg tgaacgagaa ggaactttcg tctctagctg gttcaggaga tgtgcatgca  120
caaacaactt ggccttgcgc tacagttggt gtctccgtag ccttgtgccc aactacaaag  180
tgtacaagcc agtgctaa                                                198

SEQ ID NO: 74             moltype = AA  length = 66
FEATURE                   Location/Qualifiers
source                    1..66
                          mol_type = protein
                          organism = Carnobacterium divergens
SEQUENCE: 74
MKNLKEGSYT AVNTDELKSI NGGTKYYGNG VYCNSKKCWV DWGQASGCIG QTVVGGWLGG  60
AIPGKC                                                            66

SEQ ID NO: 75             moltype = DNA  length = 201
FEATURE                   Location/Qualifiers
source                    1..201
                          mol_type = genomic DNA
                          organism = Carnobacterium divergens
SEQUENCE: 75
atgaaaaact taaaagaagg ttcatacact gctgttaata ctgatgaatt aaaaagtatc  60
aatggtggaa caaaatatta tggaatggc gtttattgca attctaaaaa atgttgggta  120
gattggggac aagcttcagg ttgtatcggt caaactgttg ttggcggatg gctaggcgga  180
gctataccag gtaaatgcta a                                            201

SEQ ID NO: 76             moltype = AA  length = 63
FEATURE                   Location/Qualifiers
source                    1..63
                          mol_type = protein
                          organism = Carnobacterium divergens
SEQUENCE: 76
MIKREKNRTI SSLGYEEISN HKLQEIQGGK GILGKLGVVQ AGVDFVSGVW AGIKQSAKDH  60
PNA                                                               63

SEQ ID NO: 77             moltype = DNA  length = 192
FEATURE                   Location/Qualifiers
source                    1..192
                          mol_type = genomic DNA
                          organism = Carnobacterium divergens
SEQUENCE: 77
atgattaaaa gagaaaagaa cagaacaatt tcttcccttg gttatgaaga aatttctaat  60
cataaattgc aagaaataca aggtggaaaa ggaattcttg gtaaactagg agtagtacag  120
gcaggagtgg attttgtatc aggagtgtgg gctggaataa aacagtctgc caaagatcat  180
cctaatgcgt aa                                                      192

SEQ ID NO: 78             moltype = AA  length = 75
FEATURE                   Location/Qualifiers
source                    1..75
                          mol_type = protein
                          organism = Carnobacterium divergens
SEQUENCE: 78
MKKQILKGLV IVVCLSGATF FSTPQQASAA APKITQKQKN CVNGQLGGML AGALGGPGGV  60
VLGGIGGAIA GGCFN                                                  75

SEQ ID NO: 79             moltype = DNA  length = 228
FEATURE                   Location/Qualifiers
source                    1..228
                          mol_type = genomic DNA
                          organism = Carnobacterium divergens
SEQUENCE: 79
atgaaaaaac aaattttaaa aggttggtt atagttgttt gtttatctgg ggcaacattt  60
ttctcaacac cacaacaagc ttctgctgct gcaccgaaaa ttactcaaaa acaaaaaaat  120
tgtgttaatg gacaattagg tggaatgctt gctggagctt tgggtggacc tggcggagtt  180
gtgttaggtg gtataggtgg tgcaatagca ggaggttgtt ttaattaa               228

SEQ ID NO: 80             moltype = AA  length = 72
FEATURE                   Location/Qualifiers
source                    1..72
```

```
                        mol_type = protein
                        organism = Enterococcus durans
SEQUENCE: 80
MQTIKELNTM ELQEIIGGEN DHRMPYELNR PNNLSKGGAK CAAGILGAGL GAVGGGPGGF  60
ISAGISAVLG CM                                                     72

SEQ ID NO: 81           moltype = DNA  length = 219
FEATURE                 Location/Qualifiers
source                  1..219
                        mol_type = genomic DNA
                        organism = Enterococcus durans
SEQUENCE: 81
atgcaaacga tcaaagaatt gaacacgatg gaattacaag aaataattgg aggtgaaaat  60
gaccatcgga tgccttacga attgaaccgt ccaaataatt tatccaaagg tggggctaag  120
tgtgctgctg gaatacttgg cgctggacta ggcgcagtag gcggtggacc tggcggattt  180
attagtgccg gaatcagtgc tgttcttggt tgtatgtaa                         219

SEQ ID NO: 82           moltype = AA  length = 72
FEATURE                 Location/Qualifiers
source                  1..72
                        mol_type = protein
                        organism = Enterococcus durans
SEQUENCE: 82
MQTIKELNTM ELQKIIGGEN DHRMPYELNR PNNLSKGGAK CAAGILGAGL GAVGGGPGGF  60
ISAGISAVLG CM                                                     72

SEQ ID NO: 83           moltype = DNA  length = 219
FEATURE                 Location/Qualifiers
source                  1..219
                        mol_type = genomic DNA
                        organism = Enterococcus durans
SEQUENCE: 83
atgcaaacga tcaaagaatt gaacacgatg gaattacaaa aaataattgg aggtgaaaat  60
gaccatcgga tgccttacga attgaaccgt ccaaataatt tatccaaagg tggagctaag  120
tgcgctgccg gaatacttgg tgctggatta ggcgcagtag gcggtggacc tggcggattt  180
attagtgccg gaatcagtgc tgttcttggt tgtatgtaa                         219

SEQ ID NO: 84           moltype = AA  length = 220
FEATURE                 Location/Qualifiers
source                  1..220
                        mol_type = protein
                        note = subsp. equisimilis
                        organism = Streptococcus dysgalactiae
SEQUENCE: 84
MKKLKRLVIS LVTSLLVISS TVPALVYANE TNNFAETQKE ITTNSEATLT NEDYTKLTSE  60
VKTIYTNLIQ YDQTKNKFYV DEDKTEQYYN YDDESIKGVY LMKDSLNDEL NNNNSSNYSE  120
IINQKISEID YVLQGNDINN LIPSNTRVKR SADFSWIQRC LEEAWGYAIS LVTLKGIINL  180
FKAGKFEAAA AKLASATAGR IAGMAALFAF VATCGATTVS                        220

SEQ ID NO: 85           moltype = DNA  length = 663
FEATURE                 Location/Qualifiers
source                  1..663
                        mol_type = genomic DNA
                        note = subsp. equisimilis
                        organism = Streptococcus dysgalactiae
SEQUENCE: 85
atgaaaaaat taaaacgtct tgttatctct cttgttactt cattactagt aatttcaagt  60
acagttccag cacttgttta cgctaatgaa acaaataact ttgcagaaac tcaaaaagaa  120
attacaacaa attcagaagc aacattaacc aatgaagact acactaaatt aacttccgaa  180
gtaaaaacaa tttatacaaa tctgattcaa tacgaccaaa caaaaaacaa attttacgtc  240
gatgaagaca aaactgaaca atattataac tacgatgatg aaagtataaa aggggtttat  300
ctcatgaaag atagtttgaa cgatgagtta aacaataata actcttcaaa ctattctgaa  360
ataattaatc aaaaaatctc tgaaattgac tatgtccttc aaggaaacga tataaataat  420
ttaattccta gcaataccag agtaaaaaga tcagcagatt tttcttggat tcaaagatgt  480
ctagaagaag catggggata tgctattagt ctagttactc taaaaggaat aatcaatcta  540
tttaaagcag gaaaatttga agctgctgct gctaaattag cttctgctac agcaggtaga  600
atcgctggaa tggctgcctt atttgctttc gtagcaactt gcggtgcgac aactgtatca  660
taa                                                                663

SEQ ID NO: 86           moltype = AA  length = 57
FEATURE                 Location/Qualifiers
source                  1..57
                        mol_type = protein
                        organism = Enterococcus faecalis
SEQUENCE: 86
MKQYKVLNEK EMKKPIGGES VFSKIGNAVG PAAYWILKGL GNMSDVNQAD RINRKKH      57

SEQ ID NO: 87           moltype = DNA  length = 174
FEATURE                 Location/Qualifiers
```

```
source                  1..174
                        mol_type = genomic DNA
                        organism = Enterococcus faecalis
SEQUENCE: 87
atgaagcaat ataaagtatt gaatgaaaaa gaaatgaaaa aacctattgg gggagagtcg  60
gtttttagta aaataggtaa tgctgtaggt ccagctgctt attggatttt aaaaggatta  120
ggtaatatga gtgatgtaaa ccaagctgat agaattaata gaaagaaaca ttaa        174

SEQ ID NO: 88           moltype = AA  length = 44
FEATURE                 Location/Qualifiers
source                  1..44
                        mol_type = protein
                        organism = Enterococcus faecalis
SEQUENCE: 88
MGAIAKLVAK FGWPIVKKYY KQIMQFIGEG WAINKIIDWI KKHI                   44

SEQ ID NO: 89           moltype = DNA  length = 135
FEATURE                 Location/Qualifiers
source                  1..135
                        mol_type = genomic DNA
                        organism = Enterococcus faecalis
SEQUENCE: 89
atgggagcaa tcgcaaaatt agtagcaaag tttggatggc caattgttaa aaagtattac  60
aaacaaatta tgcaatttat tggagaagga tgggcaatta acaaaattat tgattggatc  120
aaaaaacata tttaa                                                   135

SEQ ID NO: 90           moltype = AA  length = 43
FEATURE                 Location/Qualifiers
source                  1..43
                        mol_type = protein
                        organism = Enterococcus faecalis
SEQUENCE: 90
MGAIAKLVAK FGWPFIKKFY KQIMQFIGQG WTIDQIEKWL KRH                    43

SEQ ID NO: 91           moltype = DNA  length = 132
FEATURE                 Location/Qualifiers
source                  1..132
                        mol_type = genomic DNA
                        organism = Enterococcus faecalis
SEQUENCE: 91
atgggagcaa tcgcaaaatt agtagcaaag tttggatggc catttattaa aaaattctac  60
aaacaaatta tgcagtttat cggacaagga tggacaatag atcaaattga aaaatggtta  120
aaaagacatt ga                                                      132

SEQ ID NO: 92           moltype = AA  length = 74
FEATURE                 Location/Qualifiers
source                  1..74
                        mol_type = protein
                        organism = Enterococcus faecalis
SEQUENCE: 92
MLNKKLLENG VVNAVTIDEL DAQFGGMSKR DCNLMKACCA GQAVTYAIHS LLNRLGGDSS  60
DPAGCNDIVR KYCK                                                    74

SEQ ID NO: 93           moltype = DNA  length = 225
FEATURE                 Location/Qualifiers
source                  1..225
                        mol_type = genomic DNA
                        organism = Enterococcus faecalis
SEQUENCE: 93
atgttaaata aaaaattatt agaaaatggt gtagtaaatg ctgtaacaat tgatgaactt  60
gatgctcaat ttggtggaat gagcaaacgt gattgtaact tgatgaaggc gtgttgtgct  120
ggacaagcag taacatatgc tattcatagt cttttaaatc gattaggtgg agactctagt  180
gatccagctg gttgtaatga tattgtaaga aaatattgta aataa                  225

SEQ ID NO: 94           moltype = AA  length = 65
FEATURE                 Location/Qualifiers
source                  1..65
                        mol_type = protein
                        organism = Enterococcus faecium
SEQUENCE: 94
MKHLKILSIK ETQLIYGGTT HSGKYYGNGV YCTKNKCTVD WAKATTCIAG MSIGGFLGGA  60
IPGKC                                                              65

SEQ ID NO: 95           moltype = DNA  length = 195
FEATURE                 Location/Qualifiers
source                  1..195
                        mol_type = genomic DNA
                        organism = Enterococcus faecium
SEQUENCE: 95
```

```
atgaaacatt taaaaatttt gtctattaaa gagacacaac ttatctatgg gggtaccact  60
catagtggaa aatattatgg aaatggagtg tattgcacta aaaataaatg tacggtcgat  120
tgggccaagg caactacttg tattgcagga atgtctatag gtggtttttt aggtggagca  180
attccaggga agtgc                                                   195

SEQ ID NO: 96          moltype = AA  length = 105
FEATURE                Location/Qualifiers
source                 1..105
                       mol_type = protein
                       organism = Enterococcus faecalis
SEQUENCE: 96
MVKENKFSKI FILMALSFLG LALFSASLQF LPIAHMAKEF GIPAAVAGTV LNVVEAGGWV  60
TTIVSILTAV GSGGLSLLAA AGRESIKAYL KKEIKKKGKR AVIAW                  105

SEQ ID NO: 97          moltype = DNA  length = 318
FEATURE                Location/Qualifiers
source                 1..318
                       mol_type = genomic DNA
                       organism = Enterococcus faecalis
SEQUENCE: 97
atggttaaag aaaataaatt ttctaagatt tttattttaa tggctttgag ttttttgggg  60
ttagccttgt ttagtgcaag tcttcagttt ttgcccattg cacatatggc taaagagttc  120
ggtataccag cagcagttgc aggaactgtg cttaatgtag ttgaagctgg tggatgggtc  180
actactattg tatcaattct tactgctgta ggtagcggag gtctttcttt actcgctgca  240
gcaggaagag agtcaattaa agcatacctt aagaaagaaa ttaagaaaaa aggaaaaaga  300
gcagttattg cttggtaa                                                318

SEQ ID NO: 98          moltype = AA  length = 71
FEATURE                Location/Qualifiers
source                 1..71
                       mol_type = protein
                       organism = Enterococcus faecium
SEQUENCE: 98
MQNVKELSTK EMKQIIGGEN DHRMPNELNR PNNLSKGGAK CGAAIAGGLF GIPKGPLAWA  60
AGLANVYSKC N                                                       71

SEQ ID NO: 99          moltype = DNA  length = 216
FEATURE                Location/Qualifiers
source                 1..216
                       mol_type = genomic DNA
                       organism = Enterococcus faecium
SEQUENCE: 99
atgcaaaatg taaaagaatt aagtacgaaa gagatgaaac aaattatcgg tggagaaaat  60
gatcacagaa tgcctaatga gttaaataga cctaacaact tatctaaagg tggagcaaaa  120
tgtggtgctg caattgctgg gggattattt ggaatcccaa aaggaccact agcatgggct  180
gctgggttag caaatgtata ctctaaatgc aactaa                            216

SEQ ID NO: 100         moltype = AA  length = 58
FEATURE                Location/Qualifiers
source                 1..58
                       mol_type = protein
                       organism = Enterococcus mundtii
SEQUENCE: 100
MKKLTSKEMA QVVGGKYYGN GVSCNKKGCS VDWGKAIGII GNNSAANLAT GGAAGWKS    58

SEQ ID NO: 101         moltype = DNA  length = 177
FEATURE                Location/Qualifiers
source                 1..177
                       mol_type = genomic DNA
                       organism = Enterococcus mundtii
SEQUENCE: 101
ttgaagaaat taacatcaaa agaaatggca caagtagtag gtggaaaata ctacggtaat  60
ggagtctcat gtaataaaaa agggtgcagt gttgattggg gaaaagctat tggcattatt  120
ggaaataatt ctgctgcgaa tttagctact ggtggagcag ctggttggaa aagttaa     177

SEQ ID NO: 102         moltype = AA  length = 44
FEATURE                Location/Qualifiers
source                 1..44
                       mol_type = protein
                       organism = Enterococcus faecalis
SEQUENCE: 102
MLAKIKAMIK KFPNPYTLAA KLTTYEINWY KQQYGRYPWE RPVA                   44

SEQ ID NO: 103         moltype = DNA  length = 135
FEATURE                Location/Qualifiers
source                 1..135
                       mol_type = genomic DNA
                       organism = Enterococcus faecalis
SEQUENCE: 103
```

-continued

```
atgttagcaa aaattaaagc gatgattaag aagtttccga acccttatac tttagcagct  60
aagctaacga cttacgaaat taattggtat aaacaacaat acggtcgtta tccttgggag  120
cgccctgtag cataa                                                   135

SEQ ID NO: 104         moltype = AA  length = 71
FEATURE                Location/Qualifiers
source                 1..71
                       mol_type = protein
                       organism = Enterococcus faecium
SEQUENCE: 104
MRKKLFSLAL IGIFGLVVTN FGTKVDAATR SYGNGVYCNN SKCWVNWGEA KENIAGIVIS  60
GWASGLAGMG H                                                       71

SEQ ID NO: 105         moltype = DNA  length = 216
FEATURE                Location/Qualifiers
source                 1..216
                       mol_type = genomic DNA
                       organism = Enterococcus faecium
SEQUENCE: 105
atgagaaaaa aattatttag tttagctctt attggaatat ttgggttagt tgtgacaaat  60
tttggtacaa aagttgatgc agctacgcgt tcatatggta atggtgttta ttgtaataat  120
agtaaatgct gggttaactg gggagaagct aaagagaata ttgcaggaat cgttattagt  180
ggctgggctt ctggtttggc aggtatggga cattaa                            216

SEQ ID NO: 106         moltype = AA  length = 34
FEATURE                Location/Qualifiers
source                 1..34
                       mol_type = protein
                       organism = Enterococcus faecium
SEQUENCE: 106
MNFLKNGIAK WMTGAELQAY KKKYGCLPWE KISC                              34

SEQ ID NO: 107         moltype = DNA  length = 105
FEATURE                Location/Qualifiers
source                 1..105
                       mol_type = genomic DNA
                       organism = Enterococcus faecium
SEQUENCE: 107
atgaattttc ttaaaaatgg tatcgcaaaa tggatgaccg gtgctgaatt gcaagcgtat  60
aaaaagaaat atggatgctt gccatgggaa aaaatttctt gttaa                  105

SEQ ID NO: 108         moltype = AA  length = 76
FEATURE                Location/Qualifiers
source                 1..76
                       mol_type = protein
                       organism = Enterococcus faecalis
SEQUENCE: 108
MKKKLVKGLV ICGMIGIGFT ALGTNVEAAT YYGNGVYCNK QKCWVDWSRA RSEIIDRGVK  60
AYVNGFTKVL GGIGGR                                                  76

SEQ ID NO: 109         moltype = DNA  length = 231
FEATURE                Location/Qualifiers
source                 1..231
                       mol_type = genomic DNA
                       organism = Enterococcus faecalis
SEQUENCE: 109
atgaaaaaga aattagttaa aggcttagtt atttgtggca tgattgggat tggttttaca  60
gcattaggaa caaatgtaga agccgccacg tattacggaa atggtgtcta ttgcaataag  120
caaaaatgtt gggtagattg gagtagagca cgttctgaaa ttatagacag aggcgtaaaa  180
gcatacgtca atggatttac gaaagtgtta ggtggtatag gtggaagata a           231

SEQ ID NO: 110         moltype = AA  length = 60
FEATURE                Location/Qualifiers
source                 1..60
                       mol_type = protein
                       organism = Enterococcus faecalis
SEQUENCE: 110
MKKEELVGMA KEDFLNVICE NDNKLENSGA KCPWWNLSCH LGNDGKICTY SHECTAGCNA  60

SEQ ID NO: 111         moltype = DNA  length = 183
FEATURE                Location/Qualifiers
source                 1..183
                       mol_type = genomic DNA
                       organism = Enterococcus faecalis
SEQUENCE: 111
atgaaaaaag aagaattagt aggaatggct aaggaagact ttttaaatgt tatttgtgaa  60
aatgacaaca aactagaaaa tagtggagca aaatgtcctt ggtggaatct ttcttgtcat  120
ttaggcaatg atggtaaaat ttgcacttat tcacatgaat gtaccgcagg ttgtaatgca  180
taa                                                                183
```

```
SEQ ID NO: 112          moltype = AA  length = 61
FEATURE                 Location/Qualifiers
source                  1..61
                        mol_type = protein
                        organism = Enterococcus faecalis
SEQUENCE: 112
MTELNKRLQL KRDVSTENSL KKISNTDETH GGVTTSIPCT VMVSAAVCPT LVCSNKCGGR  60
G                                                                  61

SEQ ID NO: 113          moltype = DNA  length = 186
FEATURE                 Location/Qualifiers
source                  1..186
                        mol_type = genomic DNA
                        organism = Enterococcus faecalis
SEQUENCE: 113
atgactgaac ttaacaaaag attacaatta aaaagagatg tttcaacaga aaatagtttg  60
aaaaaaattt ctaatactga tgaaacacat gggggagtta ctacatcaat tccatgtaca  120
gtaatggtta gtgcggcagt atgtcctacc cttgtttgct cgaataaatg tggcggtaga  180
ggctag                                                             186

SEQ ID NO: 114          moltype = AA  length = 58
FEATURE                 Location/Qualifiers
source                  1..58
                        mol_type = protein
                        organism = Enterococcus faecium
SEQUENCE: 114
MQNVKEVSVK EMKQIIGGSN DSLWYGVGQF MGKQANCITN HPVKHMIIPG YCLSKILG    58

SEQ ID NO: 115          moltype = DNA  length = 177
FEATURE                 Location/Qualifiers
source                  1..177
                        mol_type = genomic DNA
                        organism = Enterococcus faecium
SEQUENCE: 115
atgcaaaatg taaaagaagt ttctgtaaaa gagatgaaac aaattatcgg tggttctaat  60
gatagtcttt ggtatggtgt aggacaattt atgggtaaac aagcaaactg tataacaaac  120
catcctgtta aacacatgat aattcctgga tattgtttat cgaaaatttt agggtaa     177

SEQ ID NO: 116          moltype = AA  length = 55
FEATURE                 Location/Qualifiers
source                  1..55
                        mol_type = protein
                        organism = Enterococcus faecium
SEQUENCE: 116
MKKYNELSKK ELLQIQGGIA PIIVAGLGYL VKDAWDHSDQ IISGFKKGWN GGRRK       55

SEQ ID NO: 117          moltype = DNA  length = 168
FEATURE                 Location/Qualifiers
source                  1..168
                        mol_type = genomic DNA
                        organism = Enterococcus faecium
SEQUENCE: 117
atgaaaaaat ataatgagtt atctaaaaaa gaacttctac agattcaagg aggaatagca  60
cctattatag ttgctggcct tggctattta gtaaaagatg catgggatca ctcagatcaa  120
ataatctcag gatttaaaaa aggttggaat ggtggacgta gaaaataa               168

SEQ ID NO: 118          moltype = AA  length = 343
FEATURE                 Location/Qualifiers
source                  1..343
                        mol_type = protein
                        organism = Enterococcus faecalis
SEQUENCE: 118
MKNILLSILG VLSIVVSLAF SSYSVNAASN EWSWPLGKPY AGRYEEGQQF GNTAFNRGGT  60
YFHDGFDFGS AIYGNGSVYA VHDGKILYAG WDPVGGGSLG AFIVLQAGNT NVIYQEFSRN  120
VGDIKVSTGQ TVKKGQLIGK FTSSHLHLGM TKKEWRSAHS SWNKDDGTWF NPIPILQGGS  180
TPTPPNPGPK NFTTNVRYGL RVLGGSWLPE VTNFNNTNDG FAGYPNRQHD MLYIKVDKGQ  240
MKYRVHTAQS GWLPWVSKGD KSDTVNGAAG MPGQAIDGVQ LNYITPKGEK LSQAYYRSQT  300
TKRSGWLKVS ADNGSIPGLD SYAGIFGEPL DRLQIGISQS NPF                    343

SEQ ID NO: 119          moltype = DNA  length = 1032
FEATURE                 Location/Qualifiers
source                  1..1032
                        mol_type = genomic DNA
                        organism = Enterococcus faecalis
SEQUENCE: 119
atgaaaaata ttttactttc tattctaggg gtattatcta tcgttgtttc tttggcgttt  60
tcttcttatt ctgtcaacgc agcttctaat gagtggtcgt ggccactggg caaaccatat  120
gcgggaagat atgaagaagg acaacaattc gggaacactg catttaaccg aggaggtact  180
```

```
tatttccatg atgggtttga ctttggttct gctatttatg gaaatggcag tgtgtatgct  240
gtgcatgatg gtaaaatttt atatgctggt tgggatcctg taggtggagg ctcattaggt  300
gcatttattg tactacaagc gggaaacaca aatgtgattt atcaagaatt tagccgaaat  360
gttggagata ttaaagttag cactggacaa actgttaaaa aaggacagct gataggaaag  420
tttacttcta gtcatttaca tttaggaatg acaaaaaaag aatggcgttc tgctcattct  480
tcttggaata aagatgatgg cacttggttt aacccaattc ctatacttca aggaggatct  540
acgcctacgc ctccaaatcc aggaccaaaa aatttcacaa caaatgttcg ttacggattg  600
cgggtcctcg gaggttcatg gttaccagaa gtaaccaact ttaacaatac caatgatggt  660
ttcgcaggtt accctaatcg tcaacatgat atgctttata taaaggtaga taaagggcaa  720
atgaaatatc gtgttcacac ggctcaaagt ggatggttgc cttgggtaag taaaggggat  780
aagagcgata cagtaaatgg agcggcaggt atgcctggac aagcaattga tggtgttcag  840
ctaaactata taactcctaa gggagaaaaa ttatcacagg cttactatcg ttcacaaact  900
acgaaacgat caggctggtt aaaagtaagt gcagataatg gttctattcc tggactagac  960
agttatgcag gaatctttgg agaaccgttg gatcgcttgc aaataggtat ttcacagtca  1020
aatccatttt aa                                                      1032

SEQ ID NO: 120          moltype = AA  length = 56
FEATURE                 Location/Qualifiers
source                  1..56
                        mol_type = protein
                        organism = Staphylococcus epidermidis
SEQUENCE: 120
MENKKDLFDL EIKKDNMENN NELEAQSLGP AIKATRQVCP KATRFVTVSC KKSDCQ      56

SEQ ID NO: 121          moltype = DNA  length = 171
FEATURE                 Location/Qualifiers
source                  1..171
                        mol_type = genomic DNA
                        organism = Staphylococcus epidermidis
SEQUENCE: 121
atggaaaaca aaaaagattt atttgattta gaaatcaaaa aagataatat ggaaaataat  60
aatgaattag aagctcaatc tcttggtcct gcaattaagg caactagaca ggtatgtcct  120
aaagcaacac gttttgttac agtttcttgt aaaaaaagtg attgtcaata g           171

SEQ ID NO: 122          moltype = AA  length = 51
FEATURE                 Location/Qualifiers
source                  1..51
                        mol_type = protein
                        organism = Staphylococcus epidermidis
SEQUENCE: 122
MAAFMKLIQF LATKGQKYVS LAWKHKGTIL KWINAGQSFE WIYKQIKKLW A           51

SEQ ID NO: 123          moltype = DNA  length = 156
FEATURE                 Location/Qualifiers
source                  1..156
                        mol_type = genomic DNA
                        organism = Staphylococcus epidermidis
SEQUENCE: 123
atggcagcat ttatgaagtt aattcagttc ttagcaacta aaggtcaaaa gtatgtttca  60
cttgcatgga aacataaagg tactatttta aaatggatta acgccggtca aagttttgaa  120
tggatttata aacaaatcaa aaaattatgg gcataa                            156

SEQ ID NO: 124          moltype = AA  length = 52
FEATURE                 Location/Qualifiers
source                  1..52
                        mol_type = protein
                        organism = Staphylococcus epidermidis
SEQUENCE: 124
MEAVKEKNDL FNLDVKVNAK ESNDSGAEPR IASKFICTPG CAKTGSFNSY CC          52

SEQ ID NO: 125          moltype = DNA  length = 159
FEATURE                 Location/Qualifiers
source                  1..159
                        mol_type = genomic DNA
                        organism = Staphylococcus epidermidis
SEQUENCE: 125
atggaagcag taaaagaaaa aaatgatctt tttaatcttg atgttaaagt taatgcaaaa  60
gaatctaacg attcaggagc tgaaccaaga attgctagta aatttatatg tactcctgga  120
tgtgcaaaaa caggtagttt taacagttat tgttgttaa                         159

SEQ ID NO: 126          moltype = AA  length = 55
FEATURE                 Location/Qualifiers
source                  1..55
                        mol_type = protein
                        organism = Staphylococcus epidermidis
SEQUENCE: 126
MNNSLFDLNL NKGVETQKSD LSPQSASVLK TSIKVSKKYC KGVTLTCGCN ITGGK        55

SEQ ID NO: 127          moltype = DNA  length = 168
```

```
FEATURE                Location/Qualifiers
source                 1..168
                       mol_type = genomic DNA
                       organism = Staphylococcus epidermidis
SEQUENCE: 127
atgaataact cattattcga tttaaaccta aacaaaggtg tagaaactca aaagagtgat  60
ttaagtccgc aatctgctag tgtcttgaag acttctatta aagtatctaa aaaatattgt  120
aaaggtgtta ctttaacatg cggttgcaat attactggtg gtaaataa               168

SEQ ID NO: 128         moltype = AA  length = 52
FEATURE                Location/Qualifiers
source                 1..52
                       mol_type = protein
                       organism = Staphylococcus gallinarum
SEQUENCE: 128
MEAVKEKNEL FDLDVKVNAK ESNDSGAEPR IASKFLCTPG CAKTGSFNSY CC          52

SEQ ID NO: 129         moltype = DNA  length = 159
FEATURE                Location/Qualifiers
source                 1..159
                       mol_type = genomic DNA
                       organism = Staphylococcus gallinarum
SEQUENCE: 129
atggaagcag taaaagagaa aaatgaactt tttgatcttg acgttaaagt aaatgcaaaa  60
gagtctaatg attcaggcgc agaaccacga attgctagta aatttttatg tactcctgga  120
tgtgccaaaa caggtagctt caatagctac tgttgttaa                         159

SEQ ID NO: 130         moltype = AA  length = 63
FEATURE                Location/Qualifiers
source                 1..63
                       mol_type = protein
                       organism = Lactococcus garvieae
SEQUENCE: 130
MENNNYTVLS DEELQKIDGG IGGALGNALN GLGTWANMMN GGGFVNQWQV YANKGKINQY  60
RPY                                                                63

SEQ ID NO: 131         moltype = DNA  length = 192
FEATURE                Location/Qualifiers
source                 1..192
                       mol_type = genomic DNA
                       organism = Lactococcus garvieae
SEQUENCE: 131
atggaaaaca acaattacac agtactttca gatgaagaac tacaaaaaat tgatggtgga  60
atcggcgggg ctcttggtaa tgctctcaac ggattaggta cctgggcaaa catgatgaac  120
ggtggaggat ttgttaatca gtggcaagtt tatgctaata aaggaaaaat aaatcaatac  180
cgtccgtatt aa                                                      192

SEQ ID NO: 132         moltype = AA  length = 63
FEATURE                Location/Qualifiers
source                 1..63
                       mol_type = protein
                       organism = Lactococcus garvieae
SEQUENCE: 132
MFDLVATGMA AGVAKTIVNA VSAGMDIATA LSLFSGAFTA AGGIMALIKK YAQKKLWKQL  60
IAA                                                                63

SEQ ID NO: 133         moltype = DNA  length = 192
FEATURE                Location/Qualifiers
source                 1..192
                       mol_type = genomic DNA
                       organism = Lactococcus garvieae
SEQUENCE: 133
atgtttgatt tagtcgcgac tggaatggct gcaggtgtag caaaaactat tgttaatgcc  60
gttagtgctg gtatggatat tgccactgct ttatcattgt tctcaggagc ttttactgca  120
gctgggggaa ttatggcact cattaaaaaa tatgctcaaa agaaattatg gaaacagctt  180
attgctgcat aa                                                      192

SEQ ID NO: 134         moltype = AA  length = 91
FEATURE                Location/Qualifiers
source                 1..91
                       mol_type = protein
                       organism = Lactobacillus gasseri
SEQUENCE: 134
MVTKYGRNLG LNKVELFAIW AVLVVALLLT TANIYWIADQ FGIHLATGTA RKLLDAMASG  60
ASLGTAFAAI LGVTLPAWAL AAAGALGATA A                                 91

SEQ ID NO: 135         moltype = DNA  length = 276
FEATURE                Location/Qualifiers
source                 1..276
```

```
                        mol_type = genomic DNA
                        organism = Lactobacillus gasseri
SEQUENCE: 135
atggttacta agtacggacg taatttaggt ttgaacaagg tagagttgtt tgcaatttgg  60
gcggttttag tagttgctct tttattgacc acagcgaaca tttattggat tgctgatcaa  120
ttcgggattc atttagcgac tggaacagcc cgtaagttat tagatgcaat ggcttctggt  180
gcctcattgg gaactgcctt tgctgctatt ttgggcgtga cattacctgc atgggctttg  240
gcagctgcag gagcattggg agcgactgca gcctag                            276

SEQ ID NO: 136          moltype = AA  length = 75
FEATURE                 Location/Qualifiers
source                  1..75
                        mol_type = protein
                        organism = Lactobacillus gasseri
SEQUENCE: 136
MKNFNTLSFE TLANIVGGRN NWAANIGGVG GATVAGWALG NAVCGPACGF VGAHYVPIAW  60
AGVTAATGGF GKIRK                                                   75

SEQ ID NO: 137          moltype = DNA  length = 228
FEATURE                 Location/Qualifiers
source                  1..228
                        mol_type = genomic DNA
                        organism = Lactobacillus gasseri
SEQUENCE: 137
atgaaaaatt ttaatacatt atcatttgaa acattggcta acatagttgg tgggagaaat  60
aattgggctg ctaatatagg tggagtaggt ggagcgacag tcgctggatg ggctcttgga  120
aatgcagttt gcggtcctgc ttgtggcttt gttggagcac actatgttcc aatagcatgg  180
gctggcgtaa cggcagctac tggtggattc ggaaagataa gaaagtag                228

SEQ ID NO: 138          moltype = AA  length = 64
FEATURE                 Location/Qualifiers
source                  1..64
                        mol_type = protein
                        organism = Lactobacillus plantarum
SEQUENCE: 138
MSKLVKTLTI SEISKAQNNG GKPAWCWYTL AMCGAGYDSG TCDYMYSHCF GIKHHSSGSS  60
SYHC                                                               64

SEQ ID NO: 139          moltype = DNA  length = 195
FEATURE                 Location/Qualifiers
source                  1..195
                        mol_type = genomic DNA
                        organism = Lactobacillus plantarum
SEQUENCE: 139
atgagtaaat tggttaagac acttactata agtgaaattt ctaaggctca aaacaacggt  60
ggaaaacctg catggtgttg gtatacttta gcaatgtgtg gtgctggtta tgattcggga  120
acctgtgatt atatgtattc gcattgtttt ggtataaagc atcatagtag tggtagtagc  180
agttatcatt gttag                                                   195

SEQ ID NO: 140          moltype = AA  length = 359
FEATURE                 Location/Qualifiers
source                  1..359
                        mol_type = protein
                        organism = Haloferax mediterranei
SEQUENCE: 140
MSKDRDGRRT SRRGTLKKIG GFSLGALSFG AVGRTQAATG SSVTTADIAP PGPNGDPKSV  60
QIDDKYTGAE MYGEGDFRVG LGTDLTMYPP VYRESLGNGS GGWEFDFTVC GSTACRFVDS  120
NGDVKEDDKA KEMWWQEINF NDINQDLYSR NDSDWVGSTP ADTQPEFDYT EFALARDGVT  180
LALTALNPAM GSLALGATYF LSDMVNWIAS QHEDDSSLKR KWDYDGLSGP LYADSSTYLL  240
ARDEMTSNSY ESFTIDNIAV AFPEFPVRTK YYVTFTAPDD PSTQSISTLE EEGIYRVPAT  300
EVAAARPPGS RRSKSAADEM VYVADPKKFI EVEPVKNPSI PDRIYEEIEQ KKKQRSRKQ   359

SEQ ID NO: 141          moltype = DNA  length = 1080
FEATURE                 Location/Qualifiers
source                  1..1080
                        mol_type = genomic DNA
                        organism = Haloferax mediterranei
SEQUENCE: 141
atgtcgaaag acagagatgg gagaaggaca agtcggcgag gcacgttaaa gaaaatcggc  60
ggtttcagtc tcggagcgct tagtttcggg gcagtcggac gaactcaagc ggcgaccggc  120
tcatcggtta cgaccgctga tatcgcacct cccggaccga acggagaccc gaagagtgtt  180
cagatagatg ataaatacac cggagccgag atgtacggcg agggtgactt cagagtcggt  240
ctcggaactg acctgacgat gtatccgccc gtgtaccgtg agagtcttgg aaatggaagc  300
gggggttggg aattcgactt caccgtttgt gggtccactg cctgtcgatt tgtggacagt  360
aacggtgacg tcaaagagga cgacaaggcg aaagaaatgt ggtggcagga aattaacttc  420
aacgacataa atcaggattt atacagtcgg aacgattccg actgggtcgg gtcgacccct  480
gccgataccc aaccggagtt cgattacacc gactttgcgc tcgctcggga cggagtgacg  540
ctcgctctca cggcactcaa ccccgcaatg ggagtcttgg cactcggtgc cacgtacttc  600
ctcagcgaca tggtgaactg gattgcgagc cagcacgaag acgacagttc gctcaagaga  660
```

```
aaatgggatt acgacgggct aagtgggccg ttgtacgccg attcgtcgac gtacctactg  720
gcacgcgacg agatgacttc gaactcgtac gaatcattca cgatcgataa catcgccgtt  780
gccttcccag agttccccgt ccggaccaag tactacgtca cattcactgc gccggatgac  840
ccgtcaacgc agtcgatatc tacgctcgaa gaggagggaa tctaccgagt gcccgctacg  900
gaagtggctg cggccagacc accggggtcc cgacgttcca aatcggcagc cgacgagatg  960
gtgtacgttg ccgatccgaa gaagttcata gaggtcgagc cggtgaagaa cccaagtatc  1020
ccggaccgaa tctacgagga gatagagcaa aaaaagaaac aacggagtag gaaacagtag  1080

SEQ ID NO: 142          moltype = AA  length = 311
FEATURE                 Location/Qualifiers
source                  1..311
                        mol_type = protein
                        note = S8a
                        organism = Haloarchaeon sp.
SEQUENCE: 142
MSDKDSINRR NVLRKIGGIG VASAVGFSGL ASGESLSDDE KQDVIDTIYK SQRVEQIKKK  60
FGGVNIEPKK VQSVTTNQSG DLVTAKLSVS DGDLVYSSVK DTTVIVQFDR SASEIGESWP  120
KNTEAFIKST SSGVDLLRTA TDEEIKDVTE GVNTSEIESA DAVNIFIDPE SQTYYMEKYD  180
FNNKVLEMFE LATGGTSSGK ISPTREDQNH EYNVREHKVF NSEKQNIQLQ SDCNINSNTA  240
ADVILCFNQV GSCALCSPTL VGGPVPTVAC LLVVCFGTPN AVSAILEEVD NSCFNLIKDV  300
ISCWDEWTSF W                                                       311

SEQ ID NO: 143          moltype = DNA  length = 936
FEATURE                 Location/Qualifiers
source                  1..936
                        mol_type = genomic DNA
                        note = S8a
                        organism = Haloarchaeon sp.
SEQUENCE: 143
atgtcggata aagacagcat taacagaaga aatgtattaa gaaaaattgg cggtatcggt  60
gtggcttcag ctgtcggatt ttctggtttg gcaagcgggg aaagtcttag cgatgatgag  120
aaacaagatg ttattgacac aatttacaaa tcacaaagag ttgaacagat aaagaaaaag  180
ttcggaggag tgaatattga gccgaaaaag gttcaatctg taacgaccaa tcagagcgga  240
gatcttgtta cggcgaagct gtcggttagt gatggggatt tggtatattc gagtgtcaaa  300
gatacaactg taatagttca gttcgataga tcggcttctg aaattggtga aagttggccc  360
aagaatactg aggcattcat caaatcgacg tcctctgggg tcgatcttct acgtacagca  420
actgatgaag aaataaagga cgttactgag ggagtcaaca catctgaaat tgaatctgcg  480
gatgctgtta acatatttat tgatcctgaa tcacagacat actatatgga gaaatatgac  540
tttaataata aggtacttga gatgtttgaa ttagcgacag gtgggacaag tagtggtaaa  600
atctccccca cacgtgaaga ccagaatcac gaatataatg ttagggaaca taaagtattt  660
aactcagaaa aacagaatat acaacttcag agtgactgta atataaacag taacaccgct  720
gctgatgtta ttctatgctt caaccaggtt ggttcttgtg cactctgctc cccgacttta  780
gtcggaggtc cagtccctac agttgcatgt ctcttagtcg tctgtttcgg cactccaaat  840
gctgtgtccg cgatacttga agaagtcgat aattcttgct ttaacttgat caaggatgta  900
atttcgtgtt gggatgaatg gactagcttc tggtga                            936

SEQ ID NO: 144          moltype = AA  length = 333
FEATURE                 Location/Qualifiers
source                  1..333
                        mol_type = protein
                        organism = Lactobacillus helveticus
SEQUENCE: 144
MKHLNETTNV RILSQFDMDT GYQAVVQKGN VGSKYVYGLQ LRKGATTILR GYRGSKINNP  60
ILELSGQAGG HTQTWEFAGD RKDINGEERA GQWFIGVKPS KIEGSKIIWA KQIARVDLRN  120
QMGPHYSNTD FPRLSYLNRA GSNPFAGNKM THAEAAVSPD YTKFLIATVE NNCIGHFTIY  180
NLDTINEKLD EKGNSEDVNL ETVKYEDSFI IDNLYGDDNN SIVNSIQGYD LDNDGNIYIS  240
SQKAPDFDGS YYAHHKQIVK IPYYARSKES EDQWRAVNLS EFGGLDIPGK HSEVESIQII  300
GENHCYLTVA YHSKNKAGEN KTTLNEIYEL SWN                                333

SEQ ID NO: 145          moltype = DNA  length = 1002
FEATURE                 Location/Qualifiers
source                  1..1002
                        mol_type = genomic DNA
                        organism = Lactobacillus helveticus
SEQUENCE: 145
atgaagcatt taaatgaaac aactaatgtt agaattttaa gtcaatttga tatggatact  60
ggctatcaag cagtagttca aaaaggcaat gtaggttcaa aatatgtata tggattacaa  120
cttcgcaaag gtgctactac tatcttgcgt ggttaccgtg gaagtaaaat taataaccct  180
attcttgaat tatctggtca agcaggtggt cacacacaga catgggaatt tgctggtgat  240
cgtaaagaca ttaatggtga agaaagagca ggtcaatggt ttataggtgt taaaccatcg  300
aaaattgaag gaagcaaaat tatttgggca aagcaaattg caagagttga tcttagaaat  360
caaatgggac ctcattattc aaatactgac tttcctcgat tatcctactt gaatcgcgcc  420
ggttctaatc catttgctgg taataagatg acgcatgccg aagccgcagt atcacctgat  480
tatactaagt ttttaattgc tactgttgaa aataactgta ttggtcattt tactatatac  540
aatttagata caattaatga aaaacttgat gaaaagggaa atagtgaaga tgttaatctc  600
gaaactgtta aatacgaaga tagttttatc attgataatt tatatggtga tgataataat  660
tctattgtaa attcaattca agggtatgat ttggataatg atggaaatat ttatatttcc  720
agtcaaaaag cgccagattt tgatggctct tattatgcac atcataagca gattgttaag  780
attccatatt atgctcggtc taaagaaagc gaagaccaat ggagagctgt aaatttaagc  840
```

```
gaattcggtg gcttggatat tccaggtaaa catagtgaag ttgaaagcat ccaaattatt  900
ggtgagaatc attgttactt aactgttgca tatcattcta aaaataaagc gggtgaaaat  960
aaaactactt tgaatgagat ttatgaatta tcttggaatt ag                     1002

SEQ ID NO: 146         moltype = AA  length = 74
FEATURE                Location/Qualifiers
source                 1..74
                       mol_type = protein
                       organism = Enterococcus hirae
SEQUENCE: 146
MKKKVLKHCV ILGILGTCLA GIGTGIKVDA ATYYGNGLYC NKEKCWVDWN QAKGEIGKII  60
VNGWVNHGPW APRR                                                    74

SEQ ID NO: 147         moltype = DNA  length = 225
FEATURE                Location/Qualifiers
source                 1..225
                       mol_type = genomic DNA
                       organism = Enterococcus hirae
SEQUENCE: 147
atgaaaaaga aagtattaaa acattgtgtt attctaggaa tattaggaac ttgtctagct  60
ggcatcggta caggaataaa agttgatgca gctacttact atggaaatgg tctttattgt  120
aacaaagaaa aatgttgggt agattggaat caagctaaag gagaaattgg aaaaattatt  180
gttaatggtt gggttaatca tggtccatgg gcacctagaa ggtag                  225

SEQ ID NO: 148         moltype = AA  length = 75
FEATURE                Location/Qualifiers
source                 1..75
                       mol_type = protein
                       organism = Lactobacillus johnsonii
SEQUENCE: 148
MKQFNYLSHK DLAVVVGGRN NWQTNVGGAV GSAMIGATVG GTICGPACAV AGAHYLPILW  60
TAVTAATGGF GKIRK                                                   75

SEQ ID NO: 149         moltype = DNA  length = 228
FEATURE                Location/Qualifiers
source                 1..228
                       mol_type = genomic DNA
                       organism = Lactobacillus johnsonii
SEQUENCE: 149
atgaaacaat ttaattattt atcacataaa gatttagcag tcgttgttgg tggaagaaat  60
aattggcaaa caaatgtggg aggagcagtg ggatcagcta tgattggggc tacagttggt  120
ggtacaattt gtggacctgc atgtgctgta gctggtgccc attatcttcc tattttatgg  180
acagcggtta cagctgcaac aggtggtttt ggcaagataa gaaagtag               228

SEQ ID NO: 150         moltype = AA  length = 62
FEATURE                Location/Qualifiers
source                 1..62
                       mol_type = protein
                       organism = Lactobacillus johnsonii
SEQUENCE: 150
MKLNDKELSK IVGGNRWGDT VLSAASGAGT GIKACKSFGP WGMAICGVGG AAIGGYFGYT  60
HN                                                                 62

SEQ ID NO: 151         moltype = DNA  length = 189
FEATURE                Location/Qualifiers
source                 1..189
                       mol_type = genomic DNA
                       organism = Lactobacillus johnsonii
SEQUENCE: 151
atgaaattaa atgacaaaga attatcaaag attgttggtg gaaatcgatg gggagatact  60
gttttatcag ctgctagtgg cgcaggaact ggtattaaag catgtaaaag ttttggccca  120
tggggaatgg caatttgtgg tgtaggaggt gcagcaatag gaggttattt tggctatact  180
cataattaa                                                          189

SEQ ID NO: 152         moltype = AA  length = 59
FEATURE                Location/Qualifiers
source                 1..59
                       mol_type = protein
                       note = subsp. lactis
                       organism = Lactococcus lactis
SEQUENCE: 152
MNKNEIETQP VTWLEEVSDQ NFDEDVFGAC STNTFSLSDY WGNNGAWCTL THECMAWCK   59

SEQ ID NO: 153         moltype = DNA  length = 180
FEATURE                Location/Qualifiers
source                 1..180
                       mol_type = genomic DNA
                       note = subsp. lactis
                       organism = Lactococcus lactis
```

```
SEQUENCE: 153
atgaacaaaa atgaaattga aacacaacca gttacatggt tggaagaagt atctgatcaa  60
aattttgatg aagatgtatt tggtgcgtgt agtactaaca cattctcgct cagtgattac  120
tggggaaata acggggcttg gtgtacactc actcatgaat gtatggcttg gtgtaaataa  180

SEQ ID NO: 154          moltype = AA  length = 65
FEATURE                 Location/Qualifiers
source                  1..65
                        mol_type = protein
                        note = subsp. lactis
                        organism = Lactococcus lactis
SEQUENCE: 154
MKEKNMKKND TIELQLGKYL EDDMIELAEG DESHGGTTPA TPAISILSAY ISTNTCPTTK  60
CTRAC                                                             65

SEQ ID NO: 155          moltype = DNA  length = 198
FEATURE                 Location/Qualifiers
source                  1..198
                        mol_type = genomic DNA
                        note = subsp. lactis
                        organism = Lactococcus lactis
SEQUENCE: 155
atgaaagaaa aaaatatgaa aaagaatgac actattgaat tacaattggg aaaatacctt  60
gaagatgata tgattgaatt agctgaaggg gatgagtctc atggaggaac aacaccagca  120
actcctgcaa tctctattct cagtgcatat attagtacca atacttgtcc aacaacaaaa  180
tgtacacgtg cttgttaa                                               198

SEQ ID NO: 156          moltype = AA  length = 51
FEATURE                 Location/Qualifiers
source                  1..51
                        mol_type = protein
                        note = subsp. lactis
                        organism = Lactococcus lactis
SEQUENCE: 156
MKEQNSFNLL QEVTESELDL ILGAKGGSGV IHTISHECNM NSWQFVFTCC S          51

SEQ ID NO: 157          moltype = DNA  length = 156
FEATURE                 Location/Qualifiers
source                  1..156
                        mol_type = genomic DNA
                        note = subsp. lactis
                        organism = Lactococcus lactis
SEQUENCE: 157
atgaaagaac aaaactcttt taatcttctt caagaagtga cagaaagtga attggacctt  60
attttaggtg caaaaggcgg cagtggagtt attcatacaa tttctcatga atgtaatatg  120
aatagctggc aatttgtatt tacttgctgc tcttaa                          156

SEQ ID NO: 158          moltype = AA  length = 53
FEATURE                 Location/Qualifiers
source                  1..53
                        mol_type = protein
                        note = subsp. lactis
                        organism = Lactococcus lactis
SEQUENCE: 158
MAGFLKVVQL LAKYGSKAVQ WAWANKGKIL DWLNAGQAID WVVSKIKQIL GIK        53

SEQ ID NO: 159          moltype = DNA  length = 162
FEATURE                 Location/Qualifiers
source                  1..162
                        mol_type = genomic DNA
                        note = subsp. lactis
                        organism = Lactococcus lactis
SEQUENCE: 159
atggcagggt ttttaaaagt agttcaatta ctagctaaat atggttctaa agctgtacaa  60
tgggcttggg caaacaaggg taagatttta gattggctta atgcaggtca ggctattgat  120
tgggtagttt cgaaaattaa gcaaatttta ggtattaagt aa                    162

SEQ ID NO: 160          moltype = AA  length = 53
FEATURE                 Location/Qualifiers
source                  1..53
                        mol_type = protein
                        note = subsp. lactis
                        organism = Lactococcus lactis
SEQUENCE: 160
MAGFLKVVQI LAKYGSKAVQ WAWANKGKIL DWINAGQAID WVVEKIKQIL GIK        53

SEQ ID NO: 161          moltype = DNA  length = 162
FEATURE                 Location/Qualifiers
source                  1..162
```

```
                        mol_type = genomic DNA
                        note = subsp. lactis
                        organism = Lactococcus lactis
SEQUENCE: 161
atggcagggt ttttaaaagt agtccaaatt ttggctaagt atggttctaa agccgtacaa  60
tgggcatggg caaataaagg aaaaatctta gattggatta atgcaggtca agctattgac  120
tgggtagttg aaaagattaa gcaaattttg ggtattaaat aa                    162

SEQ ID NO: 162          moltype = AA  length = 65
FEATURE                 Location/Qualifiers
source                  1..65
                        mol_type = protein
                        organism = Lactobacillus amylovorus
SEQUENCE: 162
MKQLNSEQLQ NIIGGNRWTN AYSAALGCAV PGVKYGKKLG GVWGAVIGGV GGAAVCGLAG  60
YVRKG                                                              65

SEQ ID NO: 163          moltype = DNA  length = 198
FEATURE                 Location/Qualifiers
source                  1..198
                        mol_type = genomic DNA
                        organism = Lactobacillus amylovorus
SEQUENCE: 163
atgaaacaat tgaattcaga acaattacaa aatattatcg gtggaaatag atggactaat  60
gcatacagcg cagctttggg atgcgctgtc cctggagtta aatatggaaa aaaacttggt  120
ggcgtatggg gtgctgtaat tggtggcgta ggcggtgcag cagtctgtgg cttggcgggt  180
tatgttcgta aaggctaa                                                198

SEQ ID NO: 164          moltype = AA  length = 68
FEATURE                 Location/Qualifiers
source                  1..68
                        mol_type = protein
                        note = L45
                        organism = Lactobacillus sakei
SEQUENCE: 164
MKTEKKVLDE LSLHASAKMG ARDVESSMNA DSTPVLASVA VSMELLPTAS VLYSDVAGCF  60
KYSAKHHC                                                           68

SEQ ID NO: 165          moltype = DNA  length = 207
FEATURE                 Location/Qualifiers
source                  1..207
                        mol_type = genomic DNA
                        note = L45
                        organism = Lactobacillus sakei
SEQUENCE: 165
atgaaaacag aaaaaaaggt tttagatgaa ctgagcttac acgcttctgc aaaaatggga  60
gcacgtgatg ttgaatccag catgaatgca gactcaacac cagttttagc atcagtcgct  120
gtatccatgg aattattgcc aactgcgtct gttctttatt cggatgttgc aggttgcttc  180
aaatattctg caaaacatca ttgttag                                      207

SEQ ID NO: 166          moltype = AA  length = 91
FEATURE                 Location/Qualifiers
source                  1..91
                        mol_type = protein
                        note = subsp. lactis
                        organism = Lactococcus lactis
SEQUENCE: 166
MKTKSLVLAL SAVTLFSAGG IVAQAEGTWQ HGYGVSSAYS NYHHGSKTHS ATVVNNNTGR  60
QGKDTQRAGV WAKATVGRNL TEKASFYYNF W                                 91

SEQ ID NO: 167          moltype = DNA  length = 276
FEATURE                 Location/Qualifiers
source                  1..276
                        mol_type = genomic DNA
                        note = subsp. lactis
                        organism = Lactococcus lactis
SEQUENCE: 167
atgaaaacca agtctctcgt attggcatta tctgcggtta cgttattctc tgccggagga  60
attgtagctc aagctgaagg aacatggcaa catggatatg gtgttagttc ggcatattca  120
aattatcatc atggtagcaa aactcattca gccacagttg taaataataa tactggccga  180
caaggtaagg atacacaacg tgccggtgtt tgggcaaaag ctactgttgg acgtaactta  240
actgaaaaag cttcatttta ttataacttt tggtaa                            276

SEQ ID NO: 168          moltype = AA  length = 75
FEATURE                 Location/Qualifiers
source                  1..75
                        mol_type = protein
                        note = subsp. cremoris
                        organism = Lactococcus lactis
```

```
SEQUENCE: 168
MKNQLNFNIV SDEELSEANG GKLTFIQSTA AGDLYYNTNT HKYVYQQTQN AFGAAANTIV  60
NGWMGGAAGG FGLHH                                                  75

SEQ ID NO: 169          moltype = DNA  length = 228
FEATURE                 Location/Qualifiers
source                  1..228
                        mol_type = genomic DNA
                        note = subsp. cremoris
                        organism = Lactococcus lactis
SEQUENCE: 169
atgaaaaatc aattaaattt taatattgtt tcagatgaag aactttcaga agctaacgga  60
ggaaaattaa catttattca atcgacagcg gctggagatt tatattacaa tactaataca  120
cacaaatatg tttaccaaca aactcaaaac gcttttgggg ctgctgctaa taccattgtt  180
aatggatgga tgggtggcgc tgctggaggt ttcgggttgc accattga               228

SEQ ID NO: 170          moltype = AA  length = 68
FEATURE                 Location/Qualifiers
source                  1..68
                        mol_type = protein
                        note = subsp. cremoris
                        organism = Lactococcus lactis
SEQUENCE: 170
MKNQLNFNIV SDEELAEVNG GSLQYVMSAG PYTWYKDTRT GKTICKQTID TASYTFGVMA  60
EGWGKTFH                                                          68

SEQ ID NO: 171          moltype = DNA  length = 207
FEATURE                 Location/Qualifiers
source                  1..207
                        mol_type = genomic DNA
                        note = subsp. cremoris
                        organism = Lactococcus lactis
SEQUENCE: 171
atgaaaaatc aattaaattt taatattgtt tctgatgaag aacttgcaga agttaatgga  60
ggaagcttgc agtatgttat gagtgctgga ccatatactt ggtataaaga tactagaaca  120
ggaaaaacaa tatgtaaaca gacaattgac acagcaagtt atacatttgg tgtaatggca  180
gaaggatggg gaaaaacatt ccactaa                                      207

SEQ ID NO: 172          moltype = AA  length = 63
FEATURE                 Location/Qualifiers
source                  1..63
                        mol_type = protein
                        note = QU 12
                        organism = Lactococcus sp.
SEQUENCE: 172
MKLIDHLGAP RWAVDTILGA IAVGNLASWV LALVPGPGWA VKAGLATAAA IVKHQGKAAA  60
AAW                                                               63

SEQ ID NO: 173          moltype = DNA  length = 192
FEATURE                 Location/Qualifiers
source                  1..192
                        mol_type = genomic DNA
                        note = QU 12
                        organism = Lactococcus sp.
SEQUENCE: 173
atgaaattaa ttgatcattt aggtgctcca agatgggccg ttgatactat tttaggtgca  60
atcgcagttg ggaacttagc aagttgggtt ctagcgcttg tccctggtcc agggtgggca  120
gtaaaagctg gtttagcaac tgctgctgcc atcgttaaac atcaaggtaa agctgccgct  180
gctgcttggt aa                                                      192

SEQ ID NO: 174          moltype = AA  length = 50
FEATURE                 Location/Qualifiers
source                  1..50
                        mol_type = protein
                        note = GI-9
                        organism = Brevibacillus sp.
SEQUENCE: 174
MACQCPDAIS GWTHTDYQCH GLENKMYRHV YAICMNGTQV YCRTEWGSSC            50

SEQ ID NO: 175          moltype = DNA  length = 153
FEATURE                 Location/Qualifiers
source                  1..153
                        mol_type = genomic DNA
                        note = GI-9
                        organism = Brevibacillus sp.
SEQUENCE: 175
atggcttgcc aatgtccaga tgcgatctca ggttggacgc atacagatta ccagtgtcac  60
ggtttggaga ataaaatgta tagacatgtt tatgcaattt gcatgaacgg tactcaagta  120
tattgcagaa cagagtgggg tagcagctgc tag                               153
```

```
SEQ ID NO: 176          moltype = AA  length = 57
FEATURE                 Location/Qualifiers
source                  1..57
                        mol_type = protein
                        organism = Leuconostoc pseudomesenteroides
SEQUENCE: 176
MNKEYNSISN FKKITNKDLQ NINGGFIGRA IGDFVYFGAK GLRESGKLLN YYYKHKH     57

SEQ ID NO: 177          moltype = DNA  length = 174
FEATURE                 Location/Qualifiers
source                  1..174
                        mol_type = genomic DNA
                        organism = Leuconostoc pseudomesenteroides
SEQUENCE: 177
atgaataaag aatataatag cattagcaat tttaaaaaaa ttactaataa agacttgcaa  60
aacataaatg gtggatttat tggtagggca ataggtgact ttgtgtactt tggagcgaag  120
ggactaagag aatctggtaa actacttaat tattactata agcataagca ttga        174

SEQ ID NO: 178          moltype = AA  length = 53
FEATURE                 Location/Qualifiers
source                  1..53
                        mol_type = protein
                        organism = Leuconostoc pseudomesenteroides
SEQUENCE: 178
MKNQLMSFEV ISEKELSTVQ GGKGLGKLIG IDWLLGQAKD AVKQYKKDYK RWH         53

SEQ ID NO: 179          moltype = DNA  length = 162
FEATURE                 Location/Qualifiers
source                  1..162
                        mol_type = genomic DNA
                        organism = Leuconostoc pseudomesenteroides
SEQUENCE: 179
atgaaaaatc agttaatgtc tttcgaagtg atatcagaaa aagaattgtc cacggtacaa  60
ggtggcaaag gcttaggtaa actcatagga attgattggc ttttgggtca agctaaggac  120
gctgttaaac agtacaagaa ggattacaaa cgttggcact aa                    162

SEQ ID NO: 180          moltype = AA  length = 61
FEATURE                 Location/Qualifiers
source                  1..61
                        mol_type = protein
                        organism = Leuconostoc gelidum
SEQUENCE: 180
MMNMKPTESY EQLDNSALEQ VVGGKYYGNG VHCTKSGCSV NWGEAFSAGV HRLANGGNGF  60
W                                                                  61

SEQ ID NO: 181          moltype = DNA  length = 186
FEATURE                 Location/Qualifiers
source                  1..186
                        mol_type = genomic DNA
                        organism = Leuconostoc gelidum
SEQUENCE: 181
atgatgaaca tgaaacctac ggaaagctat gagcaattgg ataatagtgc tctcgaacaa  60
gtcgtaggag gtaagtatta tggtaacgga gttcattgca caaaaagtgg ttgttctgta  120
aactggggag aagccttttc agctggagta catcgtttag caaatggtgg aaatggtttc  180
tggtaa                                                             186

SEQ ID NO: 182          moltype = AA  length = 61
FEATURE                 Location/Qualifiers
source                  1..61
                        mol_type = protein
                        organism = Leuconostoc carnosum
SEQUENCE: 182
MNNMKSADNY QQLDNNALEQ VVGGKYYGNG VHCTKSGCSV NWGEAFSAGV HRLANGGNGF  60
W                                                                  61

SEQ ID NO: 183          moltype = DNA  length = 186
FEATURE                 Location/Qualifiers
source                  1..186
                        mol_type = genomic DNA
                        organism = Leuconostoc carnosum
SEQUENCE: 183
atgaataaca tgaaatctgc ggataattat cagcaattgg ataataatgc tctcgaacaa  60
gtcgtaggag gtaagtatta tggtaacgga gttcattgca caaaaagtgg ttgttctgta  120
aactggggag aagccttttc agctggagta catcgtttag caaatggtgg aaatggtttc  180
tggtaa                                                             186

SEQ ID NO: 184          moltype = AA  length = 63
FEATURE                 Location/Qualifiers
```

```
source                  1..63
                        mol_type = protein
                        organism = Leuconostoc mesenteroides
SEQUENCE: 184
MFLVNQLGIS KSLANTILGA IAVGNLASWL LALVPGPGWA TKAALATAET IVKHEGKAAA  60
IAW                                                               63

SEQ ID NO: 185          moltype = DNA  length = 192
FEATURE                 Location/Qualifiers
source                  1..192
                        mol_type = genomic DNA
                        organism = Leuconostoc mesenteroides
SEQUENCE: 185
atgttcttgg taaatcagtt aggatttca aaatcgttag ctaatactat tcttggtgca  60
attgctgttg gtaatttggc cagttggtta ttagctttgg ttcctggtcc gggttgggca  120
acaaaagcag cacttgcgac agctgaaaca attgtgaagc atgaaggaaa agcagctgct  180
attgcgtggt aa                                                      192

SEQ ID NO: 186          moltype = AA  length = 74
FEATURE                 Location/Qualifiers
source                  1..74
                        mol_type = protein
                        organism = Bacillus licheniformis
SEQUENCE: 186
MSKKEMILSW KNPMYRTESS YHPAGNILKE LQEEEQHSIA GGTITLSTCA ILSKPLGNNG  60
YLCTVTKECM PSCN                                                   74

SEQ ID NO: 187          moltype = DNA  length = 225
FEATURE                 Location/Qualifiers
source                  1..225
                        mol_type = genomic DNA
                        organism = Bacillus licheniformis
SEQUENCE: 187
atgtcaaaaa aggaaatgat tctttcatgg aaaaatccta tgtatcgcac tgaatcttct  60
tatcatccag cagggaacat ccttaaagaa ctccaggaag aggaacagca cagcatcgcc  120
ggaggcacaa tcacgctcag cacttgtgcc atcttgagca agccgttagg aaataacgga  180
tacctgtgta cagtgacaaa agaatgcatg ccaagctgta actaa                  225

SEQ ID NO: 188          moltype = AA  length = 266
FEATURE                 Location/Qualifiers
source                  1..266
                        mol_type = protein
                        organism = Brevibacterium linens
SEQUENCE: 188
MNNLYRELAP IPGPAWAEIE EEARRTFKRN IAGRRIVDVA GPTGFETSAV TTGHIRDVQS  60
ETSGLQVKQR IVQEYIELRT PFTVTRQAID DVARGSGDSD WQPVKDAATT IAMAEDRAIL  120
HGLDAAGIGG IVPGSSNAAV AIPDAVEDFA DAVAQALSVL RTVGVDGPYS LLLSSAEYTK  180
VSESTDHGYP IREHLSRQLG AGEIIWAPAL EGALLVSTRG GDYELHLGQD LSIGYYSHDS  240
ETVELYLQET FGFLALTDES SVPLSL                                       266

SEQ ID NO: 189          moltype = DNA  length = 801
FEATURE                 Location/Qualifiers
source                  1..801
                        mol_type = genomic DNA
                        organism = Brevibacterium linens
SEQUENCE: 189
gtgaataacc tctatcgcga gcttgccccc atccccggcc cggcctgggc ggagatcgag  60
gaggaggctc gacggacatt caaacgcaat atcgccggcc gccggatcgt cgatgtcgca  120
gggcccacgg gcttcgagac ctccgcggtg accactggcc acatccgaga cgtccagtcg  180
gagacgagcg gactgcaggt taagcagcgc atcgtgcagg aatacatcga gctgcggacc  240
ccattcaccg tgactcggca ggccatcgat gacgtggccc gcgggtccgg tgactcggac  300
tggcagcccg tcaaggatgc ggccacgacg atcgcgatgg ctgaagatcg ggccattctc  360
cacgggctcg atgcggccgg gatcggcgga atcgttcccg gcagctcgaa tgccgcagtg  420
gccatccccg acgccgtcga ggacttcgcg gacgccgtcg cccaggcgct gagtgtgctg  480
cgcacggtgg gagtcgacgg gccctacagc ctgttgctct cctccgcgga gtacaccaag  540
gtctccgagt ccaccgacca cggctacccg atccgcgagc acctctcccg gcagctcggc  600
gccggagaga tcatctgggc gcccgcgctc gaaggggcgc tgctcgtctc cacgcgcggg  660
ggtgactacg agctccacct cggccaggac ctgtcgatcg gttactacag ccacgacagc  720
gagaccgtcg aactctatct gcaggagacc ttcggattcc tcgcgctgac cgacgaatcc  780
agtgtgcctt tgagcctctg a                                            801

SEQ ID NO: 190          moltype = AA  length = 71
FEATURE                 Location/Qualifiers
source                  1..71
                        mol_type = protein
                        organism = Listeria innocua
SEQUENCE: 190
MKKAALKFII VIAILGFSFS FFSIQSEAKS YGNGVQCNKK KCWVDWGSAI STIGNNSAAN  60
WATGGAAGWK S                                                       71
```

```
SEQ ID NO: 191          moltype = DNA  length = 216
FEATURE                 Location/Qualifiers
source                  1..216
                        mol_type = genomic DNA
                        organism = Listeria innocua
SEQUENCE: 191
ttgaagaagg cagcgttaaa atttattatt gttattgcta ttctaggttt cagtttttct  60
ttctttagca tacaatctga agctaaatct tatggaaatg gagttcagtg taataagaaa  120
aaatgttggg tagattgggg tagtgctata agtactattg gaaataattc tgcagcgaat  180
tgggctacag gtggagcagc tggttggaaa agctga                            216

SEQ ID NO: 192          moltype = AA  length = 68
FEATURE                 Location/Qualifiers
source                  1..68
                        mol_type = protein
                        organism = Bacillus sp.
SEQUENCE: 192
MSQEAIIRSW KDPFSRENST QNPAGNPFSE LKEAQMDKLV GAGDMEAACT FTLPGGGGVC  60
TLTSECIC                                                           68

SEQ ID NO: 193          moltype = DNA  length = 207
FEATURE                 Location/Qualifiers
source                  1..207
                        mol_type = genomic DNA
                        organism = Bacillus sp.
SEQUENCE: 193
atgagtcaag aagctatcat tcgttcatgg aaagatcctt tttcccgtga aaattctaca  60
caaaatccag ctggtaaccc attcagtgag ctgaaagaag cacaaatgga taagttagta  120
ggtgcgggag acatggaagc agcatgtact tttacattgc ctggtggcgg cggtgtttgt  180
actctaactt ctgaatgtat ttgttaa                                      207

SEQ ID NO: 194          moltype = AA  length = 61
FEATURE                 Location/Qualifiers
source                  1..61
                        mol_type = protein
                        organism = Leuconostoc mesenteroides
SEQUENCE: 194
MTNMKSVEAY QQLDNQNLKK VVGGKYYGNG VHCTKSGCSV NWGEAASAGI HRLANGGNGF  60
W                                                                  61

SEQ ID NO: 195          moltype = DNA  length = 186
FEATURE                 Location/Qualifiers
source                  1..186
                        mol_type = genomic DNA
                        organism = Leuconostoc mesenteroides
SEQUENCE: 195
atgacgaata tgaagtctgt ggaagcatat cagcaattag ataaccagaa tctcaagaaa  60
gttgttggtg gaaagtatta tgggaatggt gttcactgta caaaaagtgg atgctctgtt  120
aactggggag aagctgcctc agctggcata catcgtttgg ccaatggtgg aaatggattt  180
tggtaa                                                             186

SEQ ID NO: 196          moltype = AA  length = 68
FEATURE                 Location/Qualifiers
source                  1..68
                        mol_type = protein
                        note = subsp. michiganensis
                        organism = Clavibacter michiganensis
SEQUENCE: 196
MNDILETETP VMVSPRWDML LDAGEDTSPS VQTQIDAEFR RVVSPYMSSS GWLCTLTIEC  60
GTIICACR                                                           68

SEQ ID NO: 197          moltype = DNA  length = 207
FEATURE                 Location/Qualifiers
source                  1..207
                        mol_type = genomic DNA
                        note = subsp. michiganensis
                        organism = Clavibacter michiganensis
SEQUENCE: 197
atgaacgaca tcctcgagac ggagaccccc gtcatggtca gcccccggtg ggacatgctg  60
ctcgacgcgg gcgaggacac cagcccgtcc gtccagaccc agatcgacgc ggagttccgt  120
cgcgtcgtga gcccgtacat gtccagcagc ggctggctct gcacgctcac catcgaatgt  180
ggcaccatca tctgcgcgtg tcgctga                                      207

SEQ ID NO: 198          moltype = AA  length = 69
FEATURE                 Location/Qualifiers
source                  1..69
                        mol_type = protein
                        organism = Escherichia coli
```

```
SEQUENCE: 198
MELKASEFGV VLSVDALKLS RQSPLGVGIG GGGGGGGGGS CGGQGGGCGG CSNGCSGGNG  60
GSGGSGSHI                                                          69

SEQ ID NO: 199         moltype = DNA  length = 207
FEATURE                Location/Qualifiers
source                 1..207
                       mol_type = genomic DNA
                       organism = Escherichia coli
SEQUENCE: 199
atggaattaa aagcgagtga atttggtgta gttttgtccg ttgatgctct taaattatca  60
cgccagtctc cattaggtgt tggcattggt ggtggtggcg gcggcggcgg cggcggtagc  120
tgcggtggtc aaggtggcgg ttgtggtggt tgcagcaacg gttgtagtgg tggaaacggt  180
ggcagcggcg gaagtggttc acatatc                                      207

SEQ ID NO: 200         moltype = AA  length = 7
FEATURE                Location/Qualifiers
source                 1..7
                       mol_type = protein
                       organism = Escherichia coli
SEQUENCE: 200
MRTGNAN                                                            7

SEQ ID NO: 201         moltype = DNA  length = 24
FEATURE                Location/Qualifiers
source                 1..24
                       mol_type = genomic DNA
                       organism = Escherichia coli
SEQUENCE: 201
atgcgtactg gtaatgcaaa ctaa                                         24

SEQ ID NO: 202         moltype = AA  length = 99
FEATURE                Location/Qualifiers
source                 1..99
                       mol_type = protein
                       organism = Klebsiella pneumoniae
SEQUENCE: 202
MREISQKDLN LAFGAGETDP NTQLLNDLGN NMAWGAALGA PGGLGSAALG AAGGALQTVG  60
QGLIDHGPVN VPIPVLIGPS WNGSGSGYNS ATSSSGSGS                         99

SEQ ID NO: 203         moltype = DNA  length = 300
FEATURE                Location/Qualifiers
source                 1..300
                       mol_type = genomic DNA
                       organism = Klebsiella pneumoniae
SEQUENCE: 203
atgagagaaa ttagtcaaaa ggacttaaat cttgcttttg gtgcaggaga gaccgatcca  60
aatactcaac ttctaaacga ccttggaaat aatatggcat ggggtgctgc tcttggcgct  120
cctggcggat taggatcagc agctttgggg gccgcgggag gtgcattaca aactgtaggg  180
caaggattaa ttgaccatgg tcctgtaaat gtccccatcc ctgtactcat cgggccaagc  240
tggaatggta gcggtagtgg ttataacagc gcaacatcca gttccggtag tggtagttaa  300

SEQ ID NO: 204         moltype = AA  length = 75
FEATURE                Location/Qualifiers
source                 1..75
                       mol_type = protein
                       organism = Escherichia coli
SEQUENCE: 204
MREITESQLR YISGAGGAPA TSANAAGAAA IVGALAGIPG GPLGVVVGAV SAGLTTAIGS  60
TVGSGSASSS AGGGS                                                   75

SEQ ID NO: 205         moltype = DNA  length = 228
FEATURE                Location/Qualifiers
source                 1..228
                       mol_type = genomic DNA
                       organism = Escherichia coli
SEQUENCE: 205
atgcgagaaa taacagaatc acagttaaga tatatttccg gggcgggagg tgcgccagcg  60
acttcagcta atgccgcagg tgctgcagct attgttggag ctctcgccgg aatacctggt  120
ggtccacttg gggttgtagt tggagccgta tctgccggtt tgacaacagc aattggctcg  180
accgtgggaa gtggtagtgc cagttcttct gctggtggcg gtagctaa               228

SEQ ID NO: 206         moltype = AA  length = 58
FEATURE                Location/Qualifiers
source                 1..58
                       mol_type = protein
                       organism = Escherichia coli
SEQUENCE: 206
MIKHFHFNKL SSGKKNNVPS PAKGVIQIKK SASQLTKGGA GHVPEYFVGI GTPISFYG    58
```

```
SEQ ID NO: 207          moltype = DNA  length = 177
FEATURE                 Location/Qualifiers
source                  1..177
                        mol_type = genomic DNA
                        organism = Escherichia coli
SEQUENCE: 207
atgattaagc attttcattt taataaactg tcttctggta aaaaaaataa tgttccatct  60
cctgcaaagg gggttataca aataaaaaaa tcagcatcgc aactcacaaa aggtggtgca  120
ggacatgtgc ctgagtattt tgtggggatt ggtacaccta tatctttcta tggctga     177

SEQ ID NO: 208          moltype = AA  length = 90
FEATURE                 Location/Qualifiers
source                  1..90
                        mol_type = protein
                        organism = Escherichia coli
SEQUENCE: 208
MYMRELDREE LNCVGGAGDP LADPNSQIVR QIMSNAAWGP PLVPERFRGM AVGAAGGVTQ  60
TVLQGAAAHM PVNVPIPKVP MGPSWNGSKG                                   90

SEQ ID NO: 209          moltype = DNA  length = 273
FEATURE                 Location/Qualifiers
source                  1..273
                        mol_type = genomic DNA
                        organism = Escherichia coli
SEQUENCE: 209
atgtatatga gagagttaga tagagaggaa ttaaattgcg ttggtggggc tggagatccg  60
cttgcagatc ctaattccca aattgtaaga cagataatgt ctaatgcggc atggggcccg  120
cctttggtgc cagagcggtt taggggaatg gctgttggag ccgcaggtgg ggttacgcag  180
acagttcttc aaggagcagc agctcatatg ccggttaatg tccctatacc taaagttccg  240
atgggaccct catggaacgg aagtaaagga taa                               273

SEQ ID NO: 210          moltype = AA  length = 50
FEATURE                 Location/Qualifiers
source                  1..50
                        mol_type = protein
                        organism = Enterococcus mundtii
SEQUENCE: 210
MSQVVGGKYY GNGVSCNKKG CSVDWGKAIG IIGNNSAANL ATGGAAGWKS             50

SEQ ID NO: 211          moltype = DNA  length = 153
FEATURE                 Location/Qualifiers
source                  1..153
                        mol_type = genomic DNA
                        organism = Enterococcus mundtii
SEQUENCE: 211
atgtcacagg tagtaggtgg aaaatactac ggtaatggag tctcatgtaa taaaaaaggg  60
tgcagtgttg attggggaaa agcgattggc attattggaa ataattctgc tgcgaattta  120
gctactggtg gagcagctgg ttggaaaagt taa                               153

SEQ ID NO: 212          moltype = AA  length = 58
FEATURE                 Location/Qualifiers
source                  1..58
                        mol_type = protein
                        organism = Enterococcus mundtii
SEQUENCE: 212
MKKLTSKEMA QVVGGKYYGN GLSCNKKGCS VDWGKAIGII GNNSAANLAT GGAAGWKS    58

SEQ ID NO: 213          moltype = DNA  length = 177
FEATURE                 Location/Qualifiers
source                  1..177
                        mol_type = genomic DNA
                        organism = Enterococcus mundtii
SEQUENCE: 213
ttgaagaaat taacatcaaa agaaatggca caagtagtag gtgggaaata ctacggtaat  60
ggattatcat gtaataaaaa agggtgcagt gttgattggg gaaaagctat tggcattatt  120
ggaaataatt ctgctgcgaa tttagctact ggtggagcag ctggttggaa aagttaa     177

SEQ ID NO: 214          moltype = AA  length = 63
FEATURE                 Location/Qualifiers
source                  1..63
                        mol_type = protein
                        organism = Streptococcus mutans
SEQUENCE: 214
MSNTQLLEVL GTETFDVQED LFAFDTTDTT IVASNDDPDT RFKSWSLCTP GCARTGSFNS  60
YCC                                                                63

SEQ ID NO: 215          moltype = DNA  length = 192
FEATURE                 Location/Qualifiers
```

```
source                  1..192
                        mol_type = genomic DNA
                        organism = Streptococcus mutans
SEQUENCE: 215
atgtcaaaca cacaattatt agaagtcctt ggtactgaaa cttttgatgt tcaagaagat  60
ctctttgctt ttgatacaac agatactact attgtggcaa gcaacgacga tccagatact  120
cgtttcaaaa gttggagcct ttgtacgcct ggttgtgcaa ggacaggtag tttcaatagt  180
tactgttgct ga                                                      192

SEQ ID NO: 216          moltype = AA  length = 53
FEATURE                 Location/Qualifiers
source                  1..53
                        mol_type = protein
                        organism = Streptococcus mutans
SEQUENCE: 216
MNKLNSNAVV SLNEVSDSEL DTILGGNRWW QGVVPTVSYE CRMNSWQHVF TCC         53

SEQ ID NO: 217          moltype = DNA  length = 162
FEATURE                 Location/Qualifiers
source                  1..162
                        mol_type = genomic DNA
                        organism = Streptococcus mutans
SEQUENCE: 217
atgaacaagt taaacagtaa cgcagtagtt tctttgaatg aagtttcaga ttctgaattg  60
gatactattt tgggtggtaa tcgttggtgg caaggtgttg tgccaacggt ctcatatgag  120
tgtcgcatga attcatggca acatgttttc acttgctgtt aa                     162

SEQ ID NO: 218          moltype = AA  length = 57
FEATURE                 Location/Qualifiers
source                  1..57
                        mol_type = protein
                        note = subsp. lactis
                        organism = Lactococcus lactis
SEQUENCE: 218
MSTKDFNLDL VSVSKKDSGA SPRITSISLC TPGCKTGALM GCNMKTATCH CSIHVSK     57

SEQ ID NO: 219          moltype = DNA  length = 174
FEATURE                 Location/Qualifiers
source                  1..174
                        mol_type = genomic DNA
                        note = subsp. lactis
                        organism = Lactococcus lactis
SEQUENCE: 219
atgagtacaa aagattttaa cttggatttg gtatctgttt cgaagaaaga ttcaggtgca  60
tcaccacgca ttacaagtat ttcgctatgt acacccggtt gtaaaacagg agctctgatg  120
ggttgtaaca tgaaaacagc aacttgtcat tgtagtattc acgtaagcaa ataa        174

SEQ ID NO: 220          moltype = AA  length = 57
FEATURE                 Location/Qualifiers
source                  1..57
                        mol_type = protein
                        organism = Lactococcus lactis
SEQUENCE: 220
MSTKDFNLDL VSVSKKDSGA SPRITSISLC TPGCKTGALM GCNMKTATCN CSVHVSK     57

SEQ ID NO: 221          moltype = DNA  length = 171
FEATURE                 Location/Qualifiers
source                  1..171
                        mol_type = genomic DNA
                        organism = Lactococcus lactis
SEQUENCE: 221
atgagtacaa aagatttcaa cttggatttg gtatctgttt cgaagaaaga ttcaggtgca  60
tcaccacgca ttacaagtat ttcgctatgt acacccggtt gtaaaacagg agctctgatg  120
ggttgtaaca tgaaaacagc aacttgtaat tgtagcgttc acgtaagcaa a           171

SEQ ID NO: 222          moltype = AA  length = 57
FEATURE                 Location/Qualifiers
source                  1..57
                        mol_type = protein
                        organism = Lactococcus lactis
SEQUENCE: 222
MSTKDFNLDL VSVSKTDSGA STRITSISLC TPGCKTGVLM GCNLKTATCN CSVHVSK     57

SEQ ID NO: 223          moltype = DNA  length = 174
FEATURE                 Location/Qualifiers
source                  1..174
                        mol_type = genomic DNA
                        organism = Lactococcus lactis
SEQUENCE: 223
```

```
atgagtacaa aagatttcaa cttagatttg gtatctgttt caaaaacaga ttctggcgct  60
tcaacacgta ttaccagcat ttcgctttgt acaccaggtt gtaaaacagg tgttctgatg  120
ggatgtaacc tgaaaacagc aacttgtaat tgtagcgttc acgtaagcaa ataa        174

SEQ ID NO: 224         moltype = AA  length = 55
FEATURE                Location/Qualifiers
source                 1..55
                       mol_type = protein
                       organism = Streptococcus uberis
SEQUENCE: 224
MNNEDFNLDL IKISKENNSG ASPRITSKSL CTPGCKTGIL MTCPLKTATC GCHFG       55

SEQ ID NO: 225         moltype = DNA  length = 168
FEATURE                Location/Qualifiers
source                 1..168
                       mol_type = genomic DNA
                       organism = Streptococcus uberis
SEQUENCE: 225
atgaacaatg aagattttaa tttggatctc atcaaaatct caaaggaaaa caactcagga  60
gcttcacctc gaataactag taaatcatta tgtactcctg gatgtaagac gggtattttg  120
atgacttgtc cactaaaaac tgcaacctgt ggttgtcatt ttggataa               168

SEQ ID NO: 226         moltype = AA  length = 57
FEATURE                Location/Qualifiers
source                 1..57
                       mol_type = protein
                       note = subsp. lactis
                       organism = Lactococcus lactis
SEQUENCE: 226
MSTKDFNLDL VSVSKKDSGA SPRITSISLC TPGCKTGALM GCNMKTATCN CSIHVSK     57

SEQ ID NO: 227         moltype = DNA  length = 174
FEATURE                Location/Qualifiers
source                 1..174
                       mol_type = genomic DNA
                       note = subsp. lactis
                       organism = Lactococcus lactis
SEQUENCE: 227
atgagtacaa aagattttaa cttggatttg gtatctgttt cgaagaaaga ttcaggtgca  60
tcaccacgca ttacaagtat ttcgctatgt acacccggtt gtaaaacagg agctctgatg  120
ggttgtaaca tgaaaacagc aacttgtaat tgtagtattc acgtaagcaa ataa        174

SEQ ID NO: 228         moltype = AA  length = 57
FEATURE                Location/Qualifiers
source                 1..57
                       mol_type = protein
                       organism = Staphylococcus warneri
SEQUENCE: 228
MENSKVMKDI EVANLLEEVQ EDELNEVLGA KKKSGVIPTV SHDCHMNSFQ FVFTCCS     57

SEQ ID NO: 229         moltype = DNA  length = 174
FEATURE                Location/Qualifiers
source                 1..174
                       mol_type = genomic DNA
                       organism = Staphylococcus warneri
SEQUENCE: 229
atggaaaatt ctaaagttat gaaggacatt gaagtagcaa atttattaga agaggttcaa  60
gaagatgaat tgaatgaagt cttaggagct aagaaaaagt caggagtaat cccaactgtg  120
tcacacgatt gccatatgaa ttctttccaa tttgtattta cttgttgttc ataa        174

SEQ ID NO: 230         moltype = AA  length = 58
FEATURE                Location/Qualifiers
source                 1..58
                       mol_type = protein
                       organism = Paenibacillus polymyxa
SEQUENCE: 230
MAENLFDLDI QVNKSQGSVE PQVLSIVACS SGCGSGKTAA SCVETCGNRC FTNVGSLC    58

SEQ ID NO: 231         moltype = DNA  length = 177
FEATURE                Location/Qualifiers
source                 1..177
                       mol_type = genomic DNA
                       organism = Paenibacillus polymyxa
SEQUENCE: 231
atggctgaaa acttatttga tctggacatt caagtaaaca aatctcaagg ttctgtagag  60
cctcaggttc tgagcattgt tgcatgttct agcggatgtg gtagcggtaa aacagctgcc  120
agttgtgttg aaacttgtgg caaccggtgc tttactaacg ttggttcact ctgctaa     177

SEQ ID NO: 232         moltype = AA  length = 62
```

```
FEATURE                 Location/Qualifiers
source                  1..62
                        mol_type = protein
                        organism = Pediococcus acidilactici
SEQUENCE: 232
MKKIEKLTEK EMANIIGGKY YGNGVTCGKH SCSVDWGKAT TCIINNGAMA WATGGHQGNH  60
KC                                                                62

SEQ ID NO: 233          moltype = DNA  length = 189
FEATURE                 Location/Qualifiers
source                  1..189
                        mol_type = genomic DNA
                        organism = Pediococcus acidilactici
SEQUENCE: 233
atgaaaaaaa ttgaaaaatt aactgaaaaa gaaatggcca atatcattgg tggtaaatac  60
tacggtaatg ggttacttg tggcaaacat tcctgctctg ttgactgggg taaggctacc  120
acttgcataa tcaataatgg agctatggca tgggctactg gtggacatca aggtaatcat  180
aaatgctag                                                          189

SEQ ID NO: 234          moltype = AA  length = 60
FEATURE                 Location/Qualifiers
source                  1..60
                        mol_type = protein
                        organism = Pediococcus pentosaceus
SEQUENCE: 234
MTEIKVLNDK ELKNVVGGKY YGNGVHCGKK TCYVDWGQAT ASIGKIIVNG WTQHGPWAHR  60

SEQ ID NO: 235          moltype = DNA  length = 183
FEATURE                 Location/Qualifiers
source                  1..183
                        mol_type = genomic DNA
                        organism = Pediococcus pentosaceus
SEQUENCE: 235
atgactgaaa ttaaagtact aaacgataag gaactaaaaa atgtcgtagg aggaaagtat  60
tacggtaacg gagtgcattg tggtaaaaag acttgctatg tggactgggg acaagctaca  120
gctagcattg gaaaaattat agtgaacgga tggacacaac acgggccttg ggcacataga  180
taa                                                                183

SEQ ID NO: 236          moltype = AA  length = 60
FEATURE                 Location/Qualifiers
source                  1..60
                        mol_type = protein
                        organism = Staphylococcus epidermidis
SEQUENCE: 236
MKNNKNLFDL EIKKETSQNT DELEPQTAGP AIRASVKQCQ KTLKATRLFT VSCKGKNGCK  60

SEQ ID NO: 237          moltype = DNA  length = 183
FEATURE                 Location/Qualifiers
source                  1..183
                        mol_type = genomic DNA
                        organism = Staphylococcus epidermidis
SEQUENCE: 237
atgaaaaata acaaaaattt atttgattta gaaattaaaa aagaaacaag tcaaaacact  60
gatgaacttg aacctcaaac tgctggacca gcgattagag cttctgtgaa acaatgtcag  120
aaaactttga aagctacgcg tttatttaca gtgtcttgca aaggaaaaaa cggatgtaaa  180
tag                                                                183

SEQ ID NO: 238          moltype = AA  length = 62
FEATURE                 Location/Qualifiers
source                  1..62
                        mol_type = protein
                        organism = Carnobacterium maltaromaticum
SEQUENCE: 238
MKTVKELSVK EMQLTTGGKY YGNGVSCNKN GCTVDWSKAI GIIGNNAAAN LTTGGAAGWN  60
KG                                                                62

SEQ ID NO: 239          moltype = DNA  length = 189
FEATURE                 Location/Qualifiers
source                  1..189
                        mol_type = genomic DNA
                        organism = Carnobacterium maltaromaticum
SEQUENCE: 239
atgaaaactg ttaaagaact tagcgttaaa gaaatgcaac taactacagg aggtaagtat  60
tacggaaatg gcgtttcctg taataaaaat ggttgtactg tagattggag caaagctatt  120
gggattatag gaaacaatgc agcagcaaat ttgactacag gtggagccgc tggttggaac  180
aaaggataa                                                          189

SEQ ID NO: 240          moltype = AA  length = 69
FEATURE                 Location/Qualifiers
```

```
VARIANT               40
                      note = Xaa = any amino acid
source                1..69
                      mol_type = protein
                      organism = Lactobacillus plantarum
SEQUENCE: 240
MYKELTVDEL ALIDGGKKKK KKVACTWGNA ATAAASGAVX GILGGPTGAL AGAIWGVSQC  60
ASNNLHGMH                                                          69

SEQ ID NO: 241        moltype = DNA  length = 210
FEATURE               Location/Qualifiers
misc_feature          119
                      note = n = a, c, t or g
source                1..210
                      mol_type = genomic DNA
                      organism = Lactobacillus plantarum
SEQUENCE: 241
atgtataaag aattaacagt tgatgaatta gcattgattg atggaggaaa aaagaagaag  60
aaaaaagtag cttgtacttg gggaaatgca gcaacagccg ctgcttctgg tgcagttang  120
ggtattcttg gtgggcctac tggtgcactg gctggagcta tctggggcgt ttcacaatgc  180
gcgtctaaca acttacacgg catgcactaa                                    210

SEQ ID NO: 242        moltype = AA  length = 56
FEATURE               Location/Qualifiers
source                1..56
                      mol_type = protein
                      organism = Lactobacillus plantarum
SEQUENCE: 242
MMKKIEKLTE KEMANIIGGK YYGNGVTCGK HSCSVNWGQA FSCSVSHLAN FGHGKC      56

SEQ ID NO: 243        moltype = DNA  length = 171
FEATURE               Location/Qualifiers
source                1..171
                      mol_type = genomic DNA
                      organism = Lactobacillus plantarum
SEQUENCE: 243
atgatgaaaa aaattgaaaa attaactgaa aaagaaatgg ccaatatcat tggtggtaaa  60
tactatggta atggggttac ttgtggtaaa cattcctgct ctgttaactg ggccaagca  120
ttttcttgta gtgtgtcaca tttagctaac ttcggtcatg gaaagtgcta a           171

SEQ ID NO: 244        moltype = AA  length = 64
FEATURE               Location/Qualifiers
source                1..64
                      mol_type = protein
                      organism = Lactobacillus plantarum
SEQUENCE: 244
MSKLVKTLTV DEISKIQTNG GKPAWCWYTL AMCGAGYDSG TCDYMYSHCF GVKHSSGGGG  60
SYHC                                                               64

SEQ ID NO: 245        moltype = DNA  length = 195
FEATURE               Location/Qualifiers
source                1..195
                      mol_type = genomic DNA
                      organism = Lactobacillus plantarum
SEQUENCE: 245
atgagtaaac tagttaaaac attaactgtc gatgaaatct ctaagattca aaccaatggt  60
ggaaaacctg catggtgttg gtacacattg gcaatgtgcg gtgctggtta tgattcaggc  120
acttgtgatt atatgtattc acactgcttt ggtgtaaaac actctagcgg tggtggcggt  180
agctaccatt gttag                                                    195

SEQ ID NO: 246        moltype = AA  length = 56
FEATURE               Location/Qualifiers
source                1..56
                      mol_type = protein
                      organism = Lactobacillus plantarum
SEQUENCE: 246
MLQFEKLQYS RLPQKKLAKI SGGFNRGGYN FGKSVRHVVD AIGSVAGIRG ILKSIR      56

SEQ ID NO: 247        moltype = DNA  length = 171
FEATURE               Location/Qualifiers
source                1..171
                      mol_type = genomic DNA
                      organism = Lactobacillus plantarum
SEQUENCE: 247
atgctacagt ttgagaaatt acaatattcc aggttgccgc aaaaaaagct tgccaaaata  60
tctggtggtt ttaatcgggg cggttataac tttggtaaaa gtgttcgaca tgttgttgat  120
gcaattggtt cagttgcagg cattcgtggt attttgaaaa gtattcgtta a           171

SEQ ID NO: 248        moltype = AA  length = 52
```

```
FEATURE                Location/Qualifiers
source                 1..52
                       mol_type = protein
                       organism = Lactobacillus plantarum
SEQUENCE: 248
MKKFLVLRDR ELNAISGGVF HAYSARGVRN NYKSAVGPAD WVISAVRGFI HG          52

SEQ ID NO: 249         moltype = DNA  length = 159
FEATURE                Location/Qualifiers
source                 1..159
                       mol_type = genomic DNA
                       organism = Lactobacillus plantarum
SEQUENCE: 249
atgaaaaaat ttctagtttt gcgtgaccgt gaattaaatg ctatttcagg tggcgttttc  60
catgcctata gcgcgcgtgg cgttcggaat aattataaaa gtgctgttgg gcctgccgat  120
tgggtcatta gcgctgtccg aggattcatc cacggatag                         159

SEQ ID NO: 250         moltype = AA  length = 55
FEATURE                Location/Qualifiers
source                 1..55
                       mol_type = protein
                       organism = Lactobacillus plantarum
SEQUENCE: 250
MTVNKMIKDL DVVDAFAPIS NNKLNGVVGG GAWKNFWSSL RKGFYDGEAG RAIRR       55

SEQ ID NO: 251         moltype = DNA  length = 168
FEATURE                Location/Qualifiers
source                 1..168
                       mol_type = genomic DNA
                       organism = Lactobacillus plantarum
SEQUENCE: 251
atgactgtga acaaaatgat taaggatttg gatgtagtag atgcatttgc acctatttct  60
aataataagt tgaacggggt tgttggggga ggcgcttgga aaaatttctg gtctagttta  120
agaaaaggat tttatgatgg cgaagctggc agagcaatcc gtcgttaa               168

SEQ ID NO: 252         moltype = AA  length = 57
FEATURE                Location/Qualifiers
source                 1..57
                       mol_type = protein
                       organism = Lactobacillus plantarum
SEQUENCE: 252
MKIKLTVLNE FEELTADAEK NISGGRRSRK NGIGYAIGYA FGAVERAVLG GSRDYNK     57

SEQ ID NO: 253         moltype = DNA  length = 174
FEATURE                Location/Qualifiers
source                 1..174
                       mol_type = genomic DNA
                       organism = Lactobacillus plantarum
SEQUENCE: 253
atgaaaatta aattaactgt tttaaatgaa tttgaagaat taactgctga cgctgaaaag  60
aatatttctg gtggccgtcg gagtcgtaaa aatggaattg gatacgctat tggttatgcg  120
tttggcgcgg ttgaacgggc cgtgcttggt ggttcaaggg attataataa gtga        174

SEQ ID NO: 254         moltype = AA  length = 47
FEATURE                Location/Qualifiers
source                 1..47
                       mol_type = protein
                       organism = Lactobacillus plantarum
SEQUENCE: 254
MDKFEKISTS NLEKISGGDL TTKLWSSWGY YLGKKARWNL KHPYVQF                47

SEQ ID NO: 255         moltype = DNA  length = 141
FEATURE                Location/Qualifiers
source                 1..141
                       mol_type = genomic DNA
                       organism = Lactobacillus plantarum
SEQUENCE: 255
atggataaat ttgaaaaaat tagtacatct aacctagaaa agatctctgg cggtgattta  60
acaaccaagt tatggagctc ttggggatat tatcttggca agaaagcacg ttggaattta  120
aagcacccat atgttcaatt t                                            141

SEQ ID NO: 256         moltype = AA  length = 55
FEATURE                Location/Qualifiers
source                 1..55
                       mol_type = protein
                       organism = Lactobacillus plantarum
SEQUENCE: 256
MNNLNKFSTL GKSSLSQIEG GSVPTSVYTL GIKILWSAYK HRKTIEKSFN KGFYH       55
```

```
SEQ ID NO: 257         moltype = DNA  length = 168
FEATURE                Location/Qualifiers
source                 1..168
                       mol_type = genomic DNA
                       organism = Lactobacillus plantarum
SEQUENCE: 257
atgaataact tgaataaatt ttctactcta ggcaagagta gcttgtctca aattgagggc  60
ggatcagtcc caacttcagt atatacgctt ggaattaaaa ttctatggtc tgcgtataag  120
catcgcaaaa cgattgaaaa aagttttaat aaaggctttt atcattaa              168

SEQ ID NO: 258         moltype = AA  length = 55
FEATURE                Location/Qualifiers
source                 1..55
                       mol_type = protein
                       organism = Lactobacillus plantarum
SEQUENCE: 258
MNNALSFEQQ FTDFSTLSDS ELESVEGGRN KLAYNMGHYA GKATIFGLAA WALLA       55

SEQ ID NO: 259         moltype = DNA  length = 168
FEATURE                Location/Qualifiers
source                 1..168
                       mol_type = genomic DNA
                       organism = Lactobacillus plantarum
SEQUENCE: 259
atgaataacg cattaagttt tgaacaacaa tttacagact tcagcacctt atcggactct  60
gaattagaat ccgttgaggg tggccgaaat aagcttgcat ataatatggg gcattacgct  120
ggtaaggcaa ccatttttgg acttgcagca tgggcactcc ttgcatga              168

SEQ ID NO: 260         moltype = AA  length = 47
FEATURE                Location/Qualifiers
source                 1..47
                       mol_type = protein
                       organism = Lactobacillus plantarum
SEQUENCE: 260
MDKIIKFQGI SDDQLNAVIG GKKKKQSWYA AAGDAIVSFG EGFLNAW               47

SEQ ID NO: 261         moltype = DNA  length = 144
FEATURE                Location/Qualifiers
source                 1..144
                       mol_type = genomic DNA
                       organism = Lactobacillus plantarum
SEQUENCE: 261
atggataaga ttattaagtt tcaagggatt tctgatgatc aattaaatgc tgttatcggt  60
gggaaaaaga aaaaacaatc ttggtacgca gcagctggtg atgcaatcgt tagttttggt  120
gaaggatttt taaatgcttg gtaa                                        144

SEQ ID NO: 262         moltype = AA  length = 59
FEATURE                Location/Qualifiers
source                 1..59
                       mol_type = protein
                       organism = Lactobacillus plantarum
SEQUENCE: 262
MKISKIEAQA RKDFFKKIDT NSNLLNVNGA KCKWWNISCD LGNNGHVCTL SHECQVSCN   59

SEQ ID NO: 263         moltype = DNA  length = 180
FEATURE                Location/Qualifiers
source                 1..180
                       mol_type = genomic DNA
                       organism = Lactobacillus plantarum
SEQUENCE: 263
atgaaaattt ctaagattga agctcaggct cgtaaagatt tttttaaaaa aatcgatact  60
aactcgaact tattaaatgt aaatggtgcc aaatgcaagt ggtggaatat ttcgtgtgat  120
ttaggaaata atggccatgt ttgtaccttg tcacatgaat gccaagtatc ttgtaactaa  180

SEQ ID NO: 264         moltype = AA  length = 67
FEATURE                Location/Qualifiers
source                 1..67
                       mol_type = protein
                       organism = Lactobacillus plantarum
SEQUENCE: 264
MTKTSRRKNA IANYLEPVDE KSINESFGAG DPEARSGIPC TIGAAVAASI AVCPTTKCSK  60
RCGKRKK                                                           67

SEQ ID NO: 265         moltype = DNA  length = 204
FEATURE                Location/Qualifiers
source                 1..204
                       mol_type = genomic DNA
                       organism = Lactobacillus plantarum
SEQUENCE: 265
```

```
atgactaaaa ctagtcgtcg taagaatgct attgctaatt atttagaacc agtcgacgaa  60
aaaagtatta atgaatcttt tggggctggg gatccggaag caagatccgg aattccatgt  120
acaatcggcg cagctgtcgc agcatcaatt gcagtttgtc caactactaa gtgtagtaaa  180
cgttgtggca agcgtaagaa ataa                                        204

SEQ ID NO: 266          moltype = AA  length = 48
FEATURE                 Location/Qualifiers
source                  1..48
                        mol_type = protein
                        organism = Lactobacillus plantarum
SEQUENCE: 266
MKIQIKGMKQ LSNKEMQKIV GGKSSAYSLQ MGATAIKQVK KLFKKWGW              48

SEQ ID NO: 267          moltype = DNA  length = 147
FEATURE                 Location/Qualifiers
source                  1..147
                        mol_type = genomic DNA
                        organism = Lactobacillus plantarum
SEQUENCE: 267
atgaaaattc aaattaaagg tatgaagcaa cttagtaata aggaaatgca aaaaatagta  60
ggtggaaaga gtagtgcgta ttctttgcag atgggggcaa ctgcaattaa acaggtaaag  120
aaactgttta aaaaatgggg atggtaa                                     147

SEQ ID NO: 268          moltype = AA  length = 207
FEATURE                 Location/Qualifiers
source                  1..207
                        mol_type = protein
                        organism = Propionibacterium jensenii
SEQUENCE: 268
MNKTHKMATL VIAAILAAGM TAPTAYADSP GNTRITASEQ SVLTQILGHK PTQTEYNRYV  60
ETYGSVPTEA DINAYIEASE SEGSSSQTAA HDDSTSPGTS TEIYTQAAPA RFSMFFLSGT  120
WITRSGVVSL SLKPRKGGIG NEGDERTWKT VYDKFHNAGQ WTRYKNNGVD ASMKKQYMCH  180
FKYGMVKTPW NLEPHKKAAD VSPVKCN                                     207

SEQ ID NO: 269          moltype = DNA  length = 624
FEATURE                 Location/Qualifiers
source                  1..624
                        mol_type = genomic DNA
                        organism = Propionibacterium jensenii
SEQUENCE: 269
atgaacaaaa cacacaaaat ggcgacgctg gtaattgccg cgatcttggc cgccggaatg  60
accgcaccaa ctgcctatgc agattctcct ggaaacacca gaattacagc cagcgagcaa  120
agcgtcctta cccagatact cggccacaaa cctacacaaa ctgaatataa ccgatacgtt  180
gagacttacg gaagcgtacc gaccgaagca gacatcaacg catatataga agcgtctgaa  240
tctgagggat catcaagtca aacggctgct cacgatgact cgacatcacc cggcacgagt  300
accgaaatct acacgcaggc agcccctgcc aggttctcaa tgtttttcct gtccggaact  360
tggatcacta ggagtggtgt agtatcgctc tccttgaagc caaggaaggg tggtattggc  420
aacgaggggg acgagcgtac ctggaagact gtatacgaca aattccataa cgctgggcaa  480
tggacacgat acaagaacaa cggcgtagac gccagcatga aaaagcagta catgtgccac  540
ttcaagtacg ggatggtgaa gacgccatgg aatctggagc cccacaagaa ggctgcagac  600
gtcagtccag tcaagtgcaa ctag                                        624

SEQ ID NO: 270          moltype = AA  length = 96
FEATURE                 Location/Qualifiers
source                  1..96
                        mol_type = protein
                        organism = Propionibacterium thoenii
SEQUENCE: 270
MKKTLLRSGT IALATAAAFG ASLAAAPSAM AVPGGCTYTR SNRDVIGTCK TGSGQFRIRL  60
DCNNAPDKTS VWAKPKVMVS VHCLVGQPRS ISFETK                           96

SEQ ID NO: 271          moltype = DNA  length = 291
FEATURE                 Location/Qualifiers
source                  1..291
                        mol_type = genomic DNA
                        organism = Propionibacterium thoenii
SEQUENCE: 271
atgaagaaga ccctcctgcg aagtggaacg atcgcactgg cgaccgcggc tgcatttggc  60
gcatcattgg cagccgcccc atctgccatg gccgttcctg gtggttgcac gtacacaaga  120
agcaatcgcg acgtcatcgg tacctgcaag actggaagcg gccagttccg aatccgactt  180
gactgcaaca acgctccaga caaaacttca gtctgggcca agcccaaggt aatggtgtcg  240
gttcactgtc ttgttggtca accgaggtcc atctcgttcg agaccaagtg a          291

SEQ ID NO: 272          moltype = AA  length = 255
FEATURE                 Location/Qualifiers
source                  1..255
                        mol_type = protein
                        note = subsp. freudenreii
                        organism = Propionibacterium freudenreichii
```

```
SEQUENCE: 272
MNTKAVNLKS ENTTKLVSYL TENQLDEFIR RIRIDGALVE EVSQNAKQAL DNTGLNGWIN  60
TDCDEGLLSD FISKIASARW IPLAESIRPA VTDRDKYRVS CWFYQGMNIA IYANIGGVAN  120
IIGYTEAAVA TLLGAVVAVA PVVPGTPTPP KDKSSQYKEV PLAVRLSETY HEEGVRGLFD  180
ELNYSESRMI STLRRASTDG VLINSWNDGQ DTILLKKYNF QDLQLTVRSR IVGNQTIIEE  240
CKITDGRKTL SDETV                                                   255

SEQ ID NO: 273         moltype = DNA  length = 768
FEATURE                Location/Qualifiers
source                 1..768
                       mol_type = genomic DNA
                       note = subsp. freudenreii
                       organism = Propionibacterium freudenreichii
SEQUENCE: 273
atgaatacca aagctgtaaa tctgaagtca gaaaacacga ctaagttggt gagctacctt  60
acggaaaatc aattggatga gtttattaga aggattcgca ttgatggcgc tcttgtggaa  120
gaggtcagtc aaaatgctaa gcaggcctta gataatactg ggctcaatgg ctggataaat  180
actgattgcg atgaaggcct tctctctgat ttcatttcaa agatagcaag tgctagatgg  240
attccattag ctgagtcaat tcgacctgcg gtgactgaca gggataagta tcgagtaagt  300
tgctggttct accaggggat gaatatagca atttacgcaa atatcggtgg cgtggccaat  360
attatcggct atacggaggc cgcagtcgca acactccttg gtgcagttgt ggcggtagct  420
cctgtggtcc ctggaactcc aacccctcca aaggacaaga gttcgcaata taaggaggtt  480
ccccttgccg ttcgtctttc cgaaacatac cacgaagagg gagtacgagg tctattcgac  540
gagctgaact actccgagag ccgtatgatc tctactctaa ggcgagcatc aaccgatgga  600
gtcctaatta attcttggaa cgatgggcag gatacaattc tgcttaagaa gtacaatttc  660
caagacttgc aactgactgt caggagccgc attgttggga atcaaacaat aattgaagaa  720
tgcaaaatca ctgatggtag aaaaactctt tcagacgaga ctgtgtag              768

SEQ ID NO: 274         moltype = AA  length = 618
FEATURE                Location/Qualifiers
source                 1..618
                       mol_type = protein
                       organism = Pseudomonas aeruginosa
SEQUENCE: 274
MARPIADLIH FNSTTVTASG DVYYGPGGGT GIGPIARPIE HGLDSSTENG WQEFESYADV  60
GVDPRRYVPL QVKEKRREIE LQFRDAEKKL EASVQAELDK ADAALGPAKN LAPLDVINRS  120
LTIVGNALQQ KNQKLLLNQK KITSLGAKNF LTRTAEEIGE QAVREGNING PEAYMRFLDR  180
EMEGLTAAYN VKLFTEAISS LQIRMNTLTA AKASIEAAAA NKAREQAAAE AKRKAEEQAR  240
QQAAIRAANT YAMPANGSVV ATAAGRGLIQ VAQGAASLAQ AISDAIAVLG RVLASAPSVM  300
AVGFASLTYS SRTAEQWQDQ TPDSVRYALG MDAAKLGLPP SVNLNAVAKA SGTVDLPMRL  360
TNEARGNTTT LSVVSTDGVS VPKAVPVRMA AYNATTGLYE VTVPSTTAEA PPLILTWTPA  420
SPPGNQNPSS TTPVVPKPVP VYEGATLTPV KATPETYPGV ITLPEDLIIG FPADSGIKPI  480
YVMFRDPRDV PGAATGKGQP VSGNWLGAAS QGEGAPIPSQ IADKLRGKTF KNWRDFREQF  540
WIAVANDPEL SKQFNPGSLA VMRDGGAPYV RESEQAGGRI KIEIHHKVRV ADGGGVYNMG  600
NLVAVTPKRH IEIHKGGK                                                618

SEQ ID NO: 275         moltype = DNA  length = 1857
FEATURE                Location/Qualifiers
source                 1..1857
                       mol_type = genomic DNA
                       organism = Pseudomonas aeruginosa
SEQUENCE: 275
atggcacgac ccattgctga ccttatccac ttcaactcta caactgtcac ggcaagcgga  60
gacgtttatt acggccctgg gggaggtacc ggcattggcc ccattgccag acctatagag  120
cacggcttgg attcgtccac tgaaaatggc tggcaagagt ttgaaagtta tgctgatgtg  180
ggcgttgacc ccagacgcta tgttcctctt caggttaaag aaaaacgcag ggagatcgag  240
cttcagttcc gagatgccga gaaaaaactt gaggcgtcgg tacaagccga gctggataag  300
gctgatgccg ctcttggtcc ggcaaagaat cttgcaccat tggacgtcat caaccgcagt  360
ctgaccatcg ttggaaacgc cctccagcaa aagaatcaaa aactactgct gaatcagaag  420
aagattacca gcctgggtgc aaagaatttc cttacccgta cggcggaaga gatcggtgaa  480
caagcggtgc gagaaggcaa tattaacggg cctgaagcct atatgcgctt cctcgacagg  540
gaaatggaag gtctcacggc agcttataac gtaaaactct tcaccgaagc gatcagtagt  600
ctccagatcc gcatgaatac gttgaccgcc gccaaagcaa gtattgaggc ggccgcagca  660
aacaaggcgc gtgaacaagc agcggctgag gccaaacgca aagccgaaga gcaggcccgc  720
cagcaagcgg cgataagagc tgccaatacc tatgccatgc cggccaatgg cagcgttgtc  780
gccaccgccg caggccgggg tctgatccag gtcgcacaag gcgccgcatc ccttgctcaa  840
gcgatctccg atgcgattgc cgtcctgggc cgggtcctgg cttcagcacc ctcggtgatg  900
gccgtgggct ttgccagtct gacctactcc tcccggactg ccgagcaatg gcaggaccaa  960
acgcccgata gcgttcgtta cgccctgggc atggatgccg ctaaattggg gcttccccca  1020
agcgtaaacc tgaacgcggt tgcaaaagcc agcggtaccg tcgatctgcc gatgcgcctg  1080
accaacgagg cacgaggcaa cacgacgacc ctttcggtgg tcagcaccga tggtgtgagc  1140
gttccgaaag ccgttccggt ccggatggcg gcctacaatg ccacgacagg cctgtacgag  1200
gttacggttc cctctacgac cgcagaagcg ccgccactga tcctgacctg gacgccggcg  1260
agtcctccag gaaaccagaa cccttcgagt accactccgg tcgtaccgaa gccggtgccg  1320
gtatatgagg gagcgaccct tacaccggtg aaggctaccc cggaaaccta tcctggggtg  1380
attacactac cggaagacct gatcatcggc ttcccggccg actcggggat caagccgatc  1440
tatgtgatgt tcagggatcc gcgggatgta cctggtgctg cgactggcaa gggacagccc  1500
gtcagcggta attggctcgg cgccgcctct caaggtgagg ggctccaat tccaagccag  1560
attgcggata aactacgtgg taagacattc aaaaactggc gggactttcg ggaacaattc  1620
```

```
tggatagctg tggctaatga tcctgagtta agtaaacagt ttaatcctgg tagtttagct  1680
gtaatgagag atggaggggc tccttatgtc agagagtcag aacaggctgg cgggagaata  1740
aagatcgaaa tccaccacaa ggttcgagta gcagatggag gcggcgttta caatatgggg  1800
aaccttgttg cagtaacgcc aaaacgtcat atagaaatcc acaagggagg gaagtga     1857

SEQ ID NO: 276          moltype = AA  length = 689
FEATURE                 Location/Qualifiers
source                  1..689
                        mol_type = protein
                        organism = Pseudomonas aeruginosa
SEQUENCE: 276
MAVNDYEPGS MVITHVQGGG RDIIQYIPAR SSYGTPPFVP PGPSPYVGTG MQEYRKLRST  60
LDKSHSELKK NLKNETLKEV DELKSEAGLP GKAVSANDIR DEKSIVDALM DAKAKSLKAI  120
EDRPANLYTA SDFPQKSESM YQSQLLASRK FYGEFLDRHM SELAKAYSAD IYKAQIAILK  180
QTSQELENKA RSLEAEAQRA AAEVEADYKA RKANVEKKVQ SELDQAGNAL PQLTNPTPEQ  240
WLERATQLVT QAIANKKKLQ TANNALIAKA PNALEKQKAT YNADLLVDEI ASLQARLDKL  300
NAETARRKEI ARQAAIRAAN TYAMPANGSV VATAAGRGLI QVAQGAASLA QAISDAIAVL  360
GRVLASAPSV MAVGFASLTY SSRTAEQWQD QTPDSVRYAL GMDAAKLGLP PSVNLNAVAK  420
ASGTVDLPMR LTNEARGNTT TLSVVSTDGV SVPKAVPVRM AAYNATTGLY EVTVPSTTAE  480
APPLILTWTP ASPPGNQNPS STTPVVPKPV PVYEGATLTP VKATPETYPG VITLPEDLII  540
GFPADSGIKP IYVMFRDPRD VPGAATGKGQ PVSGNWLGAA SQGEGAPIPS QIADKLRGKT  600
FKNWRDFREQ FWIAVANDPE LSKQFNPGSL AVMRDGGAPY VRESEQAGGR IKIEIHHKVR  660
IADGGGVYNM GNLVAVTPKR HIEIHKGGK                                   689

SEQ ID NO: 277          moltype = DNA  length = 2070
FEATURE                 Location/Qualifiers
source                  1..2070
                        mol_type = genomic DNA
                        organism = Pseudomonas aeruginosa
SEQUENCE: 277
atggctgtca atgattacga acctggttcg atggttatta cacatgtgca gggtggtggg  60
cgtgacataa tccagtatat tcctgctcga tcaagctacg gtactccacc atttgtccca  120
ccaggaccaa gtccgtatgt cggtactgga atgcaggagt acaggaagct aagaagtacg  180
cttgataagt cccattcaga actcaagaaa aacctgaaaa atgaaaccct gaaggaggtt  240
gatgaactca agagtgaagc ggggttgcca ggtaaagcgg tcagtgccaa tgacatccgc  300
gatgaaaaga gtatcgttga tgcactcatg gatgccaaag caaaatcgct aaaggccatt  360
gaggatcgcc cggccaatct ttatacggct tcagactttc ctcagaagtc agagtcgatg  420
taccagagtc agttgctggc cagccgaaaa ttctatggag agttcctgga tcgccatatg  480
agtgagctgg ccaaagcgta cagcgccgat atctataagg cgcaaatcgc tatcttgaaa  540
caaacgtctc aagagctgga gaataaagcc cggtcattgg aagcagaagc ccagcgagcc  600
gctgctgagg tggaggcgga ctacaaggcc aggaaggcaa atgtcgagaa aaaagtgcag  660
tccgagcttg accaggctgg gaatgctttg cctcaactga ccaatccaac gccagagcag  720
tggcttgaac gcgctactca actggttacg caggcgatcg ccaataagaa gaaattgcag  780
actgcaaaca atgccttgat tgccaaggca cccaatgcac tggagaaaca aaaggcaacc  840
tacaacgccg atctcctagt ggatgaaatc gccagcctgc aagcacggct ggacaagctg  900
aacgccgaaa cggcaaggcg caaggaaatc gctcgtcaag cggcgatcag ggctgccaat  960
acttatgcca tgccagccaa tggcagcgtt gtcgccaccg ccgcaggccg gggtctgatc  1020
caggtcgcac aaggcgccgc atcccttgct caagcgatct ccgatgcgat tgccgtcctg  1080
ggccgggtcc tggcttcagc accctcggtg atggccgtgg gctttgccag tctgacctac  1140
tcctcccgga ctgccgagca atggcaggac caaacgcccg atagcgttcg ttacgccctg  1200
ggcatggatg ccgctaaatt ggggcttccc ccaagcgtaa acctgaacgc ggttgcaaaa  1260
gccagcggta ccgtcgatct gccgatgcgc ctgaccaacg aggcacgagg caacacgacg  1320
accctttcgg tggtcagcac cgatggtgtg agcgttccga aagccgttcc ggtccggatg  1380
gcggcctaca atgccacgac aggcctgtac gaggttacgg ttccctctac gaccgcagaa  1440
gcgccgccac tgatcctgac ctggacgccg gcgagtcctc caggaaacca gaacccttcg  1500
agtaccactc cggtcgtacc gaagccggtg ccggtatatg agggagcgac ccttacaccg  1560
gtgaaggcta ccccggaaac ctatcctggg gtgattacac taccggaaga cctgatcatc  1620
ggcttcccgg ccgactcggg gatcaagccg atctatgtga tgttcaggga tccgcgggat  1680
gtacctggtg ctgcgactgg caagggacag cccgtcagcg gtaattggct cggcgccgcc  1740
tctcaaggtg agggggctcc aattccaagc cagattgcgg ataaactacg tggtaagaca  1800
ttcaaaaact ggcgggactt tcgggaacaa ttctggatag ctgtggctaa tgatcctgag  1860
ttaagtaaac agtttaatcc tggtagttta gctgtaatga gagatggagg ggctccttat  1920
gtcagagagt cagaacaggc tggcgggaga ataaagatcg aaatccacca caaggttcga  1980
atagcagatg gaggcggcgt ttacaatatg ggaaccttg ttgcagtaac gccaaaacgt   2040
catatagaaa tccacaaggg agggaagtga                                  2070

SEQ ID NO: 278          moltype = AA  length = 47
FEATURE                 Location/Qualifiers
source                  1..47
                        mol_type = protein
                        organism = Ruminococcus gnavus
SEQUENCE: 278
MRNDVLTLTN PMEEKELEQI LGGGNGVLKT ISHECNMNTW QFLFTCC               47

SEQ ID NO: 279          moltype = DNA  length = 144
FEATURE                 Location/Qualifiers
source                  1..144
                        mol_type = genomic DNA
                        organism = Ruminococcus gnavus
```

```
SEQUENCE: 279
atgagaaatg acgtattaac attaacaaac ccaatggaag agaacgaact ggagcagatc  60
ttaggtggtg gcaatggtgt gttaaaaacg attagccacg aatgcaatat gaacacatgg  120
cagttcctgt ttacttgttg ctaa                                         144

SEQ ID NO: 280          moltype = AA  length = 55
FEATURE                 Location/Qualifiers
source                  1..55
                        mol_type = protein
                        organism = Lactobacillus sakei
SEQUENCE: 280
MKNAKSLTIQ EMKSITGGKY YGNGVSCNSH GCSVNWGQAW TCGVNHLANG GHGVC       55

SEQ ID NO: 281          moltype = DNA  length = 168
FEATURE                 Location/Qualifiers
source                  1..168
                        mol_type = genomic DNA
                        organism = Lactobacillus sakei
SEQUENCE: 281
atgaaaaacg caaaaagcct aacaattcaa gaaatgaaat ctattacagg tggtaaatac  60
tatggtaatg gcgttagctg taactctcac ggctgttcag taaattgggg gcaagcatgg  120
acttgtggag taaaccatct agctaatggc ggtcatggag tttgttaa               168

SEQ ID NO: 282          moltype = AA  length = 59
FEATURE                 Location/Qualifiers
source                  1..59
                        mol_type = protein
                        organism = Lactobacillus sakei
SEQUENCE: 282
MNNVKELSMT ELQTITGGAR SYGNGVYCNN KKCWVNRGEA TQSIIGGMIS GWASGLAGM   59

SEQ ID NO: 283          moltype = DNA  length = 180
FEATURE                 Location/Qualifiers
source                  1..180
                        mol_type = genomic DNA
                        organism = Lactobacillus sakei
SEQUENCE: 283
atgaataatg taaaagaatt aagtatgaca gaattacaaa caattaccgg cggtgctaga  60
tcatatggca acggtgttta ctgtaataat aaaaaatgtt gggtaaatcg ggtgaagca  120
acgcaaagta ttattggtgg tatgattagc ggctgggcta gtggtttagc tggaatgtaa  180

SEQ ID NO: 284          moltype = AA  length = 61
FEATURE                 Location/Qualifiers
source                  1..61
                        mol_type = protein
                        organism = Lactobacillus sakei
SEQUENCE: 284
MEKFIELSLK EVTAITGGKY YGNGVHCGKH SCTVDWGTAI GNIGNNAAAN WATGGNAGWN  60
K                                                                  61

SEQ ID NO: 285          moltype = DNA  length = 186
FEATURE                 Location/Qualifiers
source                  1..186
                        mol_type = genomic DNA
                        organism = Lactobacillus sakei
SEQUENCE: 285
atggaaaagt ttattgaatt atctttaaaa gaagtaacag caattacagg tggaaaatat  60
tatggtaacg gtgtacactg tggaaaacat tcatgtaccg tagactgggg aacagctatt  120
ggaaatatcg gaaataatgc agctgcaaac tgggccacag gcggaaacgc tggctggaat  180
aaataa                                                             186

SEQ ID NO: 286          moltype = AA  length = 56
FEATURE                 Location/Qualifiers
source                  1..56
                        mol_type = protein
                        organism = Streptococcus salivarius
SEQUENCE: 286
MKSTNNQSIA EIAAVNSLQE VSMEELDQII GAGNGVVLTL THECNLATWT KKLKCC       56

SEQ ID NO: 287          moltype = DNA  length = 171
FEATURE                 Location/Qualifiers
source                  1..171
                        mol_type = genomic DNA
                        organism = Streptococcus salivarius
SEQUENCE: 287
atgaaatcaa caaataatca aagtatcgca gaaattgcag cagtaaactc actacaagaa  60
gtaagtatgg aggaactaga ccaaattatt ggtgccggaa acggagtggt tcttactctt  120
actcatgaat gtaacctagc aacttggaca aaaaaactaa aatgttgcta a           171
```

```
SEQ ID NO: 288         moltype = AA  length = 51
FEATURE                Location/Qualifiers
source                 1..51
                       mol_type = protein
                       note = serotype M28
                       organism = Streptococcus pyogenes
SEQUENCE: 288
MSFMKNSKDI LTNAIEEVSE KELMEVAGGK KGSGWFATIT DDCPNSVFVC C           51

SEQ ID NO: 289         moltype = DNA  length = 156
FEATURE                Location/Qualifiers
source                 1..156
                       mol_type = genomic DNA
                       note = serotype M28
                       organism = Streptococcus pyogenes
SEQUENCE: 289
atgagtttta tgaaaaattc aaaggatatt ttgactaatg ctatcgaaga agtttctgaa  60
aaagaactta tggaagtagc tggtggtaaa aaaggttccg gttggtttgc aactattact  120
gatgactgtc cgaactcagt attcgtttgt tgttaa                            156

SEQ ID NO: 290         moltype = AA  length = 48
FEATURE                Location/Qualifiers
source                 1..48
                       mol_type = protein
                       organism = Streptococcus salivarius
SEQUENCE: 290
MKNSKDVLNN AIEEVSEKEL MEVAGGKKGP GWIATITDDC PNSIFVCC               48

SEQ ID NO: 291         moltype = DNA  length = 147
FEATURE                Location/Qualifiers
source                 1..147
                       mol_type = genomic DNA
                       organism = Streptococcus salivarius
SEQUENCE: 291
atgaaaaact caaaagatgt tttgaacaat gctatcgaag aggtttctga aaaagaactt  60
atggaagtag ctggtggtaa aaaaggtcca ggttggattg caactattac tgatgactgt  120
ccaaactcaa tattcgtttg ttgttaa                                      147

SEQ ID NO: 292         moltype = AA  length = 48
FEATURE                Location/Qualifiers
source                 1..48
                       mol_type = protein
                       organism = Streptococcus salivarius
SEQUENCE: 292
MKNSKDILNN AIEEVSEKEL MEVAGGKRGS GWIATITDDC PNSVFVCC               48

SEQ ID NO: 293         moltype = DNA  length = 147
FEATURE                Location/Qualifiers
source                 1..147
                       mol_type = genomic DNA
                       organism = Streptococcus salivarius
SEQUENCE: 293
atgaaaaact caaaagatat tttgaacaat gctatcgaag aagtttctga aaaagaactt  60
atggaagtag ctggtggtaa aagaggttca ggttggattg caactattac tgatgactgt  120
ccaaactcag tattcgtttg ttgttaa                                      147

SEQ ID NO: 294         moltype = AA  length = 62
FEATURE                Location/Qualifiers
source                 1..62
                       mol_type = protein
                       organism = Staphylococcus aureus
SEQUENCE: 294
MKSSFLEKDI EEQVTWFEEV SEQEFDDDIF GACSTNTFSL SDYWGNKGNW CTATHECMSW  60
CK                                                                 62

SEQ ID NO: 295         moltype = DNA  length = 189
FEATURE                Location/Qualifiers
source                 1..189
                       mol_type = genomic DNA
                       organism = Staphylococcus aureus
SEQUENCE: 295
atgaaaagtt ctttttttaga aaaagatata gaagaacaag tgacatggtt cgaggaagtt  60
tcagaacaag aatttgacga tgatattttt ggagcttgta gtacaaacac tttttctttg  120
agtgactatt ggggtaataa aggaaattgg tgtactgcta ctcacgaatg tatgtcttgg  180
tgtaaataa                                                          189

SEQ ID NO: 296         moltype = AA  length = 67
FEATURE                Location/Qualifiers
source                 1..67
```

```
                         mol_type = protein
                         organism = Staphylococcus aureus
SEQUENCE: 296
MKNELGKFLE ENELELGKFS ESDMLEITDD EVYAAGTPLA LLGGAATGVI GYISNQTCPT  60
TACTRAC                                                           67

SEQ ID NO: 297           moltype = DNA  length = 204
FEATURE                  Location/Qualifiers
source                   1..204
                         mol_type = genomic DNA
                         organism = Staphylococcus aureus
SEQUENCE: 297
atgaaaaatg aattaggtaa gtttttagaa gaaaacgaat tagagttagg taaatttca  60
gaatcagaca tgctagaaat tactgatgat gaagtatatg cagctggaac acctttagcc  120
ttattgggtg gagctgccac cggggtgata ggttatattt ctaaccaaac atgtccaaca  180
actgcttgta cacgcgcttg ctag                                        204

SEQ ID NO: 298           moltype = AA  length = 46
FEATURE                  Location/Qualifiers
source                   1..46
                         mol_type = protein
                         organism = Streptococcus pyogenes
SEQUENCE: 298
MNNTIKDFDL DLKTNKKDTA TPYVGSRYLC TPGSCWKLVC FTTTVK                46

SEQ ID NO: 299           moltype = DNA  length = 141
FEATURE                  Location/Qualifiers
source                   1..141
                         mol_type = genomic DNA
                         organism = Streptococcus pyogenes
SEQUENCE: 299
atgaataaca caattaaaga ctttgatctc gatttgaaaa caaataaaaa agacactgct  60
acaccttatg ttggtagccg ttacctatgt acccctggtt cttgttggaa attagtttgc  120
tttacaacaa ctgttaaata a                                           141

SEQ ID NO: 300           moltype = AA  length = 51
FEATURE                  Location/Qualifiers
source                   1..51
                         mol_type = protein
                         organism = Streptococcus pyogenes
SEQUENCE: 300
MEKNNEVINS IQEVSLEELD QIIGAGKNGV FKTISHECHL NTWAFLATCC S           51

SEQ ID NO: 301           moltype = DNA  length = 156
FEATURE                  Location/Qualifiers
source                   1..156
                         mol_type = genomic DNA
                         organism = Streptococcus pyogenes
SEQUENCE: 301
atggaaaaaa ataatgaagt aatcaactct attcaagaag ttagtcttga agaactcgat  60
caaattatcg gtgctggaaa aaatggtgtg tttaaaacaa tttctcatga gtgtcatttg  120
aatacatggg cattccttgc tacttgttgt tcataa                           156

SEQ ID NO: 302           moltype = AA  length = 51
FEATURE                  Location/Qualifiers
source                   1..51
                         mol_type = protein
                         note = serotype M49
                         organism = Streptococcus pyogenes
SEQUENCE: 302
MTKEHEIINS IQEVSLEELD QIIGAGKNGV FKTISHECHL NTWAFLATCC S           51

SEQ ID NO: 303           moltype = DNA  length = 156
FEATURE                  Location/Qualifiers
source                   1..156
                         mol_type = genomic DNA
                         note = serotype M49
                         organism = Streptococcus pyogenes
SEQUENCE: 303
atggaaaaaa ataatgaagt aatcaactct attcaagaag ttagtcttga agaactcgat  60
caaattatcg gtgctggaaa aaatggtgtg tttaaaacaa tttctcatga gtgtcatttg  120
aatacatggg cattccttgc tacttgttgc tcataa                           156

SEQ ID NO: 304           moltype = AA  length = 56
FEATURE                  Location/Qualifiers
source                   1..56
                         mol_type = protein
                         organism = Bacillus subtilis
SEQUENCE: 304
```

```
MEKLFKEVKL EELENQKGSG LGKAQCAALW LQCASGGTIG CGGGAVACQN YRQFCR      56

SEQ ID NO: 305          moltype = DNA  length = 171
FEATURE                 Location/Qualifiers
source                  1..171
                        mol_type = genomic DNA
                        organism = Bacillus subtilis
SEQUENCE: 305
atggaaaagc tatttaaaga agttaaacta gaggaactcg aaaaccaaaa aggtagtgga  60
ttaggaaaag ctcagtgtgc tgcgttgtgg ctacaatgtg ctagtggcgg tacaattggt  120
tgtggtggcg gagctgttgc ttgtcaaaac tatcgtcaat tctgcagata a           171

SEQ ID NO: 306          moltype = AA  length = 56
FEATURE                 Location/Qualifiers
source                  1..56
                        mol_type = protein
                        organism = Bacillus subtilis
SEQUENCE: 306
MSKFDDFDLD VVKVSKQDSK ITPQWKSESL CTPGCVTGAL QTCFLQTLTC NCKISK      56

SEQ ID NO: 307          moltype = DNA  length = 171
FEATURE                 Location/Qualifiers
source                  1..171
                        mol_type = genomic DNA
                        organism = Bacillus subtilis
SEQUENCE: 307
atgtcaaagt tcgatgattt cgatttggat gttgtgaaag tctctaaaca agactcaaaa  60
atcactccgc aatggaaaag tgaatcactt tgtacaccag gatgtgtaac tggtgcattg  120
caaacttgct tccttcaaac actaacttgt aactgcaaaa tctctaaata a           171

SEQ ID NO: 308          moltype = AA  length = 50
FEATURE                 Location/Qualifiers
source                  1..50
                        mol_type = protein
                        organism = Bacillus subtilis
SEQUENCE: 308
MKLPVQQVYS VYGGKDLPKG HSHSTMPFLS KLQFLTKIYL LDIHTQPFFI             50

SEQ ID NO: 309          moltype = DNA  length = 153
FEATURE                 Location/Qualifiers
source                  1..153
                        mol_type = genomic DNA
                        organism = Bacillus subtilis
SEQUENCE: 309
ttgaaattgc cggtgcaaca ggtctattcg gtctatgggg gtaaggatct cccaaaaggg  60
catagtcatt ctactatgcc ctttttaagt aaattacaat ttttaactaa aatctacctc  120
ttggatatac atacacaacc gtttttcatt tga                               153

SEQ ID NO: 310          moltype = AA  length = 43
FEATURE                 Location/Qualifiers
source                  1..43
                        mol_type = protein
                        organism = Bacillus subtilis
SEQUENCE: 310
MKKAVIVENK GCATCSIGAA CLVDGPIPDF EIAGATGLFG LWG                    43

SEQ ID NO: 311          moltype = DNA  length = 132
FEATURE                 Location/Qualifiers
source                  1..132
                        mol_type = genomic DNA
                        organism = Bacillus subtilis
SEQUENCE: 311
atgaaaaaag ctgtcattgt agaaaacaaa ggttgtgcaa catgctcgat cggagccgct  60
tgtctagtgg acggtcctat ccctgatttt gaaattgccg gtgcaacagg tctattcggt  120
ctatgggggt aa                                                      132

SEQ ID NO: 312          moltype = AA  length = 58
FEATURE                 Location/Qualifiers
source                  1..58
                        mol_type = protein
                        organism = Streptococcus thermophilus
SEQUENCE: 312
MMNATENQIF VETVSDQELE MLIGGADRGW IKTLTKDCPN VISSICAGTI ITACKNCA    58

SEQ ID NO: 313          moltype = DNA  length = 177
FEATURE                 Location/Qualifiers
source                  1..177
                        mol_type = genomic DNA
                        organism = Streptococcus thermophilus
```

```
SEQUENCE: 313
atgatgaatg ctactgaaaa ccaaattttt gttgagactg tgagtgacca agaattagaa  60
atgttaattg gtggtgcaga tcgtggatgg attaagactt taacaaaaga ttgtccaaat  120
gtaatttctt caatttgtgc aggtacaatt attacagcct gtaaaaattg tgcttaa     177

SEQ ID NO: 314          moltype = AA  length = 64
FEATURE                 Location/Qualifiers
source                  1..64
                        mol_type = protein
                        organism = Streptococcus thermophilus
SEQUENCE: 314
MKQYNGFEVL HELDLANVTG GQINWGSVVG HCIGGAIIGG AFSGGAAAGV GCLVGSGKAI  60
INGL                                                              64

SEQ ID NO: 315          moltype = DNA  length = 195
FEATURE                 Location/Qualifiers
source                  1..195
                        mol_type = genomic DNA
                        organism = Streptococcus thermophilus
SEQUENCE: 315
atgaagcagt ataatggttt tgaggttcta catgaacttg acttagcaaa tgtaactggc  60
ggtcaaatta attggggatc agttgtagga cactgtatag gtggagctat tatcggaggt  120
gcattttcag gaggtgcagc ggctggagta ggatgccttg ttgggagcgg aaaggcaatc  180
ataaatggat tataa                                                  195

SEQ ID NO: 316          moltype = AA  length = 85
FEATURE                 Location/Qualifiers
source                  1..85
                        mol_type = protein
                        organism = Streptococcus thermophilus
SEQUENCE: 316
MNTITICKFD VLDAELLSTV EGGYSGKDCL KDMGGYALAG AGSGALWGAP AGGVGALPGA  60
FVGAHVGAIA GGFACMGGMI GNKFN                                       85

SEQ ID NO: 317          moltype = DNA  length = 258
FEATURE                 Location/Qualifiers
source                  1..258
                        mol_type = genomic DNA
                        organism = Streptococcus thermophilus
SEQUENCE: 317
atgaatacaa taactatttg taaatttgat gttttagatg ctgaacttct ttcgacagtt  60
gagggtggat actctggtaa ggattgttta aaagacatgg gaggatatgc attggcagga  120
gctggaagtg gagctctgtg gggagctcca gcaggaggtg ttggagcact tccaggtgca  180
tttgtcggag ctcatgttgg ggcaattgca ggaggctttg catgtatggg tggaatgatt  240
ggtaataagt ttaactaa                                               258

SEQ ID NO: 318          moltype = AA  length = 52
FEATURE                 Location/Qualifiers
source                  1..52
                        mol_type = protein
                        organism = Bacillus cereus
SEQUENCE: 318
MSEIKKALNT LEIEDFDAIE MVDVDAMPEN EALEIMGASC TTCVCTCSCC TT         52

SEQ ID NO: 319          moltype = DNA  length = 159
FEATURE                 Location/Qualifiers
source                  1..159
                        mol_type = genomic DNA
                        organism = Bacillus cereus
SEQUENCE: 319
atgagtgaaa ttaaaaaagc attaaatacg cttgaaattg aagattttga tgcaattgaa  60
atggttgatg ttgatgctat gccagaaaac gaagcgcttg aaattatggg agcgtcatgt  120
acgacatgcg tatgtacatg cagttgttgt acaacttga                        159

SEQ ID NO: 320          moltype = AA  length = 47
FEATURE                 Location/Qualifiers
source                  1..47
                        mol_type = protein
                        organism = Bacillus cereus
SEQUENCE: 320
MEVMNNALIT KVDEEIGGNA ACVIGCIGSC VISEGIGSLV GTAFTLG               47

SEQ ID NO: 321          moltype = DNA  length = 144
FEATURE                 Location/Qualifiers
source                  1..144
                        mol_type = genomic DNA
                        organism = Bacillus cereus
SEQUENCE: 321
atggaagtta tgaacaatgc tttaattaca aaagtagatg aggagattgg aggaaacgct  60
```

```
gcttgtgtaa ttggttgtat tggcagttgc gtaattagtg aaggaattgg ttcacttgta  120
ggaacagcat ttactttagg ttaa                                          144

SEQ ID NO: 322         moltype = AA  length = 49
FEATURE                Location/Qualifiers
source                 1..49
                       mol_type = protein
                       organism = Bacillus cereus
SEQUENCE: 322
MEVLNKQNVN IIPESEEVGG WVACVGACGT VCLASGGVGT EFAAASYFL               49

SEQ ID NO: 323         moltype = DNA  length = 150
FEATURE                Location/Qualifiers
source                 1..150
                       mol_type = genomic DNA
                       organism = Bacillus cereus
SEQUENCE: 323
atggaagttt taaacaaaca aaatgtaaat attattccag aatctgaaga agtaggtgga  60
tgggtagcat gtgttggagc atgtggtaca gtatgtcttg ctagtggtgg tgttggaaca  120
gagtttgcag ctgcatctta tttcctataa                                    150

SEQ ID NO: 324         moltype = AA  length = 40
FEATURE                Location/Qualifiers
source                 1..40
                       mol_type = protein
                       organism = Bacillus thuringiensis
SEQUENCE: 324
METPVVQPRD WTCWSCLVCA ACSVELLNLV TAATGASTAS                         40

SEQ ID NO: 325         moltype = DNA  length = 123
FEATURE                Location/Qualifiers
source                 1..123
                       mol_type = genomic DNA
                       organism = Bacillus thuringiensis
SEQUENCE: 325
atggaaacac cagtagtaca accaagggat tggacttgtt ggagttgctt agtatgtgca  60
gcatgttctg tggaattatt aaatttagtt actgcggcaa caggggctag tactgcaagc  120
taa                                                                 123

SEQ ID NO: 326         moltype = AA  length = 42
FEATURE                Location/Qualifiers
source                 1..42
                       mol_type = protein
                       note = bv. trifolii
                       organism = Rhizobium leguminosarum
SEQUENCE: 326
MDNKVAKNVE VKKGSIKATF KAAVLKSKTK VDIGGSRQGC VA                      42

SEQ ID NO: 327         moltype = DNA  length = 129
FEATURE                Location/Qualifiers
source                 1..129
                       mol_type = genomic DNA
                       note = bv. trifolii
                       organism = Rhizobium leguminosarum
SEQUENCE: 327
atggataaca aggttgcgaa gaatgtcgaa gtgaagaagg gctccatcaa ggcgaccttc  60
aaggctgctg ttctgaagtc gaagacgaag gtcgacatcg gaggtagccg tcagggctgc  120
gtcgcttaa                                                           129

SEQ ID NO: 328         moltype = AA  length = 70
FEATURE                Location/Qualifiers
source                 1..70
                       mol_type = protein
                       organism = Streptococcus uberis
SEQUENCE: 328
MNTIEKFENI KLFSLKKIIG GKTVNYGNGL YCNQKKCWVN WSETATTIVN NSIMNGLTGG  60
NAGWHSGGRA                                                          70

SEQ ID NO: 329         moltype = DNA  length = 213
FEATURE                Location/Qualifiers
source                 1..213
                       mol_type = genomic DNA
                       organism = Streptococcus uberis
SEQUENCE: 329
atgaatacaa ttgaaaaatt tgaaaatatt aaactttttt cactaaagaa aattatcggt  60
ggcaaaactg taaattatgg taatggcctt tattgtaacc aaaaaaaatg ctgggtaaac  120
tggtcagaaa ctgctacaac aatagtaaat aattccatca tgaacgggct cacaggtggt  180
aatgcgggtt ggcactcagg cgggagagca taa                               213
```

```
SEQ ID NO: 330          moltype = AA  length = 76
FEATURE                 Location/Qualifiers
source                  1..76
                        mol_type = protein
                        organism = Streptococcus uberis
SEQUENCE: 330
MDILLELAGY TGIASGTAKK VVDAIDKGAA AFVIISIIST VISAGALGAV SASADFIILT  60
VKNYISRNLK AQAVIW                                                  76

SEQ ID NO: 331          moltype = DNA  length = 231
FEATURE                 Location/Qualifiers
source                  1..231
                        mol_type = genomic DNA
                        organism = Streptococcus uberis
SEQUENCE: 331
atggacattt tattagaact cgcaggatat actgggatag cctcaggtac tgcaaaaaaa  60
gttgttgatg ccattgataa aggagctgca gcctttgtta ttatttcaat tatctcaaca  120
gtaattagtg cgggagcatt gggagcagtt tcagcctcag ctgattttat tattttaact  180
gtaaaaaatt acattagtag aaatttaaaa gcacaagctg tcatttggta a          231

SEQ ID NO: 332          moltype = AA  length = 64
FEATURE                 Location/Qualifiers
source                  1..64
                        mol_type = protein
                        organism = Clostridium perfringens
SEQUENCE: 332
MDSELFKLMA TQGAFAILFS YLLFYVLKEN SKREDKYQNI IEELTELLPK IKEDVEDIKE  60
KLNK                                                               64

SEQ ID NO: 333          moltype = DNA  length = 195
FEATURE                 Location/Qualifiers
source                  1..195
                        mol_type = genomic DNA
                        organism = Clostridium perfringens
SEQUENCE: 333
atggatagtg aattatttaa gttaatggca acacaaggag cctttgcaat attattttcg  60
tatttattgt tttatgtttt aaaagagaat agtaaaagag aagataagta tcaaaatata  120
atagaggagc ttacagaatt attgccaaaa ataaaagaag atgtagaaga tataaaagaa  180
aaacttaata aatag                                                   195

SEQ ID NO: 334          moltype = AA  length = 47
FEATURE                 Location/Qualifiers
source                  1..47
                        mol_type = protein
                        organism = Micrococcus varians
SEQUENCE: 334
MTNAFQALDE VTDAELDAIL GGGSGVIPTI SHECHMNSFQ FVFTCCS                47

SEQ ID NO: 335          moltype = DNA  length = 144
FEATURE                 Location/Qualifiers
source                  1..144
                        mol_type = genomic DNA
                        organism = Micrococcus varians
SEQUENCE: 335
atgacgaacg catttcaggc actggacgaa gtcacggacg ccgagctcga cgccatcctt  60
ggcgggggca gtggtgttat tcccacgatc agccacgagt gccacatgaa ctccttccag  120
ttcgtgttca cctgctgctc ctga                                         144

SEQ ID NO: 336          moltype = AA  length = 285
FEATURE                 Location/Qualifiers
source                  1..285
                        mol_type = protein
                        note = subsp. zooepidemicus
                        organism = Streptococcus equi
SEQUENCE: 336
MKRIFFAFLS LCLFIFGTQT VSAATYTRPL DTGNITTGFN GYPGHVGVDY AVPVGTPVRA  60
VANGTVKFAG NGANHPWMLW MAGNCVLIQH ADGMHTGYAH LSKISVSTDS TVKQGQIIGY  120
TGATGQVTGP HLHFEMLPAN PNWQNGFSGR IDPTGYIANA PVFNGTTPTE PTTPTTNLKI  180
YKVDDLQKIN GIWQVRNNIL VPTDFTWVDN GIAADDVIEV TSNGTRTSDQ VLQKGGYFVI  240
NPNNVKSVGT PMKGSGGLSW AQVNFTTGGN VWLNTTSKDN LLYGK                  285

SEQ ID NO: 337          moltype = DNA  length = 858
FEATURE                 Location/Qualifiers
source                  1..858
                        mol_type = genomic DNA
                        note = subsp. zooepidemicus
                        organism = Streptococcus equi
SEQUENCE: 337
atgaaacgta tatttttgc tttcttaagt ttatgcttat ttatattcgg aacacaaacg  60
```

```
gtatctgcag ctacttatac tcggccatta gatacgggaa atatcactac agggtttaac  120
ggataccctg gtcatgttgg agtcgattat gcagtacccg ttggaactcc ggttagagca  180
gttgcaaatg gtacagtcaa atttgcaggt aatggggcta atcacccatg gatgctttgg  240
atggctggaa actgtgttct aattcaacat gctgacggga tgcatactgg atatgcacac  300
ttatcaaaaa tttcagttag cacagatagt acagttaaac aaggacaaat cataggttat  360
actggtgcca ccggccaagt taccggtcca catttgcatt ttgaaatgtt gccagcaaat  420
cctaactggc aaaatggttt ttctggaaga atagatccaa ccggatacat cgctaatgcc  480
cctgtattta atggaacaac acctacagaa cctactactc ctacaacaaa tttaaaaatc  540
tataaagttg atgatttaca aaaaattaat ggtatttggc aagtaagaaa taacatactt  600
gtaccaactg atttcacatg ggttgataat ggaattgcag cagatgatgt aattgaagta  660
actagcaatg gaacaagaac ctctgaccaa gttcttcaaa aaggtggtta ttttgtcatc  720
aatcctaata atgttaaaag tgttggaact ccgatgaaag gtagtggtgg tctatcttgg  780
gctcaagtaa actttacaac aggtggaaat gtctggttaa atactactag caaagacaac  840
ttactttacg gaaaataa                                                858

SEQ ID NO: 338          moltype = AA  length = 45
FEATURE                 Location/Qualifiers
source                  1..45
                        mol_type = protein
                        organism = Myxococcus fulvus
SEQUENCE: 338
ANCSCSTASD YCPILTFCTT GTACSYTPTG CGTGWVYCAC NGNFY                  45

SEQ ID NO: 339          moltype = DNA  length = 135
FEATURE                 Location/Qualifiers
misc_feature            1..135
                        note = Polynucleotide encoding the polypeptide of SEQ IDNO:
                         338
source                  1..135
                        mol_type = other DNA
                        organism = synthetic construct
SEQUENCE: 339
gcgaactgca gctgcagcac cgcgagcgat tattgcccga ttctgacctt ttgcaccacc  60
ggcaccgcgt gcagctatac cccgaccggc tgcggcaccg gctgggtgta ttgcgcgtgc  120
aacggcaact tttat                                                   135

SEQ ID NO: 340          moltype = AA  length = 19
FEATURE                 Location/Qualifiers
source                  1..19
                        mol_type = protein
                        organism = Streptomyces griseoluteus
SEQUENCE: 340
CANSCSYGPL TWSCDGNTK                                               19

SEQ ID NO: 341          moltype = DNA  length = 57
FEATURE                 Location/Qualifiers
misc_feature            1..57
                        note = Polynucleotide encoding the polypeptide of SEQ IDNO:
                         340
source                  1..57
                        mol_type = other DNA
                        organism = synthetic construct
SEQUENCE: 341
tgcgcgaaca gctgcagcta tggcccgctg acctggagct gcgatggcaa caccaaa     57

SEQ ID NO: 342          moltype = AA  length = 19
FEATURE                 Location/Qualifiers
source                  1..19
                        mol_type = protein
                        organism = Streptoverticillium griseoverticillatum
SEQUENCE: 342
CKQSCSFGPF TFVCDGNTK                                               19

SEQ ID NO: 343          moltype = DNA  length = 57
FEATURE                 Location/Qualifiers
misc_feature            1..57
                        note = Polynucleotide encoding the polypeptide of SEQ IDNO:
                         342
source                  1..57
                        mol_type = other DNA
                        organism = synthetic construct
SEQUENCE: 343
tgcaaacaga gctgcagctt tggcccgttt acctttgtgt gcgatggcaa caccaaa     57

SEQ ID NO: 344          moltype = AA  length = 7
FEATURE                 Location/Qualifiers
source                  1..7
                        mol_type = protein
                        organism = Carnobacterium sp.
```

```
SEQUENCE: 344
GSEIQPR                                                  7

SEQ ID NO: 345          moltype = DNA  length = 21
FEATURE                 Location/Qualifiers
misc_feature            1..21
                        note = Polynucleotide encoding the polypeptide of SEQ IDNO:
                         344
source                  1..21
                        mol_type = other DNA
                        organism = synthetic construct
SEQUENCE: 345
ggcagcgaaa ttcagccgcg c                                  21

SEQ ID NO: 346          moltype = AA  length = 39
FEATURE                 Location/Qualifiers
source                  1..39
                        mol_type = protein
                        note = subsp. lactis
                        organism = Lactococcus lactis
SEQUENCE: 346
GTWDDIGQGI GRVAYWVGKA MGNMSDVNQA SRINRKKKH               39

SEQ ID NO: 347          moltype = DNA  length = 117
FEATURE                 Location/Qualifiers
misc_feature            1..117
                        note = Polynucleotide encoding the polypeptide of SEQ IDNO:
                         346
source                  1..117
                        mol_type = other DNA
                        organism = synthetic construct
SEQUENCE: 347
ggcacctggg atgatattgg ccagggcatt ggccgcgtgg cgtattgggt gggcaaagcg  60
atgggcaaca tgagcgatgt gaaccaggcg agccgcatta accgcaaaaa aaaacat     117

SEQ ID NO: 348          moltype = AA  length = 35
FEATURE                 Location/Qualifiers
source                  1..35
                        mol_type = protein
                        note = subsp. lactis
                        organism = Lactococcus lactis
SEQUENCE: 348
KKWGWLAWVD PAYEFIKGFG KGAIKEGNKD KWKNI                   35

SEQ ID NO: 349          moltype = DNA  length = 105
FEATURE                 Location/Qualifiers
misc_feature            1..105
                        note = Polynucleotide encoding the polypeptide of SEQ IDNO:
                         348
source                  1..105
                        mol_type = other DNA
                        organism = synthetic construct
SEQUENCE: 349
aaaaaatggg gctggctggc gtgggtggat ccggcgtatg aatttattaa aggctttggc  60
aaaggcgcga ttaaagaagg caacaaagat aaatggaaaa acatt                 105

SEQ ID NO: 350          moltype = AA  length = 19
FEATURE                 Location/Qualifiers
source                  1..19
                        mol_type = protein
                        organism = Streptomyces sp.
SEQUENCE: 350
CVQSCSFGPL TWSCDGNTK                                     19

SEQ ID NO: 351          moltype = DNA  length = 57
FEATURE                 Location/Qualifiers
misc_feature            1..57
                        note = Polynucleotide encoding the polypeptide of SEQ IDNO:
                         350
source                  1..57
                        mol_type = other DNA
                        organism = synthetic construct
SEQUENCE: 351
tgcgtgcaga gctgcagctt tggcccgctg acctggagct gcgatggcaa caccaaa     57

SEQ ID NO: 352          moltype = AA  length = 19
FEATURE                 Location/Qualifiers
source                  1..19
                        mol_type = protein
```

```
                        organism = Actinoplanes liguriae
SEQUENCE: 352
SSGWVCTLTI ECGTVICAC                                              19

SEQ ID NO: 353          moltype = DNA  length = 57
FEATURE                 Location/Qualifiers
misc_feature            1..57
                        note = Polynucleotide encoding the polypeptide of SEQ IDNO:
                         352
source                  1..57
                        mol_type = other DNA
                        organism = synthetic construct
SEQUENCE: 353
agcagcggct gggtgtgcac cctgaccatt gaatgcggca ccgtgatttg cgcgtgc     57

SEQ ID NO: 354          moltype = AA  length = 38
FEATURE                 Location/Qualifiers
VARIANT                 34
                        note = Xaa = any amino acid
VARIANT                 37
                        note = Xaa = any amino acid
source                  1..38
                        mol_type = protein
                        organism = Lactobacillus curvatus
SEQUENCE: 354
YTAKQCLQAI GSCGIAGTGA GAAGGPAGAF VGAXVVXI                         38

SEQ ID NO: 355          moltype = DNA  length = 114
FEATURE                 Location/Qualifiers
misc_feature            1..114
                        note = Polynucleotide encoding the polypeptide of SEQ IDNO:
                         354
misc_feature            100..111
                        note = n = A,T,C or G
misc_feature            100..102
                        note = nnn = a codon other than a stop codon
misc_feature            109..111
                        note = nnn = a codon other than a stop codon
source                  1..114
                        mol_type = other DNA
                        organism = synthetic construct
SEQUENCE: 355
tataccgcga aacagtgcct gcaggcgatt ggcagctgcg gcattgcggg caccggcgcg  60
ggcgcggcgg gcggcccggc gggcgcgttt gtgggcgcgn nngtggtgnn natt        114

SEQ ID NO: 356          moltype = AA  length = 42
FEATURE                 Location/Qualifiers
VARIANT                 32
                        note = Xaa = any amino acid
source                  1..42
                        mol_type = protein
                        organism = Lactobacillus sakei
SEQUENCE: 356
TKYYGNGVYC NSKKCWVDWG QAAGGIGQTV VXGWLGGAIP GK                    42

SEQ ID NO: 357          moltype = DNA  length = 126
FEATURE                 Location/Qualifiers
misc_feature            1..126
                        note = Polynucleotide encoding the polypeptide of SEQ IDNO:
                         356
misc_feature            94..96
                        note = nnn = any amino acid-coding triplet
source                  1..126
                        mol_type = other DNA
                        organism = synthetic construct
SEQUENCE: 357
accaaatatt atggcaacgg cgtgtattgc aacagcaaaa aatgctgggt ggattggggc  60
caggcggcgg gcggcattgg ccagaccgtg gtgnnnggct ggctgggcgg cgcgattccg  120
ggcaaa                                                             126

SEQ ID NO: 358          moltype = AA  length = 22
FEATURE                 Location/Qualifiers
source                  1..22
                        mol_type = protein
                        organism = Streptococcus mutans
SEQUENCE: 358
FKSWSFCTPG CAKTGSFNSY CC                                          22

SEQ ID NO: 359          moltype = DNA  length = 132
```

```
FEATURE                Location/Qualifiers
misc_feature           1..132
                       note = Polynucleotide encoding the polypeptide of SEQ IDNO:
                        358
source                 1..132
                       mol_type = other DNA
                       organism = synthetic construct
SEQUENCE: 359
tttaaaagct ggagcttttg caccccgggc tgcgcgaaaa ccggcagctt taacagctat  60
tgctgcttta aaagctggag cttttgcacc ccgggctgcg cgaaaaccgg cagctttaac  120
agctattgct gc                                                      132

SEQ ID NO: 360         moltype = AA  length = 43
FEATURE                Location/Qualifiers
source                 1..43
                       mol_type = protein
                       organism = Enterococcus mundtii
SEQUENCE: 360
KYYGNGVSCN KKGCSVDWGK AIGIIGNNSA ANLATGGAAG WSK                    43

SEQ ID NO: 361         moltype = DNA  length = 129
FEATURE                Location/Qualifiers
misc_feature           1..129
                       note = Polynucleotide encoding the polypeptide of SEQ IDNO:
                        360
source                 1..129
                       mol_type = other DNA
                       organism = synthetic construct
SEQUENCE: 361
aaatattatg gcaacggcgt gagctgcaac aaaaaaggct gcagcgtgga ttggggcaaa  60
gcgattggca ttattggcaa caacagcgcg gcgaacctgg cgaccggcgg cgcggcgggc  120
tggagcaaa                                                          129

SEQ ID NO: 362         moltype = AA  length = 41
FEATURE                Location/Qualifiers
VARIANT                9..37
                       note = X= any amino acid
source                 1..41
                       mol_type = protein
                       organism = Lactobacillus sakei
SEQUENCE: 362
KYYGNGVHXG KHSXTVDWGT AIGNIGNNAA ANXATGXNAG G                      41

SEQ ID NO: 363         moltype = DNA  length = 123
FEATURE                Location/Qualifiers
misc_feature           1..123
                       note = Polynucleotide encoding the polypeptide of SEQ IDNO:
                        362
misc_feature           25..27
                       note = nnn = any amino acid-coding triplet
misc_feature           40..42
                       note = nnn = any amino acid-coding triplet
misc_feature           97..99
                       note = nnn = any amino acid-coding triplet
misc_feature           109..111
                       note = nnn = any amino acid-coding triplet
source                 1..123
                       mol_type = other DNA
                       organism = synthetic construct
SEQUENCE: 363
aaatattatg gcaacggcgt gcatnnnggc aaacatagcn nnaccgtgga ttggggcacc  60
gcgattggca acattggcaa caacgcggcg gcgaacnnng cgaccggcnn naacgcgggc  120
ggc                                                                123

SEQ ID NO: 364         moltype = AA  length = 31
FEATURE                Location/Qualifiers
source                 1..31
                       mol_type = protein
                       organism = Lactobacillus paracasei
SEQUENCE: 364
GMSGYIQGIP DFLKGYLHGI SAANKHKKGR L                                 31

SEQ ID NO: 365         moltype = DNA  length = 93
FEATURE                Location/Qualifiers
misc_feature           1..93
                       note = Polynucleotide encoding the polypeptide of SEQ IDNO:
                        364
source                 1..93
                       mol_type = other DNA
```

```
                        organism = synthetic construct
SEQUENCE: 365
ggcatgagcg gctatattca gggcattccg gattttctga aaggctatct gcatggcatt  60
agcgcggcga acaaacataa aaaaggccgc ctg                               93

SEQ ID NO: 366          moltype = AA  length = 31
FEATURE                 Location/Qualifiers
source                  1..31
                        mol_type = protein
                        organism = Leuconostoc mesenteroides
SEQUENCE: 366
KGKGFWSWAS KATSWLTGPQ QPGSPLLKKH R                                 31

SEQ ID NO: 367          moltype = DNA  length = 93
FEATURE                 Location/Qualifiers
misc_feature            1..93
                        note = Polynucleotide encoding the polypeptide of SEQ IDNO:
                         366
source                  1..93
                        mol_type = other DNA
                        organism = synthetic construct
SEQUENCE: 367
aaaggcaaag gcttttggag ctgggcgagc aaagcgacca gctggctgac cggcccgcag  60
cagccgggca gcccgctgct gaaaaaacat cgc                               93

SEQ ID NO: 368          moltype = AA  length = 43
FEATURE                 Location/Qualifiers
source                  1..43
                        mol_type = protein
                        organism = Leuconostoc mesenteroides
SEQUENCE: 368
KNYGNGVHCT KKGCSVDWGY AWTNIANNSV MNGLTGGNAG WHN                    43

SEQ ID NO: 369          moltype = DNA  length = 129
FEATURE                 Location/Qualifiers
misc_feature            1..129
                        note = Polynucleotide encoding the polypeptide of SEQ IDNO:
                         368
source                  1..129
                        mol_type = other DNA
                        organism = synthetic construct
SEQUENCE: 369
aaaaactatg gcaacggcgt gcattgcacc aaaaaaggct gcagcgtgga ttggggctat  60
gcgtggacca acattgcgaa caacagcgtg atgaacggcc tgaccggcgg caacgcgggc  120
tggcataac                                                          129

SEQ ID NO: 370          moltype = AA  length = 47
FEATURE                 Location/Qualifiers
source                  1..47
                        mol_type = protein
                        organism = Bacillus subtilis
SEQUENCE: 370
AIKLVQSPNG NFAASFVLDG TKWIFKSKYY DSSKGYWVGI YEVWDRK                47

SEQ ID NO: 371          moltype = DNA  length = 141
FEATURE                 Location/Qualifiers
misc_feature            1..141
                        note = Polynucleotide encoding the polypeptide of SEQ IDNO:
                         370
source                  1..141
                        mol_type = other DNA
                        organism = synthetic construct
SEQUENCE: 371
gcgattaaac tggtgcagag cccgaacggc aactttgcgg cgagctttgt gctggatggc  60
accaaatgga tttttaaaag caaatattat gatagcagca aaggctattg ggtgggcatt  120
tatgaagtgt gggatcgcaa a                                            141

SEQ ID NO: 372          moltype = AA  length = 12
FEATURE                 Location/Qualifiers
VARIANT                 7
                        note = Xaa = any amino acid
source                  1..12
                        mol_type = protein
                        organism = Bacillus licheniformis
SEQUENCE: 372
ISLEICXIFH DN                                                      12

SEQ ID NO: 373          moltype = DNA  length = 36
FEATURE                 Location/Qualifiers
```

```
misc_feature           1..36
                       note = Polynucleotide encoding the polypeptide of SEQ IDNO:
                        372
misc_feature           19..21
                       note = nnn = any amino acid-coding triplet
source                 1..36
                       mol_type = other DNA
                       organism = synthetic construct
SEQUENCE: 373
attagcctgg aaatttgcnn natttttcat gataac                          36

SEQ ID NO: 374         moltype = AA  length = 37
FEATURE                Location/Qualifiers
source                 1..37
                       mol_type = protein
                       note = subsp. lactis
                       organism = Lactococcus lactis
SEQUENCE: 374
TSYGNGVHCN KSKCWIDVSE LETYKAGTVS NPKDILW                         37

SEQ ID NO: 375         moltype = DNA  length = 111
FEATURE                Location/Qualifiers
misc_feature           1..111
                       note = Polynucleotide encoding the polypeptide of SEQ IDNO:
                        374
source                 1..111
                       mol_type = other DNA
                       organism = synthetic construct
SEQUENCE: 375
accagctatg gcaacggcgt gcattgcaac aaaagcaaat gctggattga tgtgagcgaa  60
ctggaaacct ataaagcggg caccgtgagc aacccgaaag atattctgtg g           111

SEQ ID NO: 376         moltype = AA  length = 9
FEATURE                Location/Qualifiers
source                 1..9
                       mol_type = protein
                       organism = Serratia plymuthica
SEQUENCE: 376
DYHHGVRVL                                                        9

SEQ ID NO: 377         moltype = DNA  length = 27
FEATURE                Location/Qualifiers
misc_feature           1..27
                       note = Polynucleotide encoding the polypeptide of SEQ IDNO:
                        376
source                 1..27
                       mol_type = other DNA
                       organism = synthetic construct
SEQUENCE: 377
gattatcatc atggcgtgcg cgtgctg                                    27

SEQ ID NO: 378         moltype = AA  length = 15
FEATURE                Location/Qualifiers
source                 1..15
                       mol_type = protein
                       organism = Halobacterium sp.
SEQUENCE: 378
DIDITGCSAC KYAAG                                                 15

SEQ ID NO: 379         moltype = DNA  length = 45
FEATURE                Location/Qualifiers
misc_feature           1..45
                       note = Polynucleotide encoding the polypeptide of SEQ IDNO:
                        378
source                 1..45
                       mol_type = other DNA
                       organism = synthetic construct
SEQUENCE: 379
gatattgata ttaccggctg cagcgcgtgc aaatatgcgg cgggc                45

SEQ ID NO: 380         moltype = AA  length = 12
FEATURE                Location/Qualifiers
VARIANT                1..6
                       note = X= any amino acid
source                 1..12
                       mol_type = protein
                       organism = Bacillus subtilis
SEQUENCE: 380
XXKEIXHIFH DN                                                    12
```

```
SEQ ID NO: 381          moltype = DNA  length = 36
FEATURE                 Location/Qualifiers
misc_feature            1..36
                        note = Polynucleotide encoding the polypeptide of SEQ IDNO:
                         380
misc_feature            1..3
                        note = nnn = any amino acid-coding triplet
misc_feature            4..6
                        note = nnn = any amino acid-coding triplet
misc_feature            16..18
                        note = nnn = any amino acid-coding triplet
source                  1..36
                        mol_type = other DNA
                        organism = synthetic construct
SEQUENCE: 381
nnnnnnaaag aaattnnnca tatttttcat gataac                            36

SEQ ID NO: 382          moltype = AA  length = 12
FEATURE                 Location/Qualifiers
source                  1..12
                        mol_type = protein
                        organism = Lactobacillus curvatus
SEQUENCE: 382
TPVVNPPFLQ QT                                                      12

SEQ ID NO: 383          moltype = DNA  length = 36
FEATURE                 Location/Qualifiers
misc_feature            1..36
                        note = Polynucleotide encoding the polypeptide of SEQ IDNO:
                         382
source                  1..36
                        mol_type = other DNA
                        organism = synthetic construct
SEQUENCE: 383
accccggtgg tgaacccgcc gtttctgcag cagacc                            36

SEQ ID NO: 384          moltype = AA  length = 10
FEATURE                 Location/Qualifiers
VARIANT                 10
                        note = Xaa = any amino acid
source                  1..10
                        mol_type = protein
                        organism = Lactobacillus curvatus
SEQUENCE: 384
VAPFPEQFLX                                                         10

SEQ ID NO: 385          moltype = DNA  length = 30
FEATURE                 Location/Qualifiers
misc_feature            1..30
                        note = Polynucleotide encoding the polypeptide of SEQ IDNO:
                         384
misc_feature            28..30
                        note = nnn = any amino acid-coding triplet
source                  1..30
                        mol_type = other DNA
                        organism = synthetic construct
SEQUENCE: 385
gtggcgccgt ttccggaaca gtttctgnnn                                   30

SEQ ID NO: 386          moltype = AA  length = 9
FEATURE                 Location/Qualifiers
source                  1..9
                        mol_type = protein
                        organism = Lactobacillus curvatus
SEQUENCE: 386
NIPQLTPTP                                                          9

SEQ ID NO: 387          moltype = DNA  length = 27
FEATURE                 Location/Qualifiers
misc_feature            1..27
                        note = Polynucleotide encoding the polypeptide of SEQ IDNO:
                         386
source                  1..27
                        mol_type = other DNA
                        organism = synthetic construct
SEQUENCE: 387
aacattccgc agctgacccc gaccccg                                      27
```

```
SEQ ID NO: 388         moltype = AA  length = 18
FEATURE                Location/Qualifiers
VARIANT                4..10
                       note = X= any amino acid
source                 1..18
                       mol_type = protein
                       note = subsp. entomocidus
                       organism = Bacillus thuringiensis
SEQUENCE: 388
DWTXWSXLVX AACSVELL                                                18

SEQ ID NO: 389         moltype = DNA  length = 54
FEATURE                Location/Qualifiers
misc_feature           1..54
                       note = Polynucleotide encoding the polypeptide of SEQ IDNO:
                        388
misc_feature           10..12
                       note = nnn = any amino acid-coding triplet
misc_feature           19..21
                       note = nnn = any amino acid-coding triplet
misc_feature           28..30
                       note = nnn = any amino acid-coding triplet
source                 1..54
                       mol_type = other DNA
                       organism = synthetic construct
SEQUENCE: 389
gattggaccn nntggagcnn nctggtgnnn gcggcgtgca gcgtggaact gctg        54

SEQ ID NO: 390         moltype = AA  length = 30
FEATURE                Location/Qualifiers
source                 1..30
                       mol_type = protein
                       organism = Lactobacillus curvatus
SEQUENCE: 390
AYPGNGVHCG KYSCTVDKQT AIGNIGNNAA                                   30

SEQ ID NO: 391         moltype = DNA  length = 90
FEATURE                Location/Qualifiers
misc_feature           1..90
                       note = Polynucleotide encoding the polypeptide of SEQ IDNO:
                        390
source                 1..90
                       mol_type = other DNA
                       organism = synthetic construct
SEQUENCE: 391
gcgtatccgg gcaacggcgt gcattgcggc aaatatagct gcaccgtgga taaacagacc  60
gcgattggca acattggcaa caacgcggcg                                   90

SEQ ID NO: 392         moltype = AA  length = 43
FEATURE                Location/Qualifiers
source                 1..43
                       mol_type = protein
                       organism = Carnobacterium divergens
SEQUENCE: 392
TKYYGNGVYC NSKKCWVDWG TAQGCIDVVI GQLGGGIPGK GKC                    43

SEQ ID NO: 393         moltype = DNA  length = 129
FEATURE                Location/Qualifiers
misc_feature           1..129
                       note = Polynucleotide encoding the polypeptide of SEQ IDNO:
                        392
source                 1..129
                       mol_type = other DNA
                       organism = synthetic construct
SEQUENCE: 393
accaaatatt atggcaacgg cgtgtattgc aacagcaaaa aatgctgggt ggattggggc  60
accgcgcagg gctgcattga tgtggtgatt ggccagctgg gcggcggcat tccgggcaaa  120
ggcaaatgc                                                          129

SEQ ID NO: 394         moltype = AA  length = 62
FEATURE                Location/Qualifiers
source                 1..62
                       mol_type = protein
                       organism = Enterococcus sp.
SEQUENCE: 394
NRWYCNSAAG GVGGAAVCGL AGYVGEAKEN IAGEVRKGWG MAGGFTHNKA CKSFPGSGWA  60
SG                                                                 62

SEQ ID NO: 395         moltype = DNA  length = 186
```

```
FEATURE                Location/Qualifiers
misc_feature           1..186
                       note = Polynucleotide encoding the polypeptide of SEQ IDNO:
                        394
source                 1..186
                       mol_type = other DNA
                       organism = synthetic construct
SEQUENCE: 395
aaccgctggt attgcaacag cgcggcgggc ggcgtgggcg gcgcggcggt gtgcggcctg  60
gcgggctatg tgggcgaagc gaaagaaaac attgcgggcg aagtgcgcaa aggctggggc  120
atggcgggcg gctttaccca taacaaagcg tgcaaaagct ttccgggcag cggctgggcg  180
agcggc                                                             186

SEQ ID NO: 396         moltype = AA  length = 39
FEATURE                Location/Qualifiers
source                 1..39
                       mol_type = protein
                       organism = Enterococcus faecium
SEQUENCE: 396
TTKNYGNGVC NSVNWCQCGN VWASCNLATG CAAWLCKLA                         39

SEQ ID NO: 397         moltype = DNA  length = 117
FEATURE                Location/Qualifiers
misc_feature           1..117
                       note = Polynucleotide encoding the polypeptide of SEQ IDNO:
                        396
source                 1..117
                       mol_type = other DNA
                       organism = synthetic construct
SEQUENCE: 397
accaccaaaa actatggcaa cggcgtgtgc aacagcgtga actggtgcca gtgcggcaac  60
gtgtgggcga gctgcaacct ggcgaccggc tgcgcggcgt ggctgtgcaa actggcg     117

SEQ ID NO: 398         moltype = AA  length = 30
FEATURE                Location/Qualifiers
source                 1..30
                       mol_type = protein
                       organism = Paenibacillus polymyxa
SEQUENCE: 398
ASIIKTTIKV SKAVCKTLTC ICTGSCSNCK                                   30

SEQ ID NO: 399         moltype = DNA  length = 90
FEATURE                Location/Qualifiers
misc_feature           1..90
                       note = Polynucleotide encoding the polypeptide of SEQ IDNO:
                        398
source                 1..90
                       mol_type = other DNA
                       organism = synthetic construct
SEQUENCE: 399
gcgagcatta ttaaaaccac cattaaagtg agcaaagcgg tgtgcaaaac cctgacctgc  60
atttgcaccg gcagctgcag caactgcaaa                                   90

SEQ ID NO: 400         moltype = AA  length = 31
FEATURE                Location/Qualifiers
source                 1..31
                       mol_type = protein
                       organism = Staphylococcus epidermidis
SEQUENCE: 400
SASIVKTTIK ASKKLCRGFT LTCGCHFTGK K                                 31

SEQ ID NO: 401         moltype = DNA  length = 93
FEATURE                Location/Qualifiers
misc_feature           1..93
                       note = Polynucleotide encoding the polypeptide of SEQ IDNO:
                        400
source                 1..93
                       mol_type = other DNA
                       organism = synthetic construct
SEQUENCE: 401
agcgcgagca ttgtgaaaac caccattaaa gcgagcaaaa aactgtgccg cggctttacc  60
ctgacctgcg gctgccattt taccggcaaa aaa                               93

SEQ ID NO: 402         moltype = AA  length = 43
FEATURE                Location/Qualifiers
source                 1..43
                       mol_type = protein
                       organism = Enterococcus faecium
SEQUENCE: 402
```

```
KYYGNGVSCN KKGCSVDWGK AIGIIGNNAA ANLTTGGKAA WAC                43

SEQ ID NO: 403          moltype = DNA  length = 129
FEATURE                 Location/Qualifiers
misc_feature            1..129
                        note = Polynucleotide encoding the polypeptide of SEQ IDNO:
                         402
source                  1..129
                        mol_type = other DNA
                        organism = synthetic construct
SEQUENCE: 403
aaatattatg gcaacggcgt gagctgcaac aaaaaaggct gcagcgtgga ttggggcaaa  60
gcgattggca ttattggcaa caacgcggcg gcgaacctga ccaccggcgg caaagcggcg  120
tgggcgtgc                                                          129

SEQ ID NO: 404          moltype = AA  length = 39
FEATURE                 Location/Qualifiers
source                  1..39
                        mol_type = protein
                        organism = Paenibacillus polymyxa
SEQUENCE: 404
ATYYGNGLYC NKQKHYTWVD WNKASREIGK ITVNGWVQH                     39

SEQ ID NO: 405          moltype = DNA  length = 117
FEATURE                 Location/Qualifiers
misc_feature            1..117
                        note = Polynucleotide encoding the polypeptide of SEQ IDNO:
                         404
source                  1..117
                        mol_type = other DNA
                        organism = synthetic construct
SEQUENCE: 405
gcgacctatt atggcaacgg cctgtattgc aacaaacaga aacattatac ctgggtggat  60
tggaacaaag cgagccgcga aattggcaaa attaccgtga acggctgggt gcagcat     117

SEQ ID NO: 406          moltype = AA  length = 35
FEATURE                 Location/Qualifiers
source                  1..35
                        mol_type = protein
                        organism = Bacillus circulans
SEQUENCE: 406
VNYGNGVSCS KTKCSVNWGI ITHQAFRVTS GVASG                         35

SEQ ID NO: 407          moltype = DNA  length = 105
FEATURE                 Location/Qualifiers
misc_feature            1..105
                        note = Polynucleotide encoding the polypeptide of SEQ IDNO:
                         406
source                  1..105
                        mol_type = other DNA
                        organism = synthetic construct
SEQUENCE: 407
gtgaactatg gcaacggcgt gagctgcagc aaaaccaaat gcagcgtgaa ctggggcatt  60
attacccatc aggcgtttcg cgtgaccagc ggcgtggcga gcggc                  105

SEQ ID NO: 408          moltype = AA  length = 30
FEATURE                 Location/Qualifiers
source                  1..30
                        mol_type = protein
                        organism = Paenibacillus polymyxa
SEQUENCE: 408
FVYGNGVTSI LVQAQFLVNG QRRFFYTPDK                               30

SEQ ID NO: 409          moltype = DNA  length = 90
FEATURE                 Location/Qualifiers
misc_feature            1..90
                        note = Polynucleotide encoding the polypeptide of SEQ IDNO:
                         408
source                  1..90
                        mol_type = other DNA
                        organism = synthetic construct
SEQUENCE: 409
tttgtgtatg gcaacggcgt gaccagcatt ctggtgcagg cgcagtttct ggtgaacggc  60
cagcgccgct ttttttatac cccggataaa                                   90

SEQ ID NO: 410          moltype = AA  length = 13
FEATURE                 Location/Qualifiers
source                  1..13
                        mol_type = protein
```

```
                        organism = Lactobacillus rhamnosus
SEQUENCE: 410
AVPAVRKTNE TLD                                                  13

SEQ ID NO: 411          moltype = DNA  length = 39
FEATURE                 Location/Qualifiers
misc_feature            1..39
                        note = Polynucleotide encoding the polypeptide of SEQ IDNO:
                         410
source                  1..39
                        mol_type = other DNA
                        organism = synthetic construct
SEQUENCE: 411
gcggtgccgg cggtgcgcaa aaccaacgaa accctggat                      39

SEQ ID NO: 412          moltype = AA  length = 69
FEATURE                 Location/Qualifiers
source                  1..69
                        mol_type = protein
                        organism = Bacillus licheniformis
SEQUENCE: 412
MKNSAAREAF KGANHPAGMV SEEELKALVG GNDVNPETTP ATTSSWTCIT AGVTVSASLC  60
PTTKCTSRC                                                       69

SEQ ID NO: 413          moltype = DNA  length = 207
FEATURE                 Location/Qualifiers
misc_feature            1..207
                        note = Polynucleotide encoding the polypeptide of SEQ IDNO:
                         412
source                  1..207
                        mol_type = other DNA
                        organism = synthetic construct
SEQUENCE: 413
atgaaaaaca gcgcggcgcg cgaagcgttt aaaggcgcga accatccggc gggcatggtg  60
agcgaagaag aactgaaagc gctggtgggc ggcaacgatg tgaacccgga aaccaccccg  120
gcgaccacca gcagctggac ctgcattacc gcgggcgtga ccgtgagcgc gagcctgtgc  180
ccgaccacca aatgcaccag ccgctgc                                   207

SEQ ID NO: 414          moltype = AA  length = 36
FEATURE                 Location/Qualifiers
source                  1..36
                        mol_type = protein
                        organism = Lactobacillus plantarum
SEQUENCE: 414
KYYGNGLSCS KKGCTVNWGQ AFSCGVNRVA TAGHGK                         36

SEQ ID NO: 415          moltype = DNA  length = 108
FEATURE                 Location/Qualifiers
misc_feature            1..108
                        note = Polynucleotide encoding the polypeptide of SEQ IDNO:
                         414
source                  1..108
                        mol_type = other DNA
                        organism = synthetic construct
SEQUENCE: 415
aaatattatg gcaacggcct gagctgcagc aaaaaaggct gcaccgtgaa ctggggccag  60
gcgtttagct gcggcgtgaa ccgcgtggcg accgcgggcc atggcaaa            108

SEQ ID NO: 416          moltype = AA  length = 24
FEATURE                 Location/Qualifiers
source                  1..24
                        mol_type = protein
                        organism = Lactobacillus acidophilus
SEQUENCE: 416
GNPKVAHCAS QIGRSTAWGA VSGA                                      24

SEQ ID NO: 417          moltype = DNA  length = 72
FEATURE                 Location/Qualifiers
misc_feature            1..72
                        note = Polynucleotide encoding the polypeptide of SEQ IDNO:
                         416
source                  1..72
                        mol_type = other DNA
                        organism = synthetic construct
SEQUENCE: 417
ggcaacccga aagtggcgca ttgcgcgagc cagattggcc gcagcaccgc gtggggcgcg  60
gtgagcggcg cg                                                   72

SEQ ID NO: 418          moltype = AA  length = 40
```

```
FEATURE                Location/Qualifiers
source                 1..40
                       mol_type = protein
                       organism = Enterococcus faecalis
SEQUENCE: 418
WLPPAGLLGR CGRWFRPWLL WLQSGAQYKW LGNLFGLGPK                        40

SEQ ID NO: 419         moltype = DNA  length = 120
FEATURE                Location/Qualifiers
misc_feature           1..120
                       note = Polynucleotide encoding the polypeptide of SEQ IDNO:
                        418
source                 1..120
                       mol_type = other DNA
                       organism = synthetic construct
SEQUENCE: 419
tggctgccgc cggcgggcct gctgggccgc tgcggccgct ggtttcgccc gtggctgctg  60
tggctgcaga gcggcgcgca gtataaatgg ctgggcaacc tgtttggcct gggcccgaaa  120

SEQ ID NO: 420         moltype = AA  length = 40
FEATURE                Location/Qualifiers
source                 1..40
                       mol_type = protein
                       organism = Anabaena variabilis
SEQUENCE: 420
NLDQWLTEQV HEFQDMYLEP QAISNQDITF KLSDLDFIHN                        40

SEQ ID NO: 421         moltype = DNA  length = 124
FEATURE                Location/Qualifiers
source                 1..124
                       mol_type = genomic DNA
                       organism = Anabaena variabilis
SEQUENCE: 421
taatttagat cagtggttaa cagaacaagt tcatgagttt caagatatgt acttggaacc  60
acaagcaata tccaatcaag acattacctt caaactatct gacctagatt ttattcataa  120
ttga                                                               124

SEQ ID NO: 422         moltype = AA  length = 40
FEATURE                Location/Qualifiers
source                 1..40
                       mol_type = protein
                       organism = Nostoc sp.
SEQUENCE: 422
NLDQWLTEQV HEFQDMYLEP QAISNQDITF KLSDLDFIHN                        40

SEQ ID NO: 423         moltype = DNA  length = 123
FEATURE                Location/Qualifiers
source                 1..123
                       mol_type = genomic DNA
                       organism = Nostoc sp.
SEQUENCE: 423
aatttagatc aatggttaac agaacaagtt catgagtttc aagatatgta cttggaacca  60
caagcaatat ccaatcaaga cattaccttc aaactgtcag acctagattt tattcataat  120
tga                                                                123

SEQ ID NO: 424         moltype = AA  length = 7
FEATURE                Location/Qualifiers
source                 1..7
                       mol_type = protein
                       organism = Nostoc azollae
SEQUENCE: 424
HREKKSA                                                            7

SEQ ID NO: 425         moltype = DNA  length = 24
FEATURE                Location/Qualifiers
source                 1..24
                       mol_type = genomic DNA
                       organism = Nostoc azollae
SEQUENCE: 425
cacagagaga aaaaatcagc atag                                         24

SEQ ID NO: 426         moltype = AA  length = 23
FEATURE                Location/Qualifiers
source                 1..23
                       mol_type = protein
                       organism = Acaryochloris marina
SEQUENCE: 426
TSNNWLAKNY LSMWNKKSSN PNL                                          23
```

```
SEQ ID NO: 427          moltype = DNA  length = 72
FEATURE                 Location/Qualifiers
source                  1..72
                        mol_type = genomic DNA
                        organism = Acaryochloris marina
SEQUENCE: 427
acaagcaata actggctagc caaaaactat ctttctatgt ggaataaaaa gagcagtaat  60
ccaaaccttt ag                                                       72

SEQ ID NO: 428          moltype = AA  length = 6
FEATURE                 Location/Qualifiers
source                  1..6
                        mol_type = protein
                        organism = Cyanothece sp.
SEQUENCE: 428
FRYFWW                                                              6

SEQ ID NO: 429          moltype = DNA  length = 21
FEATURE                 Location/Qualifiers
source                  1..21
                        mol_type = genomic DNA
                        organism = Cyanothece sp.
SEQUENCE: 429
tttagatatt tttggtggta a                                             21

SEQ ID NO: 430          moltype = AA  length = 6
FEATURE                 Location/Qualifiers
source                  1..6
                        mol_type = protein
                        organism = Cyanothece sp.
SEQUENCE: 430
FRYFWW                                                              6

SEQ ID NO: 431          moltype = DNA  length = 21
FEATURE                 Location/Qualifiers
source                  1..21
                        mol_type = genomic DNA
                        organism = Cyanothece sp.
SEQUENCE: 431
tttagatatt tttggtggta a                                             21

SEQ ID NO: 432          moltype = AA  length = 9
FEATURE                 Location/Qualifiers
source                  1..9
                        mol_type = protein
                        organism = Cyanothece sp.
SEQUENCE: 432
CGEKWRIFS                                                           9

SEQ ID NO: 433          moltype = DNA  length = 27
FEATURE                 Location/Qualifiers
source                  1..27
                        mol_type = genomic DNA
                        organism = Cyanothece sp.
SEQUENCE: 433
tgtggagaaa aatggagaat ttttagc                                       27

SEQ ID NO: 434          moltype = AA  length = 8
FEATURE                 Location/Qualifiers
source                  1..8
                        mol_type = protein
                        organism = Cyanothece sp.
SEQUENCE: 434
FRLQLWQF                                                            8

SEQ ID NO: 435          moltype = DNA  length = 24
FEATURE                 Location/Qualifiers
source                  1..24
                        mol_type = genomic DNA
                        organism = Cyanothece sp.
SEQUENCE: 435
tttcgcttac aactgtggca attt                                          24

SEQ ID NO: 436          moltype = AA  length = 16
FEATURE                 Location/Qualifiers
source                  1..16
                        mol_type = protein
                        organism = Cyanothece sp.
SEQUENCE: 436
```

```
LGCNQSSIWS IFFWNH                                            16

SEQ ID NO: 437          moltype = DNA  length = 51
FEATURE                 Location/Qualifiers
source                  1..51
                        mol_type = genomic DNA
                        organism = Cyanothece sp.
SEQUENCE: 437
ctaggatgta accagagcag tatctggtca attttttttct ggaatcatta a          51

SEQ ID NO: 438          moltype = AA  length = 40
FEATURE                 Location/Qualifiers
source                  1..40
                        mol_type = protein
                        organism = Microcoleus chthonoplastes
SEQUENCE: 438
YNLQGLPAIE SEDCIPDSVA PSDDWFSGVS SLFNRLTGLG                  40

SEQ ID NO: 439          moltype = DNA  length = 123
FEATURE                 Location/Qualifiers
source                  1..123
                        mol_type = genomic DNA
                        organism = Microcoleus chthonoplastes
SEQUENCE: 439
tataacctac aggggttgcc agcaattgag tcagaagact gtatcccaga ttctgtagcg  60
ccttcggatg attggttttc aggcgtatcg tctctgttta accgcttgac tgggttgggt  120
tag                                                                123

SEQ ID NO: 440          moltype = AA  length = 37
FEATURE                 Location/Qualifiers
source                  1..37
                        mol_type = protein
                        organism = Nostoc sp.
SEQUENCE: 440
WMAIRRILRC HPFHPGGYDP VPELGEHCCH HDSGNKG                     37

SEQ ID NO: 441          moltype = DNA  length = 114
FEATURE                 Location/Qualifiers
source                  1..114
                        mol_type = genomic DNA
                        organism = Nostoc sp.
SEQUENCE: 441
tggatggcga ttcgccgcat tttgcgttgt catccattcc acccaggggg ttatgatcct  60
gtaccagagt tgggtgagca ttgttgtcat catgatagcg ggaataaggg gtga        114

SEQ ID NO: 442          moltype = AA  length = 35
FEATURE                 Location/Qualifiers
source                  1..35
                        mol_type = protein
                        organism = Anabaena variabilis
SEQUENCE: 442
WMGIRRILRC HPFHPGGYDP VPEVGEHCCH HDSGK                       35

SEQ ID NO: 443          moltype = DNA  length = 108
FEATURE                 Location/Qualifiers
source                  1..108
                        mol_type = genomic DNA
                        organism = Anabaena variabilis
SEQUENCE: 443
tggatgggga ttcgccgcat tttgcgttgt catccattcc acccaggcgg ttatgatcct  60
gtaccagagg tgggtgagca ttgttgtcat catgatagcg ggaagtag               108

SEQ ID NO: 444          moltype = AA  length = 48
FEATURE                 Location/Qualifiers
source                  1..48
                        mol_type = protein
                        organism = Nodularia spumigena
SEQUENCE: 444
WMATRRILRC HPFHPGGYDP VPEVKHNCCD QHLSDSGKQT TEDHHKGS         48

SEQ ID NO: 445          moltype = DNA  length = 147
FEATURE                 Location/Qualifiers
source                  1..147
                        mol_type = genomic DNA
                        organism = Nodularia spumigena
SEQUENCE: 445
tggatggcga ctcggcggat tttgcgttgt catcccttcc atcctggtgg atatgatcca  60
gttccagagg taaaacacaa ttgctgcgat cagcatctgt ccgattctgg gaaacagacc  120
acagaagacc atcacaaagg ctcgtag                                      147
```

```
SEQ ID NO: 446          moltype = AA  length = 34
FEATURE                 Location/Qualifiers
source                  1..34
                        mol_type = protein
                        organism = Nostoc azollae
SEQUENCE: 446
WMATLRILRC HPFHPGGYDP VPGLAEKSCC DHHD                              34

SEQ ID NO: 447          moltype = DNA  length = 105
FEATURE                 Location/Qualifiers
source                  1..105
                        mol_type = genomic DNA
                        organism = Nostoc azollae
SEQUENCE: 447
tggatggcaa ctttgcggat tttacgctgt catcctttcc atcctggtgg ttatgatcct  60
gtaccaggac tagcggaaaa atcctgttgt gaccatcatg attga                  105

SEQ ID NO: 448          moltype = AA  length = 28
FEATURE                 Location/Qualifiers
source                  1..28
                        mol_type = protein
                        organism = Synechococcus sp
SEQUENCE: 448
WLTAKRFCRC HPLHPGGYDP VPEKKSVL                                     28

SEQ ID NO: 449          moltype = DNA  length = 87
FEATURE                 Location/Qualifiers
source                  1..87
                        mol_type = genomic DNA
                        organism = Synechococcus sp
SEQUENCE: 449
tggctaacag ccaagcgctt ttgtcgctgt catccgcttc atcctggcgg gtatgatccg  60
gtaccggaga agaaatcggt actctaa                                      87

SEQ ID NO: 450          moltype = AA  length = 23
FEATURE                 Location/Qualifiers
source                  1..23
                        mol_type = protein
                        organism = Prochlorococcus marinus
SEQUENCE: 450
WLTLRRLSRC HPFTPCGCDP VPD                                          23

SEQ ID NO: 451          moltype = DNA  length = 72
FEATURE                 Location/Qualifiers
source                  1..72
                        mol_type = genomic DNA
                        organism = Prochlorococcus marinus
SEQUENCE: 451
tggctcaccc tgcggcgcct gtctcgttgc catcctttta ccccctgtgg ttgcgacccg  60
gtgcctgatt aa                                                      72

SEQ ID NO: 452          moltype = AA  length = 69
FEATURE                 Location/Qualifiers
source                  1..69
                        mol_type = protein
                        organism = Escherichia coli
SEQUENCE: 452
MSYKKLYQLT AIFSLPLTIL LVSLSSLRIV GEGNSYVDVF LSFIIFLGFI ELIHGIRKIL  60
VWSGWKNGS                                                          69

SEQ ID NO: 453          moltype = DNA  length = 210
FEATURE                 Location/Qualifiers
source                  1..210
                        mol_type = genomic DNA
                        organism = Escherichia coli
SEQUENCE: 453
atgagttata aaaaactgta ccaattgacg gctatattta gtttacctct tactatctta  60
ttggtttcac tttcatccct tcggattgtt ggcgaaggga attcttatgt tgacgttttt  120
ctaagcttta taatatttct tggttttatt gagctgattc atgggattcg aaagattttg  180
gtctggtcag gctggaaaaa cggaagttaa                                   210

SEQ ID NO: 454          moltype = AA  length = 85
FEATURE                 Location/Qualifiers
source                  1..85
                        mol_type = protein
                        organism = Escherichia coli
SEQUENCE: 454
MGLKLDLTWF DKSTEDFKGE EYSKDFGDDG SVMESLGVPF KDNVNNGCFD VIAEWVPLLQ  60
```

```
PYFNHQIDIS DNEYFVSFDY RDGDW                                       85

SEQ ID NO: 455         moltype = DNA  length = 258
FEATURE                Location/Qualifiers
source                 1..258
                       mol_type = genomic DNA
                       organism = Escherichia coli
SEQUENCE: 455
atgggactta aattggattt aacttggttt gataaaagta cagaagattt taagggtgag  60
gagtattcaa aagattttgg agatgacggt tcagttatgg aaagtctagg tgtgcctttt  120
aaggataatg ttaataacgg ttgctttgat gttatagctg aatgggtacc tttgctacaa  180
ccatacttta atcatcaaat tgatatttcc gataatgagt attttgtttc gtttgattat  240
cgtgatggtg attggtga                                                258

SEQ ID NO: 456         moltype = AA  length = 113
FEATURE                Location/Qualifiers
source                 1..113
                       mol_type = protein
                       organism = Escherichia coli
SEQUENCE: 456
MSLRYYIKNI LFGLYCTLIY IYLITKNSEG YYFLVSDKML YAIVISTILC PYSKYAIEYI  60
AFNFIKKDFF ERRKNLNNAP VAKLNLFMLY NLLCLVLAIP FGLLGLFISI KNN         113

SEQ ID NO: 457         moltype = DNA  length = 342
FEATURE                Location/Qualifiers
source                 1..342
                       mol_type = genomic DNA
                       organism = Escherichia coli
SEQUENCE: 457
atgagcttaa gatactacat aaaaaatatt ttatttggcc tgtactgcac acttatatat  60
atatacctta taacaaaaaa cagcgaaggg tattatttcc ttgtgtcaga taagatgcta  120
tatgcaatag tgataagcac tattctatgt ccatattcaa aatatgctat tgaatacata  180
gcttttaact tcataaagaa agatttttc gaaagaagaa aaaacctaaa taacgccccc  240
gtagcaaaat taaacctatt tatgctatat aatctacttt gtttggtcct agcaatccca  300
tttggattgc taggactttt tatatcaata aagaataatt aa                     342

SEQ ID NO: 458         moltype = AA  length = 85
FEATURE                Location/Qualifiers
source                 1..85
                       mol_type = protein
                       organism = Escherichia coli
SEQUENCE: 458
MGLKLHIHWF DKKTEEFKGG EYSKDFGDDG SVIESLGMPL KDNINNGWFD VEKPWVSILQ  60
PHFKNVIDIS KFDYFVSFVY RDGNW                                       85

SEQ ID NO: 459         moltype = DNA  length = 258
FEATURE                Location/Qualifiers
source                 1..258
                       mol_type = genomic DNA
                       organism = Escherichia coli
SEQUENCE: 459
atggggctta aattacatat tcattggttt gataagaaaa ccgaagagtt taaaggcggt  60
gaatactcaa aagacttcgg tgatgatggt tctgtcattg aaagtctggg gatgccttta  120
aaggataata ttaataatgg ttggtttgat gttgaaaaac catgggtttc gatattacag  180
ccacacttta aaaatgtaat cgatattagt aaatttgatt actttgtatc ctttgtttac  240
cgggatggta actggtaa                                                258

SEQ ID NO: 460         moltype = AA  length = 86
FEATURE                Location/Qualifiers
source                 1..86
                       mol_type = protein
                       organism = Escherichia coli
SEQUENCE: 460
MELKHSISDY TEAEFLEFVK KICRAEGATE EDDNKLVREF ERLTEHPDGS DLIYYPRDDR  60
EDSPEGIVKE IKEWRAANGK SGFKQG                                      86

SEQ ID NO: 461         moltype = DNA  length = 261
FEATURE                Location/Qualifiers
source                 1..261
                       mol_type = genomic DNA
                       organism = Escherichia coli
SEQUENCE: 461
atggaactga aacatagtat tagtgattat accgaggctg aatttctgga gtttgtaaaa  60
aaaatatgta gagctgaagg tgctactgaa gaggatgaca ataaattagt gagagagttt  120
gagcgattaa ctgagcaccc agatggttca gatctgattt attatcctcg cgatgacagg  180
gaagatagtc ctgaagggat tgtcaaggaa attaaagaat ggcgagctgc taacggtaag  240
tcaggattta aacagggctg a                                            261

SEQ ID NO: 462         moltype = AA  length = 178
```

```
FEATURE                Location/Qualifiers
source                 1..178
                       mol_type = protein
                       organism = Citrobacter freundii
SEQUENCE: 462
MMNEHSIDTD NRKANNALYL FIIIGLIPLL CIFVVYYKTP DALLLRKIAT STENLPSITS  60
SYNPLMTKVM DIYCKTAPFL ALILYILTFK IRKLINNTDR NTVLRSCLLS PLVYAAIVYL  120
FCFRNFELTT AGRPVRLMAT NDATLLLFYI GLYSIIFFTT YITLFTPVTA FKLLKKRQ    178

SEQ ID NO: 463         moltype = DNA  length = 537
FEATURE                Location/Qualifiers
source                 1..537
                       mol_type = genomic DNA
                       organism = Citrobacter freundii
SEQUENCE: 463
atgatgaatg aacactcaat agatacggac aacagaaagg ccaataacgc attgtattta  60
tttataataa tcggattaat accattattg tgcattttttg ttgtttacta caaaacgcca  120
gacgctttac ttttacgtaa aattgctaca agcactgaga atctcccgtc aataacatcc  180
tcctacaacc cattaatgac aaaggttatg gatatttatt gtaaaacagc gcctttcctt  240
gccttaatac tatacatcct aacctttaaa atcagaaaat taatcaacaa caccgacagg  300
aacactgtac ttagatcttg tttattaagt ccattggtct atgcagcaat tgtttatcta  360
ttctgcttcc gaaattttga gttaacaaca gccggaaggc ctgtcagatt aatggccacc  420
aatgacgcaa cactattgtt attttatatt ggtctgtact caataatttt ctttacaacc  480
tatatcacgc tattcacacc agtcactgca tttaaattat taaaaaaaag gcagtaa     537

SEQ ID NO: 464         moltype = AA  length = 111
FEATURE                Location/Qualifiers
source                 1..111
                       mol_type = protein
                       organism = Escherichia coli
SEQUENCE: 464
MNRKYYFNNM WWGWVTGGYM LYMSWDYEFK YRLLFWCISL CGMVLYPVAK WYIEDTALKF  60
TRPDFWNSGF FADTPGKMGL LAVYTGTVFI LSLPLSMIYI LSVIIKRLSV R          111

SEQ ID NO: 465         moltype = DNA  length = 336
FEATURE                Location/Qualifiers
source                 1..336
                       mol_type = genomic DNA
                       organism = Escherichia coli
SEQUENCE: 465
atgaacagaa aatattattt taataatatg tggtggggat gggtgacggg gggatatatg  60
ctgtatatgt catgggatta tgagtttaaa tacagattac tgttctggtg tatttctctc  120
tgcggaatgg ttttgtatcc ggttgcaaaa tggtatattg aagatacagc tctaaaattt  180
acccggcctg atttctggaa cagcggtttt tttgctgata cacctggaaa aatggggttg  240
cttgcggttt atacgggtac tgttttcata ttatctcttc cgttaagtat gatatatatt  300
ctttctgtta ttataaaaag gctgtctgta agatag                            336

SEQ ID NO: 466         moltype = AA  length = 115
FEATURE                Location/Qualifiers
source                 1..115
                       mol_type = protein
                       organism = Escherichia coli
SEQUENCE: 466
MKLDISVKYL LKSLIPILII LTVFYLGWKD NQENARMFYA FIGCIISAIT FPFSMRIIQK  60
MVIRFTGKEF WQKDFFTNPV GGSLTAIFEL FCFVISVPVV AIYLIFILCK ALSGK       115

SEQ ID NO: 467         moltype = DNA  length = 348
FEATURE                Location/Qualifiers
source                 1..348
                       mol_type = genomic DNA
                       organism = Escherichia coli
SEQUENCE: 467
atgaaactgg atatatctgt aaagtattta ctgaaaagcc tgataccaat cctcattatt  60
cttacagttt tttatctggg atggaaagat aaccaggaaa atgcaagaat gttttatgcg  120
ttcatcggat gcattatcag tgccattact tttccttttt caatgaggat aatacagaaa  180
atggtaataa ggtttacagg gaaagaattc tggcaaaaag acttctttac aaatccagtt  240
ggcggaagct taactgcaat atttgaatta ttctgtttcg ttatatcagt tcctgtggtt  300
gccatttact taatttttat actctgcaaa gccctttcag gaaaatga                348

SEQ ID NO: 468         moltype = AA  length = 131
FEATURE                Location/Qualifiers
source                 1..131
                       mol_type = protein
                       organism = Escherichia coli
SEQUENCE: 468
MHNTLLEKII AYLSLPGFHS LNNPPLSEAF NLYVHTAPLA ATSLFIFTHK ELELKPKSSP  60
LRALKILTPF TILYISMIYC FLLTDTELTL SSKTFVLIVK KRSVFVFFLY NTIYWDIYIH  120
IFVLLVPYRN I                                                        131
```

```
SEQ ID NO: 469         moltype = DNA  length = 396
FEATURE                Location/Qualifiers
source                 1..396
                       mol_type = genomic DNA
                       organism = Escherichia coli
SEQUENCE: 469
atgcacaata cactcctcga aaaaatcatc gcatacctat ccctaccagg atttcattca  60
ttaaacaacc cgcccctaag cgaagcattc aatctctatg ttcatacagc ccctttagct  120
gcaaccagct tattcatatt cacacacaaa gaattagagt taaaaccaaa gtcgtcacct  180
ctgcgggcac taaagatatt aactcctttc actattcttt atatatccat gatatactgt  240
ttcttgctaa ctgacacaga actaaccttg tcatcaaaaa catttgtatt aatagtcaaa  300
aaacgatctg tttttgtctt ttttctatat aacactatat attgggatat atatattcac  360
atatttgtac ttttggttcc ttataggaac atataa                            396

SEQ ID NO: 470         moltype = AA  length = 85
FEATURE                Location/Qualifiers
source                 1..85
                       mol_type = protein
                       organism = Escherichia coli
SEQUENCE: 470
MELKNSISDY TETEFKKIIE DIINCEGDEK KQDDNLEHFI SVTEHPSGSD LIYYPEGNND  60
GSPEAVIKEI KEWRAANGKS GFKQG                                        85

SEQ ID NO: 471         moltype = DNA  length = 258
FEATURE                Location/Qualifiers
source                 1..258
                       mol_type = genomic DNA
                       organism = Escherichia coli
SEQUENCE: 471
atggaactga aaaacagcat tagtgattac actgaaactg aattcaaaaa aattattgaa  60
gacatcatca attgtgaagg tgatgaaaaa aaacaggatg ataacctcga gcattttata  120
agtgttactg agcatcctag tggttctgat ctgatttatt acccagaagg taataatgat  180
ggtagccctg aagctgttat taaagagatt aaagaatggc gagctgctaa cggtaagtca  240
ggatttaaac agggctga                                                258

SEQ ID NO: 472         moltype = AA  length = 98
FEATURE                Location/Qualifiers
source                 1..98
                       mol_type = protein
                       note = subsp. lactis
                       organism = Lactococcus lactis
SEQUENCE: 472
MKKKQIEFEN ELRSMLATAL EKDISQEERN ALNIAEKALD NSEYLPKIIL NLRKALTPLA  60
INRTLNHDLS ELYKFITSSK ASNKNLGGGL IMSWGRLF                          98

SEQ ID NO: 473         moltype = DNA  length = 297
FEATURE                Location/Qualifiers
source                 1..297
                       mol_type = genomic DNA
                       note = subsp. lactis
                       organism = Lactococcus lactis
SEQUENCE: 473
atgaaaaaaa aacaaataga atttgaaaac gagctaagaa gtatgttggc taccgccctt  60
gaaaaagaca ttagtcaaga ggaaagaaat gctctgaata ttgcagaaaa ggcgcttgac  120
aattctgaat atttaccaaa aattatttta aacctcagaa aagccctaac tccattagct  180
ataaatcgaa cacttaacca tgatttatct gaactgtata aattcattac aagttccaaa  240
gcatcaaaca aaaatttagg tggtggttta attatgtcgt ggggacgact attctaa     297

SEQ ID NO: 474         moltype = AA  length = 98
FEATURE                Location/Qualifiers
source                 1..98
                       mol_type = protein
                       note = subsp. cremoris
                       organism = Lactococcus lactis
SEQUENCE: 474
MKKKQIEFEN ELRSMLATAL EKDISQEERN ALNIAEKALD NSEYLPKIIL NLRKALTPLA  60
INRTLNHDLS ELYKFITSSK ASNKNLGGGL IMSWGRLF                          98

SEQ ID NO: 475         moltype = DNA  length = 297
FEATURE                Location/Qualifiers
source                 1..297
                       mol_type = genomic DNA
                       note = subsp. cremoris
                       organism = Lactococcus lactis
SEQUENCE: 475
atgaaaaaaa aacaaataga atttgaaaac gagctaagaa gtatgttggc taccgccctt  60
gaaaaagaca ttagtcaaga ggaaagaaat gctctgaata ttgcagaaaa ggcgcttgac  120
aattctgaat atttaccaaa aattatttta aacctcagaa aagccctaac tccattagct  180
ataaatcgaa cacttaacca tgatttatct gaactgtata aattcattac aagttccaaa  240
```

```
gcatcaaaca aaaatttagg tggtggttta attatgtcgt ggggacgact attctaa     297

SEQ ID NO: 476          moltype = AA  length = 87
FEATURE                 Location/Qualifiers
source                  1..87
                        mol_type = protein
                        organism = Escherichia coli
SEQUENCE: 476
MNKMAMIDLA KLFLASKITA IEFSERICVE RRRLYGVKDL SPNILNCGEE LFMAAERFEP  60
DADRANYEID DNGLKVEVRS ILEKFKL                                      87

SEQ ID NO: 477          moltype = DNA  length = 249
FEATURE                 Location/Qualifiers
source                  1..249
                        mol_type = genomic DNA
                        organism = Escherichia coli
SEQUENCE: 477
atgatcgatt tggcgaaatt atttttagct tcgaaaatta cagtgattga gttttcagag  60
cgaatttgtg ttgaacggag aagattgtat ggtgttaagg atttgtctcc gaatatatta  120
aattgtgggg aagagttgtc tatggctgct gagcgatttg agcctgatgc agatagggct  180
aattatgaaa ttgatgataa tggacttaag gtcgaggtcc gatctatctt ggaaaaactt  240
aaatcataa                                                          249

SEQ ID NO: 478          moltype = AA  length = 83
FEATURE                 Location/Qualifiers
source                  1..83
                        mol_type = protein
                        organism = Escherichia coli
SEQUENCE: 478
MKLSPKAAIE VCNEAAKKGL WILGIDGGHW LNPGFRIDSS ASWTYDMPEE YKSKIPENNR  60
LAIENIKDDI ENGYTAFIIT LKM                                          83

SEQ ID NO: 479          moltype = DNA  length = 243
FEATURE                 Location/Qualifiers
source                  1..243
                        mol_type = genomic DNA
                        organism = Escherichia coli
SEQUENCE: 479
atgaagttat caccaaaagc tgcaatagaa gtttgtaatg aagcagcgaa aaaaggctta  60
tggattttgg gcattgatgg tgggcattgg ctgaatcctg gattcaggat agatagttca  120
gcatcatgga catatgatat gccggagaat acaaatcaaa aatccctgaa aataatagat  180
tggctattga aaatattaaa gatgatattg agaatggata cactgctttc attatcacgt  240
taa                                                                243

SEQ ID NO: 480          moltype = AA  length = 85
FEATURE                 Location/Qualifiers
source                  1..85
                        mol_type = protein
                        organism = Escherichia coli
SEQUENCE: 480
MGLKLHINWF DKRTEEFKGG EYSKDFGDDG SVIERLGMPF KDNINNGWFD VIAEWVPLLQ  60
PYFNHQIDIS DNEYFVSFDY RDGDW                                        85

SEQ ID NO: 481          moltype = DNA  length = 258
FEATURE                 Location/Qualifiers
source                  1..258
                        mol_type = genomic DNA
                        organism = Escherichia coli
SEQUENCE: 481
atggggctta aattacatat taattggttt gataagacga ccgaggaatt taaaggtggt  60
gagtattcaa aagattttgg agatgatggc tcggtcattg aacgtcttgg aatgccttta  120
aaagataata tcaataatgg ttggtttgat gttatagctg aatgggtacc tttgctacaa  180
ccatacttta atcatcaaat tgatatttcc gataatgagt attttgtttc gtttgattat  240
cgtgatggtg attggtga                                                258

SEQ ID NO: 482          moltype = AA  length = 85
FEATURE                 Location/Qualifiers
source                  1..85
                        mol_type = protein
                        organism = Escherichia coli
SEQUENCE: 482
MELKKSIGDY TETEFKKIIE NIINCEGDEK KQDDNLEHFI SVTEHPSGSD LIYYPEGNND  60
GSPEAVIKEI KEWRAANGKS GFKQG                                        85

SEQ ID NO: 483          moltype = DNA  length = 258
FEATURE                 Location/Qualifiers
source                  1..258
                        mol_type = genomic DNA
                        organism = Escherichia coli
```

```
SEQUENCE: 483
gtggagctaa agaaaagtat tggtgattac actgaaaccg aattcaaaaa aattattgaa  60
aacatcatca attgtgaagg tgatgaaaaa aaacaggatg ataacctcga gcattttata  120
agtgttactg agcatcctag tggttctgat ctgatttatt acccagaagg taataatgat  180
ggtagccctg aagctgttat taaagagatt aaagaatggc gagctgctaa cggtaagtca  240
ggatttaaac agggctga                                                258

SEQ ID NO: 484         moltype = AA  length = 86
FEATURE                Location/Qualifiers
source                 1..86
                       mol_type = protein
                       organism = Escherichia coli
SEQUENCE: 484
MELKHSISDY TEAEFLQLVT TICNADTSSE EELVKLVTHF EEMTEHPSGS DLIYYPKEGD  60
DDSPSGIVNT VKQWRAANGK SGFKQG                                       86

SEQ ID NO: 485         moltype = DNA  length = 261
FEATURE                Location/Qualifiers
source                 1..261
                       mol_type = genomic DNA
                       organism = Escherichia coli
SEQUENCE: 485
atggaactga agcatagcat tagtgattat acagaagctg aatttttaca acttgtaaca  60
acaatttgta atgcgaacac ttccagtgaa gaagaactgg ttaaattggt tacacacttt  120
gaggaaatga ctgagcaccc tagtggtagt gatttaatat attacccaaa agaaggtgat  180
gatgactcac cttcaggtat tgtaaacaca gtaaaacaat ggcgagccgc taacggtaag  240
tcaggattta aacagggcta a                                            261

SEQ ID NO: 486         moltype = AA  length = 141
FEATURE                Location/Qualifiers
source                 1..141
                       mol_type = protein
                       organism = Escherichia coli
SEQUENCE: 486
MLTLYGYIRN VFLYRMNDRS CGDFMKVISM KFIFILTIIA LAAVFFWSED KGPACYQVSD  60
EQARTFVKND YLQRMKRWDN DVQLLGTEIP KITWEKIERS LTDVEDEKTL LVPFKAEGPD  120
GKRMYYGMYH CEEGYVEYAN D                                            141

SEQ ID NO: 487         moltype = DNA  length = 354
FEATURE                Location/Qualifiers
source                 1..354
                       mol_type = genomic DNA
                       organism = Escherichia coli
SEQUENCE: 487
atgaaagtaa ttagcatgaa atttattttt attttaacga ttattgctct tgctgctgtt  60
tttttctggt ctgaagataa aggtccggca tgctatcagg tcagcgatga acaggccaga  120
acgtttgtaa aaaatgatta cctgcaaaga atgaaacgct gggacaacga tgtacaactt  180
cttggtacag aaatcccgaa aattacatgg gaaaagattg agagaagttt aacagatgtt  240
gaagatgaaa aaacacttct tgtcccattt aaagctgaag gcccggacgg taagagaatg  300
tattatggca tgtaccattg tgaggaggga tatgttgaat atgcgaatga ctaa        354

SEQ ID NO: 488         moltype = AA  length = 175
FEATURE                Location/Qualifiers
source                 1..175
                       mol_type = protein
                       organism = Escherichia coli
SEQUENCE: 488
MTSNKDKNKK ANEILYAFSI IGIIPLMAIL ILRINDPYSQ VLYYLYNKVA FLPSITSLHD  60
PVMTTLMSNY NKTAPVMGIL VFLCTYKTRE IIKPVTRKLV VQSCFWGPVF YAILIYITLF  120
YNLELTTAGG FFKLLSHNVI TLFILYCSIY FTVLTMTYAI LLMPLLVIKY FKGRQ       175

SEQ ID NO: 489         moltype = DNA  length = 528
FEATURE                Location/Qualifiers
source                 1..528
                       mol_type = genomic DNA
                       organism = Escherichia coli
SEQUENCE: 489
atgaccagca ataaagataa gaacaagaaa gcaaacgaaa tattatatgc attttccata  60
atcgggatta ttccattaat ggctatatta atacttcgaa taaatgatcc atattctcaa  120
gtgctgtact acttatataa taaggtggca tttctccctt ctattacatc attgcatgat  180
cccgtcatga caacacttat gtcaaactac aacaagacag cgccagttat gggtattctc  240
gtttttcttt gcacatataa gacaagagaa atcataaagc cagtaacaag aaaacttgtt  300
gtgcaatcct gtttctgggg gcccgttttt tatgccattc tgatttatat cacactgttc  360
tataatctgg aactaacaac agcaggtggt ttttttaaat tattatctca taatgtcatc  420
actctgttta ttttatattg ctccatttac tttactgttt taaccatgac atatgcgatt  480
ttactgatgc cattacttgt cattaaatat tttaaaggga ggcagtaa                528

SEQ ID NO: 490         moltype = AA  length = 78
FEATURE                Location/Qualifiers
```

```
source                 1..78
                       mol_type = protein
                       organism = Escherichia coli
SEQUENCE: 490
MDRKRTKLEL LFAFIINATA IYIALAIYDC VFRGKDFLSM HTFCFSALMS AICYFVGDNY  60
YSISDKIKRR SYENSDSK                                                78

SEQ ID NO: 491         moltype = DNA  length = 237
FEATURE                Location/Qualifiers
source                 1..237
                       mol_type = genomic DNA
                       organism = Escherichia coli
SEQUENCE: 491
atggatagaa aaagaacaaa attagagttg ttatttgcat ttataataaa tgccaccgca  60
atatatattg cattagctat atatgattgt gtttttagag gaaaggactt tttatccatg  120
catacatttt gcttctctgc attaatgtct gcaatatgtt actttgttgg tgataattat  180
tattcaatat ccgataagat aaaaaggaga tcatatgaga actctgactc taaatga     237

SEQ ID NO: 492         moltype = AA  length = 113
FEATURE                Location/Qualifiers
source                 1..113
                       mol_type = protein
                       organism = Shigella sonnei
SEQUENCE: 492
MSLRYYIKNI LFGLYCALIY IYLITKNNEG YYFLASDKML YAIVISTILC PYSKYAIEHI  60
FFKFIKKDFF RKRKNLNKCP RGKIKPYLCV YNLLCLVLAI PFGLLGLVYI NKE          113

SEQ ID NO: 493         moltype = DNA  length = 342
FEATURE                Location/Qualifiers
source                 1..342
                       mol_type = genomic DNA
                       organism = Shigella sonnei
SEQUENCE: 493
atgagtttaa gatactacat aaaaaatatt ttgtttggcc tatactgcgc acttatatat  60
atataccta taacaaaaaa caacgaaggg tattatttcc tagcgtcaga taagatgcta  120
tacgcaatag tgataagcac tattctatgc ccatattcaa aatatgctat tgaacacata  180
tttttaagt tcataaagaa agattttttc agaaaaagaa aaaacctaaa taaatgcccc  240
cgtggcaaaa ttaaaccgta tttatgcgta tacaatctac tttgtttggt cctagcaatc  300
ccatttggat tgctaggact tgtttatatc aataaagaat aa                     342

SEQ ID NO: 494         moltype = AA  length = 113
FEATURE                Location/Qualifiers
source                 1..113
                       mol_type = protein
                       organism = Escherichia coli
SEQUENCE: 494
MSLRYYIKNI LFGLYCTLIY IYLITKNSEE YYFLVTDKML YAIVISTILC PYSKYAIEHI  60
AFNFIKKHFF ERRKNLNNAP VAKLNLFMLY NLLCLVLAIP FGLLGLFISI KNN          113

SEQ ID NO: 495         moltype = DNA  length = 342
FEATURE                Location/Qualifiers
source                 1..342
                       mol_type = genomic DNA
                       organism = Escherichia coli
SEQUENCE: 495
atgagcttaa gatactacat aaaaaatatt ttatttggcc tgtactgcac acttatatat  60
atataccta taacaaaaaa cagcgaagag tattatttcc ttgtgacaga taagatgcta  120
tatgcaatag tgataagcac tattctatgt ccatattcaa aatatgctat tgaacacata  180
gcttttaact tcataaagaa acattttttc gaaagaagaa aaaacctaaa taacgccccc  240
gtagcaaaat taaacctatt tatgctatat aatctacttt gtttggtcct agcaatccca  300
tttggattgc taggactttt tatatcaata aagaataatt aa                     342

SEQ ID NO: 496         moltype = AA  length = 113
FEATURE                Location/Qualifiers
source                 1..113
                       mol_type = protein
                       organism = Leuconostoc gelidum
SEQUENCE: 496
MRKNNILLDD AKIYTNKLYL LLIDRKDDAG YGDICDVLFQ VSKKLDSTKN VEALINRLVN  60
YIRITASTNR IKFSKDEEAV IIELGVIGQK AGLNGQYMAD FSDKSQFYSI FER          113

SEQ ID NO: 497         moltype = DNA  length = 342
FEATURE                Location/Qualifiers
source                 1..342
                       mol_type = genomic DNA
                       organism = Leuconostoc gelidum
SEQUENCE: 497
ttgagaaaaa ataacatttt attggacgat gctaaaatat acacgaacaa actctatttg  60
ctattaatcg atagaaaaga tgacgctggg tatggagata tttgtgatgt tttgtttcag  120
```

```
gtatccaaaa aattagatag cacaaaaaat gtagaagcat tgattaaccg attggtcaat  180
tatatacgaa ttaccgcttc aacaaacaga attaagtttt caaaagatga agaggctgta  240
attatagaac ttggtgtaat tggtcagaag gctggattaa acggccaata catggctgat  300
ttttctgaca aatctcagtt ttatagtatc tttgaaagat aa                     342

SEQ ID NO: 498         moltype = AA  length = 91
FEATURE                Location/Qualifiers
source                 1..91
                       mol_type = protein
                       note = subsp. cremoris
                       organism = Lactococcus lactis
SEQUENCE: 498
MKKKVDTEKQ ITSWASDLAS KNETKVQEKL ILSSYIQDIE NHVYFPKAMI SLEKKLRDQN  60
NICALSKEVN QFYFKVVEVN QRKSWMVGLI V                                 91

SEQ ID NO: 499         moltype = DNA  length = 276
FEATURE                Location/Qualifiers
source                 1..276
                       mol_type = genomic DNA
                       note = subsp. cremoris
                       organism = Lactococcus lactis
SEQUENCE: 499
atgaaaaaaa aagttgatac agaaaaacaa attacttctt gggcatctga cttagcttcc  60
aaaaatgaaa caaaggttca agaaaaatta atactgtctt cttatattca ggacatcgaa  120
aaccatgttt actttccaaa agcaatgatt tctttagaaa aaaaattacg agaccaaaat  180
aatatttgcg ctttatcaaa agaagtcaat cagttttatt ttaaagttgt tgaagtaaat  240
caaagaaaat cctggatggt aggtttgata gtttaa                            276

SEQ ID NO: 500         moltype = AA  length = 112
FEATURE                Location/Qualifiers
source                 1..112
                       mol_type = protein
                       organism = Pediococcus acidilactici
SEQUENCE: 500
MNKTKSEHIK QQALDLFTRL QFLLQKHDTI EPYQYVLDIL ETGISKTKHN QQTPERQARV  60
VYNKIASQAL VDKLHFTAEE NKVLAAINEL AHSQKGWGEF NMLDTTNTWP SQ          112

SEQ ID NO: 501         moltype = DNA  length = 339
FEATURE                Location/Qualifiers
source                 1..339
                       mol_type = genomic DNA
                       organism = Pediococcus acidilactici
SEQUENCE: 501
atgaataaga ctaagtcgga acatattaaa caacaagctt tggacttatt tactaggcta  60
cagtttttac tacagaagca cgatactatc gaaccttacc agtacgtttt agatattctg  120
gagactggta tcagtaaaac taaacataac cagcaaacgc ctgaacgaca agctcgtgta  180
gtctacaaca agattgccag ccaagcgtta gtagataagt tacattttac tgccgaagaa  240
aacaaagttc tagcagccat caatgaattg gcgcattctc aaaaagggtg gggcgagttt  300
aacatgctag atactaccaa tacgtggcct agccaatag                         339

SEQ ID NO: 502         moltype = AA  length = 88
FEATURE                Location/Qualifiers
source                 1..88
                       mol_type = protein
                       organism = Carnobacterium maltaromaticum
SEQUENCE: 502
MIKDEKINKI YALVKSALDN TDVKNDKKLS LLLMRIQETS INGELFYDYK KELQPAISMY  60
SIQHNFRVPD DLVKLLALVQ TPKAWSGF                                    88

SEQ ID NO: 503         moltype = DNA  length = 267
FEATURE                Location/Qualifiers
source                 1..267
                       mol_type = genomic DNA
                       organism = Carnobacterium maltaromaticum
SEQUENCE: 503
atgataaaag atgaaaaaat aaataaaatc tatgctttag ttaagagcgc acttgataat  60
acggatgtta agaatgataa aaaactttct ttacttctta tgagaataca agaaacatca  120
attaatggag aactatttta cgattataaa aaagaattac agccagctat tagtatgtac  180
tctattcaac ataactttcg ggttcctgac gatctagtaa aactgttagc attagttcaa  240
acacctaaag cttggtcagg gttttaa                                      267

SEQ ID NO: 504         moltype = AA  length = 111
FEATURE                Location/Qualifiers
source                 1..111
                       mol_type = protein
                       organism = Carnobacterium maltaromaticum
SEQUENCE: 504
MDIKSQTLYL NLSEAYKDPE VKANEFLSKL VVQCAGKLTA SNSENSYIEV ISLLSRGISS  60
YYLSHKRIIP SSMLTIYTQI QKDIKNGNID TEKLRKYEIA KGLMSVPYIY F           111
```

```
SEQ ID NO: 505          moltype = DNA  length = 336
FEATURE                 Location/Qualifiers
source                  1..336
                        mol_type = genomic DNA
                        organism = Carnobacterium maltaromaticum
SEQUENCE: 505
atggatataa agtctcaaac attatatttg aatctaagcg aggcatataa agaccctgaa  60
gtaaaagcta atgaattctt atcaaaatta gttgtacaat gtgctgggaa attaacagct  120
tcaaacagtg agaacagtta tattgaagta atatcattgc tatctagggg tatttctagt  180
tattatttat cccataaacg tataattcct tcaagtatgt taactatata tactcaaata  240
caaaaggata taaaaaacgg gaatattgac accgaaaaat taaggaaata tgagatagca  300
aaaggattaa tgtccgttcc ttatatatat ttctaa                            336

SEQ ID NO: 506          moltype = AA  length = 245
FEATURE                 Location/Qualifiers
source                  1..245
                        mol_type = protein
                        note = subsp. lactis
                        organism = Lactococcus lactis
SEQUENCE: 506
MRRYLILIVA LIGITGLSGC YQTSHKKVRF DEGSYTNFIY DNKSYFVTDK EIPQENVNNS  60
KVKFYKLLIV DMKSEKLLSS SNKNSVTLVL NNIYEASDKS LCMGINDRYY KILPESDKGA  120
VKALRLQNFD VTSDISDDNF VIDKNDSRKI DYMGNIYSIS DTTVSDEELG EYQDVLAEVR  180
VFDSVSGKSI PRSEWGRIDK DGSNSKQSRT EWDYGEIHSI RGKSLTEAFA VEINDDFKLA  240
TKVGN                                                              245

SEQ ID NO: 507          moltype = DNA  length = 738
FEATURE                 Location/Qualifiers
source                  1..738
                        mol_type = genomic DNA
                        note = subsp. lactis
                        organism = Lactococcus lactis
SEQUENCE: 507
atgagaagat atttaatact tattgtggcc ttaataggga taacaggttt atcagggtgt  60
tatcaaacaa gtcataaaaa ggtgaggttt gacgaaggaa gttatactaa ttttatttat  120
gataataaat cgtatttcgt aactgataag gagattcctc aggagaacgt taacaattcc  180
aaagtaaaat tttataagct gttgattgtt gacatgaaaa gtgagaaact tttatcaagt  240
agcaacaaaa atagtgtgac tttggtctta aataatattt atgaggcttc tgacaagtcg  300
ctatgtatgg gtattaacga cagatactat aagatacttc cagaaagtga taagggggcg  360
gtcaaagctt tgagattaca aaactttgat gtgacaagcg atatttctga tgataatttt  420
gttattgata aaaatgattc acgaaaaatt gactatatgg gaaatattta cagtatatcg  480
gacaccaccg tatctgatga agaattggga gaatatcagg atgttttagc tgaagtacgt  540
gtgtttgatt cagttagtgg caaaagtatc ccgaggtctg aatgggggag aattgataag  600
gatggttcaa attccaaaca gagtaggacg gaatgggatt atggcgaaat ccattctatt  660
agaggaaaat ctcttactga agcatttgcc gttgagataa atgatgattt taagcttgca  720
acgaaggtag gaaactag                                                738

SEQ ID NO: 508          moltype = AA  length = 261
FEATURE                 Location/Qualifiers
source                  1..261
                        mol_type = protein
                        note = bv. trifolii
                        organism = Rhizobium leguminosarum
SEQUENCE: 508
MNDEICLTGG GRTTVTRRGG VVYREGGPWS STVISLLRHL EASGFAEAPS VVGTGFDERG  60
RETLSFIEGE FVHPGPWSEE AFPQFGMMLR RLHDATASFK PPENSMWRDW FGRNLGEGQH  120
VIGHCDTGPW NIVCRSGLPV GLIDWEVAGP VRADIELAQA CWLNAQLYDD DIAERVGLGS  180
VTMRAHQVRL LLDGYGLSRK QRGGFVDKLI TFAVHDAAEQ AKEAAVTPES NDAEPLWAIA  240
WRTRSASWML HHRQTLEAAL A                                            261

SEQ ID NO: 509          moltype = DNA  length = 786
FEATURE                 Location/Qualifiers
source                  1..786
                        mol_type = genomic DNA
                        note = bv. trifolii
                        organism = Rhizobium leguminosarum
SEQUENCE: 509
atgaatgatg agatttgcct gacaggtggc ggacgaacga ctgtcacgcg gcgcggcgga  60
gtcgtgtatc gcgaaggcgg cccgtggtca tcaaccgtca tttcgctcct gcggcatctg  120
gaagcctctg gcttcgctga agctccttcc gttgtcggca ccggtttcga tgagcgcggc  180
cgggagacat tatcgtttat cgagggtgag tttgttcacc caggcccttg gtcggaggag  240
gcttttccgc aatttggaat gatgttgcgg cgactgcacg atgccaccgc ctcgttcaaa  300
cctcccgaaa actcgatgtg gcgcgattgg ttcgggcgta acctcggtga gggtcaacac  360
gtaataggac actgcgacac aggcccatgg aacattgttt gccggtcagg attgcctgtc  420
gggttgatag attgggaggt ggctgggcct gtcagggcgg atatcgaatt ggcccaggct  480
tgttggctga atgcccagct ctacgatgac gacattgcgg agagggtcgg attaggctct  540
gtgaccatga gagcgcatca agttcgcctg ctgcttgacg gctatggtct gtctcggaag  600
caacgcggcg gcttcgtcga caagctaatc acgttcgcag ttcacgatgc ggccgagcag  660
```

```
gcgaaagagg cggctgtcac gccagagtcg aacgatgcgg aaccgctatg ggcaattgcc  720
tggcgcacta gaagtgcctc ctggatgctc catcatcggc aaacactgga agcagcgctg  780
gcatag                                                             786

SEQ ID NO: 510         moltype = AA  length = 436
FEATURE                Location/Qualifiers
source                 1..436
                       mol_type = protein
                       organism = Bacillus subtilis
SEQUENCE: 510
MNNIIPIMSL LFKQLYSRQG KKDAIRIAAG LVILAVFEIG LIRQAGIDES VLRKTYIILA  60
LLLMNTYMVF LSVTSQWKES YMKLSCLLPI SSRSFWLAQS VVLFVDTCLR RTLFFFILPL  120
FLFGNGTLSG AQTLFWLGRF SFFTVYSIIF GVVLSNHFVK KKNLMFLLHA AIFACVCISA  180
ALMPAATIPL CAVHILWAVV IDFPVFLQAP PQQGKMHSFM RRSEFSFYKR EWNRFISSKA  240
MLLNYAVMAV FSGFFSFQMM NTGIFNQQVI YIVISALLLI CSPIALLYSI EKNDRMLLIT  300
LPIKRKTMFW AKYRFYSGLL AGGFLLVVMI VGFISGRSIS VLTFLQCIEL LLAGAYIRLT  360
ADEKRPSFSW QTEQQLWSGF SKYRSYLFCL PLFLAILAGT AVSLAVIPIA GLVIVYYLQK  420
QDGGFFDTSK RERLGS                                                  436

SEQ ID NO: 511         moltype = DNA  length = 1000
FEATURE                Location/Qualifiers
source                 1..1000
                       mol_type = genomic DNA
                       organism = Bacillus subtilis
SEQUENCE: 511
atgaataaca taatccctat catgtctttg ctgttcaaac agctttacag ccggcaaggg  60
aaaaaggacg ccatccgcat tgccgcaggc cttgtcattc tggccgtgtt tgaaatcggg  120
ctgatccgcc aggccggcat tgatgaatcg gtgttgcgca aaacgtatat catactcgcg  180
cttcttttga tgaacacata tatggtgttt ctttccgtga catcacaatg gaaggaatct  240
tatatgaagc tgagctgcct gctgccgatt tcttcacgga gcttttggct cgcccagagt  300
gtcgttttgt ttgtcgatac ctgtttgaga agaactttat tcttttttat tttaccgctg  360
ttcttatttg gaaacggaac gctgtcaggg gcgcaaacat tgttttggct cggcaggttt  420
tcgtttttta ccgtttactc cattattttc ggagttgtgc taagcaacca cttcgtcaaa  480
aagaagaact tgatgtttct gctgcatgcg gcgatattcg cctgtgtatg tatcagcgcc  540
gctttgatgc cggccgccac gattccgctt tgcgcggttc atatcctgtg ggcggtggtc  600
attgactttc ctgtctttct gcaggcgcct ccgcagcagg gcaagatgca ttcatttatg  660
cggcgatctg aattttcgtt ttacaaaaga gaatggaacc gatttatctc ttctaaagcg  720
atgctgttaa attacgcggt aatggcggta ttcagcggct tcttttcgtt ccagatgatg  780
aacaccggca tcttcaatca gcaagtgatt tatatcgtga tttccgcgct tttgctcatc  840
tgctcgccga tcgccctttt gtattcgatt gaaaaaaatg accggatgct gctcatcacg  900
cttccgatca agcgaaaaac gatgttttgg gcgaaatatc gcttttattc aggcctattg  960
gcaggcggat ttctccttgt cgtgatgatt gtgggtttca                        1000

SEQ ID NO: 512         moltype = AA  length = 239
FEATURE                Location/Qualifiers
source                 1..239
                       mol_type = protein
                       organism = Bacillus subtilis
SEQUENCE: 512
MSILDIHDVS VWYERDNVIL EQVDLHLEKG AVYGLLGVNG AGKTTLINTL TGVNRNFSGR  60
FTLCGIEAEA GMPQKTSDQL KTHRYFAADY PLLFTEITAK DYVSFVHSLY QKDFSEQQFA  120
SLAEAFHFSK YINRRISELS LGNRQKVVLM TGLLLRAPLF ILDEPLVGLD VESIEVFYQK  180
MREYCEAGGT ILFSSHLLDV VQRFCDYAAI LHNKQIQKVI PIGEETDLRR EFFEVIGHE   239

SEQ ID NO: 513         moltype = DNA  length = 716
FEATURE                Location/Qualifiers
source                 1..716
                       mol_type = genomic DNA
                       organism = Bacillus subtilis
SEQUENCE: 513
gcattttgga tatacacgat gtatccgttt ggtatgaacg ggacaacgtc atcttagagc  60
acgtggactt acacttagaa aaaggcgccg tttacggatt gcttggggta aacggtgccg  120
gcaaaacaac actgatcaat acgctgacag gagtgaaccg caattacagc gggggcttta  180
cgctgtgcgg cattgaagct gaggccggca tgccgcagaa aacatcagat caactgaaga  240
ttcaccgtta cttcgccgct gattatccgc tgctgtttac agaaattacg gcgaaggact  300
atgtgtcttt cgtccattcg ctttatcaaa aggatttttc agagcgacag tttgccagtt  360
tggctgaggc ctttcatttt tcaaaataca tcaacaggag aatctcggag ctgtccttgg  420
ggaacaggca aaaggttgtg ttgatgacag gattattgct gcgggctccc ctgtttattt  480
tggatgagcc gctcgtcggt ttggatgtgg aatcaataga ggtcttttat cagaaaatgc  540
gggagtactg tgaggaaggc ggaaccattt tgttttcttc ccatctgctc gatgtcgtgc  600
agagattttg tgattttgcg gccattctgc acaacaaaca gatccaaaag gtcattccga  660
ttggggagga gaccgatctg cggcgggaat tttttgaggt tatcggccat gaataa      716

SEQ ID NO: 514         moltype = AA  length = 53
FEATURE                Location/Qualifiers
source                 1..53
                       mol_type = protein
                       organism = Bacillus subtilis
SEQUENCE: 514
```

```
MSPAQRRILL YILSFIFVIG AVVYFVKSDY LFTLIFIAIA ILFGMRARKA DSR        53

SEQ ID NO: 515          moltype = DNA  length = 162
FEATURE                 Location/Qualifiers
source                  1..162
                        mol_type = genomic DNA
                        organism = Bacillus subtilis
SEQUENCE: 515
ttgtcaccag cacaaagaag aattttactg tatatccttt catttatctt tgtcatcggc  60
gcagtcgtct attttgtcaa aagcgattat ctgtttacgc tgattttcat tgccattgcc  120
attctgttcg ggatgcgcgc gcggaaggct gactcgcgat ga                     162

SEQ ID NO: 516          moltype = AA  length = 87
FEATURE                 Location/Qualifiers
source                  1..87
                        mol_type = protein
                        organism = Escherichia coli
SEQUENCE: 516
MELKNSISDY TEAEFVQLLK EIEKENVAAT DDVLDVLLEH FVKITEHPDG TDLIYYPSDN  60
RDDSPEGIVK EIKEWRAANG KPGFKQG                                      87

SEQ ID NO: 517          moltype = DNA  length = 264
FEATURE                 Location/Qualifiers
source                  1..264
                        mol_type = genomic DNA
                        organism = Escherichia coli
SEQUENCE: 517
atggaactga aaaatagtat tagtgattac acagaggctg agtttgttca acttcttaag  60
gaaattgaaa aagagaatgt tgctgcaact gatgatgtgt tagatgtgtt actcgaacac  120
tttgtaaaaa ttactgagca tccagatgga acggatctga tttattatcc tagtgataat  180
agagacgata gccccgaagg gattgtcaag gaaattaaag aatggcgagc tgctaacggt  240
aagccaggat ttaaacaggg ctga                                         264

SEQ ID NO: 518          moltype = AA  length = 87
FEATURE                 Location/Qualifiers
source                  1..87
                        mol_type = protein
                        organism = Pseudomonas aeruginosa
SEQUENCE: 518
MKSKISEYTE KEFLEFVEDI YTNNKKKFPT EESHIQAVLE FKKLTEHPSG SDLLYYPNEN  60
REDSPAGVVK EVKEWRASKG LPGFKAG                                      87

SEQ ID NO: 519          moltype = DNA  length = 264
FEATURE                 Location/Qualifiers
source                  1..264
                        mol_type = genomic DNA
                        organism = Pseudomonas aeruginosa
SEQUENCE: 519
atgaagtcca agatttccga atatacggaa aaagagtttc ttgagtttgt tgaagacata  60
tacacaaaca ataagaaaaa gttccctacc gaggagtctc atattcaagc cgtgcttgaa  120
tttaaaaaac taacggaaca cccaagcggc tcagaccttc tttactaccc caacgaaaat  180
agagaagata gcccagctgg agttgtaaag gaagttaaag aatggcgtgc ttccaagggg  240
cttcctggct ttaaggccgg ttag                                         264

SEQ ID NO: 520          moltype = AA  length = 87
FEATURE                 Location/Qualifiers
source                  1..87
                        mol_type = protein
                        organism = Pseudomonas aeruginosa
SEQUENCE: 520
MKSKISEYTE KEFLEFVKDI YTNNKKKFPT EESHIQAVLE FKKLTEHPSG SDLLYYPNEN  60
REDSPAGVVK EVKEWRASKG LPGFKAG                                      87

SEQ ID NO: 521          moltype = DNA  length = 264
FEATURE                 Location/Qualifiers
source                  1..264
                        mol_type = genomic DNA
                        organism = Pseudomonas aeruginosa
SEQUENCE: 521
atgaagtcca agatttccga atatacggaa aaagagtttc ttgagtttgt taaagacata  60
tacacaaaca ataagaaaaa gttccctacc gaggagtctc atattcaagc cgtgcttgaa  120
tttaaaaaac taacggaaca cccaagcggc tcagaccttc tttactaccc caacgaaaat  180
agagaagata gcccagctgg agttgtaaag gaagttaaag aatggcgtgc ttccaagggg  240
cttcctggct ttaaggccgg ttag                                         264

SEQ ID NO: 522          moltype = AA  length = 95
FEATURE                 Location/Qualifiers
source                  1..95
                        mol_type = protein
```

```
                         organism = Enterococcus hirae
SEQUENCE: 522
MDFTKEEKLL NAISKVYNEA TIDDYPDLKE KLFLYSKEIS EGKSVGEVSM KLSSFLGRYI  60
LKHKFGLPKS LIELQEIVSK ESQVYRGWAS IGIWS                             95

SEQ ID NO: 523           moltype = DNA  length = 288
FEATURE                  Location/Qualifiers
source                   1..288
                         mol_type = genomic DNA
                         organism = Enterococcus hirae
SEQUENCE: 523
atggatttta ctaaagaaga aaaacttta aatgcaatta gtaaagtata caatgaagca  60
actatagatg actatcctga cttaaaagaa aagctctttc tttattctaa agaaatcagt  120
gagggaaaaa gtgttggtga agttagtatg aaattaagta gttttcttgg aagatatatt  180
ttaaaacata aatttggatt acctaaatct ttaatagaat tacaagaaat tgttagtaag  240
gaatctcaag tatatagagg atgggcttct attggtattt ggagttaa               288

SEQ ID NO: 524           moltype = AA  length = 113
FEATURE                  Location/Qualifiers
source                   1..113
                         mol_type = protein
                         organism = Leuconostoc mesenteroides
SEQUENCE: 524
MKKKYRYLED SKNYTSTLYS LLVDNVDKPG YSDICDVLLQ VSKKLDNTQS VEALINRLVN  60
YIRITASTYK IIFSKKEEEL IIKLGVIGQK AGLNGQYMAD FSDKSQFYSV FDQ        113

SEQ ID NO: 525           moltype = DNA  length = 342
FEATURE                  Location/Qualifiers
source                   1..342
                         mol_type = genomic DNA
                         organism = Leuconostoc mesenteroides
SEQUENCE: 525
ttgaaaaaaa agtatcggta tttagaagat agcaaaaatt acactagtac actctattct  60
ctgttagttg ataatgttga caaacctgga tactcagata tttgcgatgt tttgcttcaa  120
gtttctaaga agttggataa tactcaaagt gttgaagcgc taattaatcg attggttaat  180
tatattcgta ttactgcttc aacatacaaa attatttttt caaaaaaaga agaggaattg  240
attataaaac ttggtgttat tggacaaaaa gctggactta atggtcagta tatggctgat  300
tttcagaca agtctcagtt ttacagcgtt ttcgatcagt aa                      342

SEQ ID NO: 526           moltype = AA  length = 93
FEATURE                  Location/Qualifiers
source                   1..93
                         mol_type = protein
                         organism = Escherichia coli
SEQUENCE: 526
MSFLNFAFSP VFFSIMACYF IVWRNKRNEF VCNRLLSIII ISFLICFIYP WLNYKIEVKY  60
YIFEQFYLFC FLSSLVAVVI NLIVYFILYR RCI                               93

SEQ ID NO: 527           moltype = DNA  length = 282
FEATURE                  Location/Qualifiers
source                   1..282
                         mol_type = genomic DNA
                         organism = Escherichia coli
SEQUENCE: 527
atgagttttc ttaattttgc attttctcct gtattcttct ccattatggc gtgttatttc  60
attgtatgga gaaataaacg aaacgaattt gtctgcaata gattgctatc aattataata  120
atatcttttt tgatatgctt catatatcca tggctaaatt acaaaatcga agttaaatat  180
tatatatttg aacagtttta tctttttgt ttttatcgt cactcgtggc tgttgtaata   240
aacctaattg tatactttat attatacagg agatgtatat ga                      282

SEQ ID NO: 528           moltype = AA  length = 96
FEATURE                  Location/Qualifiers
source                   1..96
                         mol_type = protein
                         organism = Escherichia coli
SEQUENCE: 528
MHLKYYLHNL PESLIPWILI LIFNDNDNTP LLFIFISSIH VLLYPYSKLT ISRYIKENTK  60
LKKEPWYLCK LSALFYLLMA IPVGLPSFIY YTLKRN                            96

SEQ ID NO: 529           moltype = DNA  length = 291
FEATURE                  Location/Qualifiers
source                   1..291
                         mol_type = genomic DNA
                         organism = Escherichia coli
SEQUENCE: 529
atgcatttaa aatactacct acataattta cctgaatcac ttataccatg gattcttatt  60
ttaatattta acgacaatga taacactcct ttgttattta tatttatatc atcaatacat  120
gtattgctat atccatactc taaattaacc atatctagat atatcaaaga aaatacaaag  180
ttaaaaaaag aaccctggta cttatgcaag ttatctgcat tgttttattt attaatggca  240
```

```
atcccagtag gattgccaag tttcatatat tacactctaa agagaaatta a          291

SEQ ID NO: 530          moltype = AA  length = 344
FEATURE                 Location/Qualifiers
source                  1..344
                        mol_type = protein
                        organism = Escherichia coli
SEQUENCE: 530
MMIQSHPLLA APLAVGDTIG FFSSSAPATV TAKNRFFRGV EFLQRKGFKL VSGKLTGKTD  60
FYRSGTIKER AQEFNELVYN PDITCIMSTI GGDNSNSLLP FLDYDAIIAN PKIIIGYSDT  120
TALLAGIYAK TGLITFYGPA LIPSFGEHPP LVDITYESFI KILTRKQSGI YTYTLPEKWS  180
DESINWNENK ILRPKKLYKN NCAFYGSGKV EGRVIGGNLN TLTGIWGSEW MPEILNGDIL  240
FIEDSRKSIA TIERLFSMLK LNRVFDKVSA IILGKHELFD CAGSKRRPYE VLTEVLDGKQ  300
IPVLDGFDCS HTHPMLTLPL GVKLAIDFDN KNISITEQYL STEK                  344

SEQ ID NO: 531          moltype = DNA  length = 1000
FEATURE                 Location/Qualifiers
source                  1..1000
                        mol_type = genomic DNA
                        organism = Escherichia coli
SEQUENCE: 531
atgatgatac aatctcatcc actactggcc gctcccctgg cagtaggaga tacaattggt  60
ttcttttcat catctgctcc ggcaacagtt actgcaaaaa atcgtttttt tcggggagtt  120
gagtttcttc agagaaaggg atttaagctg gtatcaggga agcttaccgg taaaacagat  180
ttttatcgtt caggtactat taaagaaaga gctcaagaat ttaatgagtt agtctacaat  240
cctgatatta cctgtataat gtcaacgatc ggtggagata acagtaattc actactaccg  300
tttctggact atgatgctat cattgcaaac cccaaaatta tcataggtta ctcagataca  360
actgctttat tagcaggaat atatgcaaaa acagggttaa taacattcta tggaccagct  420
cttattcctt cgtttggtga acatccacct cttgtggata taacatatga atcatttatt  480
aaaatactaa caagaaaaca atcaggaata tatacctaca cattacctga aaagtggagt  540
gatgagagca taaactggaa tgaaaacaag atattaaggc ctaagaagct atataaaaac  600
aactgtgcct tttatggttc cggaaaagtt gaggggcgtg taattggagg aaatctaaat  660
actttgacag gtatatgggg gagtgaatgg atgcctgaaa ttcttaatgg agatatattg  720
tttattgagg acagtcggaa aagcattgca acaattgaac gattattctc tatgctaaag  780
cttaatcgcg tgtttgataa agttagtgca ataatactcg ggaaacatga gctttttgat  840
tgtgcaggaa gtaaacgcag accatatgaa gtattaacag aggtattaga tgggaaacag  900
attcctgtac tggatggatt tgattgttca catacacatc caatgctaac tcttccactt  960
ggtgtaaaat tagctattga ctttgacaac aaaaatatat                       1000

SEQ ID NO: 532          moltype = AA  length = 90
FEATURE                 Location/Qualifiers
source                  1..90
                        mol_type = protein
                        organism = Lactobacillus sakei
SEQUENCE: 532
MKADYKKINS ILTYTSTALK NPKIIKDKDL VVLLTIIQEE AKQNRIFYDY KRKFRPAVTR  60
FTIDNNFEIP DCLVKLLSAV ETPKAWSGFS                                  90

SEQ ID NO: 533          moltype = DNA  length = 268
FEATURE                 Location/Qualifiers
source                  1..268
                        mol_type = genomic DNA
                        organism = Lactobacillus sakei
SEQUENCE: 533
ggcagattat aaaaaaataa attcaatact aacttacaca tctactgctt taaaaaaccc  60
taaaattata aaagataaag atttagtagt ccttctaact attattcaag aagaagccaa  120
acaaaataga atcttttatg attataaaag aaaatttcgt ccagcggtta ctcgctttac  180
aattgataat aattttgaga ttcctgattg tttggttaaa ctactgtcag ctgttgaaac  240
acctaaggcg tggtctggat ttagttag                                    268

SEQ ID NO: 534          moltype = AA  length = 83
FEATURE                 Location/Qualifiers
source                  1..83
                        mol_type = protein
                        organism = Escherichia coli
SEQUENCE: 534
MKLSPKAAIE VCNEAAKKGL WILGIDGGHW LNPGFRIDSS ASWTYDMPEE YKSKTPENNR  60
LAIENIKDDI ENGYTAFIIT LKM                                         83

SEQ ID NO: 535          moltype = DNA  length = 251
FEATURE                 Location/Qualifiers
source                  1..251
                        mol_type = genomic DNA
                        organism = Escherichia coli
SEQUENCE: 535
tgaagttatc accaaaagct gcaatagaag tttgtaatga agcagcgaaa aaaggcttat  60
ggattttggg cattgatggt gggcattggc tgaatcctgg attcaggata gatagttcag  120
catcatggac atatgatatg ccggaggaat acaaatcaaa aacccctgaa aataatagat  180
tggctattga aaatattaaa gatgatattg agaatggata cactgctttc attatcacgt  240
```

```
taaagatgta a                                                       251

SEQ ID NO: 536          moltype = AA  length = 436
FEATURE                 Location/Qualifiers
source                  1..436
                        mol_type = protein
                        organism = Bacillus subtilis
SEQUENCE: 536
MNNIFPIMSL LFKQLYSRQG KKDAIRIAAG LVILAVFEIG LIRQAGIDES VLGKTYIILA  60
LLLMNTYMVF LSVTSQWKES YMKLSCLLPI SSRSFWLAQS VVLFVDTCLR RTLFFFILPL  120
FLFGNGTLSG AQTLFWLGRF SFFTVYSILF GVMLSNHFVK KKNSMFLLHA AVFAFVCLSA  180
AFMPAVTIPL CAVHMLWAVI IDFPVFLQAP PHQSKMHFFM RRSEFSFYKR EWNRFISSKA  240
MLLNYVVMAA FSGFFSFQMM NTGIFNQQVI YIVISALLLI CSPIALLYSI EKNDRMLLIT  300
LPIKRRTMFW AKYRFYSGLL AGGFLLVAII VGFISGRPIS ALTFVQCMEL LLAGAFIRLT  360
ADEKRPSFGW QTEQQLWSGF SKYRSYLFCL PLFLATLAGT AVSLAVIPIA ALIIVYYLQK  420
QDGGFFDTSK RERIGS                                                  436

SEQ ID NO: 537          moltype = DNA  length = 1000
FEATURE                 Location/Qualifiers
source                  1..1000
                        mol_type = genomic DNA
                        organism = Bacillus subtilis
SEQUENCE: 537
ttggggagga gaccgatctg cggcgggaat tttttgaggt tatcggccat gaataacata  60
ttccccatca tgtcgttgct gttcaaacag ctgtacagcc ggcaagggaa aaaggacgct  120
atccgcattg ctgcagggct tgtgattctc gccgtgtttg aaatcgggct gatccgacaa  180
gccggcattg acgaatcggt gttgggaaaa acgtatatca tattggcgct tctcttaatg  240
aacacgtata tggtgtttct ttccgtgaca tcacaatgga aggaatctta tatgaagctg  300
agctgtctgc tgccgatttc atcacggagc ttttggctcg cccagagtgt cgttctgttt  360
gtcgatacct gtttgagaag aacgttattc ttttttattt taccgctgtt cttatttgga  420
aacggaacgc tgtcaggggc gcaaacattg ttttggcttg gcagattttc gttttttacc  480
gtttactcga ttctattcgg agttatgcta agcaaccatt tcgtcaaaaa gaagaactcg  540
atgtttctgc tgcatgcggc ggtattcgcc tttgtatgcc tcagtgccgc ttttatgccg  600
gccgtcacga tcccgctatg cgcggttcac atgctatggg cggtgatcat tgactttccg  660
gtctttctgc aggcgcctcc gcatcagagc aagatgcatt tttttatgcg gcgatctgaa  720
ttttcgtttt acaaaagaga atggaaccga tttatttctt ctaaagcgat gctgttaaat  780
tacgtggtga tggcggcgtt cagcggattc ttttcgttcc agatgatgaa cactggcatc  840
ttcaatcagc aagtgattta tattgtgatt tccgctctat tgctgatttg ctcgccgatc  900
gcccttttgt actctattga aaaaaacgat cgcatgctgc tcatcacgct tccaattaaa  960
agaagaacga tgttttgggc gaaatatcgc ttttattcag                        1000

SEQ ID NO: 538          moltype = AA  length = 580
FEATURE                 Location/Qualifiers
source                  1..580
                        mol_type = protein
                        organism = Escherichia coli
SEQUENCE: 538
MERKQKNSLF NYIYSLMDVR GKFLFFSMLF ITSLSSIIIS ISPLILAKIT DLLSGSLSNF  60
SYEYLVLLAC LYMFCVISNK ASVFLFMILQ SSLRINMQKK MSLKYLRELY NENITNLSKN  120
NAGYTTQSLN QASNDIYILV RNVSQNILSP VIQLISTIVV VLSTKDWFSA GVFFLYILVF  180
VIFNTRLTGS LASLRKHSMD ITLNSYSLLS DTVDNMIAAK KNNALRLISE RYEDALTQEN  240
NAQKKYWLLS SKVLLLNSLL AVILFGSVFI YNILGVLNGV VSIGHFIMIT SYIILLSTPV  300
ENIGALLSEI RQSMSSLAGF IQRHAENKAT SPSIPFLNME RKLNLSIREL SFSYSDDKKI  360
LNSVSLDLFT GKMYSLTGPS GSGKSTLVKI ISGYYKNYFG DIYLNDISLR NISDEDLNDA  420
IYYLTQDDYI FMDTLRFNLR LANYDASENE IFKVLKLANL SVVNNEPVSL DTHLINRGNN  480
YSGGQKQRIS LARLFLRKPA IIIIDEATSA LDYINESEIL SSIRTHFPDA LIINISHRIN  540
LLECSDCVYV LNEGNIVASG HFRDLMVSNE YISGLASVTE                        580

SEQ ID NO: 539          moltype = DNA  length = 1000
FEATURE                 Location/Qualifiers
source                  1..1000
                        mol_type = genomic DNA
                        organism = Escherichia coli
SEQUENCE: 539
atggaaagaa aacagaaaaa ctcattattt aattatattt attcattaat ggatgtaaga  60
ggtaaatttt tattcttttc catgttattc attacatcat tatcatcgat aatcatatct  120
atttcaccat tgattcttgc aaagattaca gatttactgt ctggctcatt gtcaaatttt  180
agttatgaat atctggtttt acttgcctgt ttatacatgt tttgcgttat atctaataaa  240
gcaagtgttt ttttatttat gatactgcaa agtagtctac gtattaacat gcagaaaaaa  300
atgtcgctaa agtatttgag agaattgtat aacgaaaata taactaactt gagtaaaaat  360
aatgctggat atacaacgca aagtcttaac caggcttcaa atgacattta tattcttgtg  420
agaaatgttt cccagaatat cctgtcacct gttatacaac ttatttccac tattgttgtt  480
gttttatcta cgaaggactg gtttctgcc  ggtgtgtttt ttctctatat tctggtattt  540
gtaatttta  ataccagact gactggcagt ttagcgtctc tcagaaaaca cagcatggat  600
atcactctta actcttatag tctgttatct gatactgttg ataacatgat agcagctaaa  660
aagaataatg cattaagact tatttctgaa cgttatgaag atgctctcac tcaggaaaac  720
aatgctcaga aaaaatactg gttactcagt tctaaagttc ttttattgaa ctctttactt  780
gctgtaatat tatttggttc tgtattcata tataatattt taggtgtgct gaatggtgta  840
gttagtatcg gccacttcat tatgattaca tcatatatca ttcttctttc aacgccagtg  900
```

```
gaaaatatag gggcattgct aagtgagatc aggcagtcaa tgtctagcct ggcaggtttt  960
attcaacgtc atgccgagaa taaagccaca tctccttcaa                        1000

SEQ ID NO: 540          moltype = AA  length = 95
FEATURE                 Location/Qualifiers
source                  1..95
                        mol_type = protein
                        organism = Klebsiella pneumoniae
SEQUENCE: 540
MTLLSFGFSP VFFSVMAFCI ISRSKFYPQR TRNKVIVLIL LTFFICFLYP LTKVYLVGSY  60
GIFDKFYLFC FISTLIAIAI NVVILTINGA KNERN                             95

SEQ ID NO: 541          moltype = DNA  length = 288
FEATURE                 Location/Qualifiers
source                  1..288
                        mol_type = genomic DNA
                        organism = Klebsiella pneumoniae
SEQUENCE: 541
atgacattac tttcatttgg attttctcct gttttctttt cagtcatggc gttctgtatc  60
atttcacgta gtaaattcta tccgcagaga acgcgaaaca aagttattgt tctgatttta  120
ctaacttttt ttatttgttt tttatatcca ttaacaaaag tgtatctggt gggaagttac  180
ggtatatttg acaaattcta cctcttttgc tttatttcta cgttaattgc aatagcaatt  240
aacgtagtga tacttacaat aaatggagct aagaatgaga gaaattag               288

SEQ ID NO: 542          moltype = RNA  length = 13
FEATURE                 Location/Qualifiers
misc_feature            1..13
                        note = Kozak sequence
source                  1..13
                        mol_type = other RNA
                        organism = synthetic construct
SEQUENCE: 542
gccgccrcca tgg                                                     13

SEQ ID NO: 543          moltype =   length =
SEQUENCE: 543
000

SEQ ID NO: 544          moltype = DNA  length = 30
FEATURE                 Location/Qualifiers
misc_feature            1..30
                        note = Lead promoter
source                  1..30
                        mol_type = other DNA
                        organism = synthetic construct
SEQUENCE: 544
gaaaaccttg tcaatgaaga gcgatctatg                                   30

SEQ ID NO: 545          moltype = DNA  length = 30
FEATURE                 Location/Qualifiers
misc_feature            1..30
                        note = FecA promoter
source                  1..30
                        mol_type = other DNA
                        organism = synthetic construct
SEQUENCE: 545
ttctcgttcg actcatagct gaacacaaca                                   30

SEQ ID NO: 546          moltype = DNA  length = 16
FEATURE                 Location/Qualifiers
misc_feature            1..16
                        note = Cu-sensitive promoter
source                  1..16
                        mol_type = other DNA
                        organism = synthetic construct
SEQUENCE: 546
atgacaaaat tgtcat                                                  16

SEQ ID NO: 547          moltype = DNA  length = 30
FEATURE                 Location/Qualifiers
misc_feature            1..30
                        note = Fe promoter
source                  1..30
                        mol_type = other DNA
                        organism = synthetic construct
SEQUENCE: 547
accaatgctg ggaacggcca gggcacctaa                                   30

SEQ ID NO: 548          moltype = DNA  length = 30
```

```
FEATURE                Location/Qualifiers
misc_feature           1..30
                       note = Fe and UV promoters
source                 1..30
                       mol_type = other DNA
                       organism = synthetic construct
SEQUENCE: 548
ctgaaagcgc ataccgctat ggagggggtt                                   30

SEQ ID NO: 549         moltype = DNA  length = 30
FEATURE                Location/Qualifiers
misc_feature           1..30
                       note = PrFe (PI + PII rus operon)
source                 1..30
                       mol_type = other DNA
                       organism = synthetic construct
SEQUENCE: 549
tagatatgcc tgaaagcgca taccgctatg                                   30

SEQ ID NO: 550         moltype = DNA  length = 30
FEATURE                Location/Qualifiers
misc_feature           1..30
                       note = Lux cassette right promoter
source                 1..30
                       mol_type = other DNA
                       organism = synthetic construct
SEQUENCE: 550
tgttatagtc gaatacctct ggcggtgata                                   30

SEQ ID NO: 551         moltype = DNA  length = 30
FEATURE                Location/Qualifiers
misc_feature           1..30
                       note = P(Las) TetO
source                 1..30
                       mol_type = other DNA
                       organism = synthetic construct
SEQUENCE: 551
ttttggtaca ctccctatca gtgatagaga                                   30

SEQ ID NO: 552         moltype = DNA  length = 30
FEATURE                Location/Qualifiers
misc_feature           1..30
                       note = P(Las) CIO
source                 1..30
                       mol_type = other DNA
                       organism = synthetic construct
SEQUENCE: 552
ctttttggta cactacctct ggcggtgata                                   30

SEQ ID NO: 553         moltype = DNA  length = 30
FEATURE                Location/Qualifiers
misc_feature           1..30
                       note = P(Rhl)
source                 1..30
                       mol_type = other DNA
                       organism = synthetic construct
SEQUENCE: 553
tacgcaagaa aatggtttgt tatagtcgaa                                   30

SEQ ID NO: 554         moltype = DNA  length = 30
FEATURE                Location/Qualifiers
misc_feature           1..30
                       note = Double Promoter (LuxR/HSL, positive / cI,negative)
source                 1..30
                       mol_type = other DNA
                       organism = synthetic construct
SEQUENCE: 554
cgtgcgtgtt gataacaccg tgcgtgttga                                   30

SEQ ID NO: 555         moltype = DNA  length = 30
FEATURE                Location/Qualifiers
misc_feature           1..30
                       note = P2 promoter in agr operon from S. aureus
source                 1..30
                       mol_type = other DNA
                       organism = synthetic construct
SEQUENCE: 555
agattgtact aaatcgtata atgacagtga                                   30
```

```
SEQ ID NO: 556          moltype = DNA  length = 30
FEATURE                 Location/Qualifiers
misc_feature            1..30
                        note = plux-cI hybrid promoter
source                  1..30
                        mol_type = other DNA
                        organism = synthetic construct
SEQUENCE: 556
gtgttgatgc ttttatcacc gccagtggta                                   30

SEQ ID NO: 557          moltype = DNA  length = 30
FEATURE                 Location/Qualifiers
misc_feature            1..30
                        note = plux-lac hybrid promoter
source                  1..30
                        mol_type = other DNA
                        organism = synthetic construct
SEQUENCE: 557
agtgtgtgga attgtgagcg gataacaatt                                   30

SEQ ID NO: 558          moltype = DNA  length = 30
FEATURE                 Location/Qualifiers
misc_feature            1..30
                        note = CinR, CinL and glucose controlled promotor
source                  1..30
                        mol_type = other DNA
                        organism = synthetic construct
SEQUENCE: 558
acatcttaaa agttttagta tcatattcgt                                   30

SEQ ID NO: 559          moltype = DNA  length = 30
FEATURE                 Location/Qualifiers
misc_feature            1..30
                        note = RhIR promoter repressible by CI
source                  1..30
                        mol_type = other DNA
                        organism = synthetic construct
SEQUENCE: 559
tacgcaagaa aatggtttgt tatagtcgaa                                   30

SEQ ID NO: 560          moltype = DNA  length = 30
FEATURE                 Location/Qualifiers
misc_feature            1..30
                        note = Reverse Lux Promoter
source                  1..30
                        mol_type = other DNA
                        organism = synthetic construct
SEQUENCE: 560
tcttgcgtaa acctgtacga tcctacaggt                                   30

SEQ ID NO: 561          moltype = DNA  length = 30
FEATURE                 Location/Qualifiers
misc_feature            1..30
                        note = rhlI promoter
source                  1..30
                        mol_type = other DNA
                        organism = synthetic construct
SEQUENCE: 561
atcctccttt agtcttcccc ctcatgtgtg                                   30

SEQ ID NO: 562          moltype = DNA  length = 30
FEATURE                 Location/Qualifiers
misc_feature            1..30
                        note = lasI promoter
source                  1..30
                        mol_type = other DNA
                        organism = synthetic construct
SEQUENCE: 562
taaaattatg aaatttgcat aaattcttca                                   30

SEQ ID NO: 563          moltype = DNA  length = 30
FEATURE                 Location/Qualifiers
misc_feature            1..30
                        note = LuxR+3OC6HSL independent R0065
source                  1..30
                        mol_type = other DNA
                        organism = synthetic construct
SEQUENCE: 563
gtgttgacta ttttacctct ggcggtgata                                   30
```

```
SEQ ID NO: 564          moltype = DNA  length = 30
FEATURE                 Location/Qualifiers
misc_feature            1..30
                        note = LasR/LasI Inducible & RHLR/RHLI repressiblePromoter
source                  1..30
                        mol_type = other DNA
                        organism = synthetic construct
SEQUENCE: 564
gaaatctggc agtttttggt acacgaaagc                                    30

SEQ ID NO: 565          moltype = DNA  length = 30
FEATURE                 Location/Qualifiers
misc_feature            1..30
                        note = pLux/cI Hybrid Promoter
source                  1..30
                        mol_type = other DNA
                        organism = synthetic construct
SEQUENCE: 565
acaccgtgcg tgttgatata gtcgaataaa                                    30

SEQ ID NO: 566          moltype = DNA  length = 30
FEATURE                 Location/Qualifiers
misc_feature            1..30
                        note = pLas promoter
source                  1..30
                        mol_type = other DNA
                        organism = synthetic construct
SEQUENCE: 566
aaaattatga aatttgtata aattcttcag                                    30

SEQ ID NO: 567          moltype = DNA  length = 30
FEATURE                 Location/Qualifiers
misc_feature            1..30
                        note = pLas/cI Hybrid Promoter
source                  1..30
                        mol_type = other DNA
                        organism = synthetic construct
SEQUENCE: 567
ggttcttttt ggtacctctg gcggtgataa                                    30

SEQ ID NO: 568          moltype = DNA  length = 30
FEATURE                 Location/Qualifiers
misc_feature            1..30
                        note = pLas/Lux Hybrid Promoter
source                  1..30
                        mol_type = other DNA
                        organism = synthetic construct
SEQUENCE: 568
tgtaggatcg tacaggtata aattcttcag                                    30

SEQ ID NO: 569          moltype = DNA  length = 30
FEATURE                 Location/Qualifiers
misc_feature            1..30
                        note = pLux
source                  1..30
                        mol_type = other DNA
                        organism = synthetic construct
SEQUENCE: 569
caagaaaatg gtttgttata gtcgaataaa                                    30

SEQ ID NO: 570          moltype = DNA  length = 30
FEATURE                 Location/Qualifiers
misc_feature            1..30
                        note = pLux/Las Hybrid Promoter
source                  1..30
                        mol_type = other DNA
                        organism = synthetic construct
SEQUENCE: 570
ctatctcatt tgctagtata gtcgaataaa                                    30

SEQ ID NO: 571          moltype = DNA  length = 30
FEATURE                 Location/Qualifiers
misc_feature            1..30
                        note = Hybrid promoter: HSL-LuxR activated, P22 C2repressed
source                  1..30
                        mol_type = other DNA
                        organism = synthetic construct
SEQUENCE: 571
```

```
tagtttataa tttaagtgtt ctttaatttc                                    30

SEQ ID NO: 572          moltype = DNA  length = 30
FEATURE                 Location/Qualifiers
misc_feature            1..30
                        note = PAI+LasR - LuxI (AI)
source                  1..30
                        mol_type = other DNA
                        organism = synthetic construct
SEQUENCE: 572
caccttcggg tgggcctttc tgcgtttata                                    30

SEQ ID NO: 573          moltype = DNA  length = 30
FEATURE                 Location/Qualifiers
misc_feature            1..30
                        note = PAI+LasR - LasI & AI+LuxR --[\m]LasI
source                  1..30
                        mol_type = other DNA
                        organism = synthetic construct
SEQUENCE: 573
aataactctg atagtgctag tgtagatctc                                    30

SEQ ID NO: 574          moltype = DNA  length = 30
FEATURE                 Location/Qualifiers
misc_feature            1..30
                        note = PAI+LasR - LasI+GFP & AI+LuxR --[\m]LasI+GFP
source                  1..30
                        mol_type = other DNA
                        organism = synthetic construct
SEQUENCE: 574
caccttcggg tgggcctttc tgcgtttata                                    30

SEQ ID NO: 575          moltype = DNA  length = 30
FEATURE                 Location/Qualifiers
misc_feature            1..30
                        note = Complex QS - LuxI & LasI circuit
source                  1..30
                        mol_type = other DNA
                        organism = synthetic construct
SEQUENCE: 575
caccttcggg tgggcctttc tgcgtttata                                    30

SEQ ID NO: 576          moltype = DNA  length = 30
FEATURE                 Location/Qualifiers
misc_feature            1..30
                        note = position 3 mutated promoter lux pR-3 (luxR &
                         HSLregulated)
source                  1..30
                        mol_type = other DNA
                        organism = synthetic construct
SEQUENCE: 576
caagaaaatg gtttgttata gtcgaataaa                                    30

SEQ ID NO: 577          moltype = DNA  length = 30
FEATURE                 Location/Qualifiers
misc_feature            1..30
                        note = position 5 mutated promoter lux pR-5 (luxR &
                         HSLregulated)
source                  1..30
                        mol_type = other DNA
                        organism = synthetic construct
SEQUENCE: 577
caagaaaatg gtttgttata gtcgaataaa                                    30

SEQ ID NO: 578          moltype = DNA  length = 30
FEATURE                 Location/Qualifiers
misc_feature            1..30
                        note = position 3&5 mutated promoter lux pR-3/5 (luxR &HSL
                         regulated)
source                  1..30
                        mol_type = other DNA
                        organism = synthetic construct
SEQUENCE: 578
caagaaaatg gtttgttata gtcgaataaa                                    30

SEQ ID NO: 579          moltype = DNA  length = 30
FEATURE                 Location/Qualifiers
misc_feature            1..30
                        note = Promoter (HSL-mediated luxR repressor)
```

```
source                  1..30
                        mol_type = other DNA
                        organism = synthetic construct
SEQUENCE: 579
ttgacacctg taggatcgta caggtataat                                    30

SEQ ID NO: 580          moltype = DNA  length = 30
FEATURE                 Location/Qualifiers
misc_feature            1..30
                        note = Promoter (luxR & HSL regulated -- lux pR)
source                  1..30
                        mol_type = other DNA
                        organism = synthetic construct
SEQUENCE: 580
caagaaaatg gtttgttata gtcgaataaa                                    30

SEQ ID NO: 581          moltype = DNA  length = 30
FEATURE                 Location/Qualifiers
misc_feature            1..30
                        note = Promoter (luxR & HSL regulated -- lux pL)
source                  1..30
                        mol_type = other DNA
                        organism = synthetic construct
SEQUENCE: 581
cacgcaaaac ttgcgacaaa caataggtaa                                    30

SEQ ID NO: 582          moltype = DNA  length = 30
FEATURE                 Location/Qualifiers
misc_feature            1..30
                        note = Promoter (RhlR & C4-HSL regulated)
source                  1..30
                        mol_type = other DNA
                        organism = synthetic construct
SEQUENCE: 582
gttagctttc gaattggcta aaaagtgttc                                    30

SEQ ID NO: 583          moltype = DNA  length = 30
FEATURE                 Location/Qualifiers
misc_feature            1..30
                        note = Promoter (cinR and HSL regulated)
source                  1..30
                        mol_type = other DNA
                        organism = synthetic construct
SEQUENCE: 583
ccattctgct ttccacgaac ttgaaaacgc                                    30

SEQ ID NO: 584          moltype = DNA  length = 30
FEATURE                 Location/Qualifiers
misc_feature            1..30
                        note = Promoter (LasR & PAI regulated)
source                  1..30
                        mol_type = other DNA
                        organism = synthetic construct
SEQUENCE: 584
ggccgcgggt tctttttggt acacgaaagc                                    30

SEQ ID NO: 585          moltype = DNA  length = 30
FEATURE                 Location/Qualifiers
misc_feature            1..30
                        note = Promoter, Standard (luxR and HSL regulated -- luxpR)
source                  1..30
                        mol_type = other DNA
                        organism = synthetic construct
SEQUENCE: 585
aagaaaatgg tttgttgata ctcgaataaa                                    30

SEQ ID NO: 586          moltype = DNA  length = 30
FEATURE                 Location/Qualifiers
misc_feature            1..30
                        note = P(Bla)
source                  1..30
                        mol_type = other DNA
                        organism = synthetic construct
SEQUENCE: 586
gtttatacat aggcgagtac tctgttatgg                                    30

SEQ ID NO: 587          moltype = DNA  length = 30
FEATURE                 Location/Qualifiers
misc_feature            1..30
```

```
                        note = P(Cat)
source                  1..30
                        mol_type = other DNA
                        organism = synthetic construct
SEQUENCE: 587
agaggttcca actttcacca taatgaaaca                                   30

SEQ ID NO: 588          moltype = DNA  length = 30
FEATURE                 Location/Qualifiers
misc_feature            1..30
                        note = P(Kat)
source                  1..30
                        mol_type = other DNA
                        organism = synthetic construct
SEQUENCE: 588
taaacaacta acggacaatt ctacctaaca                                   30

SEQ ID NO: 589          moltype = DNA  length = 30
FEATURE                 Location/Qualifiers
misc_feature            1..30
                        note = Template for Building Primer Family Member
source                  1..30
                        mol_type = other DNA
                        organism = synthetic construct
SEQUENCE: 589
acatcaagcc aaattaaaca ggattaacac                                   30

SEQ ID NO: 590          moltype = DNA  length = 30
FEATURE                 Location/Qualifiers
misc_feature            1..30
                        note = Reverse lambda cI-regulated promoter
source                  1..30
                        mol_type = other DNA
                        organism = synthetic construct
SEQUENCE: 590
gaggtaaaat agtcaacacg cacggtgtta                                   30

SEQ ID NO: 591          moltype = DNA  length = 30
FEATURE                 Location/Qualifiers
misc_feature            1..30
                        note = Key Promoter absorbs 3
source                  1..30
                        mol_type = other DNA
                        organism = synthetic construct
SEQUENCE: 591
caggccggaa taactcccta taatgcgcca                                   30

SEQ ID NO: 592          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 592
ggctagctca gtcctaggta cagtgctagc                                   30

SEQ ID NO: 593          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 593
agctagctca gtcctaggta ttatgctagc                                   30

SEQ ID NO: 594          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 594
agctagctca gtcctaggta ctgtgctagc                                   30

SEQ ID NO: 595          moltype = DNA  length = 30
FEATURE                 Location/Qualifiers
```

```
misc_feature            1..30
                        note = constitutive promoter family member
source                  1..30
                        mol_type = other DNA
                        organism = synthetic construct
SEQUENCE: 595
agctagctca gtcctaggga ttatgctagc                                   30

SEQ ID NO: 596          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 596
agctagctca gtcctaggta ttgtgctagc                                   30

SEQ ID NO: 597          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 597
ggctagctca gtcctaggta ctatgctagc                                   30

SEQ ID NO: 598          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 598
ggctagctca gtcctaggta tagtgctagc                                   30

SEQ ID NO: 599          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 599
ggctagctca gccctaggta ttatgctagc                                   30

SEQ ID NO: 600          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 600
agctagctca gtcctaggta taatgctagc                                   30

SEQ ID NO: 601          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 601
agctagctca gtcctaggga ctgtgctagc                                   30

SEQ ID NO: 602          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 602
ggctagctca gtcctaggta caatgctagc                                   30

SEQ ID NO: 603          moltype = DNA  length = 30
```

```
FEATURE               Location/Qualifiers
misc_feature          1..30
                      note = constitutive promoter family member
source                1..30
                      mol_type = other DNA
                      organism = synthetic construct
SEQUENCE: 603
ggctagctca gtcctaggta tagtgctagc                                   30

SEQ ID NO: 604        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 604
agctagctca gtcctaggga ttatgctagc                                   30

SEQ ID NO: 605        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 605
ggctagctca gtcctaggga ttatgctagc                                   30

SEQ ID NO: 606        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 606
ggctagctca gtcctaggta caatgctagc                                   30

SEQ ID NO: 607        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 607
agctagctca gcccttggta caatgctagc                                   30

SEQ ID NO: 608        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 608
agctagctca gtcctaggga ctatgctagc                                   30

SEQ ID NO: 609        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 609
agctagctca gtcctaggga ttgtgctagc                                   30

SEQ ID NO: 610        moltype = DNA  length = 30
FEATURE               Location/Qualifiers
misc_feature          1..30
                      note = constitutive promoter family member
source                1..30
                      mol_type = other DNA
                      organism = synthetic construct
SEQUENCE: 610
ggctagctca gtcctaggta ttgtgctagc                                   30
```

```
SEQ ID NO: 611          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 611
agctagctca gtcctaggta taatgctagc                                   30

SEQ ID NO: 612          moltype = DNA  length = 30
FEATURE                 Location/Qualifiers
misc_feature            1..30
                        note = 1bp mutant from J23107
source                  1..30
                        mol_type = other DNA
                        organism = synthetic construct
SEQUENCE: 612
ggctagctca gtcctaggta ttatgctagc                                   30

SEQ ID NO: 613          moltype = DNA  length = 30
FEATURE                 Location/Qualifiers
misc_feature            1..30
                        note = 1bp mutant from J23114
source                  1..30
                        mol_type = other DNA
                        organism = synthetic construct
SEQUENCE: 613
ggctagctca gtcctaggta caatgctagc                                   30

SEQ ID NO: 614          moltype = DNA  length = 30
FEATURE                 Location/Qualifiers
misc_feature            1..30
                        note = pBAD reverse
source                  1..30
                        mol_type = other DNA
                        organism = synthetic construct
SEQUENCE: 614
aaagtgtgac gccgtgcaaa taatcaatgt                                   30

SEQ ID NO: 615          moltype = DNA  length = 30
FEATURE                 Location/Qualifiers
misc_feature            1..30
                        note = NikR promoter, a protein of the ribbon
                         helix-helixfamily of trancription factors that repress
                         expre
source                  1..30
                        mol_type = other DNA
                        organism = synthetic construct
SEQUENCE: 615
gacgaatact taaaatcgtc atacttattt                                   30

SEQ ID NO: 616          moltype = DNA  length = 30
FEATURE                 Location/Qualifiers
misc_feature            1..30
                        note = lacq_Promoter
source                  1..30
                        mol_type = other DNA
                        organism = synthetic construct
SEQUENCE: 616
aaacctttcg cggtatggca tgatagcgcc                                   30

SEQ ID NO: 617          moltype = DNA  length = 30
FEATURE                 Location/Qualifiers
misc_feature            1..30
                        note = lacIQ - promoter sequence
source                  1..30
                        mol_type = other DNA
                        organism = synthetic construct
SEQUENCE: 617
tgatagcgcc cggaagagag tcaattcagg                                   30

SEQ ID NO: 618          moltype = DNA  length = 30
FEATURE                 Location/Qualifiers
misc_feature            1..30
                        note = E. Coli CreABCD phosphate sensing operon promoter
source                  1..30
                        mol_type = other DNA
                        organism = synthetic construct
```

```
SEQUENCE: 618
ttatttaccg tgacgaacta attgctcgtg                                    30

SEQ ID NO: 619          moltype = DNA  length = 30
FEATURE                 Location/Qualifiers
misc_feature            1..30
                        note = GlnRS promoter
source                  1..30
                        mol_type = other DNA
                        organism = synthetic construct
SEQUENCE: 619
catacgccgt tatacgttgt ttacgctttg                                    30

SEQ ID NO: 620          moltype = DNA  length = 30
FEATURE                 Location/Qualifiers
misc_feature            1..30
                        note = Constitutive weak promoter of lacZ
source                  1..30
                        mol_type = other DNA
                        organism = synthetic construct
SEQUENCE: 620
ttatgcttcc ggctcgtatg ttgtgtggac                                    30

SEQ ID NO: 621          moltype = DNA  length = 30
FEATURE                 Location/Qualifiers
misc_feature            1..30
                        note = Mutated LacZ promoter
source                  1..30
                        mol_type = other DNA
                        organism = synthetic construct
SEQUENCE: 621
ttatgcttcc ggctcgtatg gtgtgtggac                                    30

SEQ ID NO: 622          moltype = DNA  length = 30
FEATURE                 Location/Qualifiers
misc_feature            1..30
                        note = constitutive promoter with (TA)10 between -10 and-35
                         elements
source                  1..30
                        mol_type = other DNA
                        organism = synthetic construct
SEQUENCE: 622
atatatatat atatataatg gaagcgtttt                                    30

SEQ ID NO: 623          moltype = DNA  length = 30
FEATURE                 Location/Qualifiers
misc_feature            1..30
                        note = constitutive promoter with (TA)9 between -10 and-35
                         elements
source                  1..30
                        mol_type = other DNA
                        organism = synthetic construct
SEQUENCE: 623
atatatatat atatataatg gaagcgtttt                                    30

SEQ ID NO: 624          moltype = DNA  length = 30
FEATURE                 Location/Qualifiers
misc_feature            1..30
                        note = constitutive promoter with (C)10 between -10 and-35
                         elements
source                  1..30
                        mol_type = other DNA
                        organism = synthetic construct
SEQUENCE: 624
ccccgaaagc ttaagaatat aattgtaagc                                    30

SEQ ID NO: 625          moltype = DNA  length = 30
FEATURE                 Location/Qualifiers
misc_feature            1..30
                        note = constitutive promoter with (C)12 between -10 and-35
                         elements
source                  1..30
                        mol_type = other DNA
                        organism = synthetic construct
SEQUENCE: 625
ccccgaaagc ttaagaatat aattgtaagc                                    30

SEQ ID NO: 626          moltype = DNA  length = 30
FEATURE                 Location/Qualifiers
```

```
misc_feature          1..30
                      note = optimized (TA) repeat constitutive promoter with13
                       bp between -10 and -35 elements
source                1..30
                      mol_type = other DNA
                      organism = synthetic construct
SEQUENCE: 626
tgacaatata tatatatata taatgctagc                                   30

SEQ ID NO: 627        moltype = DNA  length = 30
FEATURE               Location/Qualifiers
misc_feature          1..30
                      note = optimized (TA) repeat constitutive promoter with15
                       bp between -10 and -35 elements
source                1..30
                      mol_type = other DNA
                      organism = synthetic construct
SEQUENCE: 627
acaatatata tatatatata taatgctagc                                   30

SEQ ID NO: 628        moltype = DNA  length = 30
FEATURE               Location/Qualifiers
misc_feature          1..30
                      note = optimized (TA) repeat constitutive promoter with17
                       bp between -10 and -35 elements
source                1..30
                      mol_type = other DNA
                      organism = synthetic construct
SEQUENCE: 628
aatatatata tatatatata taatgctagc                                   30

SEQ ID NO: 629        moltype = DNA  length = 30
FEATURE               Location/Qualifiers
misc_feature          1..30
                      note = optimized (TA) repeat constitutive promoter with19
                       bp between -10 and -35 elements
source                1..30
                      mol_type = other DNA
                      organism = synthetic construct
SEQUENCE: 629
tatatatata tatatatata taatgctagc                                   30

SEQ ID NO: 630        moltype = DNA  length = 30
FEATURE               Location/Qualifiers
misc_feature          1..30
                      note = optimized (TA) repeat constitutive promoter with21
                       bp between -10 and -35 elements
source                1..30
                      mol_type = other DNA
                      organism = synthetic construct
SEQUENCE: 630
tatatatata tatatatata taatgctagc                                   30

SEQ ID NO: 631        moltype = DNA  length = 30
FEATURE               Location/Qualifiers
misc_feature          1..30
                      note = optimized (A) repeat constitutive promoter with 17bp
                       between -10 and -35 elements
source                1..30
                      mol_type = other DNA
                      organism = synthetic construct
SEQUENCE: 631
aaaaaaaaaa aaaaaaaata taatgctagc                                   30

SEQ ID NO: 632        moltype = DNA  length = 30
FEATURE               Location/Qualifiers
misc_feature          1..30
                      note = optimized (A) repeat constitutive promoter with 18bp
                       between -10 and -35 elements
source                1..30
                      mol_type = other DNA
                      organism = synthetic construct
SEQUENCE: 632
aaaaaaaaaa aaaaaaaata taatgctagc                                   30

SEQ ID NO: 633        moltype = DNA  length = 30
FEATURE               Location/Qualifiers
misc_feature          1..30
                      note = J23101:GFP
```

```
source                  1..30
                        mol_type = other DNA
                        organism = synthetic construct
SEQUENCE: 633
caccttcggg tgggcctttc tgcgtttata                                   30

SEQ ID NO: 634          moltype = DNA  length = 30
FEATURE                 Location/Qualifiers
misc_feature            1..30
                        note = J23119:IFP
source                  1..30
                        mol_type = other DNA
                        organism = synthetic construct
SEQUENCE: 634
caccttcggg tgggcctttc tgcgtttata                                   30

SEQ ID NO: 635          moltype = DNA  length = 30
FEATURE                 Location/Qualifiers
misc_feature            1..30
                        note = J23119:HO1
source                  1..30
                        mol_type = other DNA
                        organism = synthetic construct
SEQUENCE: 635
caccttcggg tgggcctttc tgcgtttata                                   30

SEQ ID NO: 636          moltype = DNA  length = 30
FEATURE                 Location/Qualifiers
misc_feature            1..30
                        note = Infrared signal reporter (J23119:IFP:J23119:HO1)
source                  1..30
                        mol_type = other DNA
                        organism = synthetic construct
SEQUENCE: 636
caccttcggg tgggcctttc tgcgtttata                                   30

SEQ ID NO: 637          moltype = DNA  length = 30
FEATURE                 Location/Qualifiers
misc_feature            1..30
                        note = Double terminator + constitutive promoter
source                  1..30
                        mol_type = other DNA
                        organism = synthetic construct
SEQUENCE: 637
ggctagctca gtcctaggta cagtgctagc                                   30

SEQ ID NO: 638          moltype = DNA  length = 30
FEATURE                 Location/Qualifiers
misc_feature            1..30
                        note = Double terminator + Constitutive promoter + StrongRBS
source                  1..30
                        mol_type = other DNA
                        organism = synthetic construct
SEQUENCE: 638
tgctagctac tagagattaa agaggagaaa                                   30

SEQ ID NO: 639          moltype = DNA  length = 30
FEATURE                 Location/Qualifiers
misc_feature            1..30
                        note = IPTG inducible Lac promoter cassette
source                  1..30
                        mol_type = other DNA
                        organism = synthetic construct
SEQUENCE: 639
ttgtgagcgg ataacaagat actgagcaca                                   30

SEQ ID NO: 640          moltype = DNA  length = 30
FEATURE                 Location/Qualifiers
misc_feature            1..30
                        note = IPTG inducible Lac promoter cassette
source                  1..30
                        mol_type = other DNA
                        organism = synthetic construct
SEQUENCE: 640
ttgtgagcgg ataacaagat actgagcaca                                   30

SEQ ID NO: 641          moltype = DNA  length = 30
FEATURE                 Location/Qualifiers
misc_feature            1..30
```

```
                        note = IPTG inducible Lac promoter cassette
source                  1..30
                        mol_type = other DNA
                        organism = synthetic construct
SEQUENCE: 641
ttgtgagcgg ataacaagat actgagcaca                                    30

SEQ ID NO: 642          moltype = DNA  length = 30
FEATURE                 Location/Qualifiers
misc_feature            1..30
                        note = M13K07 gene I promoter
source                  1..30
                        mol_type = other DNA
                        organism = synthetic construct
SEQUENCE: 642
cctgttttta tgttattctc tctgtaaagg                                    30

SEQ ID NO: 643          moltype = DNA  length = 30
FEATURE                 Location/Qualifiers
misc_feature            1..30
                        note = M13K07 gene II promoter
source                  1..30
                        mol_type = other DNA
                        organism = synthetic construct
SEQUENCE: 643
aaatatttgc ttatacaatc ttcctgtttt                                    30

SEQ ID NO: 644          moltype = DNA  length = 30
FEATURE                 Location/Qualifiers
misc_feature            1..30
                        note = M13K07 gene III promoter
source                  1..30
                        mol_type = other DNA
                        organism = synthetic construct
SEQUENCE: 644
gctgataaac cgatacaatt aaaggctcct                                    30

SEQ ID NO: 645          moltype = DNA  length = 30
FEATURE                 Location/Qualifiers
misc_feature            1..30
                        note = M13K07 gene IV promoter
source                  1..30
                        mol_type = other DNA
                        organism = synthetic construct
SEQUENCE: 645
ctcttctcag cgtcttaatc taagctatcg                                    30

SEQ ID NO: 646          moltype = DNA  length = 30
FEATURE                 Location/Qualifiers
misc_feature            1..30
                        note = M13K07 gene V promoter
source                  1..30
                        mol_type = other DNA
                        organism = synthetic construct
SEQUENCE: 646
atgagccagt tcttaaaatc gcataaggta                                    30

SEQ ID NO: 647          moltype = DNA  length = 30
FEATURE                 Location/Qualifiers
misc_feature            1..30
                        note = M13K07 gene VI promoter
source                  1..30
                        mol_type = other DNA
                        organism = synthetic construct
SEQUENCE: 647
ctattgattg tgacaaaata aacttattcc                                    30

SEQ ID NO: 648          moltype = DNA  length = 30
FEATURE                 Location/Qualifiers
misc_feature            1..30
                        note = M13K07 gene VIII promoter
source                  1..30
                        mol_type = other DNA
                        organism = synthetic construct
SEQUENCE: 648
gtttcgcgct tggtataatc gctgggggtc                                    30

SEQ ID NO: 649          moltype = DNA  length = 30
FEATURE                 Location/Qualifiers
```

```
misc_feature          1..30
                      note = M13110
source                1..30
                      mol_type = other DNA
                      organism = synthetic construct
SEQUENCE: 649
ctttgcttct gactataata gtcagggtaa                                  30

SEQ ID NO: 650        moltype = DNA  length = 30
FEATURE               Location/Qualifiers
misc_feature          1..30
                      note = Modified promoter sequence of g3.
source                1..30
                      mol_type = other DNA
                      organism = synthetic construct
SEQUENCE: 650
aaaccgatac aattaaaggc tcctgctagc                                  30

SEQ ID NO: 651        moltype = DNA  length = 30
FEATURE               Location/Qualifiers
misc_feature          1..30
                      note = Constitutive Promoter I
source                1..30
                      mol_type = other DNA
                      organism = synthetic construct
SEQUENCE: 651
caccacactg atagtgctag tgtagatcac                                  30

SEQ ID NO: 652        moltype = DNA  length = 30
FEATURE               Location/Qualifiers
misc_feature          1..30
                      note = Constitutive Promoter II
source                1..30
                      mol_type = other DNA
                      organism = synthetic construct
SEQUENCE: 652
gccggaataa ctccctataa tgcgccacca                                  30

SEQ ID NO: 653        moltype = DNA  length = 30
FEATURE               Location/Qualifiers
misc_feature          1..30
                      note = --Specify Parts List--
source                1..30
                      mol_type = other DNA
                      organism = synthetic construct
SEQUENCE: 653
ttgacaagct tttcctcagc tccgtaaact                                  30

SEQ ID NO: 654        moltype = DNA  length = 30
FEATURE               Location/Qualifiers
misc_feature          1..30
                      note = Full-length stationary phase osmY promoter
source                1..30
                      mol_type = other DNA
                      organism = synthetic construct
SEQUENCE: 654
ggtttcaaaa ttgtgatcta tatttaacaa                                  30

SEQ ID NO: 655        moltype = DNA  length = 30
FEATURE               Location/Qualifiers
misc_feature          1..30
                      note = Minimal stationary phase osmY promoter
source                1..30
                      mol_type = other DNA
                      organism = synthetic construct
SEQUENCE: 655
ggtttcaaaa ttgtgatcta tatttaacaa                                  30

SEQ ID NO: 656        moltype = DNA  length = 30
FEATURE               Location/Qualifiers
misc_feature          1..30
                      note = htpG Heat Shock Promoter
source                1..30
                      mol_type = other DNA
                      organism = synthetic construct
SEQUENCE: 656
tctattccaa taaagaaatc ttcctgcgtg                                  30

SEQ ID NO: 657        moltype = DNA  length = 30
```

```
FEATURE                Location/Qualifiers
misc_feature           1..30
                       note = Promoter veg a constitutive promoter for B.subtilis
source                 1..30
                       mol_type = other DNA
                       organism = synthetic construct
SEQUENCE: 657
aaaaatgggc tcgtgttgta caataaatgt                                   30

SEQ ID NO: 658         moltype = DNA  length = 30
FEATURE                Location/Qualifiers
misc_feature           1..30
                       note = Promoter 43 a constitutive promoter for B.subtilis
source                 1..30
                       mol_type = other DNA
                       organism = synthetic construct
SEQUENCE: 658
aaaaaaagcg cgcgattatg taaaatataa                                   30

SEQ ID NO: 659         moltype = DNA  length = 30
FEATURE                Location/Qualifiers
misc_feature           1..30
                       note = Strong constitutive promoter for Bacillus subtilis
source                 1..30
                       mol_type = other DNA
                       organism = synthetic construct
SEQUENCE: 659
aattgcagta ggcatgacaa aatggactca                                   30

SEQ ID NO: 660         moltype = DNA  length = 30
FEATURE                Location/Qualifiers
misc_feature           1..30
                       note = PliaG
source                 1..30
                       mol_type = other DNA
                       organism = synthetic construct
SEQUENCE: 660
caagcttttc ctttataata gaatgaatga                                   30

SEQ ID NO: 661         moltype = DNA  length = 30
FEATURE                Location/Qualifiers
misc_feature           1..30
                       note = PlepA
source                 1..30
                       mol_type = other DNA
                       organism = synthetic construct
SEQUENCE: 661
tctaagctag tgtattttgc gtttaatagt                                   30

SEQ ID NO: 662         moltype = DNA  length = 30
FEATURE                Location/Qualifiers
misc_feature           1..30
                       note = Pveg
source                 1..30
                       mol_type = other DNA
                       organism = synthetic construct
SEQUENCE: 662
aatgggctcg tgttgtacaa taaatgtagt                                   30

SEQ ID NO: 663         moltype = DNA  length = 30
FEATURE                Location/Qualifiers
misc_feature           1..30
                       note = Promoter ctc for B. subtilis
source                 1..30
                       mol_type = other DNA
                       organism = synthetic construct
SEQUENCE: 663
atccttatcg ttatgggtat tgtttgtaat                                   30

SEQ ID NO: 664         moltype = DNA  length = 30
FEATURE                Location/Qualifiers
misc_feature           1..30
                       note = Promoter gsiB for B. subtilis
source                 1..30
                       mol_type = other DNA
                       organism = synthetic construct
SEQUENCE: 664
taaaagaatt gtgagcggga atacaacaac                                   30
```

```
SEQ ID NO: 665          moltype = DNA  length = 30
FEATURE                 Location/Qualifiers
misc_feature            1..30
                        note = Promoter 43 a constitutive promoter for B.subtilis
source                  1..30
                        mol_type = other DNA
                        organism = synthetic construct
SEQUENCE: 665
aaaaaaagcg cgcgattatg taaaatataa                                   30

SEQ ID NO: 666          moltype = DNA  length = 30
FEATURE                 Location/Qualifiers
misc_feature            1..30
                        note = Pspv2 from Salmonella
source                  1..30
                        mol_type = other DNA
                        organism = synthetic construct
SEQUENCE: 666
tacaaaataa ttcccctgca aacattatca                                   30

SEQ ID NO: 667          moltype = DNA  length = 30
FEATURE                 Location/Qualifiers
misc_feature            1..30
                        note = Pspv from Salmonella
source                  1..30
                        mol_type = other DNA
                        organism = synthetic construct
SEQUENCE: 667
tacaaaataa ttcccctgca aacattatcg                                   30

SEQ ID NO: 668          moltype = DNA  length = 30
FEATURE                 Location/Qualifiers
misc_feature            1..30
                        note = T7 promoter (strong promoter from T7bacteriophage)
source                  1..30
                        mol_type = other DNA
                        organism = synthetic construct
SEQUENCE: 668
agggaataca agctacttgt tctttttgca                                   30

SEQ ID NO: 669          moltype = DNA  length = 23
FEATURE                 Location/Qualifiers
misc_feature            1..23
                        note = T7 Promoter
source                  1..23
                        mol_type = other DNA
                        organism = synthetic construct
SEQUENCE: 669
taatacgact cactataggg aga                                          23

SEQ ID NO: 670          moltype = DNA  length = 28
FEATURE                 Location/Qualifiers
misc_feature            1..28
                        note = T7 Promoter
source                  1..28
                        mol_type = other DNA
                        organism = synthetic construct
SEQUENCE: 670
gaatttaata cgactcacta tagggaga                                     28

SEQ ID NO: 671          moltype = DNA  length = 19
FEATURE                 Location/Qualifiers
misc_feature            1..19
                        note = T7 consensus -10 and rest
source                  1..19
                        mol_type = other DNA
                        organism = synthetic construct
SEQUENCE: 671
taatacgact cactatagg                                               19

SEQ ID NO: 672          moltype = DNA  length = 30
FEATURE                 Location/Qualifiers
misc_feature            1..30
                        note = overlapping T7 promoter
source                  1..30
                        mol_type = other DNA
                        organism = synthetic construct
SEQUENCE: 672
gagtcgtatt aatacgactc actatagggg                                   30
```

```
SEQ ID NO: 673          moltype = DNA  length = 30
FEATURE                 Location/Qualifiers
misc_feature            1..30
                        note = more overlapping T7 promoter
source                  1..30
                        mol_type = other DNA
                        organism = synthetic construct
SEQUENCE: 673
agtgagtcgt actacgactc actatagggg                                   30

SEQ ID NO: 674          moltype = DNA  length = 30
FEATURE                 Location/Qualifiers
misc_feature            1..30
                        note = weaken overlapping T7 promoter
source                  1..30
                        mol_type = other DNA
                        organism = synthetic construct
SEQUENCE: 674
gagtcgtatt aatacgactc tctatagggg                                   30

SEQ ID NO: 675          moltype = DNA  length = 23
FEATURE                 Location/Qualifiers
misc_feature            1..23
                        note = T7 Consensus Promoter Sequence
source                  1..23
                        mol_type = other DNA
                        organism = synthetic construct
SEQUENCE: 675
taatacgact cactataggg aga                                          23

SEQ ID NO: 676          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 676
ttatacgact cactataggg aga                                          23

SEQ ID NO: 677          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 677
gaatacgact cactataggg aga                                          23

SEQ ID NO: 678          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 678
taatacgtct cactataggg aga                                          23

SEQ ID NO: 679          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 679
tcatacgact cactataggg aga                                          23

SEQ ID NO: 680          moltype = DNA  length = 30
FEATURE                 Location/Qualifiers
misc_feature            1..30
                        note = T7 strong promoter
source                  1..30
                        mol_type = other DNA
                        organism = synthetic construct
SEQUENCE: 680
```

```
taatacgact cactataggg agaccacaac                                   30

SEQ ID NO: 681          moltype = DNA  length = 30
FEATURE                 Location/Qualifiers
misc_feature            1..30
                        note = T7 weak binding and processivity
source                  1..30
                        mol_type = other DNA
                        organism = synthetic construct
SEQUENCE: 681
taattgaact cactaaaggg agaccacagc                                   30

SEQ ID NO: 682          moltype = DNA  length = 30
FEATURE                 Location/Qualifiers
misc_feature            1..30
                        note = T7 weak binding promoter
source                  1..30
                        mol_type = other DNA
                        organism = synthetic construct
SEQUENCE: 682
cgaagtaata cgactcacta ttagggaaga                                   30

SEQ ID NO: 683          moltype = DNA  length = 30
FEATURE                 Location/Qualifiers
misc_feature            1..30
                        note = pCyc (Medium) Promoter
source                  1..30
                        mol_type = other DNA
                        organism = synthetic construct
SEQUENCE: 683
acaaacacaa atacacacac taaattaata                                   30

SEQ ID NO: 684          moltype = DNA  length = 30
FEATURE                 Location/Qualifiers
misc_feature            1..30
                        note = pAdh (Strong) Promoter
source                  1..30
                        mol_type = other DNA
                        organism = synthetic construct
SEQUENCE: 684
ccaagcatac aatcaactat ctcatataca                                   30

SEQ ID NO: 685          moltype = DNA  length = 30
FEATURE                 Location/Qualifiers
misc_feature            1..30
                        note = pSte5 (Weak) Promoter
source                  1..30
                        mol_type = other DNA
                        organism = synthetic construct
SEQUENCE: 685
gatacaggat acagcggaaa caacttttaa                                   30

SEQ ID NO: 686          moltype = DNA  length = 30
FEATURE                 Location/Qualifiers
misc_feature            1..30
                        note = yeast ADH1 promoter
source                  1..30
                        mol_type = other DNA
                        organism = synthetic construct
SEQUENCE: 686
tttcaagcta taccaagcat acaatcaact                                   30

SEQ ID NO: 687          moltype = DNA  length = 30
FEATURE                 Location/Qualifiers
misc_feature            1..30
                        note = cyc100 minimal promoter
source                  1..30
                        mol_type = other DNA
                        organism = synthetic construct
SEQUENCE: 687
cctttgcagc ataaattact atacttctat                                   30

SEQ ID NO: 688          moltype = DNA  length = 30
FEATURE                 Location/Qualifiers
misc_feature            1..30
                        note = cyc70 minimal promoter
source                  1..30
                        mol_type = other DNA
                        organism = synthetic construct
```

```
SEQUENCE: 688
cctttgcagc ataaattact atacttctat                                   30

SEQ ID NO: 689          moltype = DNA  length = 30
FEATURE                 Location/Qualifiers
misc_feature            1..30
                        note = cyc43 minimal promoter
source                  1..30
                        mol_type = other DNA
                        organism = synthetic construct
SEQUENCE: 689
cctttgcagc ataaattact atacttctat                                   30

SEQ ID NO: 690          moltype = DNA  length = 30
FEATURE                 Location/Qualifiers
misc_feature            1..30
                        note = cyc28 minimal promoter
source                  1..30
                        mol_type = other DNA
                        organism = synthetic construct
SEQUENCE: 690
cctttgcagc ataaattact atacttctat                                   30

SEQ ID NO: 691          moltype = DNA  length = 30
FEATURE                 Location/Qualifiers
misc_feature            1..30
                        note = cyc16 minimal promoter
source                  1..30
                        mol_type = other DNA
                        organism = synthetic construct
SEQUENCE: 691
cctttgcagc ataaattact atacttctat                                   30

SEQ ID NO: 692          moltype = DNA  length = 30
FEATURE                 Location/Qualifiers
misc_feature            1..30
                        note = pPGK1
source                  1..30
                        mol_type = other DNA
                        organism = synthetic construct
SEQUENCE: 692
ttatctactt tttacaacaa atataaaaca                                   30

SEQ ID NO: 693          moltype = DNA  length = 30
FEATURE                 Location/Qualifiers
misc_feature            1..30
                        note = pCYC Yeast Promoter
source                  1..30
                        mol_type = other DNA
                        organism = synthetic construct
SEQUENCE: 693
acaaacacaa atacacacac taaattaata                                   30

SEQ ID NO: 694          moltype = DNA  length = 30
FEATURE                 Location/Qualifiers
misc_feature            1..30
                        note = Yeast GPD (TDH3) Promoter
source                  1..30
                        mol_type = other DNA
                        organism = synthetic construct
SEQUENCE: 694
gtttcgaata aacacacata aacaaacaaa                                   30

SEQ ID NO: 695          moltype = DNA  length = 30
FEATURE                 Location/Qualifiers
misc_feature            1..30
                        note = yeast mid-length ADH1 promoter
source                  1..30
                        mol_type = other DNA
                        organism = synthetic construct
SEQUENCE: 695
ccaagcatac aatcaactat ctcatataca                                   30

SEQ ID NO: 696          moltype = DNA  length = 30
FEATURE                 Location/Qualifiers
misc_feature            1..30
                        note = Yeast CLB1 promoter region, G2/M cell cyclespecific
source                  1..30
                        mol_type = other DNA
```

```
                         organism = synthetic construct
SEQUENCE: 696
accatcaaag gaagctttaa tcttctcata                                   30

SEQ ID NO: 697           moltype = DNA  length = 30
FEATURE                  Location/Qualifiers
misc_feature             1..30
                         note = CMV promoter
source                   1..30
                         mol_type = other DNA
                         organism = synthetic construct
SEQUENCE: 697
agaacccact gcttactggc ttatcgaaat                                   30

SEQ ID NO: 698           moltype = DNA  length = 30
FEATURE                  Location/Qualifiers
misc_feature             1..30
                         note = Ubc Promoter
source                   1..30
                         mol_type = other DNA
                         organism = synthetic construct
SEQUENCE: 698
ggccgttttt ggctttttg ttagacgaag                                    30

SEQ ID NO: 699           moltype = AA  length = 9
FEATURE                  Location/Qualifiers
source                   1..9
                         mol_type = protein
                         organism = Lactobacillus curvatus
SEQUENCE: 699
NIPQLTPTP                                                          9

SEQ ID NO: 700           moltype = DNA  length = 27
FEATURE                  Location/Qualifiers
source                   1..27
                         mol_type = genomic DNA
                         organism = Lactobacillus curvatus
SEQUENCE: 700
aacattccgc agctgacccc gaccccg                                      27

SEQ ID NO: 701           moltype = AA  length = 18
FEATURE                  Location/Qualifiers
VARIANT                  4..10
                         note = X= any amino acid
source                   1..18
                         mol_type = protein
                         organism = Bacillus thuringiensis
SEQUENCE: 701
DWTXWSXLVX AACSVELL                                                18

SEQ ID NO: 702           moltype = DNA  length = 54
FEATURE                  Location/Qualifiers
misc_feature             10..30
                         note = n = A,T,C or G
source                   1..54
                         mol_type = genomic DNA
                         organism = Bacillus thuringiensis
SEQUENCE: 702
gattggaccn nntggagcnn nctggtgnnn gcggcgtgca gcgtggaact gctg        54

SEQ ID NO: 703           moltype = AA  length = 30
FEATURE                  Location/Qualifiers
source                   1..30
                         mol_type = protein
                         note = L442
                         organism = Lactobacillus curvatus
SEQUENCE: 703
AYPGNGVHCG KYSCTVDKQT AIGNIGNNAA                                   30

SEQ ID NO: 704           moltype = DNA  length = 90
FEATURE                  Location/Qualifiers
source                   1..90
                         mol_type = genomic DNA
                         note = L442
                         organism = Lactobacillus curvatus
SEQUENCE: 704
gcgtatccgg gcaacggcgt gcattgcggc aaatatagct gcaccgtgga taaacagacc  60
gcgattggca acattggcaa caacgcggcg                                   90
```

```
SEQ ID NO: 705         moltype = AA  length = 43
FEATURE                Location/Qualifiers
source                 1..43
                       mol_type = protein
                       organism = Carnobacterium divergens
SEQUENCE: 705
TKYYGNGVYC NSKKCWVDWG TAQGCIDVVI GQLGGGIPGK GKC                   43

SEQ ID NO: 706         moltype = DNA  length = 129
FEATURE                Location/Qualifiers
source                 1..129
                       mol_type = genomic DNA
                       organism = Carnobacterium divergens
SEQUENCE: 706
accaaatatt atggcaacgg cgtgtattgc aacagcaaaa aatgctgggt ggattggggc  60
accgcgcagg gctgcattga tgtggtgatt ggccagctgg gcggcggcat tccgggcaaa  120
ggcaaatgc                                                          129

SEQ ID NO: 707         moltype = AA  length = 24
FEATURE                Location/Qualifiers
source                 1..24
                       mol_type = protein
                       note = strain 107891
                       organism = Microbispora sp.
SEQUENCE: 707
VTSWSLCTPG CTSPGGGSNC SFCC                                        24

SEQ ID NO: 708         moltype = DNA  length = 72
FEATURE                Location/Qualifiers
source                 1..72
                       mol_type = genomic DNA
                       note = strain 107891
                       organism = Microbispora sp.
SEQUENCE: 708
gtgaccagct ggagcctgtg caccccgggc tgcaccagcc cgggcggcgg cagcaactgc  60
agcttttgct gc                                                      72

SEQ ID NO: 709         moltype = AA  length = 62
FEATURE                Location/Qualifiers
source                 1..62
                       mol_type = protein
                       organism = Enterococcus sp.
SEQUENCE: 709
NRWYCNSAAG GVGGAAVCGL AGYVGEAKEN IAGEVRKGWG MAGGFTHNKA CKSFPGSGWA  60
SG                                                                 62

SEQ ID NO: 710         moltype = DNA  length = 186
FEATURE                Location/Qualifiers
source                 1..186
                       mol_type = genomic DNA
                       organism = Enterococcus sp.
SEQUENCE: 710
aaccgctggt attgcaacag cgcggcgggc ggcgtgggcg gcgcggcggt gtgcggcctg  60
gcgggctatg tgggcgaagc gaaagaaaac attgcgggcg aagtgcgcaa aggctggggc  120
atggcgggcg gctttaccca taacaaagcg tgcaaaagct ttccgggcag cggctgggcg  180
agcggc                                                             186

SEQ ID NO: 711         moltype = AA  length = 39
FEATURE                Location/Qualifiers
source                 1..39
                       mol_type = protein
                       organism = Enterococcus faecium
SEQUENCE: 711
TTKNYGNGVC NSVNWCQCGN VWASCNLATG CAAWLCKLA                         39

SEQ ID NO: 712         moltype = DNA  length = 117
FEATURE                Location/Qualifiers
source                 1..117
                       mol_type = genomic DNA
                       organism = Enterococcus faecium
SEQUENCE: 712
accaccaaaa actatggcaa cggcgtgtgc aacagcgtga actggtgcca gtgcggcaac  60
gtgtgggcga gctgcaacct ggcgaccggc tgcgcggcgt ggctgtgcaa actggcg     117

SEQ ID NO: 713         moltype = AA  length = 30
FEATURE                Location/Qualifiers
source                 1..30
                       mol_type = protein
                       organism = Paenibacillus polymyxa
```

```
SEQUENCE: 713
ASIIKTTIKV SKAVCKTLTC ICTGSCSNCK                                 30

SEQ ID NO: 714          moltype = DNA  length = 90
FEATURE                 Location/Qualifiers
source                  1..90
                        mol_type = genomic DNA
                        organism = Paenibacillus polymyxa
SEQUENCE: 714
gcgagcatta ttaaaaccac cattaaagtg agcaaagcgg tgtgcaaaac cctgacctgc  60
atttgcaccg gcagctgcag caactgcaaa                                 90

SEQ ID NO: 715          moltype = AA  length = 31
FEATURE                 Location/Qualifiers
source                  1..31
                        mol_type = protein
                        organism = Staphylococcus epidermidis
SEQUENCE: 715
SASIVKTTIK ASKKLCRGFT LTCGCHFTGK K                               31

SEQ ID NO: 716          moltype = DNA  length = 93
FEATURE                 Location/Qualifiers
source                  1..93
                        mol_type = genomic DNA
                        organism = Staphylococcus epidermidis
SEQUENCE: 716
agcgcgagca ttgtgaaaac caccattaaa gcgagcaaaa aactgtgccg cggctttacc  60
ctgacctgcg gctgccattt taccggcaaa aaa                             93

SEQ ID NO: 717          moltype = AA  length = 58
FEATURE                 Location/Qualifiers
source                  1..58
                        mol_type = protein
                        organism = Enterococcus faecium
SEQUENCE: 717
MEKLTVKEMS QVVGGKYYGN GVSCNKKGCS VDWGKAIGII GNNAAANLTT GGKAGWKG    58

SEQ ID NO: 718          moltype = DNA  length = 178
FEATURE                 Location/Qualifiers
source                  1..178
                        mol_type = genomic DNA
                        organism = Enterococcus faecium
SEQUENCE: 718
atggaaaaat taactgtgaa agaaatgtcg caagtagttg gcggaaagta ctatggtaac  60
ggagtatcat gtaataaaaa gggatgtagt gttgattggg gaaaagctat tggtattatt  120
ggaaataatg ctgctgctaa tttaactact ggcggaaaag cagggtggaa aggttaac    178

SEQ ID NO: 719          moltype = AA  length = 39
FEATURE                 Location/Qualifiers
source                  1..39
                        mol_type = protein
                        organism = Paenibacillus polymyxa
SEQUENCE: 719
ATYYGNGLYC NKQKHYTWVD WNKASREIGK ITVNGWVQH                       39

SEQ ID NO: 720          moltype = DNA  length = 93
FEATURE                 Location/Qualifiers
source                  1..93
                        mol_type = genomic DNA
                        organism = Paenibacillus polymyxa
SEQUENCE: 720
agcgcgagca ttgtgaaaac caccattaaa gcgagcaaaa aactgtgccg cggctttacc  60
ctgacctgcg gctgccattt taccggcaaa aaa                             93

SEQ ID NO: 721          moltype = AA  length = 35
FEATURE                 Location/Qualifiers
source                  1..35
                        mol_type = protein
                        organism = Bacillus circulans
SEQUENCE: 721
VNYGNGVSCS KTKCSVNWGI ITHQAFRVTS GVASG                           35

SEQ ID NO: 722          moltype = DNA  length = 105
FEATURE                 Location/Qualifiers
source                  1..105
                        mol_type = genomic DNA
                        organism = Bacillus circulans
SEQUENCE: 722
gtgaactatg gcaacggcgt gagctgcagc aaaaccaaat gcagcgtgaa ctggggcatt  60
```

```
attacccatc aggcgtttcg cgtgaccagc ggcgtggcga gcggc                105

SEQ ID NO: 723          moltype = AA  length = 30
FEATURE                 Location/Qualifiers
source                  1..30
                        mol_type = protein
                        organism = Paenibacillus polymyxa
SEQUENCE: 723
FVYGNGVTSI LVQAQFLVNG QRRFFYTPDK                                 30

SEQ ID NO: 724          moltype = DNA  length = 90
FEATURE                 Location/Qualifiers
source                  1..90
                        mol_type = genomic DNA
                        organism = Paenibacillus polymyxa
SEQUENCE: 724
tttgtgtatg gcaacggcgt gaccagcatt ctggtgcagg cgcagtttct ggtgaacggc  60
cagcgccgct ttttttatac cccggataaa                                 90

SEQ ID NO: 725          moltype = AA  length = 13
FEATURE                 Location/Qualifiers
source                  1..13
                        mol_type = protein
                        organism = Lactobacillus rhamnosus
SEQUENCE: 725
AVPAVRKTNE TLD                                                   13

SEQ ID NO: 726          moltype = DNA  length = 39
FEATURE                 Location/Qualifiers
source                  1..39
                        mol_type = genomic DNA
                        organism = Lactobacillus rhamnosus
SEQUENCE: 726
gcggtgccgg cggtgcgcaa aaccaacgaa accctggat                       39

SEQ ID NO: 727          moltype = AA  length = 60
FEATURE                 Location/Qualifiers
source                  1..60
                        mol_type = protein
                        organism = Bacillus licheniformis
SEQUENCE: 727
MKNSAAREAF KGANHPAGMV SEEELKALVG GNDVNPETTP ATTSSWTCIT AGVTVSASLC  60

SEQ ID NO: 728          moltype = DNA  length = 180
FEATURE                 Location/Qualifiers
source                  1..180
                        mol_type = genomic DNA
                        organism = Bacillus licheniformis
SEQUENCE: 728
atgaaaaaca gcgcggcgcg cgaagcgttt aaaggcgcga accatccggc gggcatggtg  60
agcgaagaag aactgaaagc gctggtgggc ggcaacgatg tgaacccgga aaccaccccg  120
gcgaccacca gcagctggac ctgcattacc gcgggcgtga ccgtgagcgc gagcctgtgc  180

SEQ ID NO: 729          moltype = AA  length = 689
FEATURE                 Location/Qualifiers
source                  1..689
                        mol_type = protein
                        organism = Pseudomonas aeruginosa
SEQUENCE: 729
MAVNDYEPGS MVITHVQGGG RDIIQYIPAR SSYGTPPFVP PGPSPYVGTG MQEYRKLRST  60
LDKSHSELKK NLKNETLKEV DELKSEAGLP GKAVSANDIR DEKSIVDALM DAKAKSLKAI  120
EDRPANLYTA SDFPQKSESM YQSQLLASRK FYGEFLDRHM SELAKAYSAD IYKAQIAILK  180
QTSQELENKA RSLEAEAQRA AAEVEADYKA RKANVEKKVQ SELDQAGNAL PQLTNPTPEQ  240
WLERATQLVT QAIANKKKLQ TANNALIAKA PNALEKQKAT YNADLLVDEI ASLQARLDKL  300
NAETARRKEI ARQAAIRAAN TYAMPANGSV VATAAGRGLI QVAQGAASLA QAISDAIAVL  360
GRVLASAPSV MAVGFASLTY SSRTAEQWQD QTPDSVRYAL GMDAAKLGLP PSVNLNAVAK  420
ASGTVDLPMR LTNEARGNTT TLSVVSTDGV SVPKAVPVRM AAYNATTGLY EVTVPSTTAE  480
APPLILTWTP ASPPGNQNPS STTPVVPKPV PVYEGATLTP VKATPETYPG VITLPEDLII  540
GFPADSGIKP IYVMFRDPRD VPGAATGKGQ PVSGNWLGAA SQGEGAPIPS QIADKLRGKT  600
FKNWRDFREQ FWIAVANDPE LSKQFNPGSL AVMRDGGAPY VRESEQAGGR IKIEIHHKVR  660
IADGGGVYNM GNLVAVTPKR HIEIHKGGK                                  689

SEQ ID NO: 730          moltype = DNA  length = 2070
FEATURE                 Location/Qualifiers
source                  1..2070
                        mol_type = genomic DNA
                        organism = Pseudomonas aeruginosa
SEQUENCE: 730
atggctgtca atgattacga acctggttcg atggttatta cacatgtgca gggtggtggg  60
```

```
cgtgacataa tccagtatat tcctgctcga tcaagctacg gtactccacc atttgtccca  120
ccaggaccaa gtccgtatgt cggtactgga atgcaggagt acaggaagct aagaagtacg  180
cttgataagt cccattcaga actcaagaaa aacctgaaaa atgaaaccct gaaggaggtt  240
gatgaactca agagtgaagc ggggttgcca ggtaaagcgg tcagtgccaa tgacatccgc  300
gatgaaaaga gtatcgttga tgcactcatg gatgccaaag caaaatcgct aaaggccatt  360
gaggatcgcc cggccaatct ttatacggct tcagactttc ctcagaagtc agagtcgatg  420
taccagagtc agttgctggc cagccgaaaa ttctatggag agttcctgga tcgccatatg  480
agtgagctgg ccaaagcgta cagcgccgat atctataagg cgcaaatcgc tatcttgaaa  540
caaacgtctc aagagctgga gaataaagcc cggtcattgg aagcagaagc ccagcgagcc  600
gctgctgagg tggaggcgga ctacaaggcc aggaaggcaa atgtcgagaa aaaagtgcag  660
tccgagcttg accaggctgg gaatgctttg cctcaactga ccaatccaac gccagagcag  720
tggcttgaac gcgctactca actggttacg caggcgatcg ccaataagaa gaaattgcag  780
actgcaaaca atgccttgat tgccaaggca cccaatgcac tggagaaaca aaaggcaacc  840
tacaacgccg atctcctagt ggatgaaatc gccagcctgc aagcacggct ggacaagctg  900
aacgccgaaa cggcaaggcg caaggaaatc gctcgtcaag cggcgatcag ggctgccaat  960
acttatgcca tgccagccaa tggcagcgtt gtcgccaccg ccgcaggccg gggtctgatc  1020
caggtcgcac aaggcgccgc atcccttgct caagcgatct ccgatgcgat tgccgtcctg  1080
ggccgggtcc tggcttcagc accctcggtg atggccgtgg gctttgccag tctgacctac  1140
tcctcccgga ctgccgagca atggcaggac caaacgcccg atagcgttcg ttacgccctg  1200
ggcatggatg ccgctaaatt ggggcttccc ccaagcgtaa acctgaacgc ggttgcaaaa  1260
gccagcggta ccgtcgatct gccgatgcgc ctgaccaacg aggcacgagg caacacgacg  1320
accctttcgg tggtcagcac cgatggtgtg agcgttccga aagccgttcc ggtccggatg  1380
gcggcctaca atgccacgac aggcctgtac gaggttacgg ttccctctac gaccgcagaa  1440
gcgccgccac tgatcctgac ctggacgccg gcgagtcctc caggaaacca gaacccttcg  1500
agtaccactc cggtcgtacc gaagccggtg ccggtatatg agggagcgac ccttacaccg  1560
gtgaaggcta ccccggaaac ctatcctggg gtgattacac taccggaaga cctgatcatc  1620
ggcttcccgg ccgactcggg gatcaagccg atctatgtga tgttcaggga tccgcgggat  1680
gtacctggtg ctgcgactgg caagggacag cccgtcagcg gtaattggct cggcgccgcc  1740
tctcaaggtg agggggctcc aattccaagc cagattgcgg ataaactacg tggtaagaca  1800
ttcaaaaact ggcgggactt tcgggaacaa ttctggatag ctgtggctaa tgatcctgag  1860
ttaagtaaac agtttaatcc tggtagttta gctgtaatga gagatggagg ggctccttat  1920
gtcagagagt cagaacaggc tggcgggaga ataaagatcg aaatccacca caaggttcga  1980
atagcagatg gaggcggcgt ttacaatatg ggaaccttg ttgcagtaac gccaaaacgt  2040
catatagaaa tccacaaggg agggaagtga                                  2070
```

```
SEQ ID NO: 731          moltype = AA  length = 36
FEATURE                 Location/Qualifiers
source                  1..36
                        mol_type = protein
                        organism = Lactobacillus plantarum
SEQUENCE: 731
KYYGNGLSCS KKGCTVNWGQ AFSCGVNRVA TAGHGK                           36

SEQ ID NO: 732          moltype = DNA  length = 108
FEATURE                 Location/Qualifiers
source                  1..108
                        mol_type = genomic DNA
                        organism = Lactobacillus plantarum
SEQUENCE: 732
aaatattatg gcaacggcct gagctgcagc aaaaaaggct gcaccgtgaa ctggggccag  60
gcgtttagct gcggcgtgaa ccgcgtggcg accgcgggcc atggcaaa              108

SEQ ID NO: 733          moltype = AA  length = 30
FEATURE                 Location/Qualifiers
source                  1..30
                        mol_type = protein
                        organism = Lactococcus lactis
SEQUENCE: 733
MKTILRFVAG YDIASHKKKT GGYPWERGKA                                  30

SEQ ID NO: 734          moltype = DNA  length = 93
FEATURE                 Location/Qualifiers
source                  1..93
                        mol_type = genomic DNA
                        organism = Lactococcus lactis
SEQUENCE: 734
atgaaaacaa tcctacgttt tgttgctggc tacgatattg ctagtcataa aaagaaaact  60
ggcggctatc catgggaacg tggaaaagct taa                              93

SEQ ID NO: 735          moltype = AA  length = 24
FEATURE                 Location/Qualifiers
source                  1..24
                        mol_type = protein
                        organism = Lactobacillus acidophilus
SEQUENCE: 735
GNPKVAHCAS QIGRSTAWGA VSGA                                        24

SEQ ID NO: 736          moltype = DNA  length = 72
FEATURE                 Location/Qualifiers
```

```
source                  1..72
                        mol_type = genomic DNA
                        organism = Lactobacillus acidophilus
SEQUENCE: 736
ggcaacccga aagtggcgca ttgcgcgagc cagattggcc gcagcaccgc gtggggcgcg  60
gtgagcggcg cg                                                      72

SEQ ID NO: 737          moltype = AA  length = 53
FEATURE                 Location/Qualifiers
source                  1..53
                        mol_type = protein
                        note = cp400
                        organism = Lactobacillus salivarius
SEQUENCE: 737
MFFNFMKKVD VKKNFGYKEV SRKDLAKVNG GKRKKHRCRV YNNGMPTGMY RWC         53

SEQ ID NO: 738          moltype = DNA  length = 162
FEATURE                 Location/Qualifiers
source                  1..162
                        mol_type = genomic DNA
                        note = cp400
                        organism = Lactobacillus salivarius
SEQUENCE: 738
atgtttttta attttatgaa aaaagtagat gtgaagaaga attttggata taaagaagtt  60
tctagaaaag atctagctaa agtaaatggt ggaaagagaa agaaacatcg ttgcagagtt  120
tataataatg gaatgcctac aggaatgtat cgttggtgct aa                     162

SEQ ID NO: 739          moltype = AA  length = 5
FEATURE                 Location/Qualifiers
REGION                  1..5
                        note = Caspase 2 consensus sequence
source                  1..5
                        mol_type = protein
                        organism = synthetic construct
SEQUENCE: 739
DVADL                                                              5

SEQ ID NO: 740          moltype = AA  length = 5
FEATURE                 Location/Qualifiers
REGION                  1..5
                        note = Caspase 2 consensus sequence
source                  1..5
                        mol_type = protein
                        organism = synthetic construct
SEQUENCE: 740
DVADI                                                              5

SEQ ID NO: 741          moltype = AA  length = 12
FEATURE                 Location/Qualifiers
REGION                  1..12
                        note = Synthetic RAP-binding peptide, RBP
source                  1..12
                        mol_type = protein
                        organism = synthetic construct
SEQUENCE: 741
FHWWQTSPAH FS                                                      12

SEQ ID NO: 742          moltype = AA  length = 12
FEATURE                 Location/Qualifiers
REGION                  1..12
                        note = Synthetic RAP-binding peptide, RBP
source                  1..12
                        mol_type = protein
                        organism = synthetic construct
SEQUENCE: 742
WPFAHWPWQY PR                                                      12

SEQ ID NO: 743          moltype = AA  length = 9
FEATURE                 Location/Qualifiers
REGION                  1..9
                        note = Synthetic AgrC ligand
VARIANT                 5..9
                        note = Thiolacton linkage between C5 and F9
source                  1..9
                        mol_type = protein
                        organism = synthetic construct
SEQUENCE: 743
GDSVCASYF                                                          9
```

```
SEQ ID NO: 744          moltype = AA  length = 7
FEATURE                 Location/Qualifiers
REGION                  1..7
                        note = Synthetic AgrC ligand
VARIANT                 3..7
                        note = Thiolacton linkage between C3 and F7
source                  1..7
                        mol_type = protein
                        organism = synthetic construct
SEQUENCE: 744
SVCASYF                                                      7

SEQ ID NO: 745          moltype = AA  length = 5
FEATURE                 Location/Qualifiers
REGION                  1..5
                        note = Synthetic Cry1Aa ligand
source                  1..5
                        mol_type = protein
                        organism = synthetic construct
SEQUENCE: 745
SKADT                                                        5

SEQ ID NO: 746          moltype = AA  length = 5
FEATURE                 Location/Qualifiers
REGION                  1..5
                        note = Synthetic Cry1Aa ligand
source                  1..5
                        mol_type = protein
                        organism = synthetic construct
SEQUENCE: 746
SKPAD                                                        5

SEQ ID NO: 747          moltype = AA  length = 11
FEATURE                 Location/Qualifiers
REGION                  1..11
                        note = Synthetic Fsr ligand
VARIANT                 3..11
                        note = Lacton linkage between S3 and A11
source                  1..11
                        mol_type = protein
                        organism = synthetic construct
SEQUENCE: 747
QNSAAAFAAW A                                                 11

SEQ ID NO: 748          moltype = AA  length = 11
FEATURE                 Location/Qualifiers
REGION                  1..11
                        note = Synthetic Fsr ligand
VARIANT                 3..11
                        note = Lacton linkage between S3 and A11
source                  1..11
                        mol_type = protein
                        organism = synthetic construct
SEQUENCE: 748
QNSAAAFGQW A                                                 11

SEQ ID NO: 749          moltype = AA  length = 7
FEATURE                 Location/Qualifiers
REGION                  1..7
                        note = Synthetic AgrC1, AgrC2
VARIANT                 4..7
                        note = Thiolacton linkage between C4 and M7)
source                  1..7
                        mol_type = protein
                        organism = synthetic construct
SEQUENCE: 749
YSTCFIM                                                      7

SEQ ID NO: 750          moltype = AA  length = 7
FEATURE                 Location/Qualifiers
REGION                  1..7
                        note = Synthetic AgrC1, AgrC2
```

-continued

```
VARIANT                3..7
                       note = Thiolacton linkage between C3 and M7
source                 1..7
                       mol_type = protein
                       organism = synthetic construct
SEQUENCE: 750
STCAFIM                                                             7
```

What is claimed is:

1. A microfluidic device for producing a specified mixture of antimicrobial peptides and/or bacteriocins, the device comprising:

discrete coding substrates that each encode a different antimicrobial peptide and/or bacteriocin, wherein the discrete coding substrates are comprised within separate chambers;

an in vitro transcription/translation solution;

a fluidic reservoir; and valves each disposed on a fluidic path between a discrete coding substrate and the fluidic reservoir, each valve configured to regulate flow between the discrete coding substrate and the fluidic reservoir, wherein the device is configured to be placed in data communication with a processor configured to:

based on the specified mixture of antimicrobial peptides and/or bacteriocins, configure the valves to place the discrete coding substrates that encode the antimicrobial peptides and/or bacteriocins of the mixture at a stoichiometry defined by a user, but not other discrete coding substrates, in fluidic communication with the fluidic reservoir;

permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;

permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

2. The microfluidic device of claim 1, wherein:

the specified mixture of antimicrobial peptides and/or bacteriocins comprises two or more submixtures each comprising a subset of antimicrobial peptides and/or bacteriocins; and the processor is configured to permit flow of each submixture into the fluidic reservoir, thereby producing the specified mixture of antimicrobial peptides and/or bacteriocins.

3. The microfluidic device of claim 2, wherein the specified mixture of antimicrobial peptides and/or bacteriocins comprises a sum of the subsets of antimicrobial peptides and/or bacteriocins in a specified stoichiometry, and wherein combination of the submixtures yields the specified stoichiometry.

4. The microfluidic device of claim 1, wherein the fluidic reservoir is configured to be placed in fluid communication with a tissue of a subject.

5. The microfluidic device of claim 1, further comprising the processor.

6. A system comprising:

the microfluidic device of claim 1, and a processor configured to:

based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir;

permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;

permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

7. The system of claim 6, wherein the microfluidic device is comprised by a cartridge, and the system further comprises a coupling for placing the cartridge in data communication with the processor.

8. The system of claim 6 wherein the in vitro transcription/translation solution is lyophilized.

9. A microfluidic device for producing a specified mixture of antimicrobial peptides and/or bacteriocins, the device comprising:

discrete coding substrates that each encode a different mixture of antimicrobial peptide(s) and/or bacteriocin(s) at a stoichiometry defined by a user, wherein the discrete coding substrates are comprised within separate chambers;

valves each disposed on a fluidic path connected to a discrete coding substrate, each valve configured to regulate flow to or from the discrete coding substrate, and wherein the device is configured to be placed in fluid communication with a fluidic reservoir of an in vitro transcription/translation solution.

10. The microfluidic device of claim 9, further comprising a reservoir of chemical or phage antibiotics configured to mix with the mixture of specified antimicrobial peptides and/or bacteriocins.

* * * * *